(12) United States Patent
Wight et al.

(10) Patent No.: US 11,840,703 B2
(45) Date of Patent: Dec. 12, 2023

(54) RECOMBINANT VERSICAN ISOFORMS AND RELATED COMPOSITIONS AND METHODS

(71) Applicant: Matrexa LLC, Seattle, WA (US)

(72) Inventors: Thomas N. Wight, Seattle, WA (US); Mervyn J. Merrilees, Auckland (NZ); Gernot Kaber, Seattle, WA (US); Ingrid A. Harten, Seattle, WA (US); Michael G. Kinsella, Seattle, WA (US)

(*) Notice: Subject to any disclaimer, the term of this patent is extended or adjusted under 35 U.S.C. 154(b) by 239 days.

(21) Appl. No.: 16/917,131

(22) Filed: Jun. 30, 2020

(65) Prior Publication Data

US 2021/0024954 A1    Jan. 28, 2021

Related U.S. Application Data

(60) Provisional application No. 62/869,438, filed on Jul. 1, 2019.

(51) Int. Cl.
*C12P 21/06* (2006.01)
*C12N 15/86* (2006.01)
(Continued)

(52) U.S. Cl.
CPC .......... *C12N 15/86* (2013.01); *C07K 14/4725* (2013.01); *A61K 9/0014* (2013.01); *A61K 38/00* (2013.01)

(58) Field of Classification Search
None
See application file for complete search history.

(56) References Cited

U.S. PATENT DOCUMENTS 4,559,157 A   12/1985   Smith et al.
4,608,392 A   8/1986    Jacquet et al.
(Continued)

FOREIGN PATENT DOCUMENTS

AU   2001253408 B2   4/2007
EP   127426 A1       12/1984
EP   1274726 B1      12/2009

OTHER PUBLICATIONS

Goh et al., "Impact of host cell line choice on glycan profile," Critical Reviews in Biotechnology, 38:6: 851-867 (Year: 2018).*
(Continued)

*Primary Examiner* — M Franco G Salvoza
(74) *Attorney, Agent, or Firm* — Schwegman Lundberg & Woessner, P.A.

(57) ABSTRACT

The disclosure provides methods and constructs for the stable production and isolation of biologically functional recombinant V3, a splice variant of the extracellular matrix proteoglycan versican, as well as the protein product and reagents for detecting the same. In one embodiment, the disclosure provides expression systems for expressing rV3. In one embodiment, the disclosure provides an expression system that properly N-glycosylates mammalian proteins, such as V3. In another embodiment, rV3 has been isolated and purified. In another embodiment, the disclosure provides a unique expression construct containing a ubiquitous chromatin opening element upstream of a strong promoter which drives expression of recombinant V3. In yet a further embodiment, the disclosure provides an isolated and purified recombinant V3 protein in amounts suitable for testing and use, and in pharmaceutical compositions thereof.

6 Claims, 33 Drawing Sheets

Specification includes a Sequence Listing.

(51) Int. Cl.
  C07K 14/47  (2006.01)
  A61K 9/00   (2006.01)
  A61K 38/00  (2006.01)

(56) References Cited

U.S. PATENT DOCUMENTS

| | | | |
|---|---|---|---|
| 4,820,508 | A | 4/1989 | Wortzman |
| 4,992,478 | A | 2/1991 | Geria |
| 5,283,173 | A | 2/1994 | Fields et al. |
| 5,468,614 | A | 11/1995 | Fields et al. |
| 7,816,335 | B2 | 10/2010 | Wight et al. |
| 8,367,619 | B2 | 2/2013 | Wight et al. |
| 8,410,067 | B2 | 4/2013 | Wight et al. |

OTHER PUBLICATIONS

Croset et al., "Differences in the glycosylation of recombinant proteins expressed in HEK and CHO cells," Journal of Biotechnology, 161: 336-348 (Year: 2012).*

Andersson-Sjoland, Annika, et al., "Versican in inflammation and tissue remodeling: the impact on lung disorders", Glycobiology vol. 25 No. 3, (Nov. 3, 2014), pp. 243-251.

Ang, Lee Cyn, et al., "Versican enhances locomotion of astrocytoma cells and reduces cell adhesion through its G1 domain", J Neuropathol Exp Neurol vol. 58 Num 6, (Jun. 1999), pp. 597-605.

Apte, Suneel S., "A disintegrin-like and metalloprotease (reprolysin-type) with thrombospondin type 1 motif (ADAMTS) superfamily: functions and mechanisms", J Biol Chem vol. 284 No. 46, (Nov. 13, 2009), pp. 31493-31497.

Bandaranayake, Ashok D., et al., "Daedalus: a robust, turnkey platform for rapid production of decigram quantities of active recombinant proteins in human cell lines using novel lentiviral vectors", Nucleic Acids Res vol. 39 No. 21, (2011), 11 pages.

Bano, Fouzia, et al., "Single-Molecule Unbinding Forces between the Polysaccharide Hyaluronan and Its Binding Proteins", Biophysical Journal 114, (Jun. 19, 2018), pp. 2910-2922.

Bode-Lesniewska, Beata, et al., "Distribution of the large aggregating proteoglycan versican in adult human tissues", The Journal of Histochemistry and Cytochemistry vol. 44 No. 4, (Apr. 1, 1996), pp. 303-312.

Brissett, Nigel C., et al., "Conserved basic residues in the C-type lectin and short complement repeat domains of the G3 region of proteoglycans", Biochem J, 329, (1998), pp. 415-424.

Cao, L, et al., "Chondrocyte apoptosis induced by aggrecan G1 domain as a result of decreased cell adhesion", Experimental Cell Research 246 vol. 246 No. 2, (Feb. 1, 1999), pp. 527-537.

Cardoso, Luiz E. M., et al., "Platelet-derived growth factor differentially regulates the expression and post-translational modification of versican by arterial smooth muscle cells through distinct protein kinase C and extracellular signal-regulated kinase pathways", The Journal of Biological Chemistry vol. 285 No. 10, (Mar. 5, 2010), pp. 6987-6995.

Chang, Yingshan, et al., "Proteoglycans synthesized by smooth muscle cells derived from monkey (*Macaca nemestrina*) aorta", The Journal of Biological chemistry vol. 258 No. 9, (05/1071983), pp. 5679-5688.

Chen, Liwen, et al., "G3 domains of aggrecan and PG-M/versican form intermolecular disulfide bonds that stabilize cell-matrix interaction", Biochemistry vol. 42 No. 27, (Jun. 20, 2003), pp. 8332-8341.

Chen, Liwen, et al., "The folded modules of aggrecan G3 domain exert two separable functions in glycosaminoglycan modification and product secretion", The Journal of Biological Chemistry vol. 277 No. 4, (Jan. 25, 2002), pp. 2657-2665.

Chen, Tung-Ling L., et al., "Aggrecan domains expected to traffic through the exocytic pathway are misdirected to the nucleus", Experimental Cell Research 263, (Feb. 1, 2001), pp. 224-235.

Clark, Michelle A., et al., "Regulation and expression of human Fabs under the control of the *Escherichia coli* arabinose promoter PBAD", Immunotechnology vol. 3 No. 3, (Oct. 1, 1997), pp. 217-226.

Du, W.W., et al., "The role of versican G3 domain in regulating breast cancer cell motility including effects on osteoblast cell growth and differentiation in vitro—evaluation towards understanding breast cancer cell bone metastasis", BioMed Central 12, Article No. 341, (Aug. 3, 2012), 16 pages.

Fanhchaksai, Kanda, et al., "Host stromal versican is essential for cancer-associated fibroblast function to inhibit cancer growth", Int J Cancer vol. 138 No. 3, (Feb. 1, 2016), pp. 630-641.

Freeze, Hudson H., "Understanding human glycosylation disorders: biochemistry leads the charge", The Journal of Biological Chemistry vol. 288 No. 10, (Mar. 8, 2013), pp. 6936-6945.

Gill, Sean, et al., "Proteoglycans: key regulators of pulmonary inflammation and the innate immune response to lung infection", The Anatomical Record 293, (Apr. 7, 2010), pp. 968-981.

Harten, Ingrid A., et al., "The synthesis and secretion of versican isoform V3 by mammalian cells: A role for N-linked glycosylation", Matrix Biology Program, (2020), pp. 27-42.

Hartwig, Sonja, et al., "Secretome profiling of primary human skeletal muscle cells", Biochimica et Biophysica Acta 1844, (2014), pp. 1011-1017.

Henderson, Deborah J., et al., "Role of the extracellular matrix in neural crest cell migration", The Journal of Anatomy vol. 191 Issue 4, (Nov. 1997), pp. 507-515.

Hernandez, Daniel, et al., "V3 versican isoform alters the behavior of human melanoma cells by interfering with CD44/ErbB-dependent signaling", The Journal of Biological Chemistry vol. 286 No. 2, (Jan. 14, 2011), pp. 1475-1485.

Hinek, Aleksander, et al., "Retrovirally mediated overexpression of versican v3 reverses impaired elastogenesis and heightened proliferation exhibited by fibroblasts from Costello syndrome and Hurler disease patients", American Journal of Pathology vol. 164 No. 1, (Jan. 2004), pp. 119-131.

Hofmann, Andreas, et al., "Epigenetic regulation of lentiviral transgene vectors in a large animal model", Molecular Therapy vol. 13 No. 1, (Jan. 2006), pp. 59-66.

Hope, Chelsea, et al., "Immunoregulatory roles of versican proteolysis in the myeloma microenvironment", Blood vol. 128 No. 5, (Aug. 4, 2016), pp. 680-685.

Hudson, Karla S., et al., "Versican G1 domain and V3 isoform overexpression results in increased chondrogenesis in the developing chick limb in ovo", The Anatomical Record 293, (Aug. 20, 2010), pp. 1669-1678.

Isogai, Zenzo, et al., "Versican interacts with fibrillin-1 and links extracellular microfibrils to other connective tissue networks", The Journal of Biological Chemistry vol. 277 No. 6, (Feb. 8, 2002), pp. 4565-4572.

Ito, Kazuo, et al., "Multiple forms of mouse PG-M, a large chondroitin sulfate proteoglycan generated by alternative splicing", The Journal of Biological Chemistry vol. 270 No. 2, (Jan. 13, 1995), pp. 958-965.

Kamiya, Nobuhiro, et al., "Versican/PG-M regulates chondrogenesis as an extracellular matrix molecule crucial for mesenchymal condensation", The Journal of Biological Chemistry vol. 281 No. 4, (Jan. 27, 2006), pp. 2390-2400.

Kang, Inkyung, et al., "Expression of V3 versican by rat arterial smooth muscle cells promotes differentiated and anti-inflammatory phenotypes", The Journal of Biological Chemistry vol. 290 No. 35, (Aug. 28, 2015), pp. 21629-21641.

Kang, Inkyung, et al., "Expression of versican V3 by arterial smooth muscle cells alters TGFß-, EGF-, and NFκB-dependent signaling pathways, creating a microenvironment that resists monocyte adhesion", The Journal of Biological Chemistry 289, (Apr. 9, 2014), pp. 15393-15404.

Kang, Inkyung, et al., "Versican Deficiency Significantly Reduces Lung Inflammatory Response Induced by Polyinosine-Polycytidylic Acid Stimulation", The Journal of Biological Chemistry vol. 292 No. 1, (Jan. 6, 2017), pp. 51-63.

(56) References Cited

OTHER PUBLICATIONS

Keire, Paul A., et al., "Expression of versican isoform V3 in the absence of ascorbate improves elastogenesis in engineered vascular constructs", Tissue Engineering Part A vol. 16 No. 2, (2010), pp. 501-512.
Keire, Paul A., et al., "Versican: Role in Cancer Tumorigenesis", Extracellular Matrix in Tumor Biology, Biology of Extracellular Matrix, (2017), pp. 51-74.
Kern, Christine B., et al., "Versican proteolysis mediates myocardial regression during outflow tract development", Developmental Dynamics 236, (Jan. 16, 2007), pp. 671-683.
Kiani, Chris, et al., "Roles of aggrecan domains in biosynthesis, modification by glycosaminoglycans and product secretion", The Biochemical Journal 354, (20012/1/), pp. 199-207.
Kohfeldt, E, et al., "Properties of the extracellular calcium binding module of the proteoglycan testican", FEBS Letters 414, (Sep. 15, 1997), pp. 557-561.
Kwaks, Ted H.K., et al., "Identification of anti-repressor elements that confer high and stable protein production in mammalian cells", Nature Biotechnology vol. 21 No. 5, (Apr. 7, 2003), pp. 553-558.
Lebaron, Richard G., et al., "Hyaluronate binding properties of versican", The Journal of Biological Chemistry vol. 267 No. 14, (May 15, 1992), pp. 10003-10010.
Lebendiker, Mario, et al., "Production of prone to aggregate proteins", FEBS Lett vol. 588 No. 2, (Jan. 21, 2014), pp. 236-246.
Lemire, Joan M., et al., "Interleukin 1beta selectively decreases the synthesis of versican by arterial smooth muscle cells", Journal of Cellular Biochemistry 101, (Jun. 2007), pp. 753-766.
Lemire, Joan M., et al., "Overexpression of the V3 variant of versican alters arterial smooth muscle cell adhesion, migration, and proliferation in vitro", Journal of Cellular Physiology 190 1 38-45, (Jan. 2002), pp. 38-45.
Lemire, Joan M., et al., "Versican PG M isoforms in vascular smooth muscle cells", Arterioscler Thromb Vasc Biol vol. 19 No. 7, (Jul. 1999), pp. 1630-1639.
Luo, Wei, et al., "Aggrecan from start to finish", J Bone Miner Metab 18 2, (Feb. 2000), pp. 51-56.
Luo, Wei, et al., "Divergent secretory behavior of the opposite ends of aggrecan", The Journal of Biological Chemistry vol. 271 No. 28, (Jul. 12, 1996), pp. 16447-16450.
Mansha, Muhammad, et al., "Problems encountered in bicistronic IRES-GFP expression vectors employed in functional analyses of GC-induced genes", Molecular Biology Reports vol. 39 Issue 12, (Dec. 2012), pp. 10227-10234.
Mauro, Vincent P., et al., "A critical analysis of codon optimization in human therapeutics", Opinion Trends in Molecular Medicine vol. 20 No. 11, (Nov. 2014), pp. 604-613.
Mayanil, C.S.K., et al., "Microarray analysis detects novel Pax3 downstream target genes", The Journal of Biological Chemistry vol. 276 No. 52, (Dec. 2001), pp. 49299-49309.
Merrilees, Mervyn J., et al., "G1 Domain of Versican Regulates Hyaluronan Organization and the Phenotype of Cultured Human Dermal Fibroblasts", Journal of Histochemistry & Cytochemistry, (2016), 11 pgs.
Merrilees, Mervyn J., et al., "Neointima After Vascular Injury Cells Induces Tropoelastin Synthesis and Elastic Fiber Formation In Vitro and in Retrovirally Mediated Overexpression of Versican V3 by Arterial Smooth Muscle", American Heart Association, (2002), 8 pgs.
Merrilees, Mervyn J., et al., "Neointima Formed by Arterial Smooth Muscle Cells Expressing Versican Variant V3 Is Resistant to Lipid and Macrophage Accumulation", Arterioscler Thromb Vasc Bio, (Jun. 2011), 8 pgs.
Merrilees, Mervyn J., et al., "Regulating Elastogenesis Using Proteoglycans", CRC Press, (Jun. 16, 2016), 30 pgs.
Merrilees, Mervyn J., et al., "Retrovirally Mediated Overexpression of Versican V3 by Arterial Smooth Muscle Cells Induces Tropoelastin Synthesis and Elastic Fiber Formation In Vitro and in Neointima After Vascular Injury", Circulation Research—American Heart Association, (2002), 8 pgs.
Merrilees, Mervyn J., et al., "Targeting the matrix: potential benefits for versican therapeutics", Elsevier Blogs Current Comments, (Mar. 28, 2012), 4 pgs.
Merrilees, Mervyn J., et al., "Use of versican variant V3 and versican antisense expression to engineer cultured human skin containing increased content of insoluble elastin", Journal of Tissue Engineering and Regenerative Medicine, (Jun. 19, 2014), 11 pgs.
Miquel-Serra, Laia, et al., "V3 versican isoform expression has a dual role in human melanoma tumor growth and metastasis", Laboratory Investigation vol. 86, No. 9, (Sep. 1, 2006), 13 pgs.
Mjaatvedt, C H., et al., "The Cspg2 gene disrupted in the hdf mutant is required for right cardiac chamber and endocardial cushion formation", Developmental Biology 202(1):, (Oct. 1998), pp. 56-66.
Mukhopadhyay, Arijit, et al., "Erosive Vitreoretinopathy and Wagner Disease Are Caused by Intronic Mutations in CSPG2/Versican That Result in an Imbalance of Splice Variants", Investigative Ophthalmology & Visual Science, vol. 47, No. 8, (Aug. 2006), 8 pgs.
Neville, Jonathan J., et al., "Ubiquitous Chromatin opening Elements UCOEs Applications in biomanufacturing and gene therapy", Biotechnology Advances 35, (May 2017), pp. 557-564.
Ohtsubo, Kazuaki, et al., "Glycosylation in Cellular Mechanisms of Health and Disease", Cell 126, (Sep. 8, 2006), 13 pgs.
Olin, Katherine E., et al., "Biglycan, a Vascular Proteoglycan, Binds Differently to HDL2 and HDL3", Arteriosclerosis, Thrombosis, and Vascular Biology—American Heart Association, (2001), 8 pgs.
Perkins, Stephen J., et al., "Immunoglobulin Fold and Tandem Repeat Structures in Proteoglycan N-terminal Domains and Link Protein", Academic Press Limited, (1989), 12 pgs.
Perkins, Stephen J., et al., "Molecular Modeling of the Multidomain Structures of the Proteoglycan Binding Region and the Link Protein of Cartilage by Neutron and Synchrotron X-ray Scattering", American Chemical Society—Biochemistry, vol. 30, No. 44, (1991), 9 pgs.
Perveen, Rahat, et al., "Refined Genetic and Physical Localization of the Wagner Disease (WGN1) Locus and the Genes CRTL1 and CSPG2 to a 2- to 2.5-cM Region of Chromosome 5q14.3", Genomics 57, (1999), 8 pgs.
Petersen, Thomas Nordahl, et al., "SignalP 4.0: Discriminating Signal Peptides From Transmembrane Regions", Nature America—Nature Methods vol. 8 No. 10, (Oct. 2011), 2 pgs.
Potter-Perigo, Susan, et al., "Polyinosine-Polycytidylic Acid Stimulates Versican Accumulation in the Extracellular Matrix Promoting Monocyte Adhesion", American Journal of Respiratory Cell and Molecular Biology vol. 43, (2010), 12 pgs.
Puttini, Stefania, et al., "MAR-Mediated iIntegration of Plasmid Vectors for In Vivo Gene Transfer and Regulation", BMC Molecular Biology, (2013), 12 pgs.
Rahmani, Maziar, et al., "Regulation of the Versican Promoter by the B-Catenin-T-cell Factor Complex in Vascular Smooth Muscle Cells", The Journal of Biological Chemistry vol. 280, No. 13, (Apr. 1, 2005), 10 pgs.
Rattan, Suresh I.S., et al., "Protein Synthesis, Post translational Modifications, and Aging", Annals of the New York Academy of Sciences, (Nov. 1992), 15 pgs.
Ricciardelli, Carmela, et al., "The biological role and regulation of versican levels in cancer", Cancer and Metastasis Reviews. Kluwer Academic Publishers vol. 28 No. 1-2, (Jan. 22, 2009), 13 pgs.
Rudd, Pauline M. et al., "Glycosylation and the Immune System", Science vol. 291, (Mar. 23, 2001), 7 pgs.
Saunders, F., et al., "Chromatin function modifying elements in an industrial antibody production platform—comparison of UCOE, MAR, STAR and cHS4 elements", PLoS One, 2015. 10(4): p. e0120096, (Apr. 7, 2015), 20 pgs.
Scatchard, George; "The Attractions of Proteins for Small Molecules and Ions", Ann. N.Y. Acad. Sci. 51, (May 1949), 13 pgs.
Schmidt, T.G., et al., "Development of the Twin-Strep-tag(R) and its application for purification of recombinant proteins from cell culture supernatants", Protein Expr Purif, 2013. 92(1): p. 54-61., (Nov. 2013), 8 pgs.
Seifter, S., et al., "Analysis for protein modifications and nonprotein cofactors", Methods Enzymol, 1990. 182: p. 626-46., (1990), 21 pgs.

(56) References Cited

OTHER PUBLICATIONS

Serra, M., et al., "V3 versican isoform expression alters the phenotype of melanoma cells and their tumorigenic potential", Int J Cancer, 2005. 114(6): p. 879-86., (2005), 8 pgs.

Seyfried, N.T., et al., "Expression and purification of functionally active hyaluronan-binding domains from human cartilage link protein, aggrecan and versican: formation of ternary complexes with defined hyaluronan oligosaccharides", J Biol Chem, 2005. 280(7): p. 5435-48., (Feb. 18, 2005), 14 pgs.

Shriver, Z., et al., "Glycomics: a pathway to a class of new and improved therapeutics", Nat Rev Drug Discov, 2004. 3(10): p. 863-73., (Oct. 2004), 12 pgs.

Spiro, R.G., "Protein glycosylation: nature, distribution, enzymatic formation, and disease implications of glycopeptide bonds", Glycobiology, 2002. 12(4): p. 43R-56R., (Jan. 30, 2002), 14 pgs.

Vertel, B.M., et al., "Nanomelic chondrocytes synthesize, but fail to translocate, a truncated aggrecan precursor", J Cell Sci, 1993. 104(Pt 3): p. 939-48., (Mar. 1993), 10 pgs.

Vertel, Barbara M., "The ins and outs of aggrecan", Trends Cell Biol, 5(12), (Dec. 5, 1995), pp. 458-464.

Watanabe, H., et al., "Identification of hyaluronan-binding domains of aggrecan", J Biol Chem, 1997. 272(44): p. 28057-65, (Oct. 31, 1997), 9 pgs.

Wight, T.N., "A role for proteoglycans in vascular disease", Matrix Biol, 2018. 71-72: p. 396-420., (Oct. 2018), 42 pgs.

Wight, T.N., et al., "Interplay of extracellular matrix and leukocytes in lung inflammation", Cell Immunol, 2017. 312: p. 1-14., (Feb. 2017), 34 pgs.

Wight, T.N., et al., "Versican and the control of inflammation", Matrix Biol, 2014. 35: p. 152-61., (Feb. 7, 2014), 10 pgs.

Wight, T.N., et al., "Versican and the regulation of cell phenotype in disease", Biochim Biophys Acta, 2014. 1840(8): p. 2441-51., (Jan. 5, 2014), 11 pgs.

Wight, Thomas N., "Versican: a versatile extracellular matrix proteoglycan in cell biology", Curr Opin Cell Biol, 2002. 14(5), (Oct. 1, 2002), pp. 617-623.

Wu, Y., et al., "Overexpression of the C-terminal PG-M/versican domain impairs growth of tumor cells by intervening in the interaction between epidermal growth factor receptor and beta1-integrin", J Cell Sci, 2004. 117(Pt 11): 2227-37., (2004), 11 pgs.

Wu, Y., et al., "The interaction of versican with its binding partners", Cell Res, 2005. 15(7): p. 483-94., (Jul. 2005), 12 pgs.

Yamaguchi, Y., "Chondroitin sulfate proteoglycans in the nervous system, in Proteoglycans: Structure, Biology, and Molecular Interactions", R. Iozzo, Editor. 2000, Marcel Dekker: New York. p. 379-402., (2000), 13 pgs.

Yang, B.L., et al., "Tandem repeats are involved in G1 domain inhibition of versican expression and secretion and the G3 domain enhances glycosaminoglycan modification and product secretion via the complement-binding protein-like motif", J Biol Chem, 2000. 275(28): p. 21255-61., (Jul. 14, 2000), 7 pgs.

Zako, M., et al., "Expression of PG-M (V3), an alternatively spliced form of PG-M without a chondroitin sulfate attachment region in mouse and human tissues", J Biol Chem, 1995. 270: p. 3914-3918., (Feb. 24, 1995), 5 pgs.

Zhang, F., et al., "A ubiquitous chromatin opening element (UCOE) confers resistance to DNA methylation-mediated silencing of lentiviral vectors", Mol Ther, 2010. 18(9): p. 1640-9., (Sep. 2010), 10 pgs.

Zhang, Y., et al., "The G3 domain of versican enhances cell proliferation via epidermal growth factor-like motifs.", J Biol Chem, 1998. 273(33): p. 21342-21351., (Aug. 14, 1998), 11 pgs.

Zheng, J., et al., "Aggrecan synthesis and secretion. A paradigm for molecular and cellular coordination of multiglobular protein folding and intracellular trafficking.", J Biol Chem, 1998. 273(21): p. 12999-3006., (May 22, 1998), 9 pgs.

Zimmermann, D., "Versican, in Proteoglycans: Structure, Biology and Molecular Interactions", R. Iozzo, Editor. 2000, Marcel Dekker, Inc.: New York. p. 327-41., (2000), 8 pgs.

Zimmermann, D.R., et al., "Extracellular matrix of the central nervous system: from neglect to challenge", Histochem Cell Biol, 2008. 130(4): p. 635-53., (Jul. 26, 2008), 20 pgs.

Zimmermann, D.R., et al., "Multiple domains of the large fibroblast proteoglycan, versican", EMBO J, 1989. 8(10): p. 2975-81., (1989), 7 pgs.

\* cited by examiner

B

Tetracycline-responsive recombinant human V3

MAR | STAR | TRE | Tagged V3 | IRES | SFFV | rtTA | P2A | GFP

SEQUENCE LISTING

```
<160> NUMBER OF SEQ ID NOS: 39

<210> SEQ ID NO 1
<211> LENGTH: 655
<212> TYPE: PRT
<213> ORGANISM: Homo sapiens

<400> SEQUENCE: 1

Met Phe Ile Asn Ile Lys Ser Ile Leu Trp Met Cys Ser Thr Leu Ile
1               5                   10                  15

Val Thr His Ala Leu His Lys Val Lys Val Gly Lys Ser Pro Pro Val
            20                  25                  30

Arg Gly Ser Leu Ser Gly Lys Val Ser Leu Pro Cys His Phe Ser Thr
        35                  40                  45

Met Pro Thr Leu Pro Pro Ser Tyr Asn Thr Ser Glu Phe Leu Arg Ile
    50                  55                  60

Lys Trp Ser Lys Ile Glu Val Asp Lys Asn Gly Lys Asp Leu Lys Glu
65                  70                  75                  80

Thr Thr Val Leu Val Ala Gln Asn Gly Asn Ile Lys Ile Gly Gln Asp
                85                  90                  95

Tyr Lys Gly Arg Val Ser Val Pro Thr His Pro Glu Ala Val Gly Asp
            100                 105                 110

Ala Ser Leu Thr Val Val Lys Leu Leu Ala Ser Asp Ala Gly Leu Tyr
        115                 120                 125
```

```
Arg Cys Asp Val Met Tyr Gly Ile Glu Asp Thr Gln Asp Thr Val Ser
130                 135                 140

Leu Thr Val Asp Gly Val Phe His Tyr Arg Ala Ala Thr Ser Arg
145                 150                 155                 160

Tyr Thr Leu Asn Phe Glu Ala Ala Gln Lys Ala Cys Leu Asp Val Gly
                165                 170                 175

Ala Val Ile Ala Thr Pro Glu Gln Leu Phe Ala Ala Tyr Glu Asp Gly
            180                 185                 190

Phe Glu Gln Cys Asp Ala Gly Trp Leu Ala Asp Gln Thr Val Arg Tyr
        195                 200                 205

Pro Ile Arg Ala Pro Arg Val Gly Cys Tyr Gly Asp Lys Met Gly Lys
210                 215                 220

Ala Gly Val Arg Thr Tyr Gly Phe Arg Ser Pro Gln Glu Thr Tyr Asp
225                 230                 235                 240

Val Tyr Cys Tyr Val Asp His Leu Asp Gly Asp Val Phe His Leu Thr
                245                 250                 255

Val Pro Ser Lys Phe Thr Phe Glu Glu Ala Ala Lys Glu Cys Glu Asn
            260                 265                 270

Gln Asp Ala Arg Leu Ala Thr Val Gly Glu Leu Gln Ala Ala Trp Arg
        275                 280                 285

Asn Gly Phe Asp Gln Cys Asp Tyr Gly Trp Leu Ser Asp Ala Ser Val
290                 295                 300

Arg His Pro Val Thr Val Ala Arg Ala Gln Cys Gly Gly Gly Leu Leu
305                 310                 315                 320

Gly Val Arg Thr Leu Tyr Arg Phe Glu Asn Gln Thr Gly Phe Pro Pro
                325                 330                 335

Pro Asp Ser Arg Phe Asp Ala Tyr Cys Phe Lys Arg Pro Asp Arg Cys
            340                 345                 350

Lys Met Asn Pro Cys Leu Asn Gly Gly Thr Cys Tyr Pro Thr Glu Thr
        355                 360                 365

Ser Tyr Val Cys Thr Cys Val Pro Gly Tyr Ser Gly Asp Gln Cys Glu
370                 375                 380

Leu Asp Phe Asp Glu Cys His Ser Asn Pro Cys Arg Asn Gly Ala Thr
385                 390                 395                 400

Cys Val Asp Gly Phe Asn Thr Phe Arg Cys Leu Cys Leu Pro Ser Tyr
                405                 410                 415

Val Gly Ala Leu Cys Glu Gln Asp Thr Glu Thr Cys Asp Tyr Gly Trp
            420                 425                 430

His Lys Phe Gln Gly Gln Cys Tyr Lys Tyr Phe Ala His Arg Arg Thr
        435                 440                 445

Trp Asp Ala Ala Glu Arg Glu Cys Arg Leu Gln Gly Ala His Leu Thr
450                 455                 460

Ser Ile Leu Ser His Glu Glu Gln Met Phe Val Asn Arg Val Gly His
465                 470                 475                 480

Asp Tyr Gln Trp Ile Gly Leu Asn Asp Lys Met Phe Glu His Asp Phe
                485                 490                 495

Arg Trp Thr Asp Gly Ser Thr Leu Gln Tyr Glu Asn Trp Arg Pro Asn
            500                 505                 510

Gln Pro Asp Ser Phe Phe Ser Ala Gly Glu Asp Cys Val Val Ile Ile
        515                 520                 525

Trp His Glu Asn Gly Gln Trp Asn Asp Val Pro Cys Asn Tyr His Leu
530                 535                 540
```

```
Thr Tyr Thr Cys Lys Lys Gly Thr Val Ala Cys Gly Gln Pro Pro Val
545                 550                 555                 560

Val Glu Asn Ala Lys Thr Phe Gly Lys Met Lys Pro Arg Tyr Glu Ile
                565                 570                 575

Asn Ser Leu Ile Arg Tyr His Cys Lys Asp Gly Phe Ile Gln Arg His
            580                 585                 590

Leu Pro Thr Ile Arg Cys Leu Gly Asn Gly Arg Trp Ala Ile Pro Lys
        595                 600                 605

Ile Thr Cys Met Asn Pro Ser Ala Tyr Gln Arg Thr Tyr Ser Met Lys
    610                 615                 620

Tyr Phe Lys Asn Ser Ser Ala Lys Asp Asn Ser Ile Asn Thr Ser
625                 630                 635                 640

Lys His Asp His Arg Trp Ser Arg Arg Trp Gln Glu Ser Arg Arg
                645                 650                 655

<210> SEQ ID NO 2
<211> LENGTH: 635
<212> TYPE: PRT
<213> ORGANISM: Homo sapiens

<400> SEQUENCE: 2

Leu His Lys Val Lys Val Gly Lys Ser Pro Val Arg Gly Ser Leu
1               5                   10                  15

Ser Gly Lys Val Ser Leu Pro Cys His Phe Ser Thr Met Pro Thr Leu
                20                  25                  30

Pro Pro Ser Tyr Asn Thr Ser Glu Phe Leu Arg Ile Lys Trp Ser Lys
            35                  40                  45

Ile Glu Val Asp Lys Asn Gly Lys Asp Leu Lys Glu Thr Thr Val Leu
50                  55                  60

Val Ala Gln Asn Gly Asn Ile Lys Ile Gly Gln Asp Tyr Lys Gly Arg
65                  70                  75                  80

Val Ser Val Pro Thr His Pro Glu Ala Val Gly Asp Ala Ser Leu Thr
                85                  90                  95

Val Val Lys Leu Leu Ala Ser Asp Ala Gly Leu Tyr Arg Cys Asp Val
            100                 105                 110

Met Tyr Gly Ile Glu Asp Thr Gln Asp Thr Val Ser Leu Thr Val Asp
        115                 120                 125

Gly Val Val Phe His Tyr Arg Ala Ala Thr Ser Arg Tyr Thr Leu Asn
    130                 135                 140

Phe Glu Ala Ala Gln Lys Ala Cys Leu Asp Val Gly Ala Val Ile Ala
145                 150                 155                 160

Thr Pro Glu Gln Leu Phe Ala Ala Tyr Glu Asp Gly Phe Glu Gln Cys
                165                 170                 175

Asp Ala Gly Trp Leu Ala Asp Gln Thr Val Arg Tyr Pro Ile Arg Ala
            180                 185                 190

Pro Arg Val Gly Cys Tyr Gly Asp Lys Met Gly Lys Ala Gly Val Arg
        195                 200                 205

Thr Tyr Gly Phe Arg Ser Pro Gln Glu Thr Tyr Asp Val Tyr Cys Tyr
    210                 215                 220

Val Asp His Leu Asp Gly Asp Val Phe His Leu Thr Val Pro Ser Lys
225                 230                 235                 240

Phe Thr Phe Glu Glu Ala Ala Lys Glu Cys Glu Asn Gln Asp Ala Arg
                245                 250                 255

Leu Ala Thr Val Gly Glu Leu Gln Ala Ala Trp Arg Asn Gly Phe Asp
            260                 265                 270
```

Gln Cys Asp Tyr Gly Trp Leu Ser Asp Ala Ser Val Arg His Pro Val
        275                 280                 285

Thr Val Ala Arg Ala Gln Cys Gly Gly Leu Leu Gly Val Arg Thr
290                 295                 300

Leu Tyr Arg Phe Glu Asn Gln Thr Gly Phe Pro Pro Asp Ser Arg
305                 310                 315                 320

Phe Asp Ala Tyr Cys Phe Lys Arg Pro Asp Arg Cys Lys Met Asn Pro
                325                 330                 335

Cys Leu Asn Gly Gly Thr Cys Tyr Pro Thr Glu Thr Ser Tyr Val Cys
                340                 345                 350

Thr Cys Val Pro Gly Tyr Ser Gly Asp Gln Cys Glu Leu Asp Phe Asp
                355                 360                 365

Glu Cys His Ser Asn Pro Cys Arg Asn Gly Ala Thr Cys Val Asp Gly
                370                 375                 380

Phe Asn Thr Phe Arg Cys Leu Cys Leu Pro Ser Tyr Val Gly Ala Leu
385                 390                 395                 400

Cys Glu Gln Asp Thr Glu Thr Cys Asp Tyr Gly Trp His Lys Phe Gln
                405                 410                 415

Gly Gln Cys Tyr Lys Tyr Phe Ala His Arg Arg Thr Trp Asp Ala Ala
                420                 425                 430

Glu Arg Glu Cys Arg Leu Gln Gly Ala His Leu Thr Ser Ile Leu Ser
            435                 440                 445

His Glu Glu Gln Met Phe Val Asn Arg Val Gly His Asp Tyr Gln Trp
            450                 455                 460

Ile Gly Leu Asn Asp Lys Met Phe Glu His Asp Phe Arg Trp Thr Asp
465                 470                 475                 480

Gly Ser Thr Leu Gln Tyr Glu Asn Trp Arg Pro Asn Gln Pro Asp Ser
                485                 490                 495

Phe Phe Ser Ala Gly Glu Asp Cys Val Val Ile Trp His Glu Asn
                500                 505                 510

Gly Gln Trp Asn Asp Val Pro Cys Asn Tyr His Leu Thr Tyr Thr Cys
            515                 520                 525

Lys Lys Gly Thr Val Ala Cys Gly Gln Pro Pro Val Val Glu Asn Ala
530                 535                 540

Lys Thr Phe Gly Lys Met Lys Pro Arg Tyr Glu Ile Asn Ser Leu Ile
545                 550                 555                 560

Arg Tyr His Cys Lys Asp Gly Phe Ile Gln Arg His Leu Pro Thr Ile
                565                 570                 575

Arg Cys Leu Gly Asn Gly Arg Trp Ala Ile Pro Lys Ile Thr Cys Met
                580                 585                 590

Asn Pro Ser Ala Tyr Gln Arg Thr Tyr Ser Met Lys Tyr Phe Lys Asn
                595                 600                 605

Ser Ser Ser Ala Lys Asp Asn Ser Ile Asn Thr Ser Lys His Asp His
610                 615                 620

Arg Trp Ser Arg Arg Trp Gln Glu Ser Arg Arg
625                 630                 635

<210> SEQ ID NO 3
<211> LENGTH: 634
<212> TYPE: PRT
<213> ORGANISM: Rattus norvegicus

<400> SEQUENCE: 3

Leu His Lys Ala Lys Met Glu Glu Asn Pro Pro Val Lys Gly Ser Leu

-continued

```
  1               5                  10                 15
Ser Gly Lys Val Ile Leu Pro Cys His Phe Ser Thr Leu Pro Thr Leu
             20                 25                 30
Pro Pro Asp Tyr Asn Thr Ser Glu Phe Leu Arg Ile Lys Trp Ser Lys
             35                 40                 45
Ile Glu Val Asp Lys Asn Gly Lys Asp Ile Lys Glu Thr Thr Val Leu
             50                 55                 60
Val Ala Gln Asp Gly Asn Ile Lys Ile Gly Gln Asp Tyr Lys Gly Arg
 65                 70                 75                 80
Val Ser Val Pro Thr His Pro Asp Asp Val Gly Asp Ala Ser Leu Thr
             85                 90                 95
Met Val Lys Leu Arg Ala Ser Asp Ala Gly Val Tyr Arg Cys Asp Val
            100                105                110
Met Tyr Gly Ile Glu Asp Thr Gln Asn Thr Met Ser Leu Ala Val Asp
            115                120                125
Gly Val Val Phe His Tyr Arg Ala Ala Thr Ser Arg Tyr Thr Leu Asn
            130                135                140
Phe Glu Ser Ala Gln Gln Ala Cys Leu Asp Ile Gly Ala Val Ile Ala
145                150                155                160
Thr Pro Glu Gln Leu Phe Ala Ala Tyr Glu Asp Gly Phe Glu Gln Cys
            165                170                175
Asp Ala Gly Trp Leu Ser Asp Gln Thr Val Arg Tyr Pro Ile Arg Ala
            180                185                190
Pro Arg Glu Gly Cys Tyr Gly Asp Met Met Gly Lys Glu Gly Val Arg
            195                200                205
Thr Tyr Gly Phe Arg Ser Pro Gln Glu Thr Tyr Asp Val Tyr Cys Tyr
            210                215                220
Val Asp His Leu Asp Gly Asp Val Phe His Ile Thr Ala Pro Ser Lys
225                230                235                240
Phe Thr Phe Glu Glu Ala Glu Ala Glu Cys Ala Asn Arg Asp Ala Arg
            245                250                255
Leu Ala Thr Val Gly Glu Leu His Ala Ala Trp Arg Asn Gly Phe Asp
            260                265                270
Gln Cys Asp Tyr Gly Trp Leu Ser Asp Ala Ser Val Arg His Pro Val
            275                280                285
Thr Val Ala Arg Ala Gln Cys Gly Gly Gly Leu Leu Gly Val Arg Thr
            290                295                300
Leu Tyr Arg Phe Glu Asn Gln Thr Cys Phe Pro Leu Pro Asp Ser Arg
305                310                315                320
Phe Asp Ala Tyr Cys Phe Lys Arg Pro Asp Leu Cys Lys Thr Asn Pro
            325                330                335
Cys Leu Asn Gly Gly Thr Cys Tyr Pro Thr Glu Thr Ser Tyr Val Cys
            340                345                350
Thr Cys Ala Pro Gly Tyr Ser Gly Asp Gln Cys Glu Leu Asp Phe Asp
            355                360                365
Glu Cys His Ser Asn Pro Cys Arg Asn Gly Ala Thr Cys Val Asp Gly
            370                375                380
Leu Asn Thr Phe Arg Cys Leu Cys Leu Pro Ser Tyr Val Gly Ala Leu
385                390                395                400
Cys Glu Gln Asp Thr Glu Thr Cys Asp Tyr Gly Trp His Lys Phe Gln
            405                410                415
Gly Gln Cys Tyr Lys Tyr Phe Ala His Arg Arg Thr Trp Asp Ala Ala
            420                425                430
```

```
Glu Arg Glu Cys Arg Leu Gln Gly Ala His Leu Thr Ser Ile Leu Ser
            435                 440                 445

His Glu Glu Gln Met Phe Val Asn Arg Val Gly His Asp Tyr Gln Trp
    450                 455                 460

Ile Gly Leu Asn Asp Lys Met Phe Glu His Asp Phe Arg Trp Thr Asp
465                 470                 475                 480

Gly Ser Ala Leu Gln Tyr Glu Asn Arg Pro Asn Gln Pro Asp Ser Phe
                485                 490                 495

Phe Ser Ala Gly Glu Asp Cys Val Val Ile Ile Trp His Glu Asn Gly
            500                 505                 510

Gln Trp Asn Asp Val Pro Cys Asn Tyr His Leu Thr Tyr Thr Cys Lys
    515                 520                 525

Lys Gly Thr Val Ala Cys Gly Gln Pro Pro Val Glu Asn Ala Lys
530                 535                 540

Thr Phe Gly Lys Met Lys Pro Arg Tyr Glu Ile Asn Ser Leu Ile Arg
545                 550                 555                 560

Tyr His Cys Lys Asp Gly Phe Ile Gln Arg His Leu Pro Thr Ile Arg
                565                 570                 575

Cys Leu Gly Asn Gly Arg Trp Ala Met Pro Lys Ile Thr Cys Met Asn
                580                 585                 590

Pro Ser Ala Tyr Gln Arg Thr Tyr Ser Lys Lys Tyr Leu Lys Asn Ser
                595                 600                 605

Ser Ser Val Lys Asp Asn Ser Ile Asn Thr Ser Lys His Glu His Arg
    610                 615                 620

Trp Ser Arg Arg Trp Gln Glu Thr Arg Arg
625                 630

<210> SEQ ID NO 4
<211> LENGTH: 635
<212> TYPE: PRT
<213> ORGANISM: Mus musculus

<400> SEQUENCE: 4

Leu His Gln Ala Lys Met Glu Thr Ser Pro Val Lys Gly Ser Leu
1               5                   10                  15

Ser Gly Lys Val Val Leu Pro Cys His Phe Ser Thr Leu Pro Thr Leu
                20                  25                  30

Pro Pro Asn Tyr Asn Thr Ser Glu Phe Leu Arg Ile Lys Trp Ser Lys
                35                  40                  45

Met Glu Val Asp Lys Asn Gly Lys Asp Ile Lys Glu Thr Thr Val Leu
50                  55                  60

Val Ala Gln Asn Gly Asn Ile Lys Ile Gly Gln Asp Tyr Lys Gly Arg
65                  70                  75                  80

Val Ser Val Pro Thr His Pro Asp Asp Val Gly Asp Ala Ser Leu Thr
                85                  90                  95

Met Val Lys Leu Arg Ala Ser Asp Ala Gly Val Tyr Arg Cys Asp Val
                100                 105                 110

Met Tyr Gly Ile Glu Asp Thr Gln Asp Thr Met Ser Leu Ala Val Asp
                115                 120                 125

Gly Val Val Phe His Tyr Arg Ala Ala Thr Ser Arg Tyr Thr Leu Asn
                130                 135                 140

Phe Ala Ala Ala Gln Gln Ala Cys Leu Asp Ile Gly Ala Val Ile Ala
145                 150                 155                 160

Ser Pro Glu Gln Leu Phe Ala Ala Tyr Glu Asp Gly Phe Glu Gln Cys
```

-continued

```
                165                 170                 175
Asp Ala Gly Trp Leu Ser Asp Gln Thr Val Arg Tyr Pro Ile Arg Ala
            180                 185                 190

Pro Arg Glu Gly Cys Tyr Gly Asp Met Met Gly Lys Glu Gly Val Arg
        195                 200                 205

Thr Tyr Gly Phe Arg Ser Pro Gln Glu Thr Tyr Asp Val Tyr Cys Tyr
    210                 215                 220

Val Asp His Leu Asp Gly Asp Val Phe His Ile Thr Ala Pro Ser Lys
225                 230                 235                 240

Phe Thr Phe Glu Glu Ala Glu Ala Glu Cys Thr Ser Arg Asp Ala Arg
                245                 250                 255

Leu Ala Thr Val Gly Glu Leu Gln Ala Ala Trp Arg Asn Gly Phe Asp
            260                 265                 270

Gln Cys Asp Tyr Gly Trp Leu Ser Asp Ala Ser Val Arg His Pro Val
        275                 280                 285

Thr Val Ala Arg Ala Gln Cys Gly Gly Gly Leu Leu Gly Val Arg Thr
    290                 295                 300

Leu Tyr Arg Phe Glu Asn Gln Thr Cys Phe Pro Leu Pro Asp Ser Arg
305                 310                 315                 320

Phe Asp Ala Tyr Cys Phe Lys Arg Pro Asp Leu Cys Lys Thr Asn Pro
                325                 330                 335

Cys Leu Asn Gly Gly Thr Cys Tyr Pro Thr Glu Thr Ser Tyr Val Cys
            340                 345                 350

Thr Cys Ala Pro Gly Tyr Ser Gly Asp Gln Cys Glu Leu Asp Phe Asp
        355                 360                 365

Glu Cys His Ser Asn Pro Cys Arg Asn Gly Ala Thr Cys Val Asp Gly
    370                 375                 380

Phe Asn Thr Phe Arg Cys Leu Cys Leu Pro Ser Tyr Val Gly Ala Leu
385                 390                 395                 400

Cys Glu Gln Asp Thr Glu Thr Cys Asp Tyr Gly Trp His Lys Phe Gln
                405                 410                 415

Gly Gln Cys Tyr Lys Tyr Phe Ala His Arg Arg Thr Trp Asp Ala Ala
            420                 425                 430

Glu Arg Glu Cys Arg Leu Gln Gly Ala His Leu Thr Ser Ile Leu Ser
        435                 440                 445

His Glu Glu Gln Met Phe Val Asn Arg Val Gly His Asp Tyr Gln Trp
    450                 455                 460

Ile Gly Leu Asn Asp Lys Met Phe Glu His Asp Phe Arg Trp Thr Asp
465                 470                 475                 480

Gly Ser Ala Leu Gln Tyr Glu Asn Trp Arg Pro Asn Gln Pro Asp Ser
                485                 490                 495

Phe Phe Ser Ala Gly Glu Asp Cys Val Val Ile Trp His Glu Asn
            500                 505                 510

Gly Gln Trp Asn Asp Val Pro Cys Asn Tyr His Leu Thr Tyr Thr Cys
        515                 520                 525

Lys Lys Gly Thr Val Ala Cys Gly Gln Pro Val Val Glu Asn Ala
    530                 535                 540

Lys Thr Phe Gly Lys Met Lys Pro Arg Tyr Glu Ile Asn Ser Leu Ile
545                 550                 555                 560

Arg Tyr His Cys Lys Asp Gly Phe Ile Gln Arg His Leu Pro Thr Ile
                565                 570                 575

Arg Cys Leu Gly Asn Gly Arg Trp Ala Met Pro Lys Ile Thr Cys Met
            580                 585                 590
```

```
Asn Pro Ser Ala Tyr Gln Arg Thr Tyr Ser Lys Lys Tyr Leu Lys Asn
        595                 600                 605

Ser Ser Ser Ala Lys Asp Asn Ser Ile Asn Thr Ser Lys His Glu His
        610                 615                 620

Arg Trp Ser Arg Arg Gln Glu Thr Arg Arg
625                 630                 635

<210> SEQ ID NO 5
<211> LENGTH: 636
<212> TYPE: PRT
<213> ORGANISM: Sus scrofa

<400> SEQUENCE: 5

Leu His Lys Val Lys Val Glu Lys Ser Pro Val Lys Gly Ser Leu
1               5                   10                  15

Ser Gly Lys Val Asn Leu Pro Cys His Phe Ser Thr Met Pro Thr Leu
                20                  25                  30

Pro Pro Ser Tyr Asn Thr Thr Ser Glu Phe Leu Arg Ile Lys Trp Ser
            35                  40                  45

Lys Ile Glu Leu Asp Lys Ser Gly Lys Asp Leu Lys Glu Thr Thr Val
50                  55                  60

Leu Val Ala Gln Asn Gly Asn Ile Lys Ile Gly Gln Gly Tyr Lys Gly
65                  70                  75                  80

Arg Val Ser Val Pro Thr His Pro Glu Asp Val Gly Asp Ala Ser Leu
                85                  90                  95

Thr Met Val Lys Leu Leu Ala Ser Asp Ala Gly Leu Tyr Arg Cys Asp
            100                 105                 110

Val Met Tyr Gly Ile Glu Asp Thr Gln Asp Ser Val Ser Leu Ala Val
        115                 120                 125

Asp Gly Val Val Phe His Tyr Arg Ala Ala Thr Ser Arg Tyr Thr Leu
130                 135                 140

Asn Phe Glu Ala Ala Gln Lys Ala Cys Leu Asp Ile Gly Ala Val Ile
145                 150                 155                 160

Ala Thr Pro Glu Gln Leu His Ala Ala Tyr Glu Asp Gly Phe Glu Gln
                165                 170                 175

Cys Asp Ala Gly Trp Leu Ser Asp Gln Thr Val Arg Tyr Pro Ile Arg
            180                 185                 190

Thr Pro Arg Glu Gly Cys Tyr Gly Asp Met Met Gly Lys Glu Gly Val
        195                 200                 205

Arg Thr Tyr Gly Phe Arg Ala Pro His Glu Thr Tyr Asp Val Tyr Cys
210                 215                 220

Tyr Val Asp His Leu Asp Gly Asp Val Phe His Ile Thr Ala Pro Asn
225                 230                 235                 240

Lys Phe Thr Phe Glu Glu Ala Glu Glu Cys Glu Asn Gln Asp Ala
                245                 250                 255

Arg Leu Ala Thr Val Gly Glu Leu Gln Ala Ala Trp Arg Asn Gly Phe
            260                 265                 270

Asp Gln Cys Asp Tyr Gly Trp Leu Leu Asp Ala Ser Val Arg His Pro
        275                 280                 285

Val Thr Val Pro Arg Ala Gln Cys Gly Gly Leu Leu Gly Val Arg
290                 295                 300

Thr Leu Tyr Arg Phe Glu Asn Gln Thr Gly Phe Pro Ser Pro Asp Ser
305                 310                 315                 320

Arg Phe Asp Ala Tyr Cys Tyr Lys Arg Pro Asp Arg Cys Lys Thr Asn
```

```
                   325                 330                 335
Pro Cys Leu Asn Gly Gly Thr Cys Tyr Pro Thr Glu Thr Ser Tyr Val
                340                 345                 350
Cys Thr Cys Val Pro Gly Tyr Ser Gly Asp Gln Cys Glu Leu Asp Phe
                355                 360                 365
Asp Glu Cys His Ser Asn Pro Cys Arg Asn Gly Ala Thr Cys Val Asp
            370                 375                 380
Gly Phe Asn Thr Phe Arg Cys Leu Cys Leu Pro Ser Tyr Val Gly Ala
385                 390                 395                 400
Leu Cys Glu Gln Asp Thr Glu Thr Cys Asp Tyr Gly Trp His Lys Phe
                405                 410                 415
Gln Gly Gln Cys Tyr Lys Tyr Phe Ala His Arg Arg Thr Trp Asp Ala
                420                 425                 430
Ala Glu Arg Glu Cys Arg Leu Gln Gly Ala His Leu Thr Ser Ile Leu
            435                 440                 445
Ser His Glu Glu Gln Met Phe Val Asn Arg Val Gly His Asp Tyr Gln
        450                 455                 460
Trp Ile Gly Leu Asn Asp Lys Met Phe Glu His Asp Phe Arg Trp Thr
465                 470                 475                 480
Asp Gly Ser Thr Leu Gln Tyr Glu Asn Trp Arg Pro Asn Gln Pro Asp
                485                 490                 495
Ser Phe Phe Ser Ser Gly Glu Asp Cys Val Val Ile Trp His Glu
                500                 505                 510
Asn Gly Gln Trp Asn Asp Val Pro Cys Asn Tyr His Leu Thr Tyr Thr
            515                 520                 525
Cys Lys Lys Gly Thr Val Ala Cys Gly Gln Pro Val Val Glu Asn
530                 535                 540
Ala Lys Thr Phe Gly Lys Met Lys Pro Arg Tyr Glu Ile Asn Ser Leu
545                 550                 555                 560
Ile Arg Tyr His Cys Lys Asp Gly Phe Ile Gln Arg His Pro Pro Thr
                565                 570                 575
Ile Arg Cys Leu Gly Asn Gly Arg Trp Ala Met Pro Lys Ile Thr Cys
            580                 585                 590
Leu Asn Pro Ser Ala Tyr Gln Arg Thr Tyr Ser Lys Lys Tyr Phe Lys
            595                 600                 605
Asn Ser Ser Ser Ala Lys Asp Asn Ser Ile Asn Thr Ser Lys His Asp
        610                 615                 620
His Arg Trp Ser Arg Arg Trp Gln Glu Ser Arg Arg
625                 630                 635
```

<210> SEQ ID NO 6
<211> LENGTH: 636
<212> TYPE: PRT
<213> ORGANISM: Bos taurus

<400> SEQUENCE: 6

```
Leu Gln Lys Val Asn Met Glu Lys Ser Pro Val Lys Gly Ser Leu
1                5                  10                  15
Ser Gly Lys Val Asn Leu Pro Cys His Phe Ser Thr Met Pro Thr Leu
                20                  25                  30
Pro Pro Ser Tyr Asn Thr Thr Ser Glu Phe Leu Arg Ile Lys Trp Ser
            35                  40                  45
Lys Ile Glu Leu Asp Lys Thr Gly Lys Asp Leu Lys Glu Thr Thr Val
        50                  55                  60
```

-continued

```
Leu Val Ala Gln Asn Gly Asn Ile Lys Ile Gly Gln Asp Tyr Lys Gly
 65                  70                  75                  80

Arg Val Ser Val Pro Thr His Pro Glu Asp Val Gly Asp Ala Ser Leu
                 85                  90                  95

Thr Met Val Lys Leu Leu Ala Ser Asp Ala Gly Arg Tyr Arg Cys Asp
            100                 105                 110

Val Met Tyr Gly Ile Glu Asp Thr Gln Asp Thr Val Ser Leu Thr Val
        115                 120                 125

Glu Gly Val Val Phe His Tyr Arg Ala Ala Thr Ser Arg Tyr Thr Leu
    130                 135                 140

Asn Phe Glu Met Ala Gln Lys Ala Cys Val Asp Ile Gly Ala Val Ile
145                 150                 155                 160

Ala Thr Pro Glu Gln Leu His Ala Ala Tyr Glu Asp Gly Phe Glu Gln
                165                 170                 175

Cys Asp Ala Gly Trp Leu Ser Asp Gln Thr Val Arg Tyr Pro Ile Arg
            180                 185                 190

Val Pro Arg Glu Gly Cys Tyr Gly Asp Met Met Gly Lys Glu Gly Val
        195                 200                 205

Arg Thr Tyr Gly Phe Arg Ala Pro His Glu Thr Tyr Asp Val Tyr Cys
    210                 215                 220

Tyr Val Asp His Leu Asp Gly Asp Val Phe His Ile Thr Ala Pro Asn
225                 230                 235                 240

Lys Phe Thr Phe Glu Glu Ala Gly Glu Glu Cys Lys Thr Gln Asp Ala
                245                 250                 255

Arg Leu Ala Thr Val Gly Glu Leu Gln Ala Ala Trp Arg Asn Gly Phe
            260                 265                 270

Asp Arg Cys Asp Tyr Gly Trp Leu Leu Asp Ala Ser Val Arg His Pro
        275                 280                 285

Val Thr Val Ala Arg Ala Gln Cys Gly Gly Gly Leu Leu Gly Val Arg
    290                 295                 300

Thr Leu Tyr Arg Phe Glu Asn Gln Thr Gly Phe Pro Thr Pro Asp Ser
305                 310                 315                 320

Arg Phe Asp Ala Tyr Cys Phe Lys Arg Pro Asp Arg Cys Lys Met Asn
                325                 330                 335

Pro Cys Leu Asn Gly Gly Thr Cys Tyr Pro Thr Glu Thr Ser Tyr Val
            340                 345                 350

Cys Thr Cys Val Pro Gly Tyr Ser Gly Asp Arg Cys Glu Leu Asp Phe
        355                 360                 365

Asp Glu Cys His Ser Asn Pro Cys Arg Asn Gly Ala Thr Cys Ile Asp
    370                 375                 380

Gly Phe Asn Thr Phe Arg Cys Leu Cys Leu Pro Ser Tyr Val Gly Ala
385                 390                 395                 400

Leu Cys Glu Gln Asp Thr Glu Thr Cys Asp Tyr Gly Trp His Lys Phe
                405                 410                 415

Gln Gly Gln Cys Tyr Lys Tyr Phe Ala His Arg Arg Thr Trp Asp Ala
            420                 425                 430

Ala Glu Arg Glu Cys Arg Leu Gln Gly Ala His Leu Thr Ser Ile Leu
        435                 440                 445

Ser His Glu Glu Gln Met Phe Val Asn Arg Val Gly His Asp Tyr Gln
    450                 455                 460

Trp Ile Gly Leu Asn Asp Lys Met Phe Glu His Asp Phe Arg Trp Thr
465                 470                 475                 480

Asp Gly Ser Thr Leu Gln Tyr Glu Asn Trp Arg Pro Asn Gln Pro Asp
```

```
            485                 490                 495
Ser Phe Ser Thr Gly Glu Asp Cys Val Ile Ile Trp His Glu
            500                 505                 510

Asn Gly Gln Trp Asn Asp Val Pro Cys Asn Tyr His Leu Thr Tyr Thr
            515                 520                 525

Cys Lys Lys Gly Thr Val Ala Cys Gly Gln Pro Val Val Glu Asn
            530                 535                 540

Ala Lys Thr Phe Gly Lys Met Lys Pro Arg Tyr Glu Ile Asn Ser Leu
545                 550                 555                 560

Ile Arg Tyr His Cys Lys Asp Gly Phe Ile Gln Arg His Leu Pro Thr
                565                 570                 575

Ile Arg Cys Leu Gly Asn Gly Arg Trp Ala Met Pro Lys Ile Thr Cys
            580                 585                 590

Leu Asn Pro Ser Ala Tyr Gln Arg Thr Tyr Ser Lys Lys Tyr Phe Lys
            595                 600                 605

Asn Ser Ser Ser Ala Lys Asp Asn Ser Ile Asn Thr Ser Lys His Asp
            610                 615                 620

His Arg Trp Ser Arg Arg Trp Gln Glu Ser Arg Arg
625                 630                 635
```

<210> SEQ ID NO 7
<211> LENGTH: 635
<212> TYPE: PRT
<213> ORGANISM: Macaca mulatta

<400> SEQUENCE: 7

```
Leu His Lys Val Lys Val Gly Lys Ser Pro Pro Leu Arg Gly Ser Leu
1               5                   10                  15

Ser Gly Lys Val Ser Leu Pro Cys His Phe Ser Thr Met Pro Thr Leu
                20                  25                  30

Pro Pro Ser Tyr Asn Thr Ser Glu Phe Leu Arg Ile Lys Trp Ser Lys
            35                  40                  45

Ile Glu Val Asp Lys Asn Gly Lys Asp Leu Lys Glu Thr Thr Val Leu
50                  55                  60

Val Ala Gln Asn Gly Asn Ile Lys Ile Gly Gln Asp Tyr Lys Gly Arg
65                  70                  75                  80

Val Ser Val Pro Thr His Pro Glu Ala Val Gly Asp Ala Ser Leu Thr
                85                  90                  95

Val Val Lys Leu Leu Ala Ser Asp Ala Gly Leu Tyr Arg Cys Asp Val
            100                 105                 110

Met Tyr Gly Ile Asp Asp Thr Gln Asp Thr Val Ser Leu Ala Val Asp
            115                 120                 125

Gly Val Val Phe His Tyr Arg Ala Ser Thr Ser Arg Tyr Thr Leu Asn
130                 135                 140

Phe Glu Ala Ala Gln Lys Ala Cys Leu Asp Ile Gly Ala Val Ile Ala
145                 150                 155                 160

Thr Pro Glu Gln Leu Phe Ala Ala Tyr Glu Asp Gly Phe Glu Gln Cys
                165                 170                 175

Asp Ala Gly Trp Leu Ala Asp Gln Thr Val Arg Tyr Pro Ile Arg Ala
            180                 185                 190

Pro Arg Val Gly Cys Tyr Gly Asp Met Met Gly Lys Ala Gly Val Arg
            195                 200                 205

Thr Tyr Gly Phe Arg Ser Pro Gln Glu Thr Tyr Asp Val Tyr Cys Tyr
            210                 215                 220
```

```
Val Asp His Leu Asp Gly Asp Val Phe His Leu Thr Ala Pro Ser Lys
225                 230                 235                 240

Phe Thr Phe Glu Glu Ala Ala Lys Glu Cys Glu Asn Gln Asp Ala Arg
            245                 250                 255

Leu Ala Thr Val Gly Glu Leu Gln Ala Ala Trp Arg Asn Gly Phe Asp
            260                 265                 270

Gln Cys Asp Tyr Gly Trp Leu Ser Asp Ala Ser Val Arg His Pro Val
        275                 280                 285

Thr Val Ala Arg Ala Gln Cys Gly Gly Leu Leu Gly Val Arg Thr
        290                 295                 300

Leu Tyr Arg Phe Glu Asn Gln Thr Gly Phe Pro Pro Pro Asp Ser Arg
305                 310                 315                 320

Phe Asp Ala Tyr Cys Phe Lys Arg Pro Asp Arg Cys Lys Met Asn Pro
                325                 330                 335

Cys Leu Asn Gly Gly Thr Cys Tyr Pro Thr Glu Thr Ser Tyr Val Cys
                340                 345                 350

Thr Cys Val Pro Gly Tyr Ser Gly Asp Gln Cys Glu Leu Asp Phe Asp
        355                 360                 365

Glu Cys His Ser Asn Pro Cys Arg Asn Gly Ala Thr Cys Val Asp Gly
    370                 375                 380

Phe Asn Thr Phe Arg Cys Leu Cys Leu Pro Ser Tyr Val Gly Ala Leu
385                 390                 395                 400

Cys Glu Gln Asp Thr Glu Thr Cys Asp Tyr Gly Trp His Lys Phe Gln
                405                 410                 415

Gly Gln Cys Tyr Lys Tyr Phe Ala His Arg Arg Thr Trp Asp Ala Ala
        420                 425                 430

Glu Arg Glu Cys Arg Leu Gln Gly Ala His Leu Thr Ser Ile Leu Ser
    435                 440                 445

His Glu Glu Gln Thr Phe Val Asn Arg Val Gly His Asp Tyr Gln Trp
    450                 455                 460

Ile Gly Leu Asn Asp Lys Met Phe Glu His Asp Phe Arg Trp Thr Asp
465                 470                 475                 480

Gly Ser Thr Leu Gln Tyr Glu Asn Trp Arg Pro Asn Gln Pro Asp Ser
            485                 490                 495

Phe Phe Ser Ala Gly Glu Asp Cys Val Val Ile Trp His Glu Asn
            500                 505                 510

Gly Gln Trp Asn Asp Val Pro Cys Asn Tyr His Leu Thr Tyr Thr Cys
        515                 520                 525

Lys Lys Gly Thr Val Ala Cys Gly Gln Pro Val Val Glu Asn Ala
    530                 535                 540

Lys Thr Phe Gly Lys Met Lys Pro Arg Tyr Glu Ile Asn Ser Leu Ile
545                 550                 555                 560

Arg Tyr His Cys Lys Asp Gly Phe Ile Gln Arg His Leu Pro Thr Ile
                565                 570                 575

Arg Cys Leu Gly Asn Gly Arg Trp Ala Ile Pro Lys Ile Thr Cys Met
            580                 585                 590

Asn Pro Ser Ala Tyr Gln Arg Thr Tyr Ser Met Lys Tyr Phe Lys Asn
            595                 600                 605

Ser Ser Ser Ala Lys Asp Asn Ser Ile Asn Thr Ser Lys His Asp His
            610                 615                 620

Arg Trp Ser Arg Arg Trp Gln Glu Thr Arg Arg
625                 630                 635
```

<210> SEQ ID NO 8
<211> LENGTH: 636
<212> TYPE: PRT
<213> ORGANISM: Canis familiaris

<400> SEQUENCE: 8

```
Leu His Lys Ala Lys Val Glu Lys Ser Pro Pro Val Lys Gly Ser Leu
1               5                   10                  15

Ser Gly Lys Val Asn Leu Pro Cys His Phe Ser Thr Met Pro Thr Leu
            20                  25                  30

Pro Pro Ser Tyr Asn Thr Ser Ser Glu Phe Leu Arg Ile Lys Trp Ser
        35                  40                  45

Lys Ile Glu Leu Asp Lys Asn Gly Lys Asp Leu Lys Glu Thr Thr Val
50                  55                  60

Leu Val Ala Gln Asn Gly Asn Val Lys Ile Gly Gln Gly Tyr Gln Gly
65                  70                  75                  80

Arg Val Ser Val Pro Thr His Ala Glu Val Val Gly Asp Ala Ser Leu
                85                  90                  95

Thr Met Val Lys Leu Arg Ala Ser Asp Ala Gly Gln Tyr Arg Cys Asp
            100                 105                 110

Val Met Tyr Gly Ile Glu Asp Thr Gln Asp Thr Val Ser Leu Ala Val
        115                 120                 125

Asp Gly Val Val Phe His Tyr Arg Ala Ala Thr Ser Arg Tyr Thr Leu
130                 135                 140

Asn Phe Glu Ala Ala Gln Lys Ala Cys Leu Asp Ile Gly Ala Val Ile
145                 150                 155                 160

Ala Thr Pro Glu Gln Leu Tyr Ala Ala Tyr Glu Asp Gly Phe Glu Gln
                165                 170                 175

Cys Asp Ala Gly Trp Leu Ser Asp Gln Thr Val Arg Tyr Pro Ile Arg
            180                 185                 190

Ala Pro Arg Val Gly Cys Tyr Gly Asp Met Met Gly Lys Glu Gly Val
        195                 200                 205

Arg Thr Tyr Gly Phe Arg Ser Pro His Glu Thr Tyr Asp Val Tyr Cys
210                 215                 220

Tyr Val Asp His Leu Asp Gly Asp Val Phe His Ile Thr Ala Pro Asn
225                 230                 235                 240

Lys Phe Thr Phe Glu Glu Ala Glu Glu Cys Glu Asn Gln Asp Ala
                245                 250                 255

Arg Leu Ala Thr Val Gly Glu Leu Gln Ala Ala Trp Arg Asn Gly Phe
            260                 265                 270

Asp Gln Cys Asp Tyr Gly Trp Leu Ser Asp Ala Ser Val Arg His Pro
        275                 280                 285

Val Thr Val Ala Arg Ala Gln Cys Gly Gly Leu Leu Gly Val Arg
290                 295                 300

Thr Leu Tyr Arg Phe Glu Asn Gln Thr Gly Phe Pro Pro Pro Asp Ser
305                 310                 315                 320

Arg Phe Asp Ala Tyr Cys Phe Lys Arg Pro Asp Arg Cys Lys Thr Asn
                325                 330                 335

Pro Cys Leu Asn Gly Gly Thr Cys Tyr Pro Thr Glu Thr Ser Tyr Val
            340                 345                 350

Cys Thr Cys Val Pro Gly Phe Ser Gly Asp Gln Cys Glu Leu Asp Phe
        355                 360                 365

Asp Glu Cys His Ser Asn Pro Cys Arg Asn Gly Ala Thr Cys Val Asp
370                 375                 380
```

```
Gly Phe Asn Thr Phe Arg Cys Leu Cys Leu Pro Ser Tyr Val Gly Ala
385                 390                 395                 400

Leu Cys Glu Gln Asp Thr Glu Thr Cys Asp Tyr Gly Trp His Lys Phe
            405                 410                 415

Gln Gly Gln Cys Tyr Lys Tyr Phe Ala His Arg Arg Thr Trp Asp Ala
        420                 425                 430

Ala Glu Arg Glu Cys Arg Leu Gln Gly Ala His Leu Thr Ser Ile Leu
    435                 440                 445

Ser His Glu Glu Gln Met Phe Val Asn Arg Val Gly His Asp Tyr Gln
450                 455                 460

Trp Ile Gly Leu Asn Asp Lys Met Phe Glu His Asp Phe Arg Trp Thr
465                 470                 475                 480

Asp Gly Ser Thr Leu Gln Tyr Glu Asn Trp Arg Pro Asn Gln Pro Asp
            485                 490                 495

Ser Phe Phe Ser Ala Gly Glu Asp Cys Val Val Ile Ile Trp His Glu
        500                 505                 510

Asn Gly Gln Trp Asn Asp Val Pro Cys Asn Tyr His Leu Thr Tyr Thr
    515                 520                 525

Cys Lys Lys Gly Thr Val Ala Cys Gly Gln Pro Pro Val Val Glu Asn
530                 535                 540

Ala Lys Thr Phe Gly Lys Met Lys Pro Arg Tyr Glu Ile Asn Ser Leu
545                 550                 555                 560

Ile Arg Tyr His Cys Lys Asp Gly Phe Ile Gln Arg His Leu Pro Thr
            565                 570                 575

Ile Arg Cys Leu Gly Asn Gly Arg Trp Ala Met Pro Lys Ile Thr Cys
        580                 585                 590

Met Asn Pro Ser Ala Tyr Gln Arg Thr Tyr Ser Lys Lys Tyr Phe Lys
    595                 600                 605

Asn Ser Ser Ala Lys Asp Asn Ser Ile Asn Thr Ser Lys His Asp
610                 615                 620

His Arg Trp Ser Arg Arg Trp Gln Glu Ser Arg Arg
625                 630                 635

<210> SEQ ID NO 9
<211> LENGTH: 609
<212> TYPE: PRT
<213> ORGANISM: Homo sapiens

<400> SEQUENCE: 9

Leu His Lys Val Lys Val Gly Lys Ser Pro Pro Val Arg Gly Ser Leu
1               5                   10                  15

Ser Gly Lys Val Ser Leu Pro Cys His Phe Ser Thr Met Pro Thr Leu
            20                  25                  30

Pro Pro Ser Tyr Asn Thr Ser Glu Phe Leu Arg Ile Lys Trp Ser Lys
        35                  40                  45

Ile Glu Val Asp Lys Asn Gly Lys Asp Leu Lys Glu Thr Thr Val Leu
    50                  55                  60

Val Ala Gln Asn Gly Asn Ile Lys Ile Gly Gln Asp Tyr Lys Gly Arg
65                  70                  75                  80

Val Ser Val Pro Thr His Pro Glu Ala Val Gly Asp Ala Ser Leu Thr
            85                  90                  95

Val Val Lys Leu Leu Ala Ser Asp Ala Gly Leu Tyr Arg Cys Asp Val
        100                 105                 110

Met Tyr Gly Ile Glu Asp Thr Gln Asp Thr Val Ser Leu Thr Val Asp
    115                 120                 125
```

```
Gly Val Val Phe His Tyr Arg Ala Ala Thr Ser Arg Tyr Thr Leu Asn
    130                 135                 140

Phe Glu Ala Ala Gln Lys Ala Cys Leu Asp Val Gly Ala Val Ile Ala
145                 150                 155                 160

Thr Pro Glu Gln Leu Phe Ala Ala Tyr Glu Asp Gly Phe Glu Gln Cys
                    165                 170                 175

Asp Ala Gly Trp Leu Ala Asp Gln Thr Val Arg Tyr Pro Ile Arg Ala
                180                 185                 190

Pro Arg Val Gly Cys Tyr Gly Asp Lys Met Gly Lys Ala Gly Val Arg
            195                 200                 205

Thr Tyr Gly Phe Arg Ser Pro Gln Glu Thr Tyr Asp Val Tyr Cys Tyr
    210                 215                 220

Val Asp His Leu Asp Gly Asp Val Phe His Leu Thr Val Pro Ser Lys
225                 230                 235                 240

Phe Thr Phe Glu Glu Ala Ala Lys Glu Cys Glu Asn Gln Asp Ala Arg
                    245                 250                 255

Leu Ala Thr Val Gly Glu Leu Gln Ala Ala Trp Arg Asn Gly Phe Asp
                260                 265                 270

Gln Cys Asp Tyr Gly Trp Leu Ser Asp Ala Ser Val Arg His Pro Val
            275                 280                 285

Thr Val Ala Arg Ala Gln Cys Gly Gly Leu Leu Gly Val Arg Thr
    290                 295                 300

Leu Tyr Arg Phe Glu Asn Gln Thr Gly Phe Pro Pro Pro Asp Ser Arg
305                 310                 315                 320

Phe Asp Ala Tyr Cys Phe Lys Arg Pro Asp Arg Cys Lys Met Asn Pro
                    325                 330                 335

Cys Leu Asn Gly Gly Thr Cys Tyr Pro Thr Glu Thr Ser Tyr Val Cys
                340                 345                 350

Thr Cys Val Pro Gly Tyr Ser Gly Asp Gln Cys Glu Leu Asp Phe Asp
            355                 360                 365

Glu Cys His Ser Asn Pro Cys Arg Asn Gly Ala Thr Cys Val Asp Gly
    370                 375                 380

Phe Asn Thr Phe Arg Cys Leu Cys Leu Pro Ser Tyr Val Gly Ala Leu
385                 390                 395                 400

Cys Glu Gln Asp Thr Glu Thr Cys Asp Tyr Gly Trp His Lys Phe Gln
                    405                 410                 415

Gly Gln Cys Tyr Lys Tyr Phe Ala His Arg Arg Thr Trp Asp Ala Ala
                420                 425                 430

Glu Arg Glu Cys Arg Leu Gln Gly Ala His Leu Thr Ser Ile Leu Ser
    435                 440                 445

His Glu Glu Gln Met Phe Val Asn Arg Val Gly His Asp Tyr Gln Trp
450                 455                 460

Ile Gly Leu Asn Asp Lys Met Phe Glu His Asp Phe Arg Trp Thr Asp
465                 470                 475                 480

Gly Ser Thr Leu Gln Tyr Glu Asn Trp Arg Pro Asn Gln Pro Asp Ser
                    485                 490                 495

Phe Phe Ser Ala Gly Glu Asp Cys Val Val Ile Ile Trp His Glu Asn
                500                 505                 510

Gly Gln Trp Asn Asp Val Pro Cys Asn Tyr His Leu Thr Tyr Thr Cys
            515                 520                 525

Lys Lys Gly Thr Val Ala Cys Gly Gln Pro Pro Val Val Glu Asn Ala
    530                 535                 540
```

```
Lys Thr Phe Gly Lys Met Lys Pro Arg Tyr Glu Ile Asn Ser Leu Ile
545                 550                 555                 560

Arg Tyr His Cys Lys Asp Gly Phe Ile Gln Arg His Leu Pro Thr Ile
            565                 570                 575

Arg Cys Leu Gly Asn Gly Arg Trp Ala Ile Pro Lys Ile Thr Cys Met
            580                 585                 590

Asn Arg Lys Trp Ser Phe Arg Lys Asn Gly Leu Pro Cys Tyr Asn Asn
        595                 600                 605

Tyr

<210> SEQ ID NO 10
<211> LENGTH: 17
<212> TYPE: PRT
<213> ORGANISM: Gaussia princeps

<400> SEQUENCE: 10

Met Gly Val Lys Val Leu Phe Ala Leu Ile Cys Ile Ala Val Ala Glu
1               5                   10                  15

Ala

<210> SEQ ID NO 11
<211> LENGTH: 1968
<212> TYPE: DNA
<213> ORGANISM: Homo sapiens

<400> SEQUENCE: 11
atgttcataa atataaagag catcttatgg atgtgttcaa ccttaatagt aacccatgcg      60
ctacataaag tcaaagtggg aaaaagccca ccggtgaggg gctccctctc tggaaaagtc    120
agcctacctt gtcattttc aacgatgcct actttgccac ccagttacaa caccagtgaa    180
tttctccgca tcaaatggtc taagattgaa gtggacaaaa atggaaaaga tttgaaagag    240
actactgtcc ttgtggccca aaatggaaat atcaagattg tcaggactac aaagggagaa    300
gtgtctgtgc ccacacatcc cgaggctgtg ggcgatgcct ccctcactgt ggtcaagctg    360
ctggcaagtg atgcgggtct ttaccgctgt gacgtcatgt acgggatatga agacacacaa    420 gacacggtgt cactgactgt ggatgggggtt gtgtttcact cagggcggc aaccagcagg    480 tacacactga ttttgaggc tgctcagaag gcttgtttgg acgttgggc agtcatagca    540 actccagagc agctctttgc tgcctatgaa gatggatttg agcagtgtga cgcaggctgg    600
ctggctgatc agactgtcag atatcccatc cgggctccca gagtaggctg ttatggagat    660
aagatgggaa aggcaggagt caggactatg ggattccgtt ctccccagga aacttacgat    720
gtgtattgtt atgtggatca tctggatggt gatgtgttcc acctcactgt ccccagtaaa    780
ttcaccttcg aggaggctgc aaaagagtgt gaaaaccagg atgccaggct ggcaacagtg    840
ggggaactcc aggcggcatg gaggaacggc tttgaccagt gcgattacgg gtggctgtcg    900
gatgccagcg tgcgccaccc tgtgactgtg ccagggccc agtgtggagg tggtctactt    960
ggggtgagaa ccctgtatcg ttttgagaac cagacaggct ccctcccc tgatagcaga   1020 tttgatgcct actgctttaa acgacctgat cgctgcaaaa tgaacccgtg ccttaacgga   1080
ggcacctgtt atcctactga aacttcctac gtatgcacct gtgtgccagg atacagcgga   1140
gaccagtgtg aacttgattt tgatgaatgt cactctaatc cctgtcgtaa tggagccact   1200
tgtgttgatg gttttaacac attcaggtgc ctctgcctc caagttatgt tggtgcactt   1260
tgtgagcaag ataccgagac atgtgactat ggctggcaca aattccaagg gcagtgctac   1320
```

| | |
|---|---:|
| aaatactttg cccatcgacg cacatgggat gcagctgaac gggaatgccg tctgcagggt | 1380 |
| gcccatctca caagcatcct gtctcacgaa gaacaaatgt tgttaatcg tgtgggccat | 1440 |
| gattatcagt ggataggcct caatgacaag atgtttgagc atgacttccg ttggactgat | 1500 |
| ggcagcacac tgcaatacga gaattggaga cccaaccagc cagacagctt cttttctgct | 1560 |
| ggagaagact gtgttgtaat catttggcat gagaatggcc agtggaatga tgttccctgc | 1620 |
| aattaccatc tcacctatac gtgcaagaaa ggaacagtcg cttgcggcca gccccctgtt | 1680 |
| gtagaaaatg ccaagacctt tggaaagatg aaacctcgtt atgaaatcaa ctccctgatt | 1740 |
| agataccact gcaaagatgg tttcattcaa cgtcaccttc caactatccg gtgcttagga | 1800 |
| aatggaagat gggctatacc taaaattacc tgcatgaacc catctgcata ccaaaggact | 1860 |
| tattctatga aatactttaa aaattcctca tcagcaaagg acaattcaat aaatacatcc | 1920 |
| aaacatgatc atcgttggag ccggaggtgg caggagtcga ggcgctga | 1968 |

<210> SEQ ID NO 12
<211> LENGTH: 1908
<212> TYPE: DNA
<213> ORGANISM: Homo sapiens

<400> SEQUENCE: 12

| | |
|---|---:|
| ctacataaag tcaaagtggg aaaaagccca ccggtgaggg gctccctctc tggaaaagtc | 60 |
| agcctacctt gtcatttttc aacgatgcct actttgccac ccagttacaa caccagtgaa | 120 |
| tttctccgca tcaatggtc taagattgaa gtggacaaaa atggaaaaga tttgaaagag | 180 |
| actactgtcc ttgtggccca aaatggaaat atcaagattg gtcaggacta caagggagaa | 240 |
| gtgtctgtgc ccacacatcc cgaggctgtg ggcgatgcct ccctcactgt ggtcaagctg | 300 |
| ctggcaagtg atgcgggtct ttaccgctgt gacgtcatgt acgggattga agacacacaa | 360 |
| gacacggtgt cactgactgt ggatggggtt gtgtttcact cagggcggc aaccagcagg | 420 |
| tacacactga tttttgaggc tgctcagaag gcttgtttgg acgttgggc agtcatagca | 480 |
| actccagagc agctctttgc tgcctatgaa gatggatttg agcagtgtga cgcaggctgg | 540 |
| ctggctgatc agactgtcag atatcccatc cgggctccca gagtaggctg ttatggagat | 600 |
| aagatgggaa aggcaggagt caggacttat ggattccgtt ctccccagga aacttacgat | 660 |
| gtgtattgtt atgtggatca tctggatggt gatgtgttcc acctcactgt ccccagtaaa | 720 |
| ttcaccttcg aggaggctgc aaaagagtgt gaaaaccagg atgccaggct ggcaacagtg | 780 |
| ggggaactcc aggcggcatg gaggaacggc tttgaccagt gcgattacgg gtggctgtcg | 840 |
| gatgccagcg tgcgccaccc tgtgactgtg gccagggccc agtgtggagg tggtctactt | 900 |
| ggggtgagaa ccctgtatcg ttttgagaac cagacaggct tccctccccc tgatagcaga | 960 |
| tttgatgcct actgctttaa acgacctgat cgctgcaaaa tgaacccgtg ccttaacgga | 1020 |
| ggcacctgtt atcctactga aacttcctac gtatgcacct gtgtgccagg atacagcgga | 1080 |
| gaccagtgtg aacttgattt tgatgaatgt cactctaatc cctgtcgtaa tggagccact | 1140 |
| tgtgttgatg gttttaacac attcaggtgc ctctgccttc caagttatgt tggtgcactt | 1200 |
| tgtgagcaag ataccgagac atgtgactat ggctggcaca aattccaagg gcagtgctac | 1260 |
| aaatactttg cccatcgacg cacatgggat gcagctgaac gggaatgccg tctgcagggt | 1320 |
| gcccatctca caagcatcct gtctcacgaa gaacaaatgt tgttaatcg tgtgggccat | 1380 |
| gattatcagt ggataggcct caatgacaag atgtttgagc atgacttccg ttggactgat | 1440 |
| ggcagcacac tgcaatacga gaattggaga cccaaccagc cagacagctt cttttctgct | 1500 |

```
ggagaagact gtgttgtaat catttggcat gagaatggcc agtggaatga tgttccctgc    1560
aattaccatc tcacctatac gtgcaagaaa ggaacagtcg cttgcggcca gccccctgtt    1620
gtagaaaatg ccaagacctt tggaaagatg aaacctcgtt atgaaatcaa ctccctgatt    1680
agataccact gcaaagatgg tttcattcaa cgtcaccttc aactatccg gtgcttagga     1740 aatggaagat gggctatacc taaaattacc tgcatgaacc catctgcata ccaaaggact    1800
tattctatga aatactttaa aaattcctca tcagcaaagg acaattcaat aaatacatcc    1860
aaacatgatc atcgttggag ccggaggtgg caggagtcga ggcgctga                 1908
```

<210> SEQ ID NO 13
<211> LENGTH: 1968
<212> TYPE: DNA
<213> ORGANISM: Homo sapiens

<400> SEQUENCE: 13

```
atgttcatca atatcaagtc catactgtgg atgtgtagta ccctcattgt gacacatgca      60
ttgcacaaag taaagttgg aaagagtccg cctgtgaggg gatcactgag tggcaaagtg     120
tcactgccct gtcactttc cactatgcca actctcccac cctcttataa cacatccgag     180
tttctccgca taaagtggtc caaaatcgag gtagacaaga acggcaaaga cctcaaagag    240
actactgtgc tcgtggcaca gaatggaaac atcaagattg gcaggacta taagggtcgt     300 gtcagcgtgc caactcaccc agaagccgtt ggcgacgcca gcttgacagt tgtgaaactg    360
cttgccagcg acgccggact gtatcgctgc gatgtcatgt atggtatcga agatacacag    420
gacacagtga gcctgaccgt ggatggggta gtctttcact atagagccgc cacatctaga    480
tacaccctga attttgaggc agctcagaag gcctgcttgg atgtgggcgc cgtgattgca    540
acgcctgagc aactgttcgc cgcctacgaa gatggattcg agcagtgtga cgcaggatgg    600
ctggccgatc agaccgttcg gtaccctatc agagctcccc gagtagggtg ctatggcgat    660
aaaatgggca aggctggcgt gaggacctac ggcttcaggt cacctcagga aacctatgac    720
gtgtactgtt atgtggacca cttggatggc gatgtctttc atctcacggt ccctctaaa    780 tttacgttcg aagaagcggc caaggagtgc gagaatcagg acgccaggct ggcaactgtg    840
ggagaactgc aggctgcctg cgcaatggg ttcgaccagt gcgattatgg gtggctgagt    900
gacgcttctg tccgccatcc cgttaccgtc gctagggcgc aatgcggtgg aggacttctg    960
ggcgttagaa ccctctatcg ctttgagaat cagactgggt ttccgccacc agattctcgg   1020
ttcgatgcgt attgcttcaa acgtcccgac cgttgtaaga tgaacccatg ccttaacggc   1080
ggaacctgtt acccaacaga aacgagctat gtttgcacct gtgtgccgg tactcaggc    1140 gaccagtgtg aactggactt tgacgaatgc cactctaatc cgtgcagaaa tggcgctacg   1200
tgcgtggacg ggttcaacac tttccgatgt ctgtgtctgc ctagctacgt cggggcactg   1260
tgcgagcagg ataccgaaac ctgtgattac gggtggcaca gtttcagggg tcagtgctac   1320
aagtactttg cgcatagaag aacatgggat gccgcagagc gagagtgtag gctgcaaggg   1380
gctcatctga catccatcct tagccatgag gaacaaatgt tgtcaacag agttggccac   1440 gactatcaat ggatcggctt gaatgacaag atgttcgagc acgacttcag gtggacagac   1500
ggctccaccc tccagtacga gaactggagg cctaatcagc ccgacagctt cttcagtgca   1560
ggagaggatt gcgtagtcat aatctggcac gaaaacggtc agtggaacga tgtgccatgc   1620
aactatcatc tgacctacac atgcaagaaa ggtactgtgg cctgtggcca acctcctgtc   1680
```

```
gtggagaatg ccaaaacatt tggtaagatg aaacccaggt acgagattaa ctcccttatt      1740
cgctaccact gtaaggatgg tttcattcaa cggcatctgc ccactattcg gtgcctggga      1800
aatgggcggt gggcaattcc gaagataacc tgtatgaacc cctctgctta ccagcgaacc      1860
tactccatga agtacttcaa gaactccagt tcagctaaag acaatagcat caacacttca      1920
aaacacgatc atcgctggag ccggcggtgg caggaaagca gacggtga                   1968

<210> SEQ ID NO 14
<211> LENGTH: 1908
<212> TYPE: DNA
<213> ORGANISM: Homo sapiens

<400> SEQUENCE: 14
ttgcacaaag taaaagttgg aaagagtccg cctgtgaggg gatcactgag tggcaaagtg        60
tcactgccct gtcacttttc cactatgcca actctcccac cctcttataa cacatccgag       120
tttctccgca taaagtggtc caaaatcgag gtagacaaga acggcaaaga cctcaaagag       180
actactgtgc tcgtggcaca gaatggaaac atcaagattg gcaggacta taagggtcgt       240 gtcagcgtgc caactcaccc agaagccgtt ggcgacgcca gcttgacagt tgtgaaactg       300
cttgccagcg acgccggact gtatcgctgc gatgtcatgt atggtatcga agatacacag       360
gacacagtga gcctgaccgt ggatggggta gtctttcact atagagccgc cacatctaga       420
tacaccctga attttgaggc agctcagaag gcctgcttgg atgtgggcgc cgtgattgca       480
acgcctgagc aactgttcgc cgcctacgaa gatggattcg agcagtgtga cgcaggatgg       540
ctggccgatc agaccgttcg gtaccctatc agagctcccc gagtagggtg ctatggcgat       600
aaaatgggca aggctggcgt gaggacctac ggcttcaggt cacctcagga aacctatgac       660
gtgtactgtt atgtggacca cttggatggc gatgtctttc atctcacggt cccctctaaa       720
tttacgttcg aagaagcggc caaggagtgc gagaatcagg acgccaggct ggcaactgtg       780
ggagaactgc aggctgcctg cgcaatgggt tcgaccagt gcgattatgg gtggctgagt       840
gacgcttctg tccgccatcc cgttaccgtc gctagggcgc aatgcggtgg aggacttctg       900
ggcgttagaa ccctctatcg ctttgagaat cagactgggt tccgccacc agattctcgg       960 ttcgatgcgt attgcttcaa acgtcccgac cgttgtaaga tgaacccatg ccttaacggc      1020
ggaacctgtt acccaacaga aacgagctat gtttgcacct gtgtgcccgg gtactcaggc      1080
gaccagtgtg aactggactt tgacgaatgc cactctaatc cgtgcagaaa tggcgctacg      1140
tgcgtggacg ggttcaacac tttccgatgt ctgtgtctgc ctagctacgt cggggcactg      1200
tgcgagcagg ataccgaaac ctgtgattac gggtggcaca gtttcagggg tcagtgctac      1260
aagtactttg cgcatagaag aacatgggat gccgcgagc gagagtgtag gctgcaaggg      1320
gctcatctga catccatcct tagccatgag gaacaaatgt ttgtcaacag agttggccac      1380
gactatcaat ggatcggctt gaatgacaag atgttcgagc acgacttcag gtggacagac      1440
ggctccaccc tccagtacga gaactggagg cctaatcagc ccgacagctt cttcagtgca      1500
ggagaggatt gcgtagtcat aatctggcac gaaaacggtc agtggaacga tgtgccatgc      1560
aactatcatc tgacctacac atgcaagaaa ggtactgtgg cctgtggcca acctcctgtc      1620
gtggagaatg ccaaaacatt tggtaagatg aaacccaggt acgagattaa ctcccttatt      1680
cgctaccact gtaaggatgg tttcattcaa cggcatctgc ccactattcg gtgcctggga      1740
aatgggcggt gggcaattcc gaagataacc tgtatgaacc cctctgctta ccagcgaacc      1800
tactccatga agtacttcaa gaactccagt tcagctaaag acaatagcat caacacttca      1860
```

```
aaacacgatc atcgctggag ccggcggtgg caggaaagca gacggtga          1908
```

<210> SEQ ID NO 15
<211> LENGTH: 1908
<212> TYPE: DNA
<213> ORGANISM: Rattus norvegicus

<400> SEQUENCE: 15

```
ctgcataaag ccaaaatgga agaaaaccca cctgttaaag gctctctgtc tggaaaagtg    60
atcctacctt gtcatttttc aaccttgccc accttaccac ccgattacaa cacgagtgaa   120
tttctcagaa tcaaatggtc taaaatagaa gtggacaaaa atggaaaaga cataaaggag   180
actactgtcc tggtggccca agacgggaac atcaagattg gtcaggacta caggggcgg    240
gtatcagtgc ctacgcatcc cgatgacgta ggcgatgcct ctctcaccat ggtcaaactc   300
cgtgctagtg acgcaggtgt ctaccgctgt gatgtcatgt atggcattga agacactcag   360
aacacgatgt cgctggccgt ggacggtgtc gtgtttcact acagggcagc gaccagcaga   420
tacactctga acttcgagtc tgctcaacag gcttgtttgg acatcggggc ggtcatagca   480
accccagagc agctgttcgc tgcctatgag gatggatttg agcagtgtga tgcaggatgg   540
ctgtctgacc aaactgtcag atatcccata cgggctcccc gagagggctg ttatggagac   600
atgatgggga aggaaggggt ccggacctat ggattccgct ctccccagga aacctatgat   660
gtgtattgct atgtggatca tctggacggc gatgtgttcc acatcactgc tcccagtaaa   720
ttcaccttcg aggaggccga agcagagtgt gcaaaccggg atgccaggct ggcgactgtt   780
ggggaacttc acgcagcttg gaggaacggc tttgaccagt gcgattacgg ctggctgtcg   840
gatgccagcg tgcggcaccc tgtgactgtg gccaggggcc agtgtggagg tggtctactt   900
ggggtgagaa ccctgtatcg ttttgagaac cagacatgct tccctctccc tgatagcaga   960
tttgatgcct actgctttaa acgacctgat ctctgcaaaa caaacccatg cctcaatgga  1020
ggcacctgct atcctactga acttcctat gtgtgcacct gtgcacctgg ctacagtgga  1080
gaccagtgtg aactggattt tgatgaatgt cactctaacc cttgtcggaa tggagccacc  1140
tgtgtggacg gtctgaatac atttagatgc ctctgccttc cgagttatgt cggtgcactc  1200
tgcgaacaag acactgagac atgcgactat ggctggcaca aattccaagg gcaatgctac  1260
aagtactttg ctcatcgccg tacatgggat gctgctgaaa gggagtgtcg cctgcagggt  1320
gcccacctca aagcatcct ttctcatgag gaacaaatgt tgtgaatcg tgtgggccat  1380
gattaccagt ggattggcct caatgacaag atgtttgaac atgacttccg ctggactgac  1440
ggcagcgcac tgcaatatga gaactggaga cccaaccagc cagacagctt cttttctgct  1500
ggagaagact gcgttgtgat catttggcat gagaatggcc agtggaatga cgtccctgc   1560
aactaccacc tcacctacac ctgcaagaag ggaacagttg cttgcggcca accccctgtt  1620
gtagaaaatg ccaagaccct tggaaagatg aaaccacgtt atgaaatcaa ctccttgatt  1680
agataccact gcaaagatgg tttcattcag cgtcaccttc caactatccg gtgcctagga  1740
aatgggagat gggcaatgcc taaaataacc tgcatgaacc catctgcata ccaaaggact  1800
tattctaaga aatacttaaa aaattcctca tcagtcaagg acaattctat aaatacgtca  1860
aaacatgagc atcgctggag ccggaggtgg caggaaacga ggcgctga              1908
```

<210> SEQ ID NO 16
<211> LENGTH: 1908
<212> TYPE: DNA

<213> ORGANISM: Mus musculus

<400> SEQUENCE: 16

```
ctacatcaag ccaaaatgga aaccagccca cctgttaaag gctctctgtc tggaaaagtg      60
gtcctacctt gtcattttc aaccttacct accttaccac ccaattacaa cacgagtgaa     120
tttctcagaa tcaaatggtc taagatggaa gtggacaaaa atggaaaaga tataaaggag     180
acgactgtct tggtggccca gaacggaaat atcaagattg tcaggacta caaggggcga     240
gtgtccgtgc ctacacatcc cgatgatgta ggtgatgctt ccctcaccat ggtcaaactc     300
cgggctagtg atgcaggcgt ctaccgatgt gatgtcatgt atgggattga agacactcag     360
gacaccatgt cactggctgt ggatggtgtt gtgtttcact acagggcagc caccagcagg     420
tacactctga actttgccgc tgctcaacag gcttgtttgg atatcggggc ggtcatagca     480
agcccagagc agctgtttgc cgcctatgag gatggatttg agcagtgtga tgcaggatgg     540
ctgtctgatc aaactgtcag atatcccata cgggctcccc gagagggctg ttacggagac     600
atgatgggga aggaagggt tcggacctat ggattccgct ctcccagga aacctatgat     660
gtgtattgtt atgtggatca tctggatggc gatgtgttcc acatcactgc tcccagtaag     720
ttcaccttcg aggaggccga agcagagtgt acaagcaggg atgcgaggct ggcgactgtt     780
ggagaacttc aggcagcttg gagaaatggc tttgaccaat gcgattacgg ctggctgtcg     840
gatgccagcg tgcggcaccc tgtgactgtg gccagggccc agtgtggagg aggtctactt     900
ggggtgagaa ccctgtatcg ttttgagaac cagacatgct tccctctccc tgatagcaga     960
tttgatgcct actgctttaa acgacctgat ctctgcaaaa caaacccatg cctcaacgga    1020
ggcacctgtt atcctaccga gacttcctat gtgtgcacct gtgcacctgg atacagcgga    1080
gaccagtgtg aacttgattt tgatgaatgt cactctaacc cttgtcggaa tggtgccacc    1140
tgtgtggatg gttttaatac atttagatgt ctctgtctcc caagttatgt tggtgcactc    1200
tgtgaacaag acactgagac atgtgactat ggctggcaca aattccaagg acagtgctac    1260
aagtactttg ctcatcgacg cacatgggat gctgctgaaa gggagtgtcg cctgcagggt    1320
gcccacctca caagcatcct ttctcatgag gaacaaatgt tgtgaatcg tgtgggccat    1380
gattaccagt ggatcggcct caatgacaag atgtttgaac atgacttccg ctggactgac    1440
ggcagtgcac tgcaatatga gaactggaga cccaaccagc cagacagttt ctttctgca    1500
ggagaagact gcgttgtgat catttggcat gaaaatggtc agtggaatga cgtcccctgc    1560
aattaccacc tcacctacac ttgcaagaag ggaacagttg cttgcggcca accccctgtt    1620
gtagaaaatg ccaagacctt tggaaagatg aaaccacgct atgaaatcaa ctccttgatt    1680
agatatcact gcaaagatgg tttcattcag cgacaccttc caactatccg gtgcctagga    1740
aacgggagat gggcaatgcc taaaataacc tgcatgaacc catctgcata ccaaaggact    1800
tattctaaga aatacttaaa aaattcctca tccgcaaagg acaattctat aaatacatca    1860
aaacatgagc atcgctggag ccggaggcgg caggaaacca ggcgctga              1908
```

<210> SEQ ID NO 17
<211> LENGTH: 1911
<212> TYPE: DNA
<213> ORGANISM: Sus scrofa

<400> SEQUENCE: 17

```
ctacataaag tcaaagtgga aaaagcccca cctgtcaagg gctccctctc tggaaaagtc      60
aacctacctt gtcattttc aactatgcct accttaccac ccagttacaa caccaccagt     120
```

```
gaatttctcc gaattaaatg gtctaagatt gaattggaca agagtggaaa agatttaaag      180
gagactactg ttcttgtggc ccaaaatggg aatatcaaga ttggtcaggg ctacaaagga      240
agagtgtcgg tgcctacaca tccggaggat gtgggtgatg cctcactcac catggtcaaa      300
ctccttgcca gtgatgcagg cctttaccgc tgtgatgtca tgtatgggat agaagacaca      360
caagactccg tgtcattggc tgtggatgga gttgtgtttc actacagggc agcgacgagc      420
aggtacactc tgaattttga ggctgcrcag aaggcttgtc tggatatcgg agcagtcata      480
gcaaccccag agcagctcca tgccgcctat gaagacggat ttgagcaatg tgatgcaggc      540
tggctgtctg atcagactgt tagatatccc atccggactc cccgagaagg ctgttacgga      600
gatatgatgg ggaaggaagg agtcaggacc tacggattcc gtgctcccca tgagacttac      660
gatgtgtatt gttacgtgga ccatctggat ggtgatgtgt tccacatcac tgctcccaat      720
aaattcacct ttgaggaggc tgaagaagag tgtgaaaacc aggatgcccg cctggcaaca      780
gtgggggaac tccaagcagc gtggaggaac ggctttgacc agtgtgatta cgggtggcta      840
ttggatgcca gtgttcgcca ccctgtgact gtgcccaggg cccagtgtgg aggtggttta      900
cttggggtga gaaccctgta tcgttttgag accagacag gcttcccttc ccctgatagc      960
agatttgatg cctactgcta taaacgaccc gatcgttgca aaaccaaccc gtgccttaat     1020
gggggcacct gctaccctac tgaaacgtcc tatgtgtgca cctgcgtgcc aggatacagt     1080
ggcgaccaat gtgaacttga ttttgatgaa tgtcactcta cccctgtcg caacggagcc     1140 acatgcgttg acggttttaa tacctttagg tgtctctgcc tcccgagcta tgtaggtgca     1200 cttttgtgagc aagacacgga gacatgtgac tatggctggc acaaatttca agggcagtgc     1260
tacaagtact tcgcccaccg acgtacgtgg gatgcagctg aacgggagtg ccgtcttcag     1320
ggtgcccatc tcaccagcat tctgtctcat gaggaacaaa tgtttgtgaa tcgtgtgggc     1380
catgattatc agtggattgg tctcaatgac aagatgtttg agcatgactt ccgttggacc     1440
gatggcagca cactgcaata tgagaactgg aggcccaacc agccagacag cttctttttct     1500 tctggagaag actgcgttgt gatcatatgg catgagaatg gccagtggaa tgatgttccc     1560
tgcaattacc atctcaccta cacctgcaag aaaggaacag ttgcttgcgg ccagcccccct     1620 gttgtagaaa atgccaagac ctttggaaag atgaaacctc gttatgaaat caactccctg     1680
attagatatc actgcaaaga tggtttcatt caacgccacc ctccaactat ccgttgccta     1740
ggaaatggaa gatgggctat gcccaaaatt acctgcctga cccatccgc ataccaaagg     1800 acttattcta agaaatactt taaaaattcc tcatcagcaa aggacaattc aataaacaca     1860
tccaaacatg atcaccgttg gagtcggagg tggcaagagt caaggcgctg a             1911
```

<210> SEQ ID NO 18
<211> LENGTH: 1911
<212> TYPE: DNA
<213> ORGANISM: Bos taurus

<400> SEQUENCE: 18

```
ctacagaaag tcaacatgga aaaaagccca cctgttaagg gctccctctc tggaaaagtc       60
aacctaccct gtcatttctc aaccatgcct accttaccac ccagttataa caccaccagt      120
gaatttctgc gaatcaaatg gtctaagatt gaattggaca agacgggaaa agatttaaag      180
gagactactg ttctcgtggc ccaaaatggg aatatcaaga tcggtcaaga ctacaaaggg      240
agagtgtcgg tgcctacaca tccgaggat gtgggcgatg cctcactcac catggtcaaa      300
```

```
ctgctggcca gtgatgcagg ccgctaccgc tgtgacgtca tgtacgggat tgaagacaca    360
caggacacgg tgtcactgac cgtggagggg gttgtgtttc actacagggc ggcaaccagc    420
aggtacaccc tgaactttga gatggcacag aaggcttgtg tggacatcgg ggccgtcata    480
gccaccccag agcagctgca tgccgcctat gaagatggtt ttgagcagtg tgatgcagga    540
tggctgtcag atcagactgt taggtatccc atccgggttc cccgagaagg ctgctatgga    600
gacatgatgg ggaaggaagg agtccggacc tacggattcc gtgctcctca tgaaacttac    660
gatgtgtatt gttacgtgga ccatctggat ggtgatgtgt tccacatcac tgctcccaac    720
aagttcacct tgaggaagc tggagaagag tgtaaaaccc aggacgcccg cctggcgacc    780
gtgggggagc tccaagcagc gtggaggaac ggcttcgacc ggtgtgatta cgggtggctg    840
ttggacgcca gcgttcgcca ccctgtgact gtggccaggg cccagtgtgg aggtggttta    900
cttggggtga aaccctgta tcgttttgag aaccagacag gcttccctac ccctgatagc    960
agatttgatg cctactgctt taaacgacct gatcgttgca aaatgaaccc gtgcctcaat   1020
gggggcacct gttatcctac tgaaacttcc tacgtgtgca cctgcgtgcc aggatacagt   1080
ggtgatcggt gtgaacttga ttttgatgaa tgtcattcta atccttgtcg caatggagcc   1140
acatgtattg acgttttaa taccttcagg tgtctctgcc tcccgagcta cgttggtgcg   1200
cttttgtgagc aagacacgga gacatgtgac tatggctggc acaaatttca agggcagtgc   1260
tacaagtact ttgcccatcg acggacgtgg gatgcagctg aacgggaatg ccgtctgcag   1320
ggcgcccatc tcaccagtat cctgtctcac gaggaacaaa tgtttgtgaa tcgtgtgggc   1380
catgattatc agtggatagg tctcaatgac aagatgtttg agcatgactt ccgttggact   1440
gatggcagca cactgcaata tgagaactgg aggccgaacc aaccagacag cttcttttct   1500
actgagaaag attgtgttgt gattatatgg catgagaatg ccagtggaa tgacgttccc   1560
tgcaattacc atctcaccta cacctgcaag aaaggaacag ttgcttgcgg ccagcccct   1620
gttgtagaaa atgccaagac cttttggaaag atgaaacctc gttatgaaat caactccttg   1680
attagatatc actgcaaaga tggtttcatt caacgccacc ttccaactat ccgttgccta   1740
ggaaatggaa gatgggctat gcctaaaatt acctgcctga acccatctgc ataccaaagg   1800
acttattcta agaaatattt taaaaattcc tcatcagcaa aggacaattc aataaataca   1860
tcaaaacatg atcaccgttg gagccgaagg tggcaagaat caaggcgctg a           1911
```

<210> SEQ ID NO 19
<211> LENGTH: 1908
<212> TYPE: DNA
<213> ORGANISM: Macaca mulatta

<400> SEQUENCE: 19

```
ctacataaag tcaaagtggg aaaaagccca cctctgaggg gctccctctc tggaaaagtc     60
agcctacctt gtcatttttc aaccatgcct actttgccac ccagttacaa caccagtgaa    120
tttctccgca tcaaatggtc taagattgaa gtggacaaaa atggaaaaga tttgaaagaa    180
actactgtcc ttgtggccca aaatggaaat atcaagattg gtcaggacta caaagggaga    240
gtgtctgtgc ccacacatcc cgaggccgtg ggcgatgcct ccctcactgt ggtcaagctg    300
ctggcaagtg atgcgggcct ctaccgctgt gatgtcatgt acggattga tgacacgcaa    360
gacacggtgt cactggctgt ggatggggtt gtgtttcact acagggcgtc aaccagcagg    420
tacacactga attttgaggc tgctcagaag gcttgtttgg acattgggc ggtcatagca    480
actccagagc agctctttgc cgcctatgaa gatggatttg agcagtgtga cgcaggctgg    540
```

```
ctggctgatc agactgtcag atatcccatc cgggctcccc gagtaggctg ttacggagat      600
atgatgggaa aggcaggagt caggacctat ggattccgtt ctccccagga aacttacgat      660
gtgtattgtt atgtggatca tctggatggt gatgtgttcc acctcactgc ccccagtaaa      720
ttcaccttcg aggaggccgc aaaagagtgt gaaaaccagg acgccaggct ggcaacagtg      780
ggggaactcc aggcggcgtg gaggaacggc tttgaccagt gcgattacgg gtggctgtcg      840
gatgccagcg tgcgccaccc tgtgactgtg gccagggccc agtgtggagg tggtctactt      900
ggggtgagaa ccctgtatcg ttttgagaac cagacaggct ccctccccc tgatagcaga      960 tttgatgcct actgctttaa cgacctgat cgttgcaaaa tgaacccgtg ccttaacgga     1020
ggcacctgtt atcctactga aacttcctat gtatgcacct gtgtgccagg atacagtgga     1080
gaccagtgtg aacttgattt tgatgaatgt cactctaatc cctgtcggaa tggagccact     1140
tgtgttgatg gttttaacac attcaggtgc ctctgccttc aagttatgt tggtgcactt     1200 tgtgaacaag acactgagac atgtgactat ggctggcaca aattccaagg gcagtgctac     1260
aaatactttg cccatcgacg cacatgggat gcagctgaac gggaatgccg tctgcagggt     1320
gcccatctca caagcatcct gtctcacgaa gaacaaacgt ttgttaatcg tgtgggccat     1380
gattatcagt ggataggcct caatgacaag atgtttgagc atgacttccg ctggactgat     1440
ggcagcacac tgcaatacga gaattggagg cccaaccagc cagacagctt cttttctgct     1500
ggagaagact gtgttgtaat catttggcat gagaatggcc agtggaatga tgttccctgc     1560
aattaccatc tcacctatac gtgcaagaaa ggaacagttg cttgcggcca gcccctgtt     1620 gtagaaaatg ccaagaccctt tggaaagatg aaacctcgtt atgaaatcaa ctccctgatt     1680
agataccact gcaaagatgg tttcattcaa cgtcaccttc caaccatccg gtgcctagga     1740
aatggaagat gggctatacc taaaattacc tgcatgaacc catctgcata ccaaaggact     1800
tattctatga aatactttaa aaattcctca tcagcaaagg acaattcaat aaatacatcc     1860
aaacatgatc atcgttggag ccggaggtgg caggagacga ggcgctga                  1908
```

<210> SEQ ID NO 20
<211> LENGTH: 1911
<212> TYPE: DNA
<213> ORGANISM: Canis familiaris

<400> SEQUENCE: 20

```
ctacataaag ccaaagtgga aaaaagccca cctgttaagg gctccctgtc tggaaaagtc       60
aacctacctt gccattttc cactatgcct accttaccgc ccagttacaa cacctccagc      120
gaatttctca gaatcaaatg gtctaagatt gaattggaca agaatggaaa ggatttgaag      180
gagactaccg tccttgtagc ccaaaatggg aatgtcaaga ttggtcaggg ctatcaagga      240
agggtgtccg tgcctacaca tgctgaggtg gtgggtgatg cctccctcac catggtcaaa      300
ctgcgtgcca gtgacgcggg ccagtaccgc tgcgacgtca tgtacgggat tgaagacaca      360
caagacacgg tatcgttggc ggtggacggg gttgtgtttc actacagagc ggcaaccagc      420
aggtatacac tgaattttga ggctgcacag aaggcttgtt tggatattgg agcagtcata      480
gcaaccccag agcagctcta tgctgcctac gaagatggat ttgagcagtg tgatgcaggc      540
tggctgtctg atcagaccgt cagatatccc atccgggctc cccgagtagg ctgttacgga      600
gatatgatgg ggaaggaagg agtcaggacc tacggattcc gttcgcctca tgagacttac      660
gatgtgtact gctacgtgga ccacctggat ggtgatgtgt tccatatcac tgctcccaat      720
```

```
aaatttacct tgaggaggc cgaagaagag tgtgagaacc aggacgcccg gctggcgaca    780
gtggggaac tccaagcagc ttggaggaat ggctttgacc agtgcgatta tgggtggctg    840
tccgacgcca gcgttcgcca ccctgtgact gtggccaggg cccagtgtgg aggtggtttg    900
cttggggtga gaaccctgta tcgttttgag aaccagacag gcttccctcc ccctgatagc    960
agatttgatg cctactgctt taaacgaccc gatcgttgta aaacgaaccc gtgccttaat   1020
ggaggcacct gttatcctac tgaaacttcc tacgtatgta cctgtgtgcc aggattcagt   1080
ggcgaccagt gtgagcttga tttcgatgaa tgtcactcta accctgtcg caatggagcc    1140
acgtgtgtgg atggttttaa tacgttcagg tgcctctgcc ttccgagcta cgttggtgca   1200
ctttgtgaac aagacacaga gacgtgtgac tacggctggc acaaattcca aggccagtgc   1260
tacaaatact cgcccatcg gcgcacgtgg gacgcagctg aacgggaatg ccgtctgcag    1320
ggcgcgcatc tcacaagcat cctgtctcac gaggaacaga tgtttgtgaa ccgtgtgggg   1380
catgattatc agtggatagg cctcaatgac aagatgtttg aacatgactt ccgttggacc   1440
gatggcagca cactgcaata tgagaactgg aggcccaacc agccagacag cttcttttct   1500
gctggagagg actgtgttgt aatcatttgg catgagaatg ccagtggaa tgatgttccc    1560
tgcaattatc atctcactta tacctgcaag aaaggaacag ttgcttgcgg ccagccccct   1620
gttgtagaaa atgccaagac ctttggaaag atgaaacctc gttatgaaat caactccctg   1680
attagatatc actgcaaaga tggtttcatt caacgccacc ttccaactat ccgttgccta   1740
ggaaatggaa gatgggctat gcctaaaatt acctgcatga acccgtctgc ataccaaagg   1800
acttactcta agaaatactt taaaaattct tcatcagcaa aggacaattc aataaatatca  1860
tcaaaacatg atcaccgttg gagccgaagg tggcaggagt ccaggcgctg a            1911
```

<210> SEQ ID NO 21
<211> LENGTH: 1831
<212> TYPE: DNA
<213> ORGANISM: Homo sapiens

<400> SEQUENCE: 21

```
ctacataaag tcaaagtggg aaaaagccca ccggtgaggg gctccctctc tggaaaagtc     60
agcctacctt gtcatttttc aacgatgcct actttgccac ccagttacaa caccagtgaa    120
tttctccgca tcaaatggtc taagattgaa gtggacaaaa atggaaaaga tttgaaagag    180
actactgtcc ttgtggccca aaatggaaat atcaagattg gtcaggacta caaagggaga    240
gtgtctgtgc ccacacatcc cgaggctgtg ggcgatgcct ccctcactgt ggtcaagctg    300
ctggcaagtg atgcgggtct ttaccgctgt gacgtcatgt acgggattga agacacacaa    360
gacacggtgt cactgactgt ggatgggggtt gtgtttcact acagggcggc aaccagcagg    420
tacacactga atttttgaggc tgctcagaag gcttgtttgg acgttggggc agtcatagca    480
actccagagc agctctttgc tgcctatgaa gatggatttg agcagtgtga cgcaggctgg    540
ctggctgatc agactgtcag atatcccatc cgggctccca gagtaggctg ttatggagat    600
aagatgggaa aggcaggagt caggacttat ggattccgtt ctccccagga aacttacgat    660
gtgtattgtt atgtggatca tctggatggt gatgtgttcc acctcactgt ccccagtaaa    720
ttcaccttcg aggaggctgc aaaagagtgt gaaaaccagg atgccaggct ggcaacagtg    780
ggggaactcc aggcggcatg gaggaacggc tttgaccagt gcgattacgg gtggctgtcg    840
gatgccagcg tgcgccaccc tgtgactgtg gccaggccc agtgtggagg tggtctactt     900
ggggtgagaa ccctgtatcg ttttgagaac cagacaggct tccctccccc tgatagcaga    960
```

-continued

```
tttgatgcct actgctttaa acgacctgat cgctgcaaaa tgaacccgtg ccttaacgga    1020
ggcacctgtt atcctactga aacttcctac gtatgcacct gtgtgccagg atacagcgga    1080
gaccagtgtg aacttgattt tgatgaatgt cactctaatc cctgtcgtaa tggagccact    1140
tgtgttgatg gttttaacac attcaggtgc ctctgccttc aagttatgt tggtgcactt     1200 tgtgagcaag ataccgagac atgtgactat ggctggcaca aattccaagg gcagtgctac    1260
aaatactttg cccatcgacg cacatgggat gcagctgaac gggaatgccg tctgcagggt    1320
gcccatctca aagcatcct gtctcacgaa gaacaaatgt tgttaatcg tgtgggccat      1380 gattatcagt ggataggcct caatgacaag atgtttgagc atgacttccg ttggactgat    1440
ggcagcacac tgcaatacga gaattggaga cccaaccagc cagacagctt cttttctgct    1500
ggagaagact gtgttgtaat catttggcat gagaatggcc agtggaatga tgttccctgc    1560
aattaccatc tcacctatac gtgcaagaaa ggaacagtcg cttgcggcca gccccctgtt    1620
gtagaaaatg ccaagacctt tggaaagatg aaacctcgtt atgaaatcaa ctccctgatt    1680
agataccact gcaaagatgg tttcattcaa cgtcaccttc caactatccg gtgcttagga    1740
aatggaagat gggctatacc taaaattacc tgcatgaacc gtaagtggtc ctttagaaag    1800
aatggactac cgtgctataa caactactag a                                   1831
```

<210> SEQ ID NO 22
<211> LENGTH: 3474
<212> TYPE: DNA
<213> ORGANISM: Artificial Sequence
<220> FEATURE:
<223> OTHER INFORMATION: A synthetic oligonucleotide sequence

<400> SEQUENCE: 22

```
ctgcagctag acagcgtcct acaggtgctt tacgtgtgaa attttggtttt ttatggtgct     60 ttgctctgag ccagcccacc agtttggaat gactcctttt tatgacttga attttcaagt    120
ataaagtcta gtgctaaatt taatttgaac aactgtatag ttttttgctgg ttgggggaag    180 gaaaaaaaat ggtggcagtg tttttttcag aattagaagt gaaatgaaaa cttgttgtgt    240
gtgaggattt ctaatgacat gtggtggttg catactgagt gaagccggtg agcattctgc    300
catgtcaccc cctcgtgctc agtaatgtac tttacagaaa tcctaaactc aaaagattga    360
tataaaccat gcttcttgtg tatatccggt ctcttctctg ggtagtctca ctcagcctgc    420
atttctgcca acgcgtgtgg catctgaagc accaccagcg agcgagagct agagagaagg    480
aaagccacct acttcaccgc ctccgagctg ctccgggtcg cgggtctgca gcgtctccgg    540
ccctccgcgc ctacagctca agccacatcc aaggggggag ggagccggga gctgcgcgcg    600
gggccgccgg ggggagggt ggcaccgccc acgccgggcg ccacgaagg gcggggcagc      660 gggcgcgcgc ccggcggggg gaggggccgc gcgccgcgcc cgctgggaat tggggcccta    720
gggggagggc ggaggcgccg acgaccgcgg cacttaccgt tcgcggcgtg gcgcccggtg    780
gtccccaagg ggagggaagg gggaggcggg gcgaggacag tgaccggagt ctcctcagcg    840
gtggcttttc tgcttggcag cctcagcggc tggcgccaaa accggactcc gcccacttcc    900
tcgcccctgc ggtgcgaggg tgtggaatcc tccagacgct gggggagggg gagttgggag    960
cttaaaaact agtaccccct tgggaccact ttcagcagcg aactctcctg tacaccaggg    1020
gtcagttcca cagacgcggg ccaggggtgg gtcattgcgg cgtgaacaat aatttgacta    1080
gaagttgatt cgggtgtttc cggaattcct agctgcagta acgccatttt gcaaggcatg    1140
```

-continued

```
gaaaaatacc aaaccaagaa tagagaagtt cagatcaagg gcgggtacat gaaaatagct    1200
aacgttgggc caaacaggat atctgcggtg agcagtttcg gccccggccc ggggccaaga    1260
acagatggtc accgcagttt cggccccggc ccgaggccaa gaacagatgg tccccagata    1320
tggcccaacc ctcagcagtt tcttaagacc catcagatgt ttccaggctc ccccaaggac    1380
ctgaaatgac cctgcgcctt atttgaatta accaatcagc ctgcttctcg cttctgttcg    1440
cgcgcttctg cttcccgagc tctataaaag agctcacaac ccctcactcg gcgcgccagt    1500
cctccgacag actgagtcat gggcgtgaag gtgctgttcg ccctgatctg catcgccgtg    1560
gccgaggcct tgcacaaagt aaaagttgga aagagtccgc ctgtgagggg atcactgagt    1620
ggcaaagtgt cactgccctg tcactttcc actatgccaa ctctcccacc ctcttataac    1680
acatccgagt ttctccgcat aaagtggtcc aaaatcgagg tagacaagaa cggcaaagac    1740
ctcaaagaga ctactgtgct cgtggcacag aatggaaaca tcaagattgg gcaggactat    1800
aagggtcgtg tcagcgtgcc aactcaccca gaagccgttg gcgacgccag cttgacagtt    1860
gtgaaactgc ttgccagcga cgccggactg tatcgctgcg atgtcatgta tggtatcgaa    1920
gatacacagg acacagtgag cctgaccgtg gatgggtag tctttcacta tagagccgcc    1980
acatctagat acaccctgaa ttttgaggca gctcagaagg cctgcttgga tgtgggcgcc    2040
gtgattgcaa cgcctgagca actgttcgcc gcctacgaag atggattcga gcagtgtgac    2100
gcaggatggc tggccgatca gaccgttcgg tacccctatca gagctccccg agtagggtgc    2160
tatggcgata aaatgggcaa ggctggcgtg aggacctacg gcttcaggtc acctcaggaa    2220
acctatgacg tgtactgtta tgtggaccac ttggatggcg atgtctttca tctcacggtc    2280
ccctctaaat ttacgttcga agaagcggcc aaggagtgcg agaatcagga cgccaggctg    2340
gcaactgtgg gagaactgca ggctgcctgg cgcaatgggt tcgaccagtg cgattatggg    2400
tggctgagtg acgcttctgt ccgccatccc gttaccgtcg ctagggcgca atgcggtgga    2460
ggacttctgg gcgttagaac cctctatcgc tttgagaatc agactgggtt tccgccacca    2520
gattctcggt tcgatgcgta ttgcttcaaa cgtcccgacc gttgtaagat gaacccatgc    2580
cttaacggcg gaacctgtta cccaacagaa acgagctatg tttgcacctg tgtgcccggg    2640
tactcaggcg accagtgtga actggacttt gacgaatgcc actctaatcc gtgcagaaat    2700
ggcgctacgt gcgtggacgg gttcaacact ttccgatgtc tgtgtctgcc tagctacgtc    2760
ggggcactgt gcgagcagga taccgaaacc tgtgattacg ggtggcacaa gtttcagggt    2820
cagtgctaca agtactttgc gcatagaaga acatgggatg ccgcagagcg agagtgtagg    2880
ctgcaagggg ctcatctgac atccatcctt agccatgagg aacaaatgtt tgtcaacaga    2940
gttggccacg actatcaatg gatcggcttg aatgacaaga tgttcgagca cgacttcagg    3000
tggacagacg gctccaccct ccagtacgag aactggaggc ctaatcagcc cgacagcttc    3060
ttcagtgcag gagaggattg cgtagtcata atctggcacg aaaacggtca gtggaacgat    3120
gtgccatgca actatcatct gacctacaca tgcaagaaag gtactgtggc ctgtggccaa    3180
cctcctgtcg tggagaatgc caaaacattt ggtaagatga acccaggta cgagattaac    3240
tcccttattc gctaccactg taaggatggt ttcattcaac ggcatctgcc cactattcgg    3300
tgcctgggaa atgggcggtg ggcaattccg aagataacct gtatgaaccc ctctgcttac    3360
cagcgaacct actccatgaa gtacttcaag aactccagtt cagctaaaga caatagcatc    3420
aacacttcaa aacacgatca tcgctggagc cggcggtggc aggaaagcag acgg         3474
```

<210> SEQ ID NO 23
<211> LENGTH: 5202
<212> TYPE: DNA
<213> ORGANISM: Artificial Sequence
<220> FEATURE:
<223> OTHER INFORMATION: A synthetic oligonucleotide sequence

<400> SEQUENCE: 23

| | | | | | |
|---|---|---|---|---|---|
| agaaagggca | taaactgctt | tatccagtgt | tatattaaaa | gcttaatgta | tataatcttt | 60 |
| tagaggtaaa | atctacagcc | agcaaaagtc | atggtaaata | ttctttgact | gaactctcac | 120 |
| taaactcctc | taaattatat | gtcatattaa | ctggttaaat | taatataaat | ttgtgacatg | 180 |
| accttaactg | gttaggtagg | atattttttct | tcatgcaaaa | atatgactaa | taataattta | 240 |
| gcacaaaaat | atttcccaat | actttaattc | tgtgatagaa | aaatgtttaa | ctcagctact | 300 |
| ataatcccat | aattttgaaa | actatttatt | agcttttgtg | tttgacccttt | ccctagccaa | 360 |
| aggcaactat | ttaaggaccc | tttaaaactc | ttgaaactac | tttagagtca | ttaagttctg | 420 |
| cagctagaca | gcgtcctaca | ggtgcttac | gtgtgaaatt | ttggttttta | tggtgctttg | 480 |
| ctctgagcca | gcccaccagt | ttggaatgac | tccttttat | gacttgaatt | ttcaagtata | 540 |
| aagtctagtg | ctaaatttaa | tttgaacaac | tgtatagttt | ttgctggttg | ggggaaggaa | 600 |
| aaaaaatggt | ggcagtgttt | ttttcagaat | tagaagtgaa | atgaaaactt | gttgtgtgtg | 660 |
| aggatttcta | atgacatgtg | gtggttgcat | actgagtgaa | gccggtgagc | attctgccat | 720 |
| gtcaccccct | cgtgctcagt | aatgtacttt | acagaaatcc | taaactcaaa | agattgatat | 780 |
| aaaccatgct | tcttgtgtat | atccggtctc | ttctctgggt | agtctcactc | agcctgcatt | 840 |
| tctgccaacg | cgtgtggcat | ctgaagcacc | accagcgagc | gagagctaga | gagaaggaaa | 900 |
| gccaccgact | tcaccgcctc | cgagctgctc | cgggtcgcgg | gtctgcagcg | tctccggccc | 960 |
| tccgcgccta | cagctcaagc | cacatccgaa | ggggagggga | gccgggagct | gcgcgcgggg | 1020 |
| ccgccggggg | gaggggtggc | accgccacg | ccgggcggcc | acgaagggcg | gggcagcggg | 1080 |
| cgcgcgcccg | gcgggggag | gggccgcgcg | ccgcgcccgc | tgggaattgg | ggccctaggg | 1140 |
| ggagggcgga | ggcgccgacg | accgcggcac | ttaccgttcg | cggcgtggcg | cccggtggtc | 1200 |
| cccaagggga | gggaaggggg | aggcgggcg | aggacagtga | ccggagtctc | ctcagcggtg | 1260 |
| gcttttctgc | ttggcagcct | cagcggctgg | cgccaaaacc | ggactccgcc | cacttcctcg | 1320 |
| cccctgcggt | gcgagggtgt | ggaatcctcc | agacgctggg | ggaggggag | ttgggagctt | 1380 |
| aaaaactagt | accccttgg | gaccactttc | agcagcgaac | tctcctgtac | accaggggtc | 1440 |
| agttccacag | acgcgggcca | ggggtgggtc | attgcgcgt | gaacaataat | ttgactagaa | 1500 |
| gttgattcgg | gtgtttccgg | aattcctagc | tgcagtaacg | ccattttgca | aggcatggaa | 1560 |
| aaataccaaa | ccaagaatag | agaagttcag | atcaagggcg | ggtacatgaa | aatagctaac | 1620 |
| gttgggccaa | acaggatatc | tgcggtgagc | agtttcggcc | ccggcccggg | gccaagaaca | 1680 |
| gatggtcacc | gcagtttcgg | ccccggcccg | aggccaagaa | cagatggtcc | ccagatatgg | 1740 |
| cccaacccctc | agcagtttct | taagacccat | cagatgtttc | caggctcccc | caaggacctg | 1800 |
| aaatgaccct | gcgccttatt | tgaattaacc | aatcagcctg | cttctcgctt | ctgttcgcgc | 1860 |
| gcttctgctt | cccgagctct | ataaagagc | tcacaacccc | tcactcggcg | cgccagtcct | 1920 |
| ccgacagact | gagtcgcccg | ctcgaggtcg | acggtatcga | taagcttgcc | accatggtga | 1980 |
| gcaagggcga | ggagctgttc | accggggtgg | tgcccatcct | ggtcgagctg | gacggcgacg | 2040 |
| taaacggcca | caagttcagc | gtgtccggcg | agggcgaggg | cgatgccacc | tacggcaagc | 2100 |

```
tgaccctgaa gttcatctgc accaccggca agctgcccgt gccctggccc accctcgtga    2160 ccacccctgac ctacggcgtg cagtgcttca gccgctaccc cgaccacatg aagcagcacg   2220
acttcttcaa gtccgccatg cccgaaggct acgtccagga gcgcaccatc ttcttcaagg    2280
acgacggcaa ctacaagacc cgcgccgagg tgaagttcga gggcgacacc ctggtgaacc    2340
gcatcgagct gaagggcatc gacttcaagg aggacggcaa catcctgggg cacaagctgg    2400
agtacaacta caacagccac aacgtctata tcatggccga caagcagaag aacggcatca    2460
aggtgaactt caagatccgc cacaacatcg aggacggcag cgtgcagctc gccgaccact    2520
accagcagaa cacccccatc ggcgacggcc ccgtgctgct gcccgacaac cactacctga    2580
gcacccagtc cgccctgagc aaagacccca acgagaagcg cgatcacatg gtcctgctgg    2640
agttcgtgac cgccgccggg atcactctcg gcatggacga gctgtacaag catatggcca    2700
agttgaccag tgccgttccg gtgctcaccg cgcgcgacgt cgccggagcg tcgagttct    2760 ggaccgaccg gctcgggttc tcccgggact tcgtggagga cgacttcgcc ggtgtggtcc    2820
gggacgacgt gaccctgttc atcagcgcgg tccaggacca ggtggtgccg acaacaccc    2880 tggcctgggt gtgggtgcgc ggcctggacg agctgtacgc cgagtggtcg gaggtcgtgt    2940
ccacgaactt ccgggacgcc tccggccgg ccatgaccga gatcggcgag cagccgtggg    3000
ggcgggagtt cgccctgcgc gacccggccg gcaactgcgt gcacttcgtg gccgaggagc    3060
aggacgaaag cggagctact aacttcagcc tgctgaagca ggctggtgac gtggaggaga    3120
atcccggccc tagcatgggc gtgaaggtgc tgttcgccct gatctgcatc gccgtggccg    3180
aggccttgca caaagtaaaa gttggaaaga gtccgcctgt gagggatca ctgagtggca    3240 aagtgtcact gccctgtcac ttttccacta tgccaactct cccaccctct tataacacat    3300
ccgagtttct ccgcataaag tggtccaaaa tcgaggtaga caagaacggc aaagacctca    3360
aagagactac tgtgctcgtg gcacagaatg aaacatcaa gattgggcag gactataagg     3420
gtcgtgtcag cgtgccaact cacccagaag ccgttggcga cgccagcttg acagttgtga    3480
aactgcttgc cagcgacgcc ggactgtatc gctgcgatgt catgtatggt atcgaagata    3540
cacaggacac agtgagcctg accgtggatg gggtagtctt tcactataga gccgccacat    3600
ctagatacac cctgaatttt gaggcagctc agaaggcctg cttggatgtg gcgcgcgtga    3660
ttgcaacgcc tgagcaactg ttcgccgcct acgaagatgg attcgagcag tgtgacgcag    3720
gatggctggc cgatcagacc gttcggtacc ctatcagagc tccccgagta gggtgctatg    3780
gcgataaaat gggcaaggct ggcgtgagga cctacggctt caggtcacct caggaaacct    3840
atgacgtgta ctgttatgtg gaccacttgg atggcgatgt ctttcatctc acggtccct    3900 ctaaatttac gttcgaagaa gcggccaagg agtgcgagaa tcaggacgcc aggctggcaa    3960
ctgtgggaga actgcaggct gcctggcgca atgggttcga ccagtgcgat tatgggtggc    4020
tgagtgacgc ttctgtccgc catcccgtta ccgtcgctag ggcgcaatgc ggtggaggac    4080
ttctgggcgt tagaaccctc tatcgctttg agaatcagac tgggtttccg ccaccagatt    4140
ctcggttcga tgcgtattgc ttcaaacgtc ccgaccgttg taagatgaac ccatgcctta    4200
acggcggaac ctgttaccca acagaaacga gctatgtttg cacctgtgtg cccgggtact    4260
caggcgacca gtgtgaactg gactttgacg aatgccactc taatccgtgc agaaatggcg    4320
ctacgtgcgt ggacgggttc aacactttcc gatgtctgtg tctgcctagc tacgtcgggg    4380
cactgtgcga gcaggatacc gaaacctgtg attacgggtg gcacaagttt cagggtcagt    4440
gctacaagta ctttgcgcat agaagaacat gggatgccgc agagcgagag tgtaggctgc    4500
```

```
aaggggctca tctgacatcc atccttagcc atgaggaaca atgtttgtc aacagagttg    4560 gccacgacta tcaatggatc ggcttgaatg acaagatgtt cgagcacgac ttcaggtgga    4620
cagacggctc caccctccag tacgagaact ggaggcctaa tcagcccgac agcttcttca    4680
gtgcaggaga ggattgcgta gtcataatct ggcacgaaaa cggtcagtgg aacgatgtgc    4740
catgcaacta tcatctgacc tacacatgca agaaaggtac tgtggcctgt ggccaacctc    4800
ctgtcgtgga gaatgccaaa acatttggta agatgaaacc caggtacgag attaactccc    4860
ttattcgcta ccactgtaag gatggtttca ttcaacggca tctgcccact attcggtgcc    4920
tgggaaatgg gcggtgggca attccgaaga taacctgtat gaacccctct gcttaccagc    4980
gaacctactc catgaagtac ttcaagaact ccagttcagc taaagacaat agcatcaaca    5040
cttcaaaaca cgatcatcgc tggagccggc ggtggcagga agcagacgg tatccttatg    5100 acgtgcctga ttacgcttgg agccacccc agttcgagaa gggtggaggt tctggcggtg    5160
gatcgggagg ttcagcgtgg agccacccgc agttcgagaa at    5202
```

<210> SEQ ID NO 24
<211> LENGTH: 5039
<212> TYPE: DNA
<213> ORGANISM: Artificial Sequence
<220> FEATURE:
<223> OTHER INFORMATION: A synthetic oligonucleotide sequence

<400> SEQUENCE: 24

```
agaaagggca taaactgctt tatccagtgt tatattaaaa gcttaatgta tataatcttt      60
tagaggtaaa atctacagcc agcaaaagtc atggtaaata ttctttgact gaactctcac     120
taaactcctc taaattatat gtcatattaa ctggttaaat taatataaat ttgtgacatg     180
accttaactg gttaggtagg atatttttct tcatgcaaaa atatgactaa taataattta     240
gcacaaaaat atttcccaat actttaattc tgtgatagaa aaatgtttaa ctcagctact     300
ataatcccat aattttgaaa actatttatt agcttttgtg tttgacccct ccctagccaa     360
aggcaactat ttaaggaccc tttaaaactc ttgaaactac tttagagtca ttaagttctg     420
cagctagaca gcgtcctaca ggtgctttac gtgtgaaatt ttggttttta tggtgctttg     480
ctctgagcca gcccaccagt ttggaatgac tccttttat gacttgaatt ttcaagtata     540
aagtctagtg ctaaatttaa tttgaacaac tgtatagttt ttgctggttg ggggaaggaa     600
aaaaaatggt ggcagtgttt ttttcagaat tagaagtgaa atgaaaactt gttgtgtgtg     660
aggatttcta atgacatgtg gtggttgcat actgagtgaa gccggtgagc attctgccat     720
gtcaccccct cgtgctcagt aatgtacttt acagaaatcc taaactcaaa agattgatat     780
aaaccatgct tcttgtgtat atccggtctc ttctctgggt agtctcactc agcctgcatt     840
tctgccacga gtttactccc tatcagtgat agagaacgta tgtcgagttt actccctatc     900
agtgatagag aacgatgtcg agtttactcc ctatcagtga tagagaacgt atgtcgagtt     960
tactccctat cagtgataga gaacgtatgt cgagtttact ccctatcagt gatagagaac    1020
gtatgtcgag tttatcccta tcagtgatag agaacgtatg tcgagtttac tccctatcag    1080
tgatagagaa cgtatgtcga ggtaggcgtg tacggtggga ggcctatata gcagagctc    1140 gtttaatggg cgtgaaggtg ctgttcgccc tgatctgcat cgccgtggcc gaggccttgc    1200
acaaagtaaa agttggaaag agtccgcctg tgagggatc actgagtggc aaagtgtcac    1260
tgccctgtca cttttccact atgccaactc tcccacccct ttataacaca tccgagtttc    1320
```

```
tccgcataaa gtggtccaaa atcgaggtag acaagaacgg caaagacctc aaagagacta    1380
ctgtgctcgt ggcacagaat ggaaacatca agattgggca ggactataag ggtcgtgtca    1440
gcgtgccaac tcacccagaa gccgttggcg acgccagctt gacagttgtg aaactgcttg    1500
ccagcgacgc cggactgtat cgctgcgatg tcatgtatgg tatcgaagat acacaggaca    1560
cagtgagcct gaccgtggat ggggtagtct ttcactatag agccgccaca tctagataca    1620
ccctgaattt tgaggcagct cagaaggcct gcttggatgt gggcgccgtg attgcaacgc    1680
ctgagcaact gttcgccgcc tacgaagatg gattcgagca gtgtgacgca ggatggctgg    1740
ccgatcagac cgttcggtac cctatcagag ctccccgagt agggtgctat ggcgataaaa    1800
tgggcaaggc tggcgtgagg acctacggct tcaggtcacc tcaggaaacc tatgacgtgt    1860
actgttatgt ggaccacttg gatggcgatg tctttcatct cacggtcccc tctaaattta    1920
cgttcgaaga agcggccaag gagtgcgaga atcaggacgc caggctggca actgtgggag    1980
aactgcaggc tgcctggcgc aatgggttcg accagtgcga ttatgggtgg ctgagtgacg    2040
cttctgtccg ccatcccgtt accgtcgcta gggcgcaatg cggtggagga cttctgggcg    2100
ttagaaccct ctatcgcttt gagaatcaga ctgggtttcc gccaccagat tctcggttcg    2160
atgcgtattg cttcaaacgt cccgaccgtt gtaagatgaa cccatgcctt aacggcggaa    2220
cctgttaccc aacagaaacg agctatgttt gcacctgtgt gcccgggtac tcaggcgacc    2280
agtgtgaact ggactttgac gaatgccact ctaatccgtg cagaaatggc gctacgtgcg    2340
tggacgggtt caacactttc cgatgtctgt gtctgcctag ctacgtcggg gcactgtgcg    2400
agcaggatac cgaaacctgt gattacgggt ggcacaagtt tcagggtcag tgctacaagt    2460
actttgcgca tagaagaaca tgggatgccg cagagcgaga gtgtaggctg caaggggctc    2520
atctgacatc catccttagc catgaggaac aaatgtttgt caacagagtt ggccacgact    2580
atcaatggat cggcttgaat gacaagatgt tcgagcacga cttcaggtgg acagacggct    2640
ccaccctcca gtacgagaac tggaggccta atcagcccga cagcttcttc agtgcaggag    2700
aggattgcgt agtcataatc tggcacgaaa acggtcagtg gaacgatgtg ccatgcaact    2760
atcatctgac ctacacatgc aagaaaggta ctgtggcctg tggccaacct cctgtcgtgg    2820
agaatgccaa acatttggt aagatgaaac ccaggtacga gattaactcc cttattcgct    2880
accactgtaa ggatggtttc attcaacggc atctgcccac tattcggtgc ctgggaaatg    2940
ggcggtgggc aattccgaag ataacctgta tgaacccctc tgcttaccag cgaacctact    3000
ccatgaagta cttcaagaac tccagttcag ctaaagacaa tagcatcaac acttcaaaac    3060
acgatcatcg ctggagccgg cggtggcagg aaagcagacg gcgcgtgtgg catctgaagc    3120
accaccagcg agcgagagct agagagaagg aaagccaccg acttcaccgc ctccgagctg    3180
ctccgggtcg cgggtctgca gcgtctccgg ccctccgcgc ctacagctca agccacatcc    3240 gaaggggag ggagccggga gctgcgcgcg gggccgccgg gggaggggt ggcaccgccc    3300 acgccgggcg gccacgaagg gcgggcagc gggcgcgcgc ccggcggggg gaggggccgc    3360
gcgccgcgcc cgctgggaat tggggcccta gggggagggc ggaggcgccg acgaccgcgg    3420
cacttaccgt tcgcggcgtg gcgcccggtg gtccccaagg ggagggaagg gggaggcggg    3480
gcgaggacag tgaccggagt ctcctcagcg gtggcttttc tgcttggcag cctcagcggc    3540
tggcgccaaa accggactcc gcccacttcc tcgcccctgc ggtgcgaggg tgtggaatcc    3600
tccagacgct gggggagggg gagttgggag cttaaaaact agtaccccctt tgggaccact    3660 ttcagcagcg aactctcctg tacaccaggg gtcagttcca cagacgcggg ccaggggtgg    3720
```

```
gtcattgcgg cgtgaacaat aatttgacta gaagttgatt cgggtgtttc cggtatcctt    3780
atgacgtgcc tgattacgct tggagccacc cccagttcga aagggtgga ggttctggcg    3840 gtggatcggg aggttcagcg tggagccacc cgcagttcga aaatctagc tgcagtaacg    3900 ccattttgca aggcatggaa aataccaaa ccaagaatag agaagttcag atcaagggcg    3960
ggtacatgaa aatagctaac gttgggccaa acaggatatc tgcggtgagc agtttcggcc    4020
ccggcccggg gccaagaaca gatggtcacc gcagtttcgg ccccggcccg aggccaagaa    4080
cagatggtcc ccagatatgg cccaacccctc agcagtttct taagacccat cagatgtttc    4140
caggctcccc caaggacctg aaatgaccct gcgccttatt tgaattaacc aatcagcctg    4200
cttctcgctt ctgttcgcgc gcttctgctt cccgagctct ataaagagc tcacaacccc    4260 tcactcggcg cgccagtcct ccgacagact gagtcatgtc cagactggac aagagcaaag    4320
tcataaacgg agctctggaa ttactcaatg gtgtcggtat cgaaggcctg acgacaagga    4380
aactcgctca aaagctggga gttgagcagc ctaccctgta ctggcacgtg aagaacaagc    4440
gggccctgct cgatgccctg ccaatcgaga tgctggacag gcatcatacc cacttctgcc    4500
ccctggaagg cgagtcatgg caagactttc tgcggaacaa cgccaagtca taccgctgtg    4560
ctctcctctc acatcgcgac ggggctaaag tgcatctcgg cacccgccca acagagaaac    4620
agtacgaaac cctggaaaat cagctcgcgt tcctgtgtca gcaaggcttc tcctggaga    4680 acgcactgta cgctctgtcc gccgtgggcc actttacact gggctgcgta ttggaggaac    4740
aggagcatca gtagcaaaa gaggaaagag agacacctac caccgattct atgcccccac    4800
ttctgagaca agcaattgag ctgttcgacc ggcagggagc cgaacctgcc ttccttttcg    4860
gcctggaact aatcatatgt ggcctggaga aacagctaaa gtgcgaaagc ggcgggccga    4920
ccgacgccct tgacgatttt gacttagaca tgctcccagc cgatgccctt gacgactttg    4980
accttgatat gctgcctgct gacgctcttg acgattttga ccttgacatg ctccccggg    5039
```

<210> SEQ ID NO 25
<211> LENGTH: 51
<212> TYPE: DNA
<213> ORGANISM: Gaussia princeps

<400> SEQUENCE: 25
atgggagtga aagttctttt tgcccttatt tgtattgctg tggccgaggc c    51

<210> SEQ ID NO 26
<211> LENGTH: 51
<212> TYPE: DNA
<213> ORGANISM: Gaussia princeps

<400> SEQUENCE: 26
atgggcgtga aggtgctgtt cgccctgatc tgcatcgccg tggccgaggc c    51

<210> SEQ ID NO 27
<211> LENGTH: 654
<212> TYPE: PRT
<213> ORGANISM: Rattus norvegicus

<400> SEQUENCE: 27

Met Leu Ile Asn Met Asn Gly Ile Leu Trp Met Cys Ser Thr Leu Leu
1               5                   10                  15

Leu Thr His Ala Leu His Lys Ala Lys Met Glu Glu Asn Pro Pro Val
            20                  25                  30

```
Lys Gly Ser Leu Ser Gly Lys Val Ile Leu Pro Cys His Phe Ser Thr
             35                  40                  45

Leu Pro Thr Leu Pro Pro Asp Tyr Asn Thr Ser Glu Phe Leu Arg Ile
 50                  55                  60

Lys Trp Ser Lys Ile Glu Val Asp Lys Asn Gly Lys Asp Ile Lys Glu
 65                  70                  75                  80

Thr Thr Val Leu Val Ala Gln Asp Gly Asn Ile Lys Ile Gly Gln Asp
                 85                  90                  95

Tyr Lys Gly Arg Val Ser Val Pro Thr His Pro Asp Asp Val Gly Asp
                100                 105                 110

Ala Ser Leu Thr Met Val Lys Leu Arg Ala Ser Asp Ala Gly Val Tyr
                115                 120                 125

Arg Cys Asp Val Met Tyr Gly Ile Glu Asp Thr Gln Asn Thr Met Ser
    130                 135                 140

Leu Ala Val Asp Gly Val Val Phe His Tyr Arg Ala Ala Thr Ser Arg
145                 150                 155                 160

Tyr Thr Leu Asn Phe Glu Ser Ala Gln Gln Ala Cys Leu Asp Ile Gly
                165                 170                 175

Ala Val Ile Ala Thr Pro Glu Gln Leu Phe Ala Ala Tyr Glu Asp Gly
                180                 185                 190

Phe Glu Gln Cys Asp Ala Gly Trp Leu Ser Asp Gln Thr Val Arg Tyr
                195                 200                 205

Pro Ile Arg Ala Pro Arg Glu Gly Cys Tyr Gly Asp Met Met Gly Lys
                210                 215                 220

Glu Gly Val Arg Thr Tyr Gly Phe Arg Ser Pro Gln Glu Thr Tyr Asp
225                 230                 235                 240

Val Tyr Cys Tyr Val Asp His Leu Asp Gly Asp Val Phe His Ile Thr
                245                 250                 255

Ala Pro Ser Lys Phe Thr Phe Glu Glu Ala Glu Ala Glu Cys Ala Asn
                260                 265                 270

Arg Asp Ala Arg Leu Ala Thr Val Gly Glu Leu His Ala Ala Trp Arg
                275                 280                 285

Asn Gly Phe Asp Gln Cys Asp Tyr Gly Trp Leu Ser Asp Ala Ser Val
                290                 295                 300

Arg His Pro Val Thr Val Ala Arg Ala Gln Cys Gly Gly Gly Leu Leu
305                 310                 315                 320

Gly Val Arg Thr Leu Tyr Arg Phe Glu Asn Gln Thr Cys Phe Pro Leu
                325                 330                 335

Pro Asp Ser Arg Phe Asp Ala Tyr Cys Phe Lys Arg Pro Asp Leu Cys
                340                 345                 350

Lys Thr Asn Pro Cys Leu Asn Gly Gly Thr Cys Tyr Pro Thr Glu Thr
                355                 360                 365

Ser Tyr Val Cys Thr Cys Ala Pro Gly Tyr Ser Gly Asp Gln Cys Glu
                370                 375                 380

Leu Asp Phe Asp Glu Cys His Ser Asn Pro Cys Arg Asn Gly Ala Thr
385                 390                 395                 400

Cys Val Asp Gly Leu Asn Thr Phe Arg Cys Leu Cys Leu Pro Ser Tyr
                405                 410                 415

Val Gly Ala Leu Cys Glu Gln Asp Thr Glu Thr Cys Asp Tyr Gly Trp
                420                 425                 430

His Lys Phe Gln Gly Gln Cys Tyr Lys Tyr Phe Ala His Arg Arg Thr
                435                 440                 445

Trp Asp Ala Ala Glu Arg Glu Cys Arg Leu Gln Gly Ala His Leu Thr
```

```
                450             455             460
Ser Ile Leu Ser His Glu Glu Gln Met Phe Val Asn Arg Val Gly His
465                 470                 475                 480

Asp Tyr Gln Trp Ile Gly Leu Asn Asp Lys Met Phe Glu His Asp Phe
                485                 490                 495

Arg Trp Thr Asp Gly Ser Ala Leu Gln Tyr Glu Asn Arg Pro Asn Gln
            500                 505                 510

Pro Asp Ser Phe Phe Ser Ala Gly Glu Asp Cys Val Val Ile Ile Trp
        515                 520                 525

His Glu Asn Gly Gln Trp Asn Asp Val Pro Cys Asn Tyr His Leu Thr
    530                 535                 540

Tyr Thr Cys Lys Lys Gly Thr Val Ala Cys Gly Gln Pro Pro Val Val
545                 550                 555                 560

Glu Asn Ala Lys Thr Phe Gly Lys Met Lys Pro Arg Tyr Glu Ile Asn
                565                 570                 575

Ser Leu Ile Arg Tyr His Cys Lys Asp Gly Phe Ile Gln Arg His Leu
                580                 585                 590

Pro Thr Ile Arg Cys Leu Gly Asn Gly Arg Trp Ala Met Pro Lys Ile
            595                 600                 605

Thr Cys Met Asn Pro Ser Ala Tyr Gln Arg Thr Tyr Ser Lys Lys Tyr
        610                 615                 620

Leu Lys Asn Ser Ser Val Lys Asp Asn Ser Ile Asn Thr Ser Lys
625                 630                 635                 640

His Glu His Arg Trp Ser Arg Arg Trp Gln Glu Thr Arg Arg
                645                 650

<210> SEQ ID NO 28
<211> LENGTH: 6
<212> TYPE: PRT
<213> ORGANISM: Homo sapiens

<400> SEQUENCE: 28

Ala Asp Ala Met Thr Ser
1               5

<210> SEQ ID NO 29
<211> LENGTH: 2076
<212> TYPE: DNA
<213> ORGANISM: Artificial Sequence
<220> FEATURE:
<223> OTHER INFORMATION: A synthetic oligonucleotide sequence

<400> SEQUENCE: 29
atgttcatca atatcaagtc catactgtgg atgtgtagta ccctcattgt gacacatgca      60
ttgcacaaag taaagttgg aaagagtccg cctgtgaggg gatcactgag tggcaaagtg     120
tcactgccct gtcactttc cactatgcca actctcccac cctcttataa cacatccgag     180
tttctccgca taagtggtc caaaatcgag gtagacaaga acggcaaaga cctcaaagag     240
actactgtgc tcgtggcaca gaatggaaac atcaagattg gcaggacta taagggtcgt     300 gtcagcgtgc caactcaccc agaagccgtt ggcgacgcca gcttgacagt tgtgaaactg     360
cttgccagcg acgccggact gtatcgctgc gatgtcatgt atggtatcga agatacacag     420
gacacagtga gcctgaccgt ggatgggta gtctttcact atagagccgc cacatctaga     480 tacacccctga attttgaggc agctcagaag gcctgcttgg atgtgggcgc cgtgattgca     540
acgcctgagc aactgttcgc cgcctacgaa gatggattcg agcagtgtga cgcaggatgg     600
```

```
ctggccgatc agaccgttcg gtaccctatc agagctcccc gagtagggtg ctatggcgat    660
aaaatgggca aggctggcgt gaggacctac ggcttcaggt cacctcagga aacctatgac    720
gtgtactgtt atgtggacca cttggatggc gatgtctttc atctcacggt cccctctaaa    780
tttacgttcg aagaagcggc caaggagtgc gagaatcagg acgccaggct ggcaactgtg    840
ggagaactgc aggctgcctg gcgcaatggg ttcgaccagt gcgattatgg gtggctgagt    900
gacgcttctg tccgccatcc cgttaccgtc gctagggcgc aatgcggtgg aggacttctg    960
ggcgttagaa ccctctatcg ctttgagaat cagactgggt ttccgccacc agattctcgg   1020
ttcgatgcgt attgcttcaa acgtcccgac cgttgtaaga tgaacccatg ccttaacggc   1080
ggaacctgtt acccaacaga aacgagctat gtttgcacct gtgtgcccgg gtactcaggc   1140
gaccagtgtg aactggactt tgacgaatgc cactctaatc cgtgcagaaa tggcgctacg   1200
tgcgtggacg ggttcaacac tttccgatgt ctgtgtctgc ctagctacgt cggggcactg   1260
tgcgagcagg ataccgaaac ctgtgattac gggtggcaca gtttcaggg tcagtgctac   1320
aagtactttg cgcatagaag aacatgggat gccgcagagc gagagtgtag gctgcaaggg   1380
gctcatctga catccatcct tagccatgag gaacaaatgt ttgtcaacag agttggccac   1440
gactatcaat ggatcggctt gaatgacaag atgttcgagc acgacttcag gtggacagac   1500
ggctccaccc tccagtacga gaactggagg cctaatcagc ccgacagctt cttcagtgca   1560
ggagaggatt gcgtagtcat aatctggcac gaaaacggtc agtggaacga tgtgccatgc   1620
aactatcatc tgacctacac atgcaagaaa ggtactgtgg cctgtggcca acctcctgtc   1680
gtggagaatg ccaaaacatt tggtaagatg aaacccaggt acgagattaa ctcccttatt   1740
cgctaccact gtaaggatgg tttcattcaa cggcatctgc ccactattcg gtgcctggga   1800
aatgggcggt gggcaattcc gaagataacc tgtatgaacc cctctgctta ccagcgaacc   1860
tactccatga agtacttcaa gaactccagt tcagctaaag acaatagcat caacacttca   1920
aaacacgatc atcgctggag ccggcggtgg caggaaagca gacggtatcc ttatgacgtg   1980
cctgattacg cttggagcca ccccagttc gagaagggtg gaggttctgg cggtggatcg   2040
ggaggttcag cgtggagcca cccgcagttc gagaaa                             2076
```

<210> SEQ ID NO 30
<211> LENGTH: 23
<212> TYPE: DNA
<213> ORGANISM: Artificial Sequence
<220> FEATURE:
<223> OTHER INFORMATION: A synthetic oligonucleotide sequence

<400> SEQUENCE: 30
caggcttccc tccccctgat agc                                              23

<210> SEQ ID NO 31
<211> LENGTH: 23
<212> TYPE: DNA
<213> ORGANISM: Artificial Sequence
<220> FEATURE:
<223> OTHER INFORMATION: A synthetic oligonucleotide sequence

<400> SEQUENCE: 31
gctgtatcct ggcacacagg tgc                                              23

<210> SEQ ID NO 32
<211> LENGTH: 20
<212> TYPE: DNA
<213> ORGANISM: Artificial Sequence

```
<220> FEATURE:
<223> OTHER INFORMATION: A synthetic oligonucleotide sequence

<400> SEQUENCE: 32
tgcaggtccc tgtcatgctt                                           20

<210> SEQ ID NO 33
<211> LENGTH: 22
<212> TYPE: DNA
<213> ORGANISM: Artificial Sequence
<220> FEATURE:
<223> OTHER INFORMATION: A synthetic oligonucleotide sequence

<400> SEQUENCE: 33
gaatgagtag cagcaggtga gt                                        22

<210> SEQ ID NO 34
<211> LENGTH: 20
<212> TYPE: DNA
<213> ORGANISM: Artificial Sequence
<220> FEATURE:
<223> OTHER INFORMATION: A synthetic oligonucleotide sequence

<400> SEQUENCE: 34
aaccgaagtc atagccacac                                           20

<210> SEQ ID NO 35
<211> LENGTH: 21
<212> TYPE: DNA
<213> ORGANISM: Artificial Sequence
<220> FEATURE:
<223> OTHER INFORMATION: A synthetic oligonucleotide sequence

<400> SEQUENCE: 35
tttctccgtt acttggggac a                                         21

<210> SEQ ID NO 36
<211> LENGTH: 46
<212> TYPE: DNA
<213> ORGANISM: Artificial Sequence
<220> FEATURE:
<223> OTHER INFORMATION: A synthetic oligonucleotide sequence

<400> SEQUENCE: 36
ttttactagt gccaccatgt tgataaatat gaacggcatc ctatgg              46

<210> SEQ ID NO 37
<211> LENGTH: 60
<212> TYPE: DNA
<213> ORGANISM: Artificial Sequence
<220> FEATURE:
<223> OTHER INFORMATION: A synthetic oligonucleotide sequence

<400> SEQUENCE: 37
tttttctaga tcaagcgtaa tctggaacat cgtatgggta gcgcctcgtt tcctgccacc    60

<210> SEQ ID NO 38
<211> LENGTH: 24
<212> TYPE: DNA
<213> ORGANISM: Artificial Sequence
<220> FEATURE:
<223> OTHER INFORMATION: A synthetic oligonucleotide sequence

<400> SEQUENCE: 38
agcagatttg atgcctactg cttt                                      24
```

```
<210> SEQ ID NO 39
<211> LENGTH: 20
<212> TYPE: DNA
<213> ORGANISM: Artificial Sequence
<220> FEATURE:
<223> OTHER INFORMATION: A synthetic oligonucleotide sequence

<400> SEQUENCE: 39
gcacaggtgc acacatagga                                              20
```

RECOMBINANT VERSICAN ISOFORMS AND RELATED COMPOSITIONS AND METHODS

PRIORITY PARAGRAPH

This application claims the benefit of priority to U.S. Provisional Patent Application Ser. No. 62/869,438, filed Jul. 1, 2019, the content of which is incorporated herein by reference in its entirety.

STATEMENT OF GOVERNMENT LICENSE RIGHTS

This invention was made with Government support under 1R41HL106967-01A1 and 1R01EB012558-01A1 awarded by the National Institutes of Health. The Government has certain rights in the invention.

BACKGROUND

Versican is a multifunctional extracellular matrix (ECM) molecule belonging to the family of large chondroitin sulfate (CS) proteoglycans and is encoded by the VCAN gene. The expression of versican is observed in various tissues such as blood vessels, skin, and the developing heart. Vascular smooth muscle cells (SMCs), skin epithelial cells, and the cells of the central and peripheral nervous system are a few examples of cell types that express versican physiologically. Its versatility, as its name suggests, is derived from its ability to interact with a variety of binding partners including hyaluronan (also referred to as hyaluronic acid or HA), a host of ECM proteins, chemokines, lipids and cell surface proteins. These myriad and diverse interactions lead versican to have roles in regulating cellular functions including adhesion, proliferation and migration, as well as ECM assembly. For example, versican is involved in development, in part, by guiding embryonic cell migration in the formation of the heart and outlining the path for neural crest cell migration. Versican is also a factor in inflammation, interacting with adhesion molecules on the surfaces of inflammatory leukocytes and with chemokines that are involved in recruiting inflammatory cells. Furthermore CS-containing versican isoforms inhibit the assembly of elastic fiber networks required for tissue integrity and normal function. With these roles, versican expression can have impact on tissue development and disease.

Versican is structured into three molecular domains. The amino-terminal globular domain (G1) contains two link modules and has the ability to bind HA. The carboxy-terminal globular domain (G3) contains epidermal growth factor (EGF) repeats, a C-type lectin domain, and a complement regulatory protein (CRP)-like domain. The middle region between the G1 and G3 domains of the versican core protein is encoded by two large exons that specify the CS attachment regions of versican.

Alternative splicing of the VCAN gene generates at least four major isoforms (splice variants V0, V1, V2, and V3) with different numbers of CS glycosaminoglycans (GAGs) attached to the protein core. The isoforms are temporally and spatially regulated in a specific manner, although the biological significance of alternative splicing for versican is yet to be fully determined. The splice junction joining the G1 and G3 regions occurs between residues 348 and 349 of SEQ ID NO:1. Variants of isoforms V1 and V3 include an alternatively spliced C-terminus referred to as a Vint tail.

The spatiotemporal expression pattern and accumulation of the larger isoforms V0. V1, and V2 have been characterized. V0 is transiently expressed at high levels during embryogenesis, whereas V1 is most abundant in adult tissues. V1 is also the isoform most prominent in repair and remodeling associated with injury and disease, except for the nervous system where V2 is most abundant. V3 mRNA is expressed in a variety of tissues, but detection of V3 protein in tissues or cells is a challenge due to the lack of a functional antibody that specifically recognizes native V3 and not the other isoforms.

While there is information available on the expression and accumulation of the CS-containing V0, V1, and V2 isoforms, little is known about the V3 isoform, the smaller splice variant, which consists solely of the N-terminal and C-terminal portions with no attached GAGs. Moreover, V3 is unique among the other isoforms of versican in that it lacks a major ADAMTS cleavage site present in the βGAG region of V0 and V1 isoforms, preventing the production of a bioactive proinflammatory V3 cleavage product. A number of studies have shown that forced expression of V3 by a variety of cells and tissues dramatically influences their phenotype. For example, overexpression of V3 appears to counter the effects of CS-containing versican isoforms (primarily V0 and V1) by inhibiting of cell proliferation and migration, dampening tissue inflammation by preventing inflammatory infiltrate, and restoring elastic fiber networks in damaged tissues.

A wide range of diseases and conditions have been associated with excessive CS-containing versican isoforms (primarily V0 and V1) expression and/or activity, including those of the vascular system (e.g. aortic aneurysm and atherosclerosis), of skin (e.g. keloid scarring, chronic wounds, Costello syndrome, and mucopolysaccharidoses, such as Hurler syndrome), of the lung (e.g. COPD, emphysema, and asthma), of the nervous system (e.g. spinal cord injury and Wagner's disease), and many types of cancers and tumors.

The mechanisms responsible for these functions and activity of V3 have not been fully elucidated, exacerbated by the fact that, despite extensive efforts, V3 has been difficult to isolate and characterize. Isolation and purification of V3 from cells and tissues (e.g. extracting V3 from cells and tissues and removing non-V3 molecules and contaminants to obtain purified protein) for characterization and use has been precluded by factors such as extremely low levels of native expression, difficulty maintaining stable expression using traditional recombinant methods, as well as significant secretion and solubility issues. Thus, unique methods and stable expression systems need to be developed to generate stable and soluble recombinant V3 (rV3) protein, including biologically active recombinant human V3 (rhV3).

SUMMARY OF THE INVENTION

The Summary of the Invention below is not intended to limit the scope and embodiments of the invention(s) as more fully described and claimed in the entirety of this application.

Biologically active rV3, including rhV3, has never been exogenously generated, isolated and then purified in soluble stable form, or in quantities sufficient for characterization and use. The present invention provides methods and reagents (e.g., cDNA constructs, expression vectors and cassettes and expression systems) for increasing stable expression of soluble recombinant versican isoforms, including rV3, further including rhV3, and variants and mutants thereof, with sufficient yields for isolating and purifying these protein products. The isolated and purified rhV3 is soluble in aqueous solution and suitable for storage, pharmaceutical compositions and other uses, and remains stable in storage. Stable rV3 expression is sustained for at least about 3 days post-transduction, or at least about 4 weeks or more. The methods described herein will produce at least 0.5 µg/ml of rhV3, or at least about 100 µg/ml, or at least about 1 mg/ml in conditioned media. This level of production can be confirmed by isolating V3 from conditioned media collected over a 1-7-day period using an affinity tag-based system as described in the invention.

In one embodiment, the invention provides a method for increasing production of soluble rV3. In one of the embodiments, the method comprises the step of providing an expression vector comprising an expression cassette and transfecting a host cell or tissue capable of N-glycosylation of the rV3 at the appropriate sites for increased levels of secretion and/or solubility of the expressed protein compared to non-glycosylated protein. In another embodiment, the cassette further comprises cDNA sequences coding for a recombinant V3 (rV3), an efficient signal peptide, operatively and contiguously linked to and upstream of the rV3 sequence, a strong promoter, operatively linked and upstream of the rV3 sequence, a chromatin function modifying element, further comprising universal chromatin opening element (UCOE), operatively linked to and upstream of the strong promoter sequence. In another embodiment the efficient signal peptide is non-native. In yet another embodiment, the non-native signal peptide is codon-optimized.

In another embodiment, the invention provides an expression system for production of a recombinant mammalian versican V3 isoform protein, including rhV3, variants and/or mutants thereof. In one of the embodiments of the present invention, the expression system comprises an expression vector comprising an expression cassette further comprising a cDNA for rV3 and variant or mutants thereof, and a host cell or tissue transfected with the vector, wherein the host cell or tissue is capable of N-glycosylating the expressed rV3 protein at the proper sites and in the proper conformation, providing for increased levels of protein secretion, and/or solubility in aqueous solution, as compared to a non-N-glycosylated form of the expressed rV3 protein. Increased levels of secretion using the methods and constructs of the present invention are at least about a 10-fold increase, at least about a 50-fold increase, or at least about a 100-fold increase or more, as compared to a non-N-glycosylated form of the rV3 protein. Increased solubility of the rV3 of the present invention is at least about 50%, at least about 75%, to at least about 90% of isolated and purified rV3 protein remaining dissolved in aqueous solution for more than 24 hours at 4° C. It will also be appreciated that, when used herein, transfection refers to a general process by which DNA is transferred into a host cell and can encompass transfection, transduction and/or transformation.

Another embodiment of the vector of the invention comprises an expression cassette further comprising cDNA sequence coding for a V3 protein, variant or mutant thereof, a signal peptide contiguous to and upstream of the cDNA coding for rV3, a strong promoter operatively linked and upstream of the cDNA sequence coding for rV3, and a ubiquitous chromatin opening element (UCOE) upstream of the promoter. In another embodiment, the invention provides a rV3 expression cassette further includes a more efficient non-native signal peptide, to increase expression and secretion of the rV3 protein. In another embodiment, the invention provides a host cell, aggregations of cells, progeny thereof, or tissue transfected with a vector as described herein. The host cell or tissue is selected to properly N-glycosylate the expressed protein to impart solubility to the protein, which is necessary for characterization and further use, and also desirable for storage of the protein.

In other embodiments the vector further contains a selection marker, such as an antibiotic resistance selection marker or a fluorescent marker, to help select the protein product, an identification tag to help identify the protein through antibody binding to the tag if no antibody specific for the protein is available, and/or a purification/affinity tag to help isolate and purify the rV3 protein. In yet another embodiment, the rV3 is isolated and purified after expression. In another embodiment, an rV3 protein of the invention produced by the methods and systems of the invention has amino acid sequence similarity or identity to its corresponding native or consensus V3 sequence (i.e. that of its species) sufficient for biological activity of the rV3.

In another embodiment, the invention provides a method for stably producing increasing yield of recombinant mammalian versican isoforms, including mammalian rV3, or variants, or mutants thereof, including human rV3. The isolated and purified rV3 protein can be in a form suitable for long-term storage. In some embodiments, the soluble protein is stored in water or other aqueous solutions. In some embodiments, the protein is lyophilized. In other embodiments, the protein is in frozen solution. Increased yield using the methods and expression constructs of the invention are at least about 100 µg/ml, or at least about 1 mg/ml, or more of soluble rV3 are isolated and purified from the conditioned culture media generated by the host cells.

In some embodiments, the method comprises the step of transfecting a host cell or tissue with a vector comprising a cDNA sequence encoding the rV3 (i.e. cDNA variants or mutants thereof), wherein the vector further comprises a strong promoter operatively linked to the V3 cDNA sequence and a ubiquitous chromatin opening element (UCOE) upstream of a strong promoter, followed by N-glycosylation of the rV3. In another embodiment the rV3 is human. In other embodiments the cDNA coding for rV3 has been codon optimized. In yet other embodiments the non-native signal peptide has also been codon optimized In one embodiment, the expression vector or cassette is bicistronic (i.e. the cassette contains two genes of interest) where the rV3 is positioned downstream of a fluorescent selection marker, or even tricistronic (three genes of interest).

It will be appreciated that V3 variants, such as the Vint-tailed variant, and V3 mutants, including N-glycosylation and deletion mutants described below, can be produced using the methods and systems of this invention. Yet another embodiment of the invention provides a method for producing soluble protein through proper post-translational N-glycosylation of the protein in a host cell selected for such capability.

Another embodiment of the invention comprises an expression cassette as illustrated in FIG. 9A, in a non-adherent human embryonic kidney (HEK) host cell cultured in animal protein-free medium, wherein a rV3 protein is isolated from conditioned media using the STREP tag system and purified to achieve at least about 80%, 81%, 82%, 83%, 84%, 85%, 86%, 87%, 88%, or 89% rV3 protein purity, and approaching at least about 90%, 91%, 92%, 93%, 94%, 95%, 96%, 97%, 98%, 99% or to at least about 100%. In another of the invention's embodiments, the rV3 protein is recombinant human V3 (rhV3).

The above methods, expression systems, and vector constructs of the invention provide increased and stable production of stable recombinant proteins of versican isoforms, variants and/or mutant proteins, for example, mammalian rV3 and rhV3, which are stable, biologically active and soluble. In another embodiment, the invention provides isolated and purified protein obtained according to the methods described herein. In some embodiments, the protein is soluble in water or other aqueous solution. In some embodiments, the protein is lyophilized. In some embodiments, the protein is in frozen solution.

The rV3, such as rhV3, of the invention produced in the described methods has several advantageous applications, including uses as an anti-adhesive molecule, an anti-fibrotic molecule, an anti-inflammatory molecule, and a promoter of elastic fiber network formation in tissues, such as, but not limited to skin, lung, and the vasculature.

Another embodiment of the invention provides a composition comprising an exogenously produced mammalian molecular complex of purified exogenously rV3, or a portion thereof, bound to a hyaluronan molecule (rV3/HA) in a pharmaceutically acceptable carrier. Other embodiments of the invention include methods of producing the composition and its administration to a mammal including humans. Pharmaceutical compositions of the invention comprising the rV3/HA molecular complexes can be useful in skin, vascular and lung applications to counter tissue inflammation, prevent fibrosis and promote elastic fiber network formation. Other beneficial uses of the rV3/HA composition include aesthetic applications such as treatments for aging, wrinkled and/or inflamed, reddened or irritated skin.

Another embodiment of the invention provides compositions, including pharmaceutical and cosmetic compositions, comprising rV3 or the rV3/HA molecular complex. These compositions of the invention can be combined with a carrier, wherein the carrier comprises a matrix, dressing, scaffold or sheet. Another embodiment of the invention provides compositions comprising a coating, gel, lotion, foam, cream or ointment further comprising the rV3 or the rV3/HA complex of the invention.

Antibodies specifically raised to the rV3 of the present invention are also contemplated to be within the scope of this invention. Additionally, the methods and compositions of the invention lend themselves to use as research tools (e.g. for investigation of the biology of versican in health and disease) and veterinary uses when a pharmaceutically acceptable composition of mammalian rV3 is of the appropriate species.

On embodiment provides for a method to improve tissue healing, reduce the signs of aging, and/or treat conditions where elastic fiber formation is inadequate or disrupted comprising administering the compositions described herein to a subject in need thereof. In one embodiment, the tissue is skin, lung and/or vascular tissue. In one embodiment, said tissue healing improvement is a reduction in inflammation, reduction in fibrosis and/or scarring, and/or an increase in organized elastic fiber network formation. In one embodiment, the administration is topical. In another embodiment, the carrier comprises a wound dressing, biodressing or skin substitute, cellular or decellularized extracellular matrix, a synthetic or naturally derived scaffold, layer, gel or sheet. In one embodiment, the administration of rhV3 in vivo did not increase markers of inflammation, exhibited trends towards increased elastin expression, and reduced expression of markers of fibrosis, without adversely affecting the rate of wound closure. Thus, in vivo administration of rhV3 is useful in improving tissue healing.

Potential applications for the recombinant V3 protein herein are also described but not limited to those described in U.S. Pat. No. 7,816,335, European Patent No. 1274726, Australian Patent No. 2001253408, U.S. Pat. Nos. 8,367, 619, and 8,410,067, each of which is incorporated herein by reference in its entirety, and specifically for the disclosure of uses of versican and isoforms thereof.

DESCRIPTION OF THE DRAWINGS

The foregoing embodiments and many of the attendant advantages of this invention will become more readily appreciated as the same become better understood by reference to the following detailed description, when taken in conjunction with the accompanying drawings, wherein:

FIG. 1A illustrates that bacterially-expressed GST-HuV3-HApHis is highly insoluble. It will be appreciated that while HA is the accepted acronym for hyaluronic acid (hyaluronan), the abbreviation HA also commonly refers to a hemagglutinin tag when used in the context of nucleic acid constructs, their Seq ID's and/or protein identification tags. Applicants have not deviated from this accepted scientific nomenclature since one of ordinary skill in the art will easily be able to distinguish references to hyaluronan from references to hemagglutinin tags from the context of the disclosure. FIGS. 1B and 1C illustrate that thrombin did not efficiently remove the GST moiety. FIGS. 1D and 1E illustrate that the G3 domain was less soluble than the G1 domain.

FIG. 9B is a cartoon schematic of a representative alternative embodiment of the vector for expression of tagged V3. The expression vector contains a TET-ON system for driving stable recombinant V3 expression. MAR=matrix attachment region; STAR=DNA stabilizing anti-repressor element; TRE=tetracycline responsive element; Tagged V3=V3 cDNA sequence with a c-terminal detection tag; UCOE=Ubiquitous chromatin opening element; SFFV=spleen focus forming virus promoter; rtTA=reverse tetracycline-responsive transactivator; P2A=porcine teschovirus-1 2A self-cleaving peptide; GFPz=bifunctional fluorescent and chemical selection marker.

FIG. 10A shows the domain structure of the 4 major isoforms of versican. FIG. 10B shows full-length rat V3 containing a c-terminal hemagglutinin tag cloned into the pSLIK lentiviral vector which confers tetra/doxycycline-inducible expression of V3 and constitutive hygromycin resistance under control of the human ubiquitin C promoter. FIG. 10C shows full-length rat V3 containing a c-terminal hemagglutinin tag cloned into the pGL11 lentiviral vector which confers tetra/doxycycline-inducible expression of V3 and constitutive GFP expression and zeocin resistance under control of the SFFV promoter. FIG. 10D shows stable expression of V3 up to 8 days after induction with doxycycline.

FIG. 11A shows V3 expression in transduced NIH 3T3 fibroblasts was induced with 500 ng/ml doxycycline (Dox) for 48 h±50 µM Brefeldin A (BrefA) added to the medium. Conditioned medium was collected, and proteins were separated on a 10% SDS-PAGE gel under denaturing conditions. After transfer to a nitrocellulose membrane. V3 secreted into the culture medium was detected with an antibody directed against the c-terminal hemagglutinin tag. The large bands below V3 are non-specific antibody binding to serum albumin in the culture medium. Thin arrow indicates soluble monomeric V3, whereas filled arrowhead indicates putative aggregated multimeric V3. Dashed line indicates where lanes were digitally cut form original gel and rearranged. FIGS. 11B-11D show the same NIH 3T3 cells used in FIG. 11A were seeded on coverslips, fixed with 10% NBF and stained for V3 (anti-hemagglutinin tag; orange), F-actin (phalloidin; green) and nuclei (DAPI; blue). FIGS. 11E and 11F show higher magnification of the images shown in FIGS. 11C and 11D, revealing the extracellular localization of V3 in the Dox only control cells (FIG. 1E, yellow arrowheads) and the intracellular and vesicular localization in the cells treated with Dox and BrefA (FIG. 11F, white arrowheads).

FIG. 12A shows a map of the exons and domains for the V3 mutants containing deletions in exon 3 (rE3), exons 4-6 (rE456), and exons 11-13 (rE1113) which were expressed in NIH 3T3 cells in a Dox-inducible manner. FIG. 12B shows western blot of cell lysates probed for hemagglutinin-tagged V3. FIG. 12C shows conditioned media probed for hemagglutinin-tagged V3. Red arrows indicate secreted V3, all other bands are non-specific due to presence of 10% fetal bovine serum in the conditioned media.

FIG. 14A shows V3 expression in transduced NIH 3T3 fibroblasts was induced by addition of 500 ng/ml Dox for 48 h±10 µM tunicamycin (Tun) to block N-glycosylation. Cellular protein was collected, and proteins were separated on a 10% SDS-PAGE gel under denaturing conditions. After transfer to a nitrocellulose membrane, V3 was detected with an antibody directed against the c-terminal hemagglutinin tag. FIG. 14B shows cellular protein harvested from V3-expressing cells was subjected to enzymatic deglycosylation with PNGase F (N), sialidase (S) and O-glycanase (O) for 24 h.

FIGS. 15A-15C show NIH 3T3 cells seeded on cover slips were fixed in formalin after induction of V3 expression for 48 h in the presence or absence of 10 µM Tun to block N-glycosylation. Cells were stained for hemagglutinin-tagged V3 (red). F-actin (green), and nuclei (blue). FIG. 15D shows medium from the cells in FIG. 15A was collected and proteins were separated on a 10% SDS-PAGE gel under denaturing conditions. After transfer to a nitrocellulose membrane. V3 was detected with an antibody directed against the c-terminal hemagglutinin tag. Dashed lines indicate where lanes were digitally cut form original gel and rearranged.

FIG. 17 illustrates that N-glycosylation prediction results by NetNGlyc. Full-length rat V3 contains twelve possible N-glycosylation sites (SEQ ID NO: 27). Three of these sites, at amino acid (AA) positions 57, 330 and 613 relative to the start methionine, are predicted to be potential N-glycosylation sites by NetNGlyc, a web-based N-glycosylation prediction algorithm. Of these predicted attachment sites, only AA position 57 is expected to be glycosylated by two other prediction algorithms (GlycoEP and NGlycPred).

In FIG. 19A, immunohistochemistry of NIH 3T3 cells expressing native (Ctrl) and mutant (N57Q and N330Q) probed for V3 (red) shows a marked reduction in V3 secreted into the extracellular space in mutant cells which is abolished with Tun treatment. Nuclei are stained in blue. FIG. 19B is a western blot of conditioned media from control and mutant V3-expressing NIH 3T3 cultures probed for hemagglutinin tag. Secretion of hypo-glycosylated mutant V3 into the conditioned media is markedly reduced compared to native V3.

FIG. 20A shows NIH 3T3 cells incubated with 1 µg/ml high molecular weight hyaluronic acid (HA) labeled with fluorescein (green) with or without addition of Dox. After washing, the cells were fixed and counterstained for V3 (red) and nuclei (blue). Cells overexpressing V3 demonstrate HA retained at the cell surface. FIG. 20B shows V3 exon deletion mutants have less HA retained around cells. FIG. 20C shows digital quantification of the amount of HA shown in FIG. 20A. FIG. 20D shows digital quantification of the amount of HA shown in FIG. 20B.

FIG. 22A illustrates that wounds treated with rhV3 protein administered in DMEM buffer were able to heal at a nearly identical rate to wounds treated with buffer only. FIG. 22B illustrates a separate set of experiments where wounds were either allowed to heal with no treatment, with a gel containing cross-linked hyaluronan (Glycosil™) or a dermal substitute (Endoform™). A subset of wounds was treated with rhV3 incorporated into the gel or dermal substitute. Results from these experiments also show similar rates of wound healing between controls and rhV3 treated wounds thus indicating that the use of rhV3 protein isolated in the method of this invention is safe to use in vivo and does not have deleterious effects on dermal wound healing, such as inflammatory reactivity. Wounds were imaged every 2-3 days for the entire course of wound healing and digital image analysis (ImageJ) was used to measure the area of the wounds on each day. Wound size data are expressed as a percentage of initial wound size.

DEFINITIONS

Figures 7A, 7B, 7C, 7D:
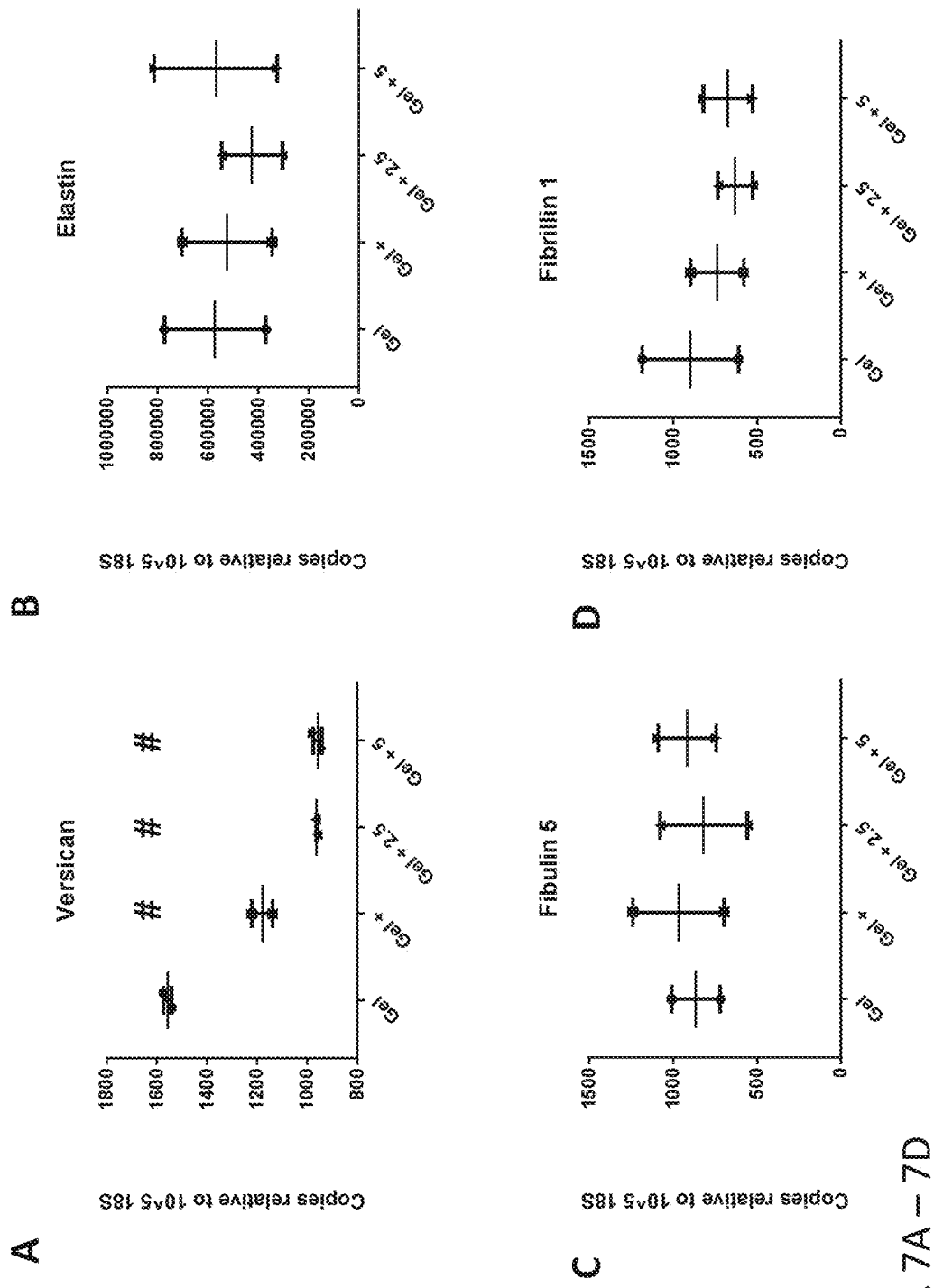
FIGS. 7A-7D graphically illustrate that FRSMC exposed to rhV3 suppress VCAN expression.
Figures 7E, 7F, 7G:
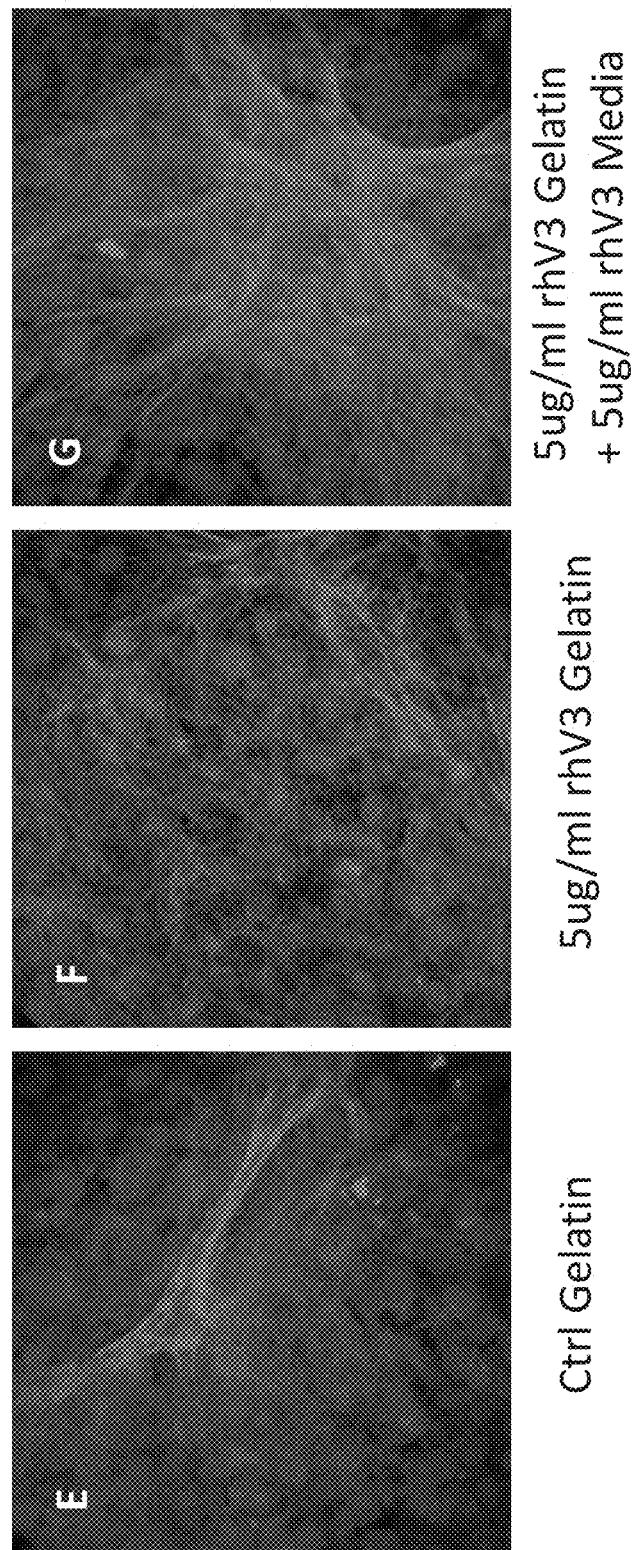
FIGS. 7E-7G are photomicrographs illustrating the enhanced elastin deposition by FRSMC grown on Gelatin +rhV3 for 2 wks.
Figure 7H:
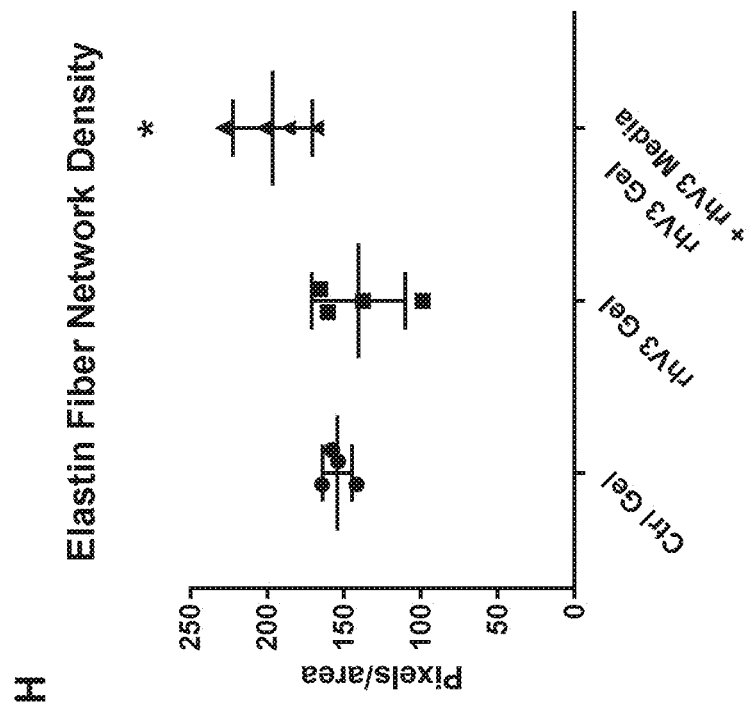
FIG. 7H graphically illustrates that the enhanced elastin deposition by FRSMC grown on gelatin +rhV3 for 2 wks.
Figures 8A, 8B, 8C, 8D:
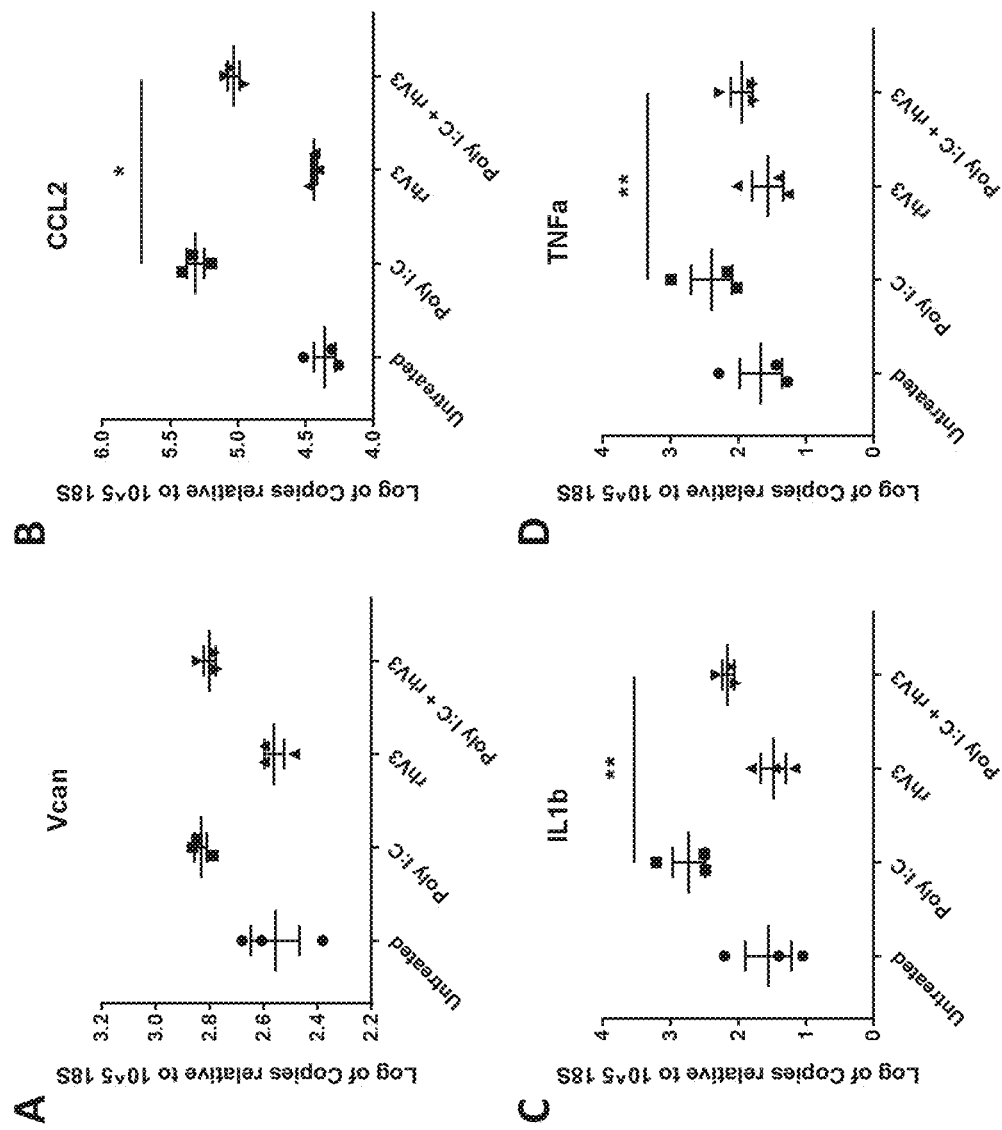
FIGS. 8A-8D graphically illustrate that soluble rhV3 dampens Toll-like receptor 3 (TLR3) inflammatory response in mouse lung fibroblasts (MLF).
Figure 8E:
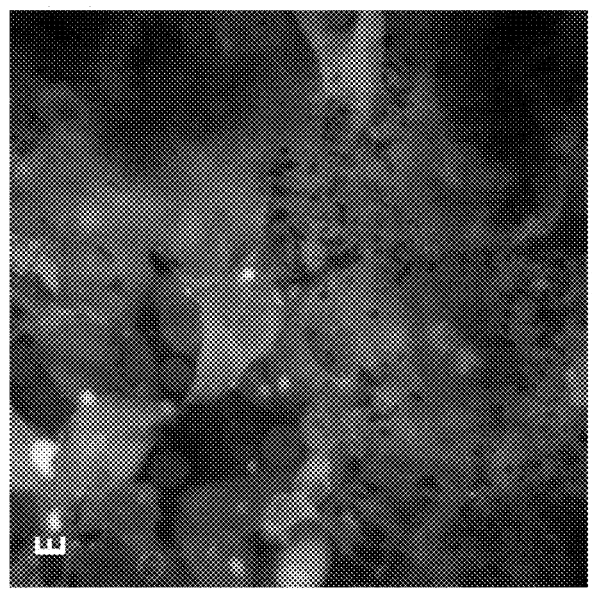
FIG. 8E is a photomicrograph illustrating that rhV3-coated surfaces inhibit HEK cell adhesion.
Figure 8F:
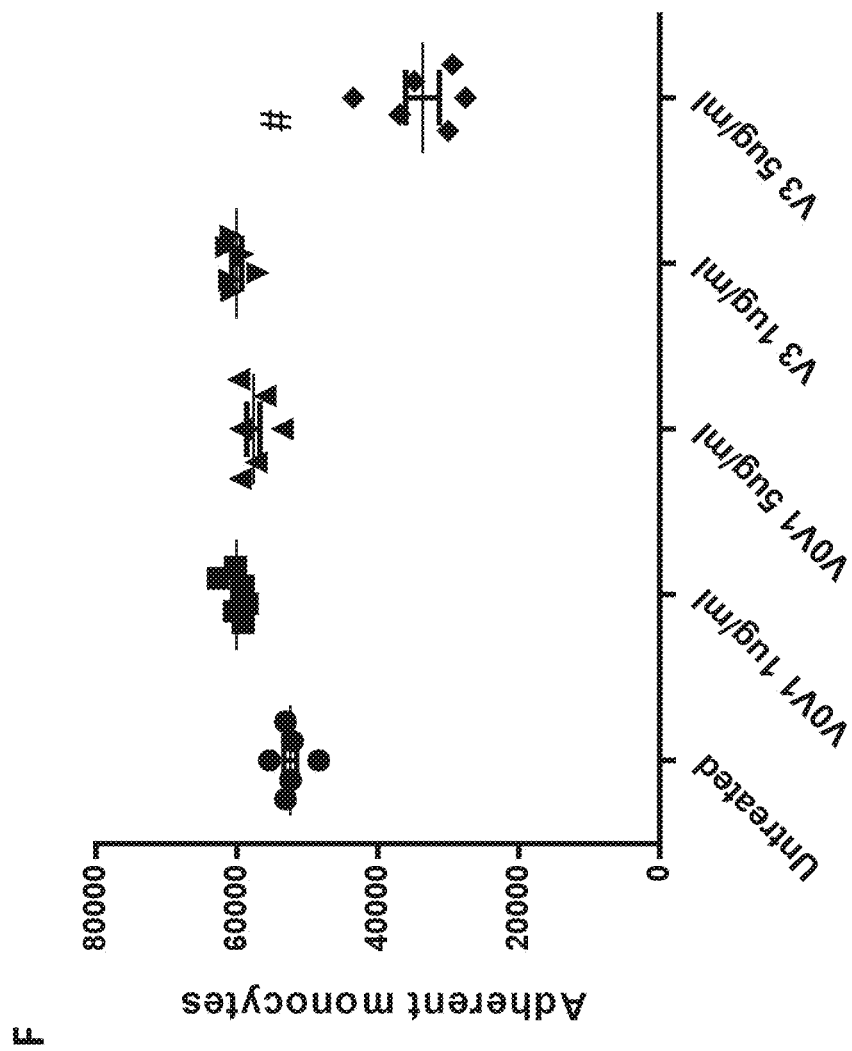
FIG. 8F graphically illustrates that rhV3 inhibits monocyte adhesion.
Figure 9A:
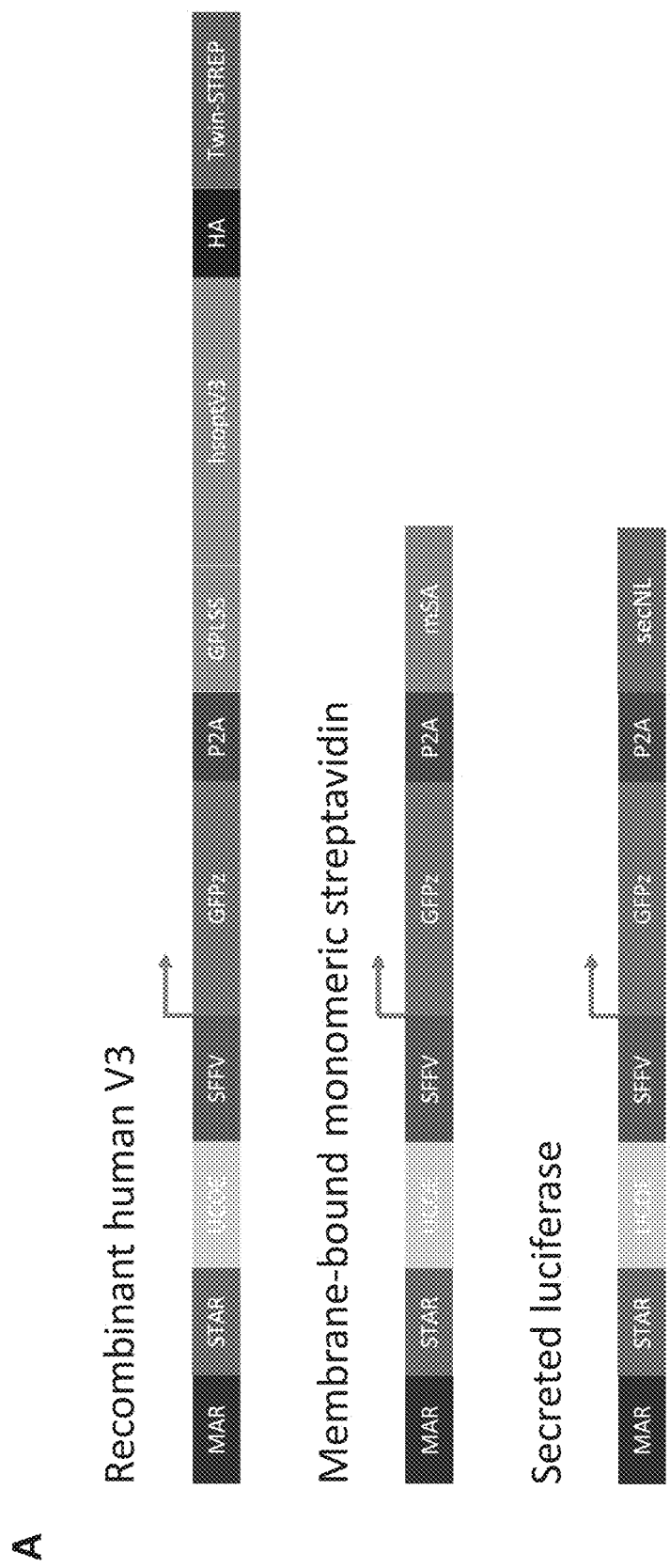
FIG. 9A is a series of cartoon schematics illustrating several embodiments of lentiviral vector constructs according to the present disclosure. The recombinant V3 vector provides for high levels of recombinant expression. MAR=matrix attachment region; STAR=DNA stabilizing anti-repressor element; UCOE=Ubiquitous chromatin opening element; SFFV=spleen focus-forming virus promoter; GFPz=bifunctional fluorescent and chemical selection marker; P2A=porcine teschovirus-1 2A self-cleaving peptide; GPLSS=*Gaussia princeps* luciferase signal peptide; hsoptV3=human sequence-optimized V3; HA=C-terminal hemagglutinin tag; STREP=C-terminal STREP tag.

Except as otherwise indicated in the specification, various terms and meanings are set forth below:

Biologically active: A protein or polypeptide, including fragments thereof, that is biologically active means that the protein or polypeptide elicits a biological response from a cell or organism. An rV3 protein or polypeptide of the invention is considered biologically active when it exhibits at least one of the following in cells or tissues: the ability to increase the density of elastic fiber network formation (see FIGS. 7E-7H), the ability to increase tropoelastin gene expression in cells (as described in U.S. Pat. No. 7,816,335), the ability to reduce or inhibit total (i.e. all isoforms) versican gene expression in cells (as shown in FIG. 7A), the ability to inhibit the expression of at least one marker of inflammation, including but not limited to those described in Kang et al. 2015 (Kang I, Barth J L, Sproul E P, Yoon D W, Braun K R, Argraves W S, et al. Expression of V3 versican by rat arterial smooth muscle cells promotes differentiated and anti-inflammatory phenotypes. J Biol Chem. 2015; 290:21629-41; also see FIGS. 8B-8D), and/or the ability to reduce the expression of at least one marker of fibrosis including but not limited to Acta2 or Col1a1 (see FIG. 24). The term "biological activity" includes the ability of the protein or polypeptide to bind to a binding partner which elicits or results in a biological response in a cell or organism. For example, the rV3 of the present invention has the ability to bind hyaluronic acid (HA), which can be demonstrated or confirmed by the methods described for FIG. 21, and which promotes the accumulation of HA at the cell surface (see FIGS. 20A-20D). Other biological activities of rV3 can include the ability to increase adhesion of mammalian cells, decrease proliferation of mammalian cells, improve the seeding capacity of mammalian cells in a tissue graft, improve the growth of mammalian cells on a scaffold, reduce or eliminate wrinkles, prevent or treat emphysema, prevent lesion formation in mammalian blood vessels following angioplasty, promote the amount of elastic fiber in mammalian cartilage, promote wound healing, treat or prevent Marfan's syndrome, or prevent or treat a pathological condition. The activity of a protein or polypeptide molecule of the invention can be determined by methods well known to the art.

Cell line or host cell(s): This term includes well-characterized homogenous, biologically pure populations of cells. These cells may be eukaryotic cells that are neoplastic or which have been "immortalized" in vitro by methods known in the art, as well as primary cells, or prokaryotic cells. The cell line or host cell includes those of mammalian origin, but cell lines or host cells of non-mammalian origin may be employed, including plant, insect, yeast, fungal or bacterial sources.

Chromatin function modifying elements: Chromatin function modifying elements are genetic regulatory elements that confer a transcriptionally permissive state (Neville J J, Orlando J, Mann K, McCloskey B. Antoniou M N. Ubiquitous Chromatin-opening Elements (UCOEs): Applications in biomanufacturing and gene therapy. Biotechnol Adv. 2017 September; 35(5):557-564.) by affecting the chromatin environment to enhance transgene expression. These can be broadly grouped into those that actively function through dominant chromatin remodeling mechanisms, such as locus control regions (LCRs) and ubiquitous chromatin opening elements (UCOEs), and those that function as boundary elements by restricting the spread of heterochromatin marks into regions of euchromatin, which include scaffold/matrix attachment regions (S/MARs), and stabilizing anti-repressor (STAR) elements. Constructs of the present invention include chromatin function modifying elements, including, but not limited to, UCOE, MAR, STAR, and cHS4 (see Saunders F. Sweeney B, Antoniou M N, Stephens P, Cain K. Chromatin function modifying elements in an industrial antibody production platform—comparison of UCOE. MAR, STAR and cHS4 elements. PLoS One. 2015 Apr. 7:10(4):e0120096.).

Codon/Codon Optimization: A codon is a sequence of three contiguous DNA or RNA nucleotides that corresponds with a specific amino acid or stop signal during protein synthesis. Codon optimization improves the codon composition of a recombinant gene or cDNA sequence based on various criteria without altering the amino acid sequence for which it codes in order to maximize expression. This is possible because most amino acids are encoded by more than one codon (i.e., redundancy). Codon optimization programs include Codon Adaption Index (CAI) and GenScript, as was used for sequences in the present invention. (Mauro V P, Chappell S A. A critical analysis of codon optimization in human therapeutics. Trends Mol Med. 2014 November; 20(11):604-13. doi: 10.1016/j.molmed.2014.09.003. Epub 2014 Sep. 25. PubMed PMID: 25263172: PubMed Central PMCID: PMC4253638.)

Complementary DNA (cDNA): A "complementary DNA," or "cDNA" gene includes recombinant coding sequences or "recombinant genes" synthesized by reverse transcription of mRNA and from which intervening sequences (introns) have been removed.

DNA Construct: A DNA construct is an artificially constructed segment of nucleic acid. A DNA construct is typically created for transfer (e.g. transfection, transduction, or infection) via a vector into a target tissue or cell. It often contains a gene or cDNA encoding a protein of interest, with the DNA being subcloned into the vector.

Expression: Expression is the process by which a protein or polypeptide is produced from a structural gene. The process involves transcription of the gene into mRNA and the translation of such mRNA into polypeptide(s). In the case of a recombinant protein, the cDNA coding for the protein of interest in the expression vector in expressed.

Expression vector or expression construct: An expression vector is used to introduce a specific gene into a target cell and utilize the machinery within the cell for protein synthesis to produce the protein encoded by the gene. An expression vector is typically a double stranded DNA plasmid or virus designed for gene expression.

Expression cassette: An expression cassette is a DNA construct within the expression vector consisting of a gene and regulatory sequences to be expressed by the cell into which it has been incorporated (e.g. transfection or transduction). In each successful transfection, the expression cassette directs the cell's machinery to make RNA and protein(s). The gene to be expressed is usually placed under the control of (i.e., operably/operatively linked to) certain control sequences such as promoter sequences. Promoter sequences may be either constitutive or inducible.

Homologous/Nonhomologous: When considering "homology" from an evolutionary perspective, homology is the similarity attributed to descent from and common ancestor. Homologous biological components (genes, proteins, structures) are called homologs, but do not always share significant sequence similarity. (See "An Introduction to Sequence Similarity (Homology") Searching, William R Pearson and BLAST Glossary at ncbi.nih.gov.)

As commonly used, however, sequence "homology" or "homologous sequence" often refers to the subunit sequence similarity between two polymeric molecules, e.g., between two nucleic acid molecules, e.g., two DNA molecules or two RNA molecules, or between two polypeptide molecules. When a subunit position in both of the two molecules is occupied by the same monomeric subunit, e.g., if a position in each of two DNA molecules is occupied by adenine, then they are homologous at that position. The homology between two sequences is a direct function of the number of matching or homologous positions, e.g., if half (e.g., five positions in a polymer ten subunits in length) of the positions in two compound sequences are homologous then the two sequences are 50% homologous, if 90% of the positions. e.g., 9 of 10, are matched or homologous, the two sequences share 90% homology. By way of example, the DNA sequences 3'ATTGCC5' and 3'TATGGC share 50% homology. Thus, as used herein, "homology" is sometimes used synonymously with "identity" as herein defined.

Hybridization: Hybridization, both stringent and moderate and very stringent are described and defined in U.S. Pat. No. 7,816,335, which is herein incorporated by reference.

Identification or Affinity tag: An identification tag is a short polypeptide sequence, typically no greater than about 20 aa, added to the C- or N-terminus of a recombinant protein commonly used for identification of the protein using antibodies to the tag when specific antibodies to the protein are not available, such as the hemagglutinin tag used in an embodiment of the present invention. A purification or affinity tag is a short polypeptide sequence, typically no greater than about 20 aa, added to the C- or N-terminus of a recombinant protein which binds to a substrate and allows for the isolation and purification of the protein from a mixture of other molecules, such as cell lysate. Examples include His tag (immobilized metal affinity) or Twin-Strep-Tag® (streptactin affinity) systems. It will be appreciated that some tags can serve as both identification and purification tags (e.g. HA, His and Twin-Strep-Tags®) (see Schmidt T G, Batz L, Bonet L. Carl U. Holzapfel G, Kiem K, et al. Development of the Twin-Strep-Tag® and its application for purification of recombinant proteins from cell culture supernatants. Protein Expr Purif. 2013; 92:54-61).

Identity or Sequence Identity: This term refers to a measure of the identity of nucleotide sequences or amino acid sequences. In general, the sequences are aligned so that the highest order match is obtained. "Identity" per se has an art-recognized meaning and can be calculated using published techniques. (See, e.g., Computational Molecular Biology, Lesk, A. M., ed., Oxford University Press, New York, 1988: Biocomputing: Informatics and Genome Projects, Smith, D. W., ed., Academic Press, New York, 1993; Computer Analysis of Sequence Data, Part I, Griffin, A. M., and Griffin, H. G., eds., Humana Press, New Jersey, 1994; Sequence Analysis in Molecular Biology, von Heinje, G., Academic Press, 1987; and Sequence Analysis Primer. Gribskov, M. and Devereux, J., eds., M. Stockton Press, New York, 1991). While there exist a number of methods to measure identity between two polynucleotide or polypeptide sequences, the term "identity" is well known to skilled artisans (Carillo, H. and Lipton, D., SIAM Applied Math., 48, 1073 (1988)). Methods commonly employed to determine identity or similarity between two sequences include, but are not limited to, those disclosed in Guide to Huge Computers, Martin J. Bishop, ed., Academic Press, San Diego, 1994, and Carillo, H. and Lipton, D., SIAM J. Applied Math., 48, 1073 (1988). Methods to determine identity and similarity are codified in computer programs and algorithms. Computer program methods to determine identity and similarity between two sequences include, but are not limited to, GCS program package (Devereux, J., et al., Nucleic Acids Research, 12(I), 387 (1984)), BLASTP, BLASTN, FASTA (Altschul. S. F. et al., J. Mol. Biol., 215.403 (1990)).

Therefore, as used herein, the term "identity" represents a comparison between a test sequence (sequence of interest) and reference polynucleic acid or polypeptide sequence. For example, identity at a level of 90% or more is indicative of the fact that, assuming for exemplification purposes a test and reference sequence length of 100 units, that no more than 10% (i.e., 10 out of 100) units in the test sequence differ from that of the reference sequence. Such differences may be randomly distributed over the entire length of a sequence or they may be clustered in one or more locations of varying length in any position in the sequence up to the maximum allowable 10-unit difference. Differences are defined as substitutions, deletions or additions of sequence. In the embodiments of the present invention, nucleic acid and polypeptide sequences include those that have at least about 85%, 86%, 87%, 88%, 89%, 90%, 91%, 92%, 93%, 94%, 95%, 96%, 97%, 98%, 99% or up to at least about 100%, including at least about 95% sequence identity to a reference sequence.

N-glycosylation: N-glycosylation is a process wherein oligosaccharides (saccharide polymers containing a small number (typically three to ten) of monosaccharides (simple sugars), sometimes also referred to glycans), are attached to the amide nitrogen of an asparagine (Asn) residue of a protein.

Oligonucleotide or Primer: These terms include naturally occurring, and modified nucleotides linked together by naturally occurring, and non-naturally occurring oligonucleotide linkages. Oligonucleotides are a polynucleotide subset with 200 or fewer bases in length. Oligonucleotides are about 10 to about 60 bases in length, from about 12 to 20, to about 40 bases in length. Oligonucleotides are usually single stranded. e.g., for probes, although oligonucleotides may be double stranded. e.g., for use in the construction of a variant. Oligonucleotides can be either sense or antisense oligonucleotides.

Operably or operatively linked: This term means that the nucleic acids are placed in a functional relationship with another nucleic acid sequence. For example, DNA for a presequence or secretory leader is operably or operatively linked to DNA for a peptide or polypeptide if it is expressed as a preprotein that participates in the secretion of the peptide or polypeptide; a promoter or enhancer is operably linked to a coding sequence if it affects the transcription of the sequence; or a ribosome binding site is operably linked to a coding sequence if it is positioned so as to facilitate translation. Generally, but not always. "operably linked" or "operatively linked" means that the DNA sequences being linked are contiguous and, in the case of a secretory leader, contiguous and in reading phase. Linking is accomplished by ligation at convenient restriction sites. If such sites do not exist, the synthetic oligonucleotide adaptors or linkers may be used in accord with conventional practice. However, enhancers and transactivators do not have to be contiguous, such as in a construct of the present invention utilizing tetracycline-controlled gene expression elements, where expression of the rtTA (reverse tetracycline transactivator) drives the TRE (tetracycline response element) promoter, elements which are not contiguous in the construct. When elements are not contiguous, the term "operatively or operably positioned" may sometimes be used.

Pharmaceutically acceptable carrier: This term includes any and all solvents, dispersion media, excipients, fillers, inert solids, colloids, gels, coatings, antibacterial and antifungal agents, isotonic and absorption delaying agents, and the like. The use of such media and agents for pharmaceutically active substances is well known in the art. Except insofar as any conventional media or agent is incompatible with the active ingredient, its use in the pharmaceutical compositions is contemplated. Supplemental active ingredients can also be incorporated into the compositions.

Polynucleic acid: This term generally refers to any polyribonucleotide or polydeoxyribonucleotide, which may be unmodified RNA or DNA or modified RNA or DNA. "Polynucleic acids" include, without limitation, single- and double-stranded DNA. DNA that is a mixture of single- and double-stranded regions, single- and double-stranded RNA, and RNA that is a mixture of single- and double-stranded regions, hybrid molecules including DNA and RNA that may be single-stranded or, more typically, double-stranded or a mixture of single- and double-stranded regions. In addition, "polynucleic acid" refers to triple-stranded regions of RNA or DNA or both RNA and DNA. The term polynucleic acid also includes DNAs or RNAs containing one or more modified bases and DNAs or RNAs with backbones modified for stability or for other reasons. "Modified" bases include, for example, tritylated bases and unusual bases such as inosine. A variety of modifications have been made to DNA and RNA.

Thus, "polynucleic acid" embraces chemically, enzymatically or metabolically modified forms of polynucleotides as typically found in nature, as well as the chemical forms of DNA and RNA characteristic of viruses and cells. "Polynucleic acid" also embraces relatively short polynucleotides, often referred to as oligonucleotides.

Polypeptide: This term refers to any peptide or protein having two or more amino acids joined to each other by peptide bonds or modified peptide bonds, i.e., peptide isosteres. "Polypeptide" refers to both short chains, commonly referred to as peptides, oligopeptides or oligomers, and to longer chains, generally referred to as proteins. Polypeptides may contain amino acids other than the 20 gene-encoded amino acids. Polypeptides can include amino acid sequences modified either by natural processes, such as post-translational processing, or by chemical modification techniques which are well known in the art. Such modifications are well described in basic texts and in more detailed monographs, as well as in a voluminous research literature. Modifications can occur anywhere in a polypeptide, including the peptide backbone, the amino acid side-chains and the amino or carboxyl termini. It will be appreciated that the same type of modification may be present in the same or varying degrees at several sites in a given polypeptide. Also, a given polypeptide may contain many types of modifications. Polypeptides may be branched as a result of ubiquitization, and they may be cyclic, with or without branching. Cyclic, branched and branched cyclic polypeptides may result from post-translation natural processes or may be made by synthetic methods. Modifications include acetylation, acylation. ADPribosylation, amidation, covalent attachment of flavin, covalent attachment of a heme moiety, covalent attachment of a nucleotide or nucleotide derivative, covalent attachment of a lipid of lipid derivative, covalent attachment of phosphotidylinositol, cross-linking, cyclization, disulfide bond formation, demethylation, formation of covalent cross-links, formation of cystine, formation of pyroglutamate, formylation, gamma-carboxylation, glycosylation, including N-glycosylation, CPI anchor formation, hydroxylation, iodination, methylation, myristylation, oxidation, proteolytic processing, phosphorylation, prenylation, racemization, selenoylation, sulfation, transfer-RNA mediated addition of amino acids to proteins such as arginylation, and ubiquitination. Sec, for instance, Proteins-Structure and Molecular Properties, 2nd Ed., T. E. Creighton. W. H., Freeman and Company, New York, 1993 and Wold, F., Posttranslational Protein Modifications: Perspectives and Prospects, pgs. 1-12 in Posttranslational Covalent Modification of Proteins, B. C. Johnson. Ed., Academic Press, New York, 193; Seifter et al., "Analysis for protein modifications and nonprotein cofactors," Methods in Enzymol, 182: 626-646 (1990) and Rattan et al., "Protein Synthesis: Posttranslational Modifications and Aging." Ann. N.Y. Acad. Sci., 663, 48-62 (1992). In an embodiment of the rV3 protein produced by the methods of the present invention, post-translational N-glycosylation is required for efficient secretion and solubility of the rV3 protein. Although a number of putative N-glycosylation sites are contained within the V3 amino acid sequence (see FIG. 17), not all sites are post-translationally N-glycosylated or critical for efficient secretion and solubility.

Promoter/Strong Promoter: A DNA sequence generally described as the 5' region of a gene, located proximal to the start codon. The transcription of an adjacent gene(s) is initiated at the promoter region. If a promoter is an inducible promoter, then the rate of transcription increases in response to an inducing agent. In contrast, the rate of transcription is not regulated by an inducing agent if the promoter is a constitutive promoter. A promoter is classified as strong or weak according to its affinity for RNA polymerase (and/or sigma factor); this is related to how closely the promoter sequence resembles the ideal consensus sequence for the polymerase (a strong promoter leads to a high rate of transcription initiation). In some constructs of the present invention, strong promoters include, but are not limited to, SFFV, CMV, and TRE.

Selection Marker: A selection marker is a protein coding sequence that confers a selective advantage or disadvantage to host cell. A common type of selection marker is one that confers resistance to a particular drug or antibiotic, such as the Zeocin resistance gene used in one embodiment of the present invention. Fluorescent proteins can also be used for selection of cells using flow sorting.

Signal Peptide: A signal peptide (sometimes referred to as signal sequence, targeting signal, localization signal, localization sequence, transit peptide, leader sequence or leader peptide) is a short peptide (usually 16-30 amino acids long) present at the N-terminus of the majority of newly synthesized proteins that are destined towards the secretory pathway. A non-native signal peptide is a signal peptide sequence from one species operatively linked to a gene sequence of another species is an effort to maximize expression and secretion of the recombinant protein (e.g. the *Gaussia princeps* luciferase: Petersen T N, Brunak S, von Heijne G. Nielsen H. SignalP 4.0: discriminating signal peptides from transmembrane regions. Nat Methods. 2011; 8:785-6.)

Substantially homologous: As used herein, a "substantially homologous sequence" includes those amino acid sequences which have at least about 85%, 86%, 87%, 88%, 89%, 90%, 91%, 92%, 93%, 94%, 95%, 96%, 97%, 98%, 99% or up to at least about 100% homology, including at least about 95% homology, to the sequence of a reference sequence. Amino acid sequences similarity or identity can be computed using, for example, the BLASTP and TBLASTN programs which employ the BLAST (basic local alignment search tool) algorithm. The default setting used for these programs are suitable for identifying substantially similar amino acid sequences for purposes of the present invention.

It will be appreciated although the term "substantial homology" may be more commonly associated with amino acid sequences, it may be applied to nucleic acid sequences, although the term "identity" is more commonly used.

Substantially pure: By "substantially pure", in the context of proteins of the invention, including V3, rV3 and rhV3, is meant that the protein is purified to at least about 80%, to at least about 85%, and to at least about 90%. "Substantially pure" encompasses purity of at least about 80%, 81%, 82%, 83%, 84%, 85%, 86%, 87%, 88%, 89%, 90%, 91%, 92%, 93%, 94%, 95%, 96%, 97%, 98%, 99%, to at least about 100% as assessed by methods accepted in the art, such as SDS-PAGE and mass spectrometry.

Substantially similar: A protein or polypeptide molecule is said to be "substantially similar" to another molecule if the sequence of amino acids in both molecules is substantially the same, and if both molecules possess a similar biological activity. Thus, provided that two molecules possess a similar activity, they are considered variants as that term is used herein even if one of the molecules contains additional amino acid residues not found in the other, or if the sequence of amino acid residues is not identical.

Variant or Variation: As used herein. V3 molecules are intended to encompass polynucleic acid and polypeptide molecules with substitutions, such that the variant polynucleic acid or polypeptide differs in sequence from a consensus V3 polynucleic acid molecule or polypeptide, respectively, but retains biological activity. Changes in the nucleotide sequence of the variant may or may not alter the amino acid sequence of a polypeptide encoded by the consensus V3 polynucleic acid. Nucleotide changes may result in amino acid substitutions, additions, deletions, fusions and truncations in the polypeptide encoded by the consensus V3 sequence.

A typical variant of a polypeptide differs in amino acid sequence from a consensus V3 polypeptide. Generally, differences are limited so that the sequences of the consensus V3 polypeptide and the variant are substantially similar, and, in many regions, have identity. A variant and consensus polypeptide may differ in amino acid sequence by one or more substitutions, additions, deletions in any combination. A substituted or inserted amino acid residue may or may not be one encoded by the genetic code, e.g., a D-amino acid or one other than an alpha amino acid, such as 3-amino propionic acid, or taurine. A variant of a polynucleotide or polypeptide may be naturally occurring such as an allelic variant, or it may be a variant that is not known to occur naturally. Non-naturally occurring variants of polynucleotides and polypeptides may be made by mutagenesis techniques or by direct synthesis.

For example, a variant of SEQ ID NO:2 is a polypeptide that has at least about 85%, at least about 90%, at least about 95%, but less than 100%, contiguous amino acid sequence homology or identity to the amino acid sequence corresponding to SEQ ID NO:2 and is biologically active.

Vector: In molecular biology, a vector is a DNA molecule used as a vehicle to carry a DNA construct into another cell, where it can be replicated and/or expressed (e.g. plasmid, virus, cosmid. Lambda phages). A vector can be a cloning vector. i.e. one that can independently replicate in the host cell or tissue, or an expression vector, capable of enhancing a gene or cDNA into which it has been cloned after it has been incorporated or transferred into a host. Vectors can include additional DNA sequences that provide for easy identification, selection, amplification, transformation of the DNA construct in prokaryotic and eukaryotic cells. The additional DNA sequences can include origins of replication to provide for autonomous replication of the vector, selectable marker genes, e.g. encoding antibiotic or herbicide resistance, unique multiple cloning sites providing for multiple sites to insert DNA sequences or genes encoded in the expression construct, and sequences that enhance transformation of prokaryotic and eukaryotic cells.

General Terms: The use of the term "or" in the claims is used to mean "and/or" unless explicitly indicated to refer to alternatives only or the alternatives are mutually exclusive, although the disclosure supports a definition that refers to only alternatives and "and/or." Following long-standing patent law, the words "a" and "an," when used conjunction with the word "comprising" in the claims or specification, denotes one or more, unless specifically noted. Unless the context clearly requires otherwise, throughout the description and the claims, the words "comprise," "comprising," and the like, are to be construed in an inclusive sense as opposed to an exclusive or exhaustive sense; that is to indicate, in the sense of "including, but not limited to." Words using the singular or plural number also include the plural and singular number, respectively. Additionally, the words "herein," "above," and "below," and words of similar import, when used in this application, shall refer to this application as a whole and not to any particular portions of the application.

Unless stated otherwise, the term "about" implies minor variation around the stated value of no more than 10%. The term "about" as used herein can allow for a degree of variability in a value or range, for example, within 10%, within 9%, within 8%, within 7%, within 6%, within 5%, within 4%, within 3%, within 2%, within 1%, within 0.5%, within 0.4%, within 0.3%, within 0.2%, within 0.1%, within 0.05%, within 0.01%, within 0.005%, or within 0.001% of a stated value or of a stated limit of a range and includes the exact stated value or range.

DETAILED DESCRIPTION

The present disclosure is based on the inventors' investigations into the expression and characterization of the V3 isoform of versican, and its effects on cells.

V3 is the smallest splice variant of versican, which unlike larger isoforms, lacks glycosaminoglycan chains. Overexpression of V3 often has effects that resemble CS-containing versican isoform inhibition, which make V3 an attractive therapeutic candidate. Despite employing a variety of approaches, this elusive protein has never been isolated from tissues. Thus, unique methods are needed to generate recombinant protein, including human, in sufficient quantities for characterization and use. Since the biological activity of isolated extracellular matrix molecules introduced exogenously it is not necessarily identical to that of the endogenously-generated molecule, isolated recombinant human V3 (rhV3) protein, produced in accordance with the methods described below, was tested for its effectiveness in modulating cellular phenotypes in vitro to determine if its biological activity mimicked that of the endogenously-generated recombinant molecule.

Functional biologically active rhV3 was generated in a mammalian expression system using a lentiviral expression vector containing chromatin function modifying elements. When isolated rhV3 protein was added to smooth muscle cell cultures, elastin fiber network formation was increased in a dose-dependent manner, similar to what is observed when rV3 is expressed endogenously. Adding rhV3 to cultured lung fibroblasts exposed to a TLR3 agonist resulted in a blunted inflammatory response and, interestingly, surfaces coated with the protein inhibited the binding of inflammatory cells. Furthermore, adding rhV3 to cultured dermal fibroblasts resulted in a dose-dependent reduction in Acta2 and Col1a1 gene expression, both of which are markers of fibrosis. These properties demonstrate that rhV3 can be an elastic fiber network-promoting anti-fibrotic, and anti-inflammatory biologic for use in the treatment of diseases where versican is a major contributor to pathogenesis, where organized elastic fiber formation is inadequate or disrupted, and/or where inflammation is present. Such pathologies and conditions include vascular diseases, such as aneurysm and restenosis, inflammatory and fibrotic lung diseases, such as asthma and interstitial lung disease, urogenital and gastrointestinal pathologies, as well as dermal pathologies and conditions such as non-healing wounds, burns, scarring and keloid. Dermal applications can also include aesthetic treatments and cosmetic formulations for skin exhibiting, for example, wrinkles, redness and/or irritation.

It will be appreciated that prior to the present invention it was not definitive that V3 was actually N-glycosylated. In fact, N-glycosylation prediction algorithms varied widely in number and location of potential N-glycosylation sites (see FIG. 17). Initial attempts to produce the protein in a bacterial system (lacking the ability to properly N-glycosylate proteins) failed to produce soluble, functional protein (see FIG. 1A). Additionally, although production in a plant would, in theory, provide appropriate N-glycosylation, expression in tobacco was not successful (see FIG. 2). This left the question of N-glycosylation unanswered. As such, the inventors examined the question in more detail and explored the addition of other essential and desirable elements of the expression system to achieve adequate expression of rV3. This in turn allowed for post-translational glycosylation studies with surprising results in which only certain sites were N-glycosylated, and that such glycosylation was essential for efficient secretion and solubility of the rV3 protein.

In one study, the inventors used lentiviral generation of doxycycline-inducible rat V3 with a C-terminal tag in stable NIH 3T3 cell lines and demonstrated that V3 is processed through the classical secretory pathway, and that N-linked glycosylation is required for efficient secretion and to maintain solubility. By site-directed mutagenesis, the inventors generated V3 glycosylation mutants, in which amino acids 57 or 330 were substituted to prevent N-glycosylation, demonstrated amino acids 57 and 330 as being N-linked glycosylation sites in rat V3. Furthermore, mutant exon deletion constructs of V3 missing either exons 4-6, 9-10 or 11-13 (i.e., V3 exon deletion mutants) revealed that exons 11-13 which code for portions of the G3 domain, are essential for V3 processing and secretion. Once outside the cell, rV3 associates with hyaluronan (HA) along the cell membrane and within the ECM. These results establish critical parameters for the processing, solubility, and targeting of the V3 isoform by mammalian cells.

In accordance with the foregoing, the present disclosure provides methods and reagents (e.g., expression vectors, cassette constructs, host cells, expression systems) for stably expressing and isolating recombinant versican and its variants/mutants and their protein products.

One embodiment of the invention provides a cDNA construct coding for a versican variant, namely the V3 isoform, and the recombinant protein product, rV3, which is isolated and purified. The rV3 is post-translationally N-glycosylated to impart increased levels of expression, secretion and solubility rendering it suitable for isolation and purification for further use.

In another embodiment, the disclosure provides an expression system for production of recombinant mammalian versican protein isoforms, variants, or mutants thereof. The expression system comprises: an expression vector and a host cell or tissue transfected, transduced or transformed with the vector.

The vector comprises an expression cassette further comprising a cDNA sequence coding for a versican V3 isoform protein, a signal peptide which is upstream, contiguous and operatively linked to the cDNA coding for the rV3, a strong promoter upstream of and operatively linked to the cDNA sequence coding for rV3, and a ubiquitous chromatin opening element operatively linked to and upstream of the promoter. The host cell or tissue properly N-glycosylates the expressed rV3 protein at amino acid residues 57 and 330 of the reference sequence SEQ ID NO:1 or the corresponding residues in SEQ ID NOs:2-9 (i.e. residues 37 and 310).

Figures 20A, 20B, 20C, 20D:
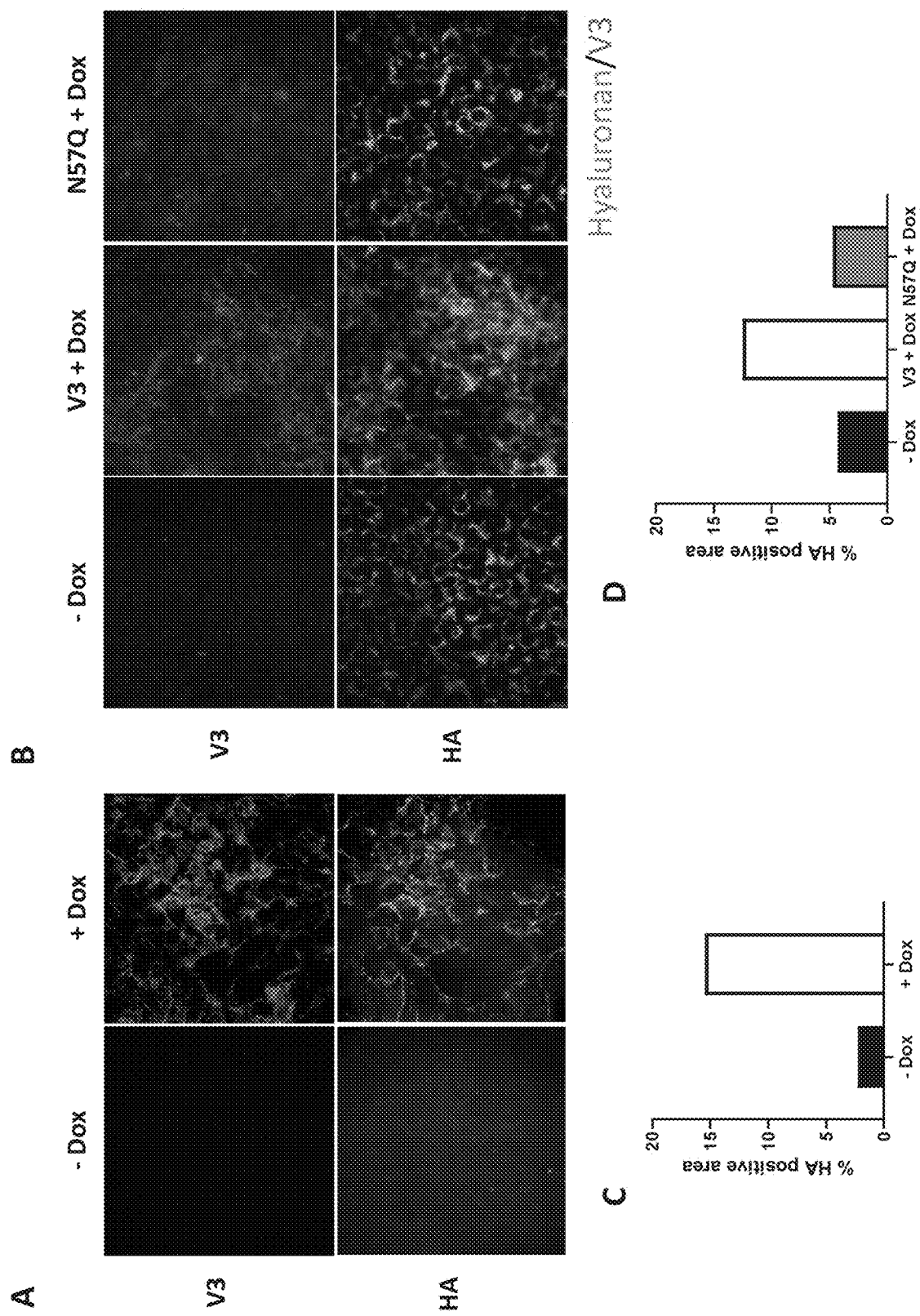
FIGS. 20A-20D illustrate that overexpression of V3 increases the amount of HA at the cell surface and that V3 glycosylation mutants reduce that amount.
Figure 21:
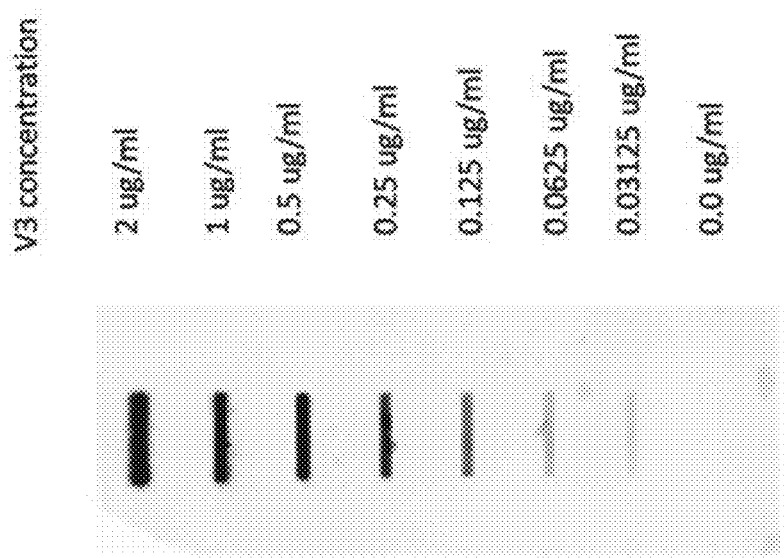
FIG. 21 illustrates that hyaluronan binds to V3 in a dose-dependent manner. Exogenously produced V3 was serially diluted and bound to nitrocellulose via slot blotting. The membrane was blocked, probed with 1 µg/ml fluoresceinated high molecular weight hyaluronan, washed and scanned using a Typhoon scanner (Amersham Biosciences).

In another embodiment, the disclosed rV3 produced by the methods and systems of the invention has sufficient sequence identity to amino acid residues 21-655 of SEQ ID NO:1 (i.e. SEQ ID 1 is the consensus sequence with native signal peptide) and to the sequence of SEQ ID NO:2 for biological activity of V3, such as the ability to bind hyaluronan (HA) via the link modules in the G1 globular region of the molecule, which can be demonstrated or confirmed by the methods described in FIGS. 20 and 21. Other biological activities of V3 include, but are not limited to, the ability to increase tropoelastin gene expression in cells (as described in U.S. Pat. No. 7,816,335), the ability to enhance elastic fiber network formation by cells, and/or the ability to reduce or inhibit total (i.e. all isoforms) versican gene expression in cells (see FIG. 7A). In yet another embodiment, the rV3 protein of the invention includes a non-native signal peptide sequence (for example, but not limited to, SEQ ID NO:10). In another embodiment, the secreted rV3 of the invention has at least about 85% amino acid sequence identity to one of SEQ ID NOs: 2-9. The rV3 protein of the invention can have at least about 85%, 86%, 87%, 88%, 89%, 90%, 91%, 92%, 93%, 94%, 95%, 96%, 97%, 98%, 99%, or to at least about 100% sequence identity to the reference sequences, said reference sequences being any one of SEQ ID NOs: 1, as described below, or SEQ ID NO:2, 3, 4, 5, 6, 7, 8, or 9. The reference sequences include amino acid residues 21-655, of SEQ ID NO:1 and/or SEQ ID NO:2, with sequence identity of the rV3 being at least about 85%, 86%, 87%, 88%, 89%, 90%, 91%, 92%, 93%, 94%, 95%, 96%, 97%, 98%, 99%, or 100%, 92% to about 100%, including at least about 95% to about 100%, further including about 100% to these reference sequences. It should be noted that the reference sequences SEQ ID NOs: 2-9 lack signal peptides which are absent from the secreted and isolated rV3 protein. The rV3 protein of the invention includes human recombinant V3 (i.e., rhV3), including rhV3 wherein any deviation from SEQ ID NOs:1 and/or 2 are conservative substitutions or substitutions that preserve rV3 biological activity.

In one embodiment, the expression cassette further comprises at least one of the following operatively linked to the V3 cDNA sequence or operatively positioned within the cassette: a chromatin function modifying element(s), a sequence coding for a non-native signal peptide, a sequence coding for a selection marker, a sequence coding for an identification tag, and/or a purification tag. In another embodiment, the cassette includes one or more additional chromatin function modifying elements operatively linked therein.

The term "operatively linked" indicates that the two or more domains exist in the same nucleic acid or amino acid polymer such that they are functionally linked as intended. For example, a promoter sequence is operatively linked to a coding sequence in a vector molecule when the promoter is able to recruit appropriate transcription factors to enable transcription. Operatively linking certain types of chromatin function modifying elements, namely ubiquitous chromatin opening elements (UCOEs), Scaffold or Matrix Attachment Regions (S/MARs). Stabilizing Anti Repressor (STAR) elements and insulators to the promoter and downstream gene of interest can reduce or negate epigenetic processes from negatively affecting transgene expression even if the gene has been integrated into an area of closed heterochromatin (Saunders F, Sweeney B. Antoniou M N, Stephens P. Cain K. Chromatin function modifying elements in an industrial antibody production platform—comparison of UCOE, MAR, STAR and cHS4 elements. PLoS One. 2015 Apr. 7; 10(4):e0120096.). A signal peptide (sometimes referred to as signal sequence, targeting signal, localization signal, localization sequence, transit peptide, leader sequence or leader peptide) is a short peptide (usually 16-30 amino acids long) present at the N-terminus of the majority of newly synthesized proteins that are destined towards the secretory pathway. A non-native signal peptide is a signal peptide sequence from one species operatively linked to a gene sequence of another species is an effort to maximize expression and secretion of the recombinant protein (i.e. the *Gaussia princeps* luciferase: Petersen T N, Brunak S, von Heijne G. Nielsen H. SignalP 4.0: discriminating signal peptides from transmembrane regions. Nat Methods. 2011; 8:785-6.). A selection marker is a protein coding sequence that confers a selective advantage or disadvantage to host cell. A common type of selection marker is one that confers resistance to a particular antibiotic, such as the Zeocin resistance gene used in one embodiment of the present invention. Fluorescent proteins can also be used for selection of cells using flow sorting. An identification tag is a polypeptide sequence added to the C- or N-terminus of a recombinant protein commonly used for identification of the protein using antibodies to the tag when specific antibodies to the protein are not available, such as the hemagglutinin tag used in an embodiment of the present invention. A purification or affinity tag is a polypeptide sequence added to the C- or N-terminus of a recombinant protein which binds to a substrate and allows for the isolation and purification of the protein from a mixture of other molecules, such as cell lysate. Examples include His tag (metal affinity) or Twin-Strep-Tag® systems. It will be appreciated that some tags can serve as both identification and purification tags (e.g. His and Twin-Strep-Tags®).

In one embodiment, the cDNA sequence is codon optimized for expression of the rV3 protein in the host cell or tissue. In one embodiment, any variance in the cDNA sequence encoding the Hyaluronan binding site and G3 domain encodes for one or more conservative amino acid substitutions. In one embodiment, the ubiquitous chromatin opening element is or comprises UCOE. In one embodiment, the promoter is selected from the group consisting of SFFV, CMV, EF1, and the like. In one embodiment, the selection marker is cleavable or separately transcribed.

In another embodiment, the expression vector increases production of recombinant mammalian versican protein, or variants or mutants thereof. The expression vector includes any embodiment as described above. In some embodiments, the vector comprises DNA sequence encoding a protein having at least about 85%, at least about 90%, or at least about 95% sequence identity to any one of SEQ ID NOs: 1-9, a promoter operatively linked within the vector to the DNA sequence, and a ubiquitous chromatin opening element upstream of the strong promoter.

In some embodiments, the expression vector further comprises a cDNA sequence coding for a non-native signal peptide replacing amino acids positions 1-20 of SEQ ID NO:1 or a wild-type V3 sequence w/a signal peptide, wherein the non-native signal peptide need not replace the native 20 amino acids on a one-to one basis. In some embodiments, a non-native, more efficient rV3 signal peptide, (e.g. from *Gaussia princeps* luciferase as in SEQ ID NO:10), is used to enhance trafficking of the recombinant protein to the extracellular space. In some embodiments, the expression vector further comprises: a cDNA sequence coding for a selection marker positioned upstream of the rV3 cDNA, and a cDNA sequence coding for a purification tag at the C-terminal end of the rV3 protein. In some embodiments, the cDNA sequence coding for the selection marker codes for a fluorescent protein and/or antibiotic resistance. In some embodiments, the vector further comprises a 2A self-cleaving peptide multi-gene expression component positioned within the vector. In some embodiments, the vector comprises an encoded purification tag selected from His, GST, and/or STREP. In some embodiments, the expression vector further comprises a DNA sequence coding for an identification tag upstream of the purification tag, wherein the identification tag is Hemagglutinin. STREP, His, and/or Flag.

In embodiments of the expression vector, expression cassette or expression system described herein, the cDNA sequence coding for rV3 isoform protein is or comprises SEQ ID NO:12 or 14, wherein the promoter is SFFV, wherein the ubiquitous chromatin opening element is UCOE, and wherein the chromatin enhancing element is selected from the group consisting of matrix attachment region element (MAR), stabilizing anti-repressor element (STAR), and/or insulator sequence (cHS4).

In one embodiment, the expression vector contains the same essential elements as the embodiments described above which are arranged as depicted in FIG. 9A. This embodiment appears to be one of the most effective, of the embodiments tested, at producing increased amounts of rV3. This specific embodiment of the expression vector is constitutively active and comprises:

An expression vector readily able to transduce any mammalian cell line of choice (i.e. lentivirus) and stably express the recombinant V3 protein;

Chromatin function modifying elements (e.g. STAR, MAR) upstream of a V3 cDNA to stabilize the DNA and enhance transcription;

A ubiquitous chromatin opening element (e.g. UCOE) upstream of a bicistronic cassette containing:

a selection marker (e.g. GFPz) cDNA which is operatively linked to and upstream of;

a 2A self-cleaving peptide to allow for the simultaneous expression of both selection marker and the V3 which is upstream of;

An efficient non-native signal peptide (e.g. *Gaussia princeps* luciferase signal peptide) upstream and contiguous with the V3 cDNA.

The bicistronic cassette is driven by a strong promoter (e.g. CMV, SFFV) to maximize transcription of V3.

The C-terminal end of the V3 must contain a tag for identification (e.g. HA-tag) and selection (e.g. Twin-Strep-Tag®).

In another embodiment, the expression vector can contain a tetracycline response element (TRE) and a reverse tetracycline-controlled transactivator (rtTA) such that transcription of, e.g., V3, is reversibly activated (TET-ON) in the presence of the antibiotic tetracycline or one of its derivatives (e.g. doxycycline). This embodiment with the addition of the elements required for tetracycline responsiveness. However, the arrangement of the elements differs from the embodiment to enable the functionality of this inducible alternative form.

This specific embodiment of the expression vector comprises:

An expression vector readily able to transduce any mammalian cell line of choice (i.e. lentivirus) and stably express the recombinant V3 protein;

Use of 2nd generation (or later) tetracycline responsive elements to minimize "leakiness" or V3 expression in the absence of tetracycline;

Chromatin function modifying elements (e.g. STAR, MAR) upstream of tetracycline responsive elements and V3 to stabilize DNA and enhance transcription;

A ubiquitous chromatin opening element upstream if the rtTA element driven by a strong promoter (e.g. CMV, SFFV) to maximize transcription of the rtTA.

A 2A self-cleaving peptide to allow for the simultaneous expression of both rtTA and a selection marker (e.g. GFPz); and If a selection marker is not desired and a 2A peptide is not used, then the C-terminal end of the V3 must contain a tag for identification and selection.

A schematic of this embodiment of the vector is illustrated in FIG. 9B.

Another embodiment of the invention comprises the nucleic acid sequence and/or expression system(s) described herein, wherein the cDNA coding for rV3 has at least about 85%, at least about 90%, or at least about 95% sequence identity with SEQ IDs 12, 14-21. In another embodiment, the invention comprises a nucleic acid having at least 85%, at least 90%, or at least 95% sequence identity to SEQ ID NO:13, 22, 23, or 24, including those that have at least about 85%, 86%, 87%, 88%, 89%, 90%, 91%, 92%, 93%, 94%, 95%, 96%, 97%, 98%, 99% or up to at least about 100%, including at least about 95%, including at least about 92% to about 100%, including at least about 95% to about 100%, further including about 100% sequence identity.

In another embodiment of the invention a host cell, aggregations of cells, progeny thereof, or tissue transduced, transfected or transformed with a vector as described herein is provided.

In yet another embodiment of the invention provides a method for producing and/or increasing yield of mammalian rV3, variants or mutants thereof. In some embodiments, the host cells are adherent in culture. In other embodiments, the host cells are non-adherent and are grown in suspension culture. The use of mammalian host cells facilitates proper N-glycosylation of the expressed protein.

In some embodiments, the suspension culture is free of animal proteins and/or the pH is not at the protein's isoelectric point. In some embodiments, the method comprises the step of isolating the mammalian rV3 protein. In some embodiments, the recombinant protein is purified or substantially purified, such as by chromatographic, affinity tag, binding partner interactions, or other strategies known in the art. The host cells can be mammalian cells or cell lines. Examples include HEK and CHO cell lines, although any cell line capable of reliably N-glycosylating mammalian proteins are contemplated. In some embodiments, the method incorporates use of lab ware for culture and isolation that comprise polypropylene, polycarbonate, polyether sulfone, and/or methacrylate, and do not comprise nitrocellulose and sepharose. The culture systems can require serum or, alternatively, be serum-free.

Another embodiment of the invention provides an isolated and purified rV3 obtained in the methods described herein. The protein can be in a form suitable for long-term storage. In some embodiments, the protein is soluble in water. In some embodiments, the protein is lyophilized. In some embodiments, the protein is in frozen solution. In some embodiments, the protein is detectably labeled.

Equivalent DNA constructs that encode various additions or substitutions of amino acid residues or sequences, or deletions of terminal or internal residues or sequences not needed for biological activity are also encompassed by the invention. For example, another embodiment of the invention is where any nucleotide substitutions are silent, meaning that when silent nucleotide substitutions are present in a codon, the same amino acid is encoded as without the substitutions. For example, valine is encoded by the codon GTT, GTC, GTA and GTG. A change in the third nucleotide in a codon for valine, will still result in valine at that position. (see Appendix D in Sambrook et al., Molecular Cloning: A Laboratory Manual (1989)). Nucleotide substitutions can be introduced into DNA segments by methods well known to the art. Likewise, nucleic acid molecules encoding mammalian, including human, V3 polypeptides may be modified in a similar manner. Moreover, the DNAs of the invention may be modified in a similar manner so as to result in polypeptides that have deletions, mutations, or additions.

Amino acid substitutions which do not adversely affect biological activity of the rV3 protein are also within the scope of this invention. Conservative amino acid substitutions include, for example, aspartic-glutamic as acidic amino acids; lysine/arginine/histidine as basic amino acids; leucine/isoleucine, methionine/valine, alanine/valine as hydrophobic amino acids; serine/glycine/alanine/threonine as hydrophilic amino acids. Conservative amino acid substitution also includes groupings based on side chains. Members in each group can be substituted for one another. For example, a group of amino acids having aliphatic side chains is glycine, alanine, valine, leucine, and isoleucine. These may be substituted for one another. A group of amino acids having aliphatic-hydroxyl side chains is serine and threonine. A group of amino acids having amide-containing side chains is asparagine and glutamine. A group of amino acids having aromatic side chains is phenylalanine, tyrosine and tryptophan. A group of amino acids having basic side chains is lysine, arginine, and histidine. A group of amino acids having sulfur-containing side chains is cysteine and methionine. For example, replacement of a leucine with an isoleucine or valine, an aspartate with a glutamate, a threonine with a serine, or a similar replacement of an amino acid with a structurally related amino acid may be accomplished to produce a variant polypeptide of the invention.

In some embodiments, the method comprises steps of transducing a host cell or tissue with a vector comprising a nucleic acid sequence encoding rV3, its vint-tailed variant, or its above-described N-glycosylation or exon deletion mutants thereof, wherein the vector further comprises a strong promoter operatively linked to the nucleic acid sequence and a ubiquitous chromatin opening element upstream of the strong promoter. In some embodiments, the method further comprises isolating and/or purifying the recombinant protein.

In another embodiment, the invention provides isolated and purified protein obtained according to the methods described herein. In some embodiments, the protein is soluble in water or other aqueous solution. In some embodiments, the protein is lyophilized. In some embodiments, the protein is in frozen solution. In some embodiments, the protein is detectably labeled.

In another embodiment of the present invention provides an antibody or antigen binding fragment or derivative thereof, that binds to the recombinant protein described herein. It will be appreciated that previous efforts by the inventors utilizing synthesized polypeptides comprising the specific G1-G3 globular domain splice junction of V3, to raise functional antibodies specific to the versican V3 isoform, were only successful in binding to rV3 in an unglycosylated form generated in a bacterial expression system, but failed to bind to N-glycosylated rV3 of the present invention. Thus, monoclonal antibodies, antigen binding fragments, and derivatives thereof, contemplated within the scope of this invention, are alternatively generated using peptides unique to rV3 which are also readily exposed on the isolated rV3, using any technique commonly known in the art. It will be appreciated that the polypeptide sequences may vary from primary wild-type or consensus V3 amino sequence. Monoclonal antibodies can be prepared using a wide variety of techniques known in the art including the use of hybridoma, recombinant, and phage display technologies, or a combination thereof. In other embodiments, the antibody or antigen binding fragment or derivative thereof specifically binds to rhV3.

As used herein, the term "antibody" generally encompasses antibodies and antibody fragments and derivatives thereof, as obtained or derived from any antibody-producing mammal (e.g., mouse, rat, rabbit, and primate including human), that specifically bind to an antigen of interest (e.g., V3). Exemplary antibodies multi-specific antibodies (e.g., bispecific antibodies); humanized antibodies; murine antibodies; chimeric, mouse-human, mouse-primate, primate-human monoclonal antibodies; and anti-idiotype antibodies. The antigen-binding molecule can be or comprise any intact antibody molecule or fragment thereof (e.g., with a functional antigen-binding domain).

An antibody fragment is a portion derived from or related to a full-length antibody, and can include the complementarity-determining regions (CDRs), antigen binding regions, or variable regions thereof. Illustrative examples of antibody fragments and derivatives useful in the present disclosure include Fab. Fab', $F(ab)_2$, $F(ab')_2$ and Fv fragments, nanobodies (e.g., $V_HH$ fragments and $V_{NAR}$ fragments), linear antibodies, single-chain antibody molecules, multi-specific antibodies formed from antibody fragments, and the like. Single-chain antibodies include single-chain variable fragments (scFv) and single-chain Fab fragments (scFab). A "single-chain Fv" or "scFv" antibody fragment, for example, comprises the $V_H$ and $V_L$ domains of an antibody, wherein these domains are present in a single polypeptide chain. The Fv polypeptide can further comprise a polypeptide linker between the $V_H$ and $V_L$ domains, which enables the scFv to form the desired structure for antigen binding. Single-chain antibodies can also include diabodies, triabodies, and the like. Antibody fragments can be produced recombinantly, or through enzymatic digestion.

Production of antibodies or antibody-like molecules (e.g., antibody fragments and derivatives) can be accomplished using any technique commonly known in the art. Monoclonal antibodies can be prepared using a wide variety of techniques known in the art including the use of hybridoma, recombinant, and phage display technologies, or a combination thereof. For example, monoclonal antibodies can be produced using hybridoma techniques including those known in the art and taught, for example, in Harlow et al., *Antibodies: A Laboratory Manual* (Cold Spring Harbor Laboratory Press, 2nd ed. 1988); Hammerling et al., in: *Monoclonal Antibodies and T-Cell Hybridomas* 563-681 (Elsevier, N.Y., 1981), incorporated herein by reference in their entireties. The term "monoclonal antibody" refers to an antibody that is derived from a single clone, including any eukaryotic, prokaryotic, or phage clone, and not the method by which it is produced. Methods for producing and screening for specific antibodies using hybridoma technology are routine and well known in the art. Once a monoclonal antibody is identified for inclusion within the bi-specific molecule, the encoding gene for the relevant binding domains can be cloned into an expression vector that also comprises nucleic acids encoding the remaining structure(s) of the bi-specific molecule.

Antibody fragments that recognize specific epitopes can be generated by any technique known to those of skill in the art. For example. Fab and $F(ab')_2$ fragments of the invention can be produced by proteolytic cleavage of immunoglobulin molecules, using enzymes such as papain (to produce Fab fragments) or pepsin (to produce $F(ab')_2$ fragments). F(ab')2 fragments contain the variable region, the light chain constant region and the CHI domain of the heavy chain. Further, the antibodies of the present invention can also be generated using various phage display methods known in the art.

As used herein, "specifically binds" refers to an association or union of a binding domain (e.g., as a domain of an antibody, or antibody fragment or derivative) to a target (e.g., V3) and bind to the target molecule with an affinity or $K_a$ (i.e., an equilibrium association constant of a particular binding interaction with units of 1/M) equal to or greater than $10^5$ M$^{-1}$, while not significantly associating or uniting with any other molecules or components in a sample. Binding domains can be classified as "high affinity" binding domains or "low affinity" binding domains. "High affinity" binding domains refer to those binding domains with a $K_a$ of at least $10^7$ M$^{-1}$, at least $10^8$ M$^{-1}$, at least $10^9$ M$^{-1}$, at least $10^{10}$ M$^{-1}$, at least $10^{11}$ M$^{-1}$, at least $10^{12}$ M$^{-1}$, or at least $10^{13}$ M$^{-1}$. "Low affinity" binding domains refer to those binding domains with a $K_a$ of up to $10^7$ M$^{-1}$, up to $10^6$ M$^{-1}$, up to $10^5$ M$^{-1}$. Alternatively, affinity can be defined as an equilibrium dissociation constant (Kd) of a particular binding interaction with units of M (e.g., $10^{-5}$ M to $10^{-13}$ M). In certain embodiments, a binding domain may have "enhanced affinity," which refers to a selected or engineered binding domain with stronger binding to a target antigen than a wild type (or parent) binding domain. For example, enhanced affinity may be due to a $K_a$ (equilibrium association constant) for the target antigen that is higher than the wild type binding domain, or due to a $K_d$ (dissociation constant) for the target antigen that is less 10 than that of the wild type binding domain, or due to an off-rate ($K_{off}$) for the target antigen that is less than that of the wild type binding domain. A variety of assays are known for identifying binding domains of the present disclosure that specifically bind a particular target, as well as determining binding domain or fusion protein affinities, such as Western blot, ELISA, and BIACORE® analysis (see also, e.g., Scatchard et al., *Ann. N.Y. Acad. Sci.* 51:660, 1949; and U.S. Pat. Nos. 5,283,173, 5,468,614, or the equivalent).

In some embodiments, the antibody or antigen binding fragment or derivative thereof is detectably labeled. Detectable labels and methods of attaching them to affinity reagents as described herein are known in the art The methods, expression systems and vector constructs of the invention provide increased and stable production of rV3. Thus, the inventors determined that in embodiments described herein, stable V3 expression, (i.e., sustained for at least 3 days post-transduction to at least 4 weeks or more) was achieved in accordance with the methods of the invention. Additionally, in some embodiments, the method of the invention will produce at least about 0.5 μg/ml of rV3 in conditioned media, to at least about 6.75 μg/ml or greater. This level of production can be confirmed by isolating V3 from conditioned media collected over a 1-7 day period using an affinity tag-based embodiment of the system as described below.

In this embodiment, the vector construct includes the following components as selection markers to aid in identification of protein-producing cells as well as the protein itself:

- 2A self-cleaving peptide multi-gene expression component to allow for simultaneous expression of recombinant protein and selection marker;
- Green fluorescent protein (GFP) and the Zeocin-resistance gene Shble (ZeoR) fused together to generate a bifunctional protein (GFPz) for the identification and selection of transfected mammalian cells;
- Placement of the selection marker cDNA cassette upstream and the V3 cDNA cassette downstream of the 2A peptide; and
- Addition of one or more C-terminal tags to help identify (e.g. HA-6, Flag, His) and purify (e.g. His, STREP) the secreted recombinant protein.

The inventors have also found that in some embodiments, a C-terminal tag provides for easier detection to distinguish it from other isoforms of versican. However, other methods can be employed including chromatography and antibodies, which can now be developed and employed.

In accordance with the studies described below, the inventors determined that when simultaneous expression of rV3 and a selection marker are desired, a 2A peptide is required for sustained expression of both proteins, as attempts to use other bicistronic elements such as IRES were less successful. Surprisingly we discovered that the V3 cDNA must be placed downstream of the 2A peptide for expression to occur. There was no way to predict this previously and it had to be determined empirically.

Finally, the recombinant V3 isoform protein produced in the disclosed methods has several advantageous applications, including its use in combination with other molecules.

For example, the present invention further comprises a composition comprising a molecular complex of purified rV3, or a portion thereof, bound to a hyaluronan molecule, either native or modified, capable of binding to the rV3 or rV3 portion, wherein the rV3 has been isolated from a cell or tissue and/or has been exogenously produced, in a pharmaceutically acceptable carrier. Production and uses of this composition are also contemplated to be within the scope of this invention. Given that V3 has never been isolated purified in protein form or recombinantly produced, it has never been exogenously complexed or bound to any other molecule including hyaluronan (HA), nor has any pharmaceutically acceptable composition containing such a complex been produced or administered. The G1 domain of versican, which is included in rV3, contains a binding region that is specific for hyaluronan and when complexed with hyaluronan has a measured bond strength of 37 pN. (LeBaron, R. G., Zimmermann, D. R., and Ruoslahti, E. (1992) *J. Biol. Chem.* 267, 10003-10010; Bano, F. Tammi, M I. Kang, D W, Harris, E N. and Richter, R P. (2018) *Biophys J.* 114(12), 2910-2922). However, it should also be appreciated that overexpression of V3 does not necessarily result in increased association of that V3 with endogenously produced hyaluronan (Hudson K S, Andrews K, Early J. Mjaatvedt C H, Capehart A A. (2010) *Anatomical record,* 293(10):1669-1678; Kang I, Yoon D W, Braun K R, Wight T N. (2014) *The Journal of Biological Chemistry,* 289(22):15393-15404). It should be noted that despite the presence of an HA binding region within the full-length V3 isoform, until the present invention no V3/HA complexes had been identified as present in mammalian tissue. The presence of the HA binding site in the full-length molecule did not guarantee actual binding activity to HA, similar to the inventors' demonstration that the identification of multiple N-glycosylation sites did not result in glycosylation at all of these sites.

Although full-length versican V0 has been exogenously produced and complexed to hyaluronan and the G1 region of versican has been exogenously produced and complexed to hyaluronan, as noted above. V3 has never been isolated and purified and is not being used in any applications, including in compositions containing HA (LeBaron, R. G., Zimmermann, D. R., and Ruoslahti, E. (1992) *J. Biol. Chem.* 267, 10003-10010; Bano, F, Tammi, M I, Kang. D W, Harris, E N. and Richter, R P. (2018) *Biophys Jl.* 114(12), 2910-2922).

Thus another embodiment of a composition of the present invention comprises a molecular complex further comprising rV3 which is isolated and purified from a cell or tissue and/or has been exogenously produced and HA which is purified from a cell or tissue and/or has been exogenously produced, as well as methods of administration of the complex to mammals, including humans. In some embodiments, this complex is formulated for cosmetic use. In one embodiment the HA is of an average molecular weight greater than about 250 kDa, and in another embodiment of an average molecular weight greater than about 1000 kDa (i.e. high molecular weight) and may be isolated to a narrow molecular weight range with a standard deviation of no more than about 200 kDa. Depending on the specific application of the molecular complex, the hyaluronan may be chemically modified to include thiol groups to aid in crosslinking.

Another embodiment of the present invention is a gel composition comprising the rV3/HA complex of the present invention. The gel can be produced as follows: exogenously produced rV3 is isolated and purified as described in our system and remains in aqueous solution, and lyophilized hyaluronan, which may be further modified with thiol groups to aid in crosslinking, is solubilized in aqueous solution. The rV3 and hyaluronan solutions are then combined into a solution containing a crosslinking acceleration agent, such as Extralink (ESIBio) to allow the molecular complex to gel. While the gel is still in liquid form, it is poured into a mold of appropriate size for a given application, which may also contain another carrier, to be either impregnated by or act as a carrier for, the rV3/HA gel. In another embodiment, the rV3 is incorporated into a gel impregnated with HA.

In another embodiment of this invention, addition of Link Protein to the rV3/HA complex is employed to help stabilize and strengthen the rV3/HA interaction (Seyfried, N T, McVey, D F, Almond, A, Mahoney. D J, Dudhia, J J, and Day, A J. (2005) *Biol. Chem.* 280:5435-5448).

Another embodiment of the present invention provides a pharmaceutically acceptable composition comprising a purified exogenously produced rV3/HA complex in a pharmaceutically acceptable carrier such as those, for example, described herein. In another embodiment the composition is administered to a mammal, including human, to treat a condition where V3 and/or the complex is useful and beneficial, including those described herein.

The inventors have also established the utility of the rV3 as an anti-adhesive molecule. Briefly, the inventors demonstrated that protein adheres readily to many surface materials such as certain plastics and glass but that rhV3-coated surfaces resist inflammatory cell (U937 monocytic line) binding (see below for additional detail.) Accordingly, the disclosure provides for the use of the recombinant V3 isoform protein as an anti-adhesive molecule.

The inventors have also established the utility of the recombinantly expressed V3 isoform protein as an anti-inflammatory molecule. Briefly, the inventors demonstrated that isolated rhV3 has anti-inflammatory activity, including dampening expression of chemokine CCL2 and cytokines IL1β and TNFα in response to TLR-3 activation (see below for additional detail). This effect of V3 on pro-inflammatory molecule profile has only been demonstrated using overexpressed endogenous V3 protein and this is the first time exogenously produced rhV3 protein has been used as an anti-inflammatory. Accordingly, the disclosure provides for the use of the recombinant V3 isoform protein as an anti-inflammatory molecule.

Similarly, the inventors have also established the utility of the recombinantly expressed V3 isoform protein as promoter of elastin fiber network formation. Briefly, the effect of V3 on pro-inflammatory molecule profile has only been demonstrated using overexpressed endogenous V3 protein, and this is the first time exogenously produced rV3 protein has been used as to enhance elastin fiber network formation. Accordingly, the disclosure provides for the use of the rV3 isoform protein as a promoter of elastin fiber network formation. Both medical and veterinary applications are contemplated to be within the scope of the present invention. The inventors have further determined the utility of rV3 in reducing expression of molecules involved in the fibrotic process, supporting its use as an antifibrotic therapeutic. In in vitro analyses, the addition of isolated rV3 to cultured lung and dermal fibroblasts resulted in a dose-dependent reduction in the expression of alpha smooth muscle actin, a marker of myofibroblasts and type 1 collagen, the major molecule in fibrotic tissues. References addressing potential applications for the recombinant V3 protein disclosed herein include U.S. Pat. No. 7,816,335, European Patent No. 1274726, Australian Patent No. 2001253408. U.S. Pat. Nos. 8,367,619, and 8,410,067, each of which is incorporated herein by reference in its entirety, and specifically for the disclosure of uses of versican and isoforms thereof.

An rV3 protein or pharmaceutical composition containing rV3 and/or the rV3/HA complex of the invention can be formulated as pharmaceutical compositions and administered to an animal, including a mammal, such as a human, or to a veterinary patient in a variety of forms adapted to the chosen route of administration, i.e., orally or parenterally, by intravenous, intramuscular, topical, inhalation, or subcutaneous routes.

The rV3 compositions of the invention (e.g., rV3 or rV3/HA complex) can be administered in combination with a pharmaceutically acceptable vehicle suitable for its administration route. The amount of active agent in such therapeutically useful compositions is such that an effective dosage level will be obtained.

The rV3 compositions of the invention can be provided as a coating or topical gel, foam, ointment, lotion or in an aqueous solution. Examples of useful dermatological compositions which can be used to deliver compositions of the invention are known to the art; for example, see Jacquet et al. (U.S. Pat. No. 4,608,392), Geria (U.S. Pat. No. 4,992,478), Smith et al. (U.S. Pat. No. 4,559,157) and Wortzman (U.S. Pat. No. 4,820,508).

The rV3 compositions of the invention may also be coated onto or impregnate a carrier which delivers the rV3 or its complex, such carriers, including synthetic or naturally derived scaffolds, biodressings, wound dressings, natural or bioengineered skin graft and skin substitutes, and cellular, acellular, and decellularized matrices. The compositions of this invention can also be provided in aerosol form.

Sterile solutions are prepared by incorporating the rV3 compositions of the invention in the required amount in the appropriate solvent with various of the other ingredients enumerated above, as required, followed by filter or other sterilization. Methods of preparation include those suitable for long-term storage, which include vacuum drying, freezing, and freeze drying techniques. Long-term storage is contemplated to be at least about 3 months, to at least about 6 months, without losing more than at least about least about 10%, or at least about 25%, or at least about 50%, or at least about 75%, or at least about 90% of its biological activity prior to storage.

Unless specifically defined herein, all terms used herein have the same meaning as they would to one skilled in the art of the present invention. Practitioners are particularly directed to Sambrook J., et al. (eds.) Molecular Cloning: A Laboratory Manual, 3rd ed., Cold Spring Harbor Press, Plainsview, New York (2001); Ausubel, F. M., et al. (eds.), Current Protocols in Molecular Biology, John Wiley & Sons, New York (2010); and Coligan, J. E., et al. (eds.), Current Protocols in Immunology, John Wiley & Sons, New York (2010) for definitions and terms of art.

Disclosed are materials and compositions that can be used for, can be used in conjunction with, can be used in preparation for, or are products of the disclosed methods and compositions. It is understood that, when combinations, subsets, interactions, groups, etc., of these materials are disclosed, each of various individual and collective combinations is specifically contemplated, even though specific reference to each and every single combination and permutation of these compounds may not be explicitly disclosed. This concept applies to all aspects of this disclosure including, but not limited to, steps in the described methods. Thus, specific elements of any foregoing embodiments can be combined or substituted for elements in other embodiments. For example, if there are a variety of additional steps that can be performed, it is understood that each of these additional steps can be performed with any specific method steps or combination of method steps of the disclosed methods, and that each such combination or subset of combinations is specifically contemplated and should be considered disclosed. Additionally, it is understood that the embodiments described herein can be implemented using any suitable material such as those described elsewhere herein or as known in the art.

Publications, including patents, cited herein and the subject matter for which they are cited are hereby specifically incorporated by reference in their entireties.

Specific Studies

Study 1: "Production of Recombinant Human V3 and In Vitro Proof-of-Concept for its Development as a Biologic".

Introduction:

The structure of versican is responsible for enabling its many functional interactions. Like all proteoglycans, versican is comprised of a core protein with attached sulfated glycosaminoglycan (GAG) side chains. Both its core protein and CS GAG side chains participate in these interactions, and the presence or absence of the GAG chains has a major impact on versican function. The versican gene contains 15 alternatively-spliced exons with exons 3-6 encoding the G1 domain, which binds hyaluronan, exons 7-8 encoding the GAG attachment regions, and exons 9-14 encoding the G3 domain, which bind ECM proteins including fibrillin-1 and fibulin-2 and cell surface molecules such as integrin β1. RNA splicing occurs in exons 7 and 8, resulting in the expression of four isoforms denoted V0, V1, V2 and V3, each with a differential GAG binding arrangement.

Unlike the other isoforms of versican, V3 contains only the G1 and G3 domains and thus lacks GAG side chains. Additionally, V3 lacks a major ADAMTS (SEQ ID NO: 28) cleavage site present in the βGAG region of V0 and V1 isoforms, preventing the production of a bioactive cleavage product, versikine, which although critical for embryogenesis, acts as a pro-inflammatory damage-associated molecular pattern (DAMP), CS-containing versican isoforms interact with cytokines and chemokines via their GAG chains, thus V3 is predicted to lack this ability and therefore have altered function.

Indeed, the inventors have shown that V3 expression can actually have similar cellular effects as total versican inhibition. Specifically, elastogenesis was enhanced in dermal fibroblasts by either forced expression of V3 or antisense to decrease levels of versican variant V1. Whereas CS-containing isoforms of versican are necessary for smooth muscle cell proliferation and migration, and versican is abundant in the neointima of injured blood vessels, retroviral V3 expression was able to retard growth and migration in vitro as well as reduce neointimal formation by enhancing elastin fiber formation and limiting inflammatory cell infiltration in injured blood vessels in vivo. Similar cell growth retardation induced by V3 expression has also been observed in cancer cells in vitro, as well as reduced tumor size in vivo.

Notwithstanding these striking observations V3 as a therapeutic in conditions where versican is a major contributor to disease, such as vein graft failure due to restenosis, V3 has been difficult to isolate. Furthermore, gene therapies have met with unintended clinical side effects and other barriers to near-term clinical use. Accordingly, the present inventors describe here development of a system to generate recombinant human V3 (rhV3) protein and establish its effectiveness in modulating cellular phenotypes similar to those observed by cells overexpressing the V3 gene.

Figure 1A:
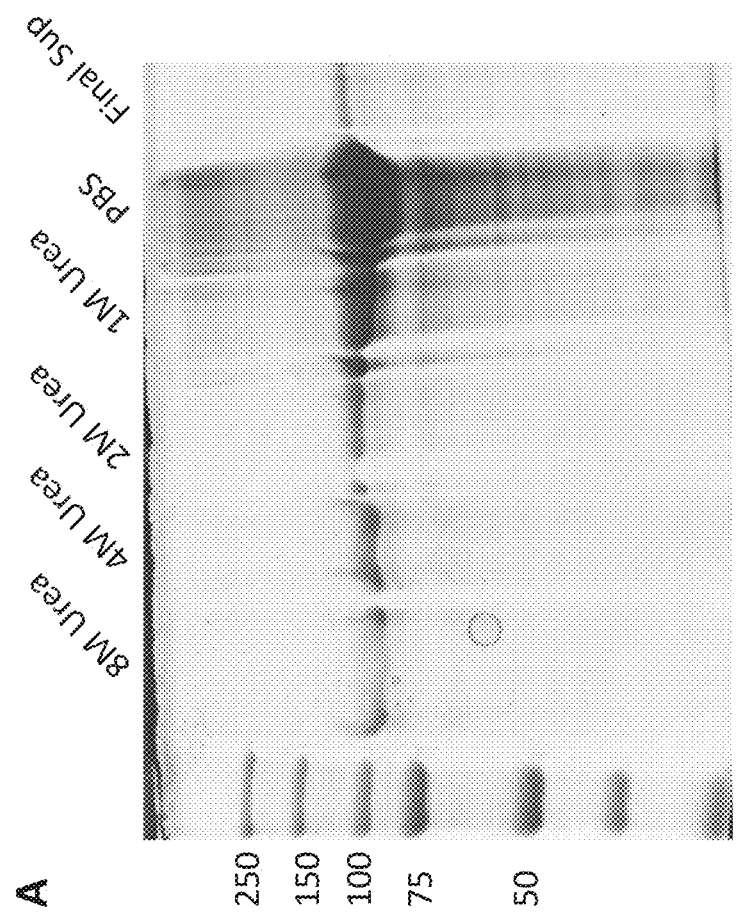
FIGS. 1A-1E are blots addressing the expression of V3 protein.
Figure 2:
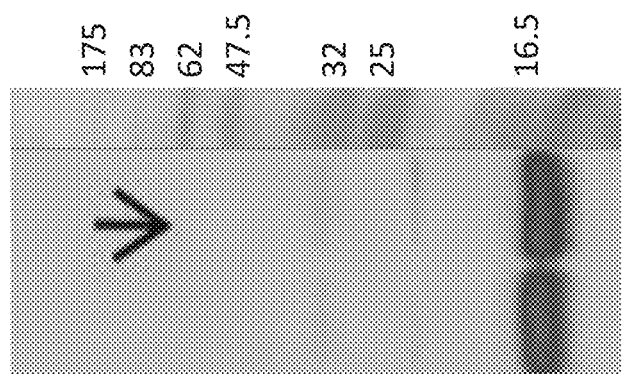
FIG. 2 is a blot illustrating that inoculated tobacco plants failed to produce soluble rhV3.
Figures 3A, 3B:
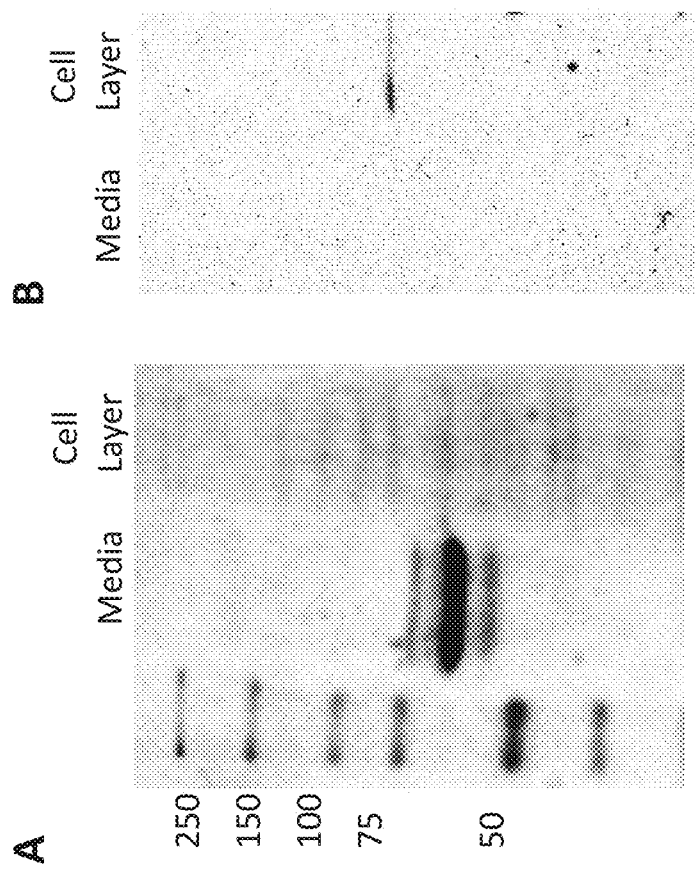
FIGS. 3A and 3B are blots that illustrate the transient transfection of HEK cells.
Figures 4A, 4B:
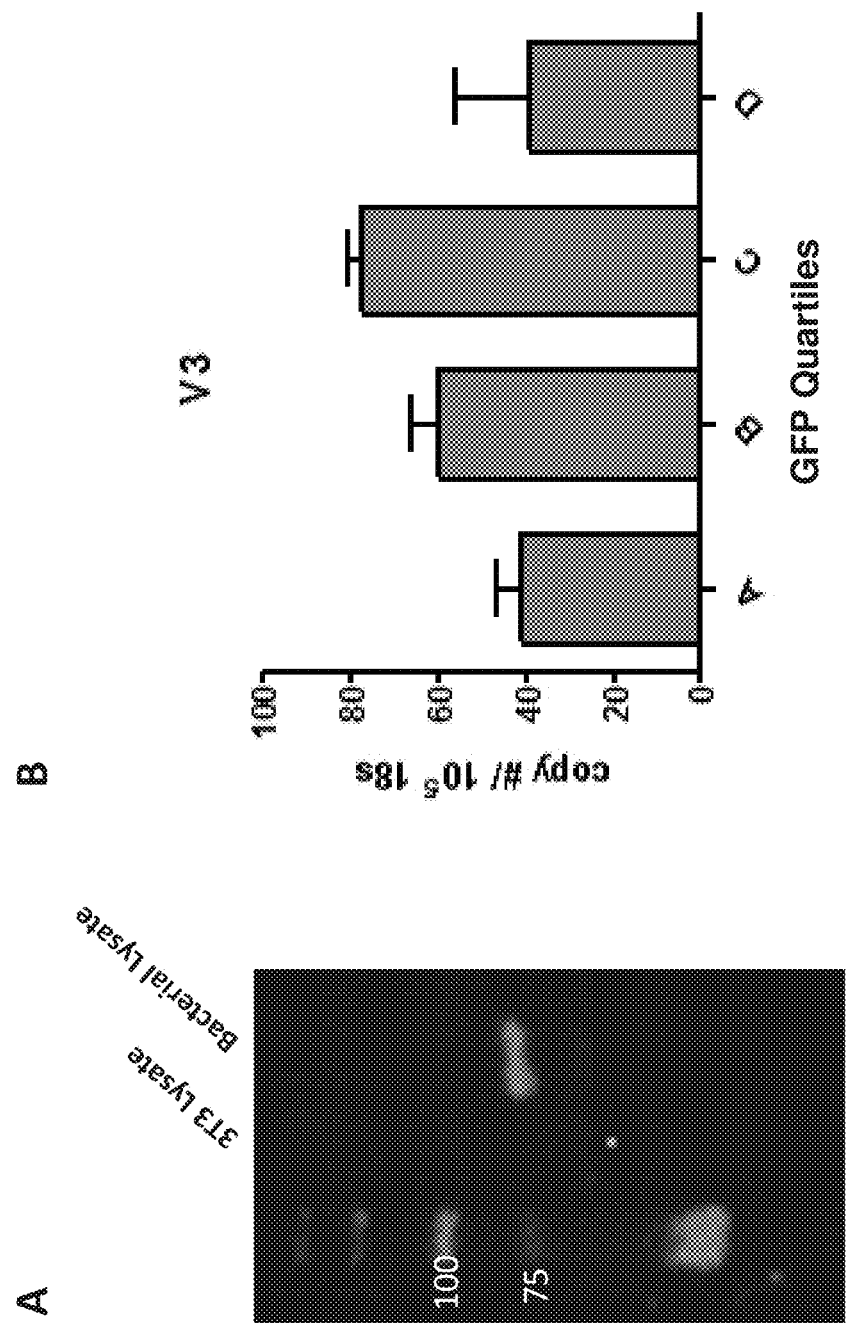
FIGS. 4A and 4B illustrate the observed loss of V3 expression with lentivirus.
Figure 4C:
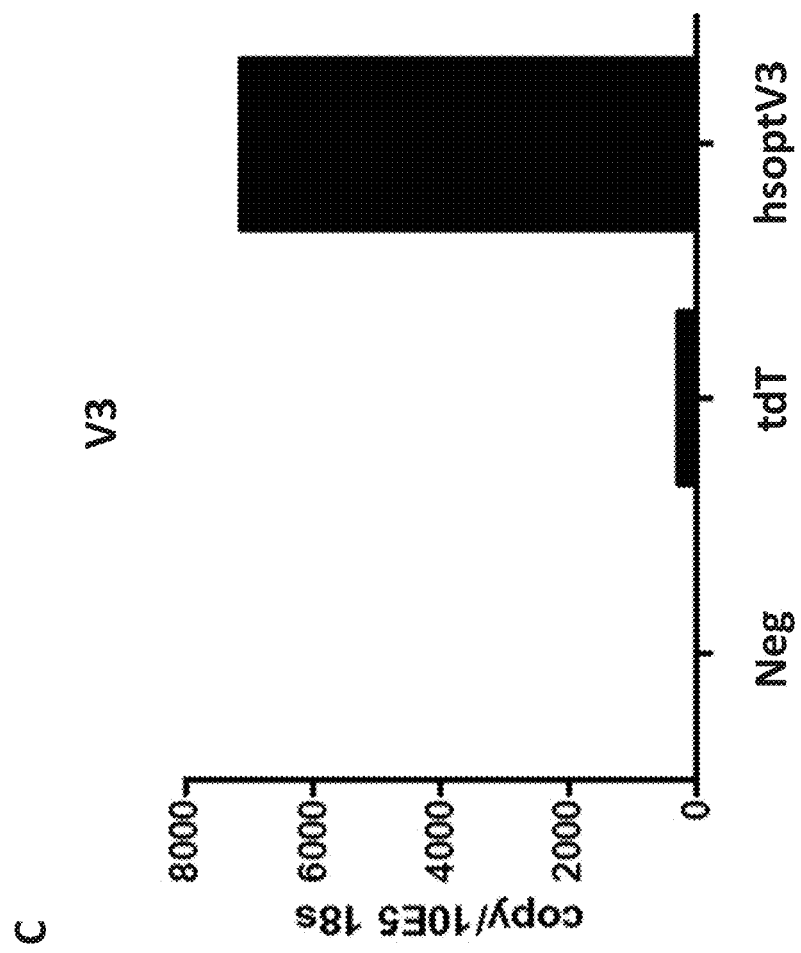
FIG. 4C graphically illustrates the highly efficient expression of V3 with the UCOE-containing pCVLU lentivirus.
Figure 5A:
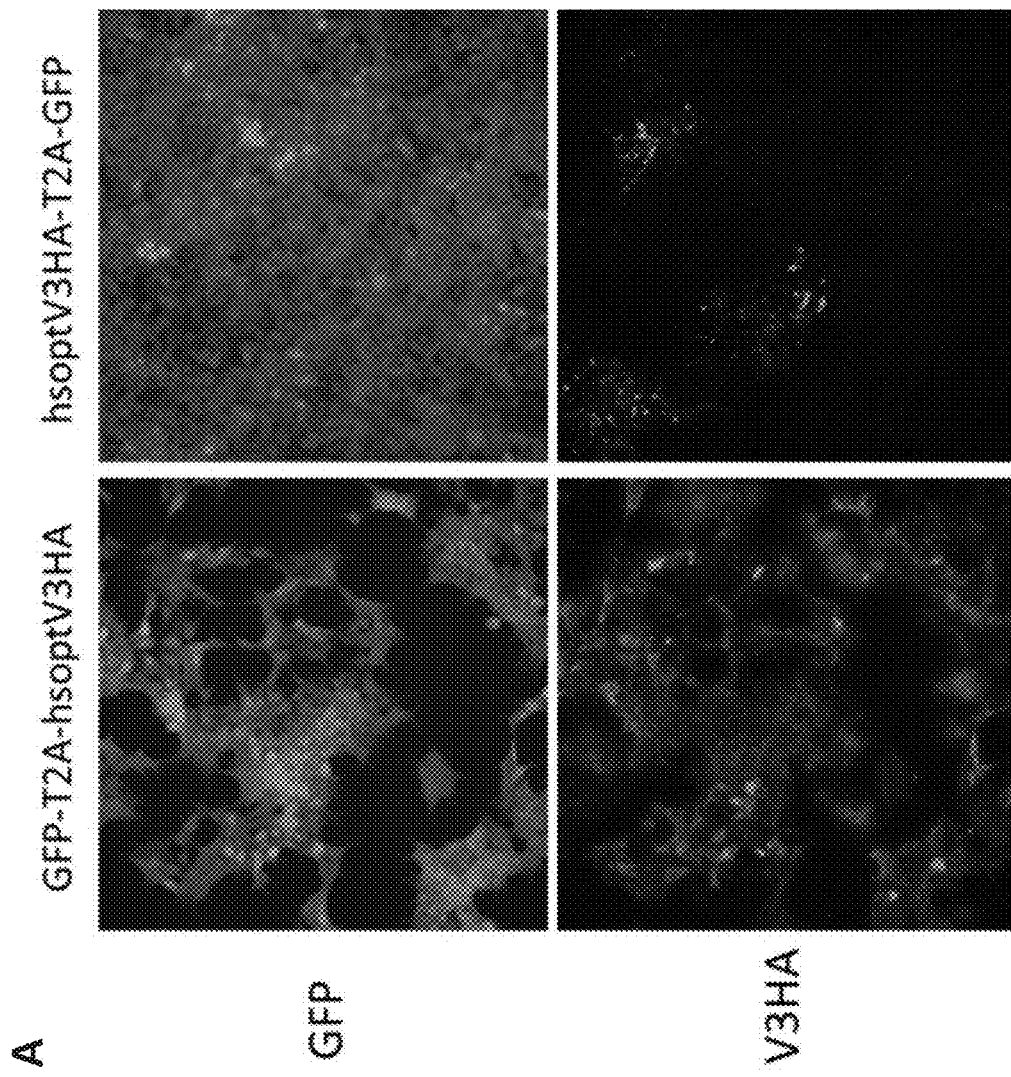
FIG. 5A is a series of photomicrographs demonstrating that rhV3 expression has positional specificity around the 2A element.
Figure 5B:
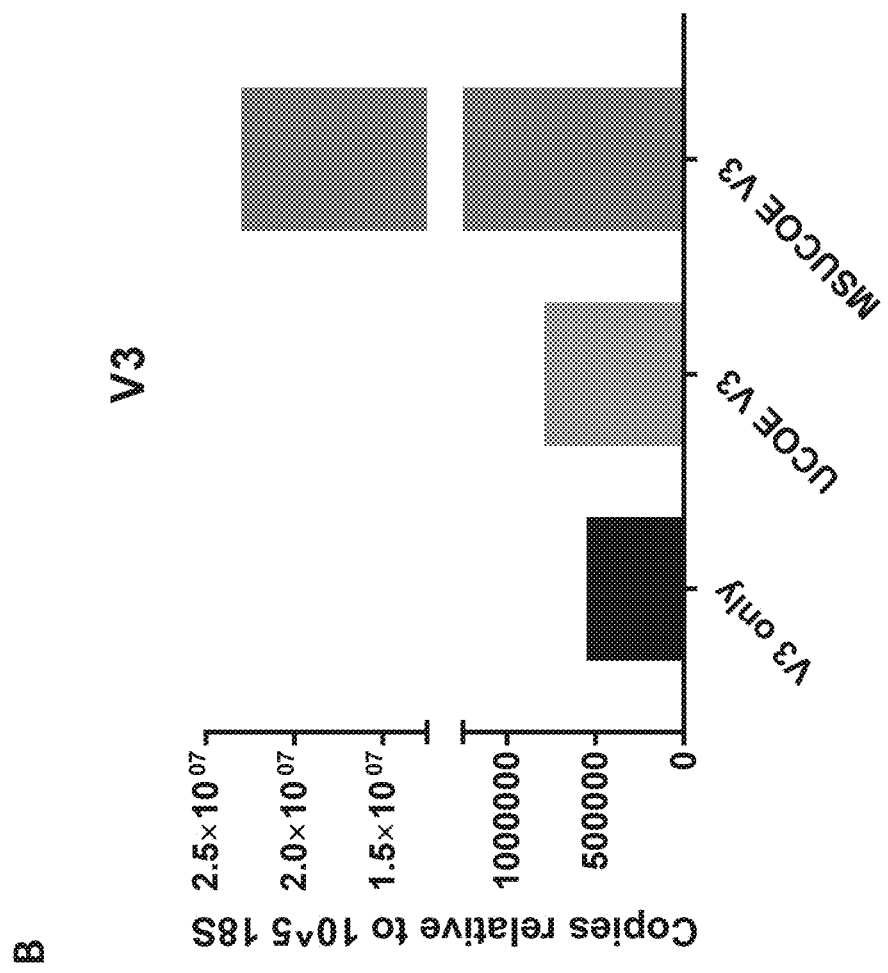
FIG. 5B graphically illustrates that MAR and STAR elements upstream of UCOE markedly increase V3 expression.
Figures 6A, 6B:
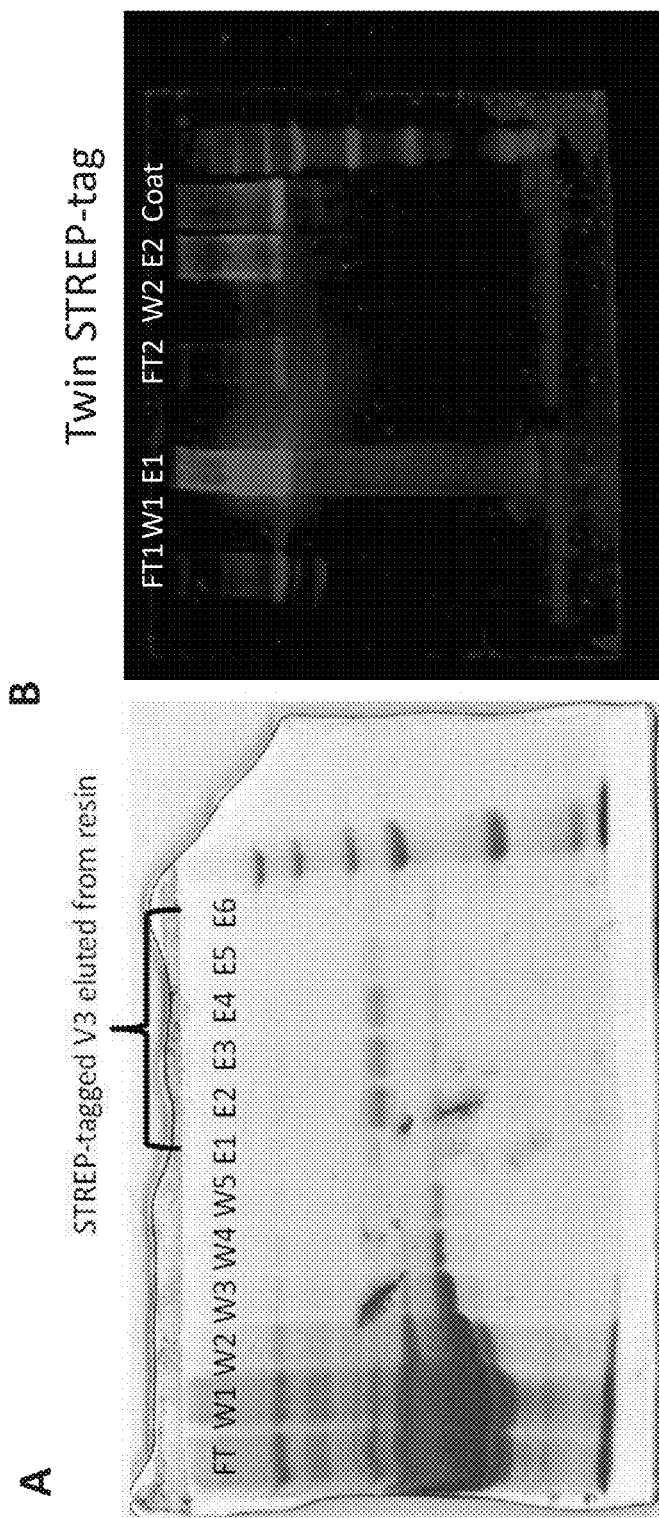
FIGS. 6A and 6B are blots demonstrating that C-terminal STREP-tag allows for isolation and purification of soluble hrV3 from HEK cells.

Discussion of Results:

Sequestration in inclusion bodies and insolubility of isolated rhV3 when produced in E. coli: Initial attempts to produce rhV3 were carried out in a BL21 bacterial expression system generating a fusion protein with C-terminal epitope (hemagglutinin; HA) and affinity (polyhistidine;

pHis) tags, as well as a secondary means (glutathione S-transferase; GST) of purification in physiological buffers on glutathione-agarose columns (GST-HuV3-HApHis). A bacterial system was chosen for its efficiency and also due to a lack of clarity in the literature regarding the glycosylation status of V3. However, the resulting bacterial rhV3 was exclusively present as insoluble protein in inclusion bodies, regardless of bacterial growth or induction conditions. Inclusion body-packaged rhV3 was soluble in dissociative solvents, such as buffers containing 6 M guanidine (GuHCl) or 8 M urea, which allowed for purification on immobilized metal affinity chromatography (IMAC) columns, such as TALON. On-column renaturation to generate functional and soluble GST-HuV3-HApHis was first attempted by stepwise dialysis through decreasing urea concentrations to PBS, with recombinant GST-HuV3-HApHis quantitatively precipitating between 1M and 2M urea (FIG. 1A). A large number of modifications of the step-wise dialysis renaturation approach were attempted, including different redox systems, such as glutathione, cysteine, dithiothreitol (DTT) and beta mercaptoethanol, as well as known refolding enhancers, such as arginine, acetamide, and a variety of detergents, without appreciable increases in recombinant protein solubility (data not shown).

Figures 1B, 1C:
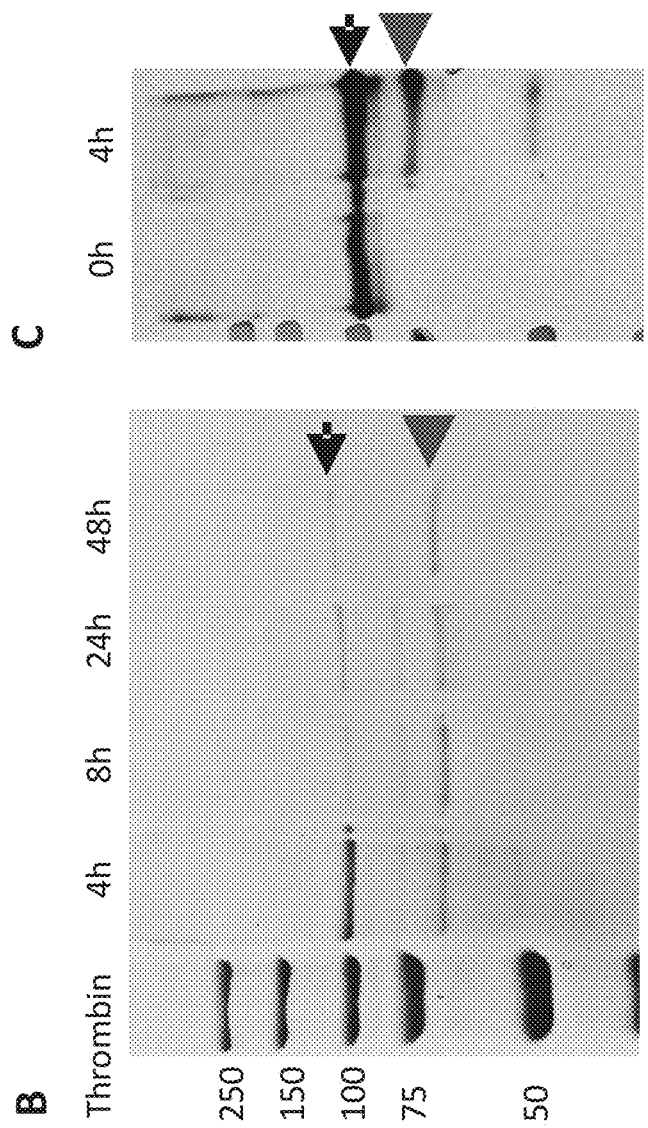
Figures 1D, 1E:
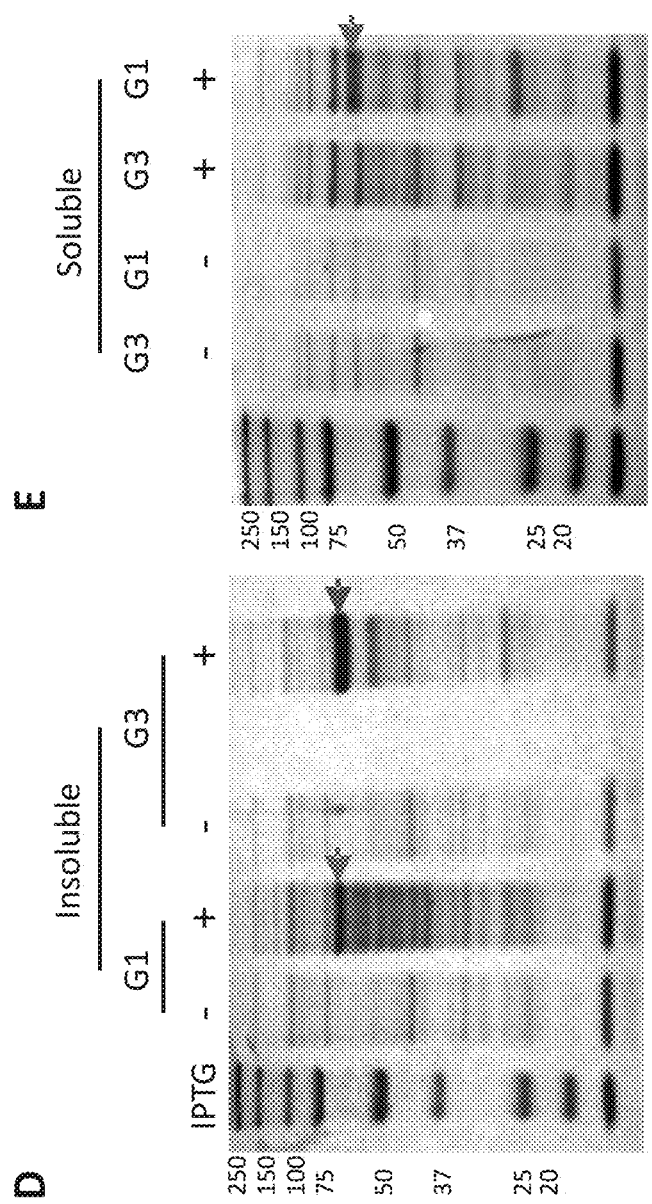

An additional challenge caused by the insolubility of the GST-HuV3-HApHis protein was thrombin digestion to remove the GST moiety from the minimally modified, recombinant protein. In these experiments, thrombin did not efficiently remove the GST moiety of the fusion protein, even at prolonged incubation times (FIGS. 1B and 1C). In an effort to gain understanding of the relative insolubility of the GST-HuV3-HApHis fusion protein, expression vectors were prepared with either the N-terminal G1 domain (known to be soluble), GST-HuG1-HApHis, or the C-terminal G3 domain. GST-HuG3-HApHis. When expressed in *E. coli* under standard conditions, a significant amount of GST-HuG1-HApHis was found in the soluble phase of the bacterial extracts, while GST-HuG3-HApHis was found exclusively as an insoluble product in the inclusion bodies (FIGS. 1D and 1E). This suggested that elements in the G3 domain were rendering the full length rhV3 molecule insoluble in the BL21 bacterial expression systems. This is in direct contrast to work suggesting the G1 domain is responsible for a reduction in versican solubility in a transient mammalian expression system (Kiani, C., et al. (2001) Roles of aggrecan domains in biosynthesis, modification by glycosaminoglycans and product secretion. *Biochem J* 354, 199-207).

Subsequent to these studies, work proceeded with the analysis of bacterially-expressed rhV3 using the pBAD expression system which has been shown to be ideal for optimizing protein solubility (Clark, M. A., et al. (1997) Regulation and expression of human Fabs under the control of the *Escherichia coli* arabinose promoter, PBAD. *Immunotechnology* 3, 217-226; incorporated herein by reference in its entirety). Expression constructs were designed to generate rhV3 fusion proteins that contained solubility enhancers, including glutathione and maltose binding protein. Although appreciable yield of protein was generated, again no soluble product was isolated. Explosive dilution (1:10,000-fold) of isolates was successful in generating soluble protein, but both time and re-concentration of the solution resulted in protein precipitation. These results led us to suspect that some manner of post-translational modification to V3, such as glycosylation, was necessary to achieve soluble protein. In a separate study, this question is explored in more detail (see below).

Lack of secreted rhV3 from transfected tobacco plants: As plant expression systems are known to glycosylate proteins in a manner similar to that of mammalian cells, a commercial entity was engaged to determine if it could produce soluble rhV3 in a tobacco (*Nicotiana benthamiana*) system (Agrenvec, Spain). There was reason to believe this method might work as the entity had previously been able to produce the G1 domain of versican, which was both soluble and functional (Merrilees, M. J., et al. (2016) G1 Domain of Versican Regulates Hyaluronan Organization and the Phenotype of Cultured Human Dermal Fibroblasts. *J Histochem Cytochem* 64, 353-363). However, after several attempts, no rhV3 could be generated in the plant system (FIG. 2). Thus, a mammalian culture system was explored for generating soluble rhV3.

Lack of secreted rhV3 from transiently transfected HEK cells: To prepare rhV3 without endotoxin contamination, expression of rhV3 was attempted with C-terminal epitope HA and pHis tags in mammalian (HEK) cells, which had been optimized for protein expression into low-serum media after transfection with the expression vector. A C-terminal site for tag addition was selected to avoid problems with signal peptide processing by mammalian cells. Western blots of HEK cell media (concentrated 50-fold) and cell layer extracts indicated very low amounts of material recovered from cell layers, with undetectable amounts in media samples (FIGS. 3A and 3B). The apparent lack of recovery of soluble recombinant protein from conditioned media or physiological (non-denatured) extracts of transiently huV3-HApHis-transfected HEK cells in these preliminary experiments suggested that this mammalian system would not meet practical demands for generating sufficient quantities of soluble and functional rhV3.

Low levels and unstable expression of rhV3 in a mammalian lentiviral system: It was reasoned that perhaps stable expression of V3 would be required to generate appreciable amounts of recombinant protein. The initial approach used expression of C-terminally HA-tagged V3, driven by the human ubiquitin C promoter (hUbc) in a pCDH vector, in NIH 3T3 fibroblasts. Initial mRNA expression results appeared promising; however, no rhV3 protein could be detected by western blot (FIG. 4A) after 5 days in culture, suggesting that expression of V3 had been turned off in these cells. In a separate set of experiments, 4T1 cells expressing V3 and a GFP (green fluorescent protein) selection marker driven by a separate EF1a promotor were grown for a week in culture. It was found that the fraction of cells displaying the highest GFP expression no longer had the highest V3 expression (FIG. 4B). This suggests that cells might actively suppress expression of V3 via epigenetic means despite the use of a non-viral promoter. The biological reason for V3 suppression in this system remains to be determined, however reports suggest that lentiviral integrants in higher order mammalian systems can experience epigenetic silencing through DNA methylation.

To enable the generation of stably expressing cells and to prevent promoter silencing, V3 was cloned into the pCVL-UCOE0.7-SFFV-muScn-IRES-GFP lentiviral vector (pCVLU) using the unique Xho I and Bam HI restriction sites, replacing the muScn sequence. The truncated ubiquitous chromatin opening element (UCOE) was chosen for its reported ability to stabilize high-level expression of recombinant proteins (Bandaranayake. A. D., et al. (2011) Daedalus: a robust, turnkey platform for rapid production of decigram quantities of active recombinant proteins in human cell lines using novel lentiviral vectors. Nucleic acids research 39, e143) via its ability to negate DNA methylation and silencing the SFFV promoter (Zhang, Fang et al. "A ubiquitous chromatin opening element (UCOE) confers resistance to DNA methylation-mediated silencing of lentiviral vectors." *Molecular Therapy*, vol. 18.9 (2010): 1640-9). This vector also contains an internal ribosomal entry site (IRES) to allow for the expression of a fluorescent protein marker for rapid non-chemical selection. Using cell sorting, cultures expressing sustained high levels of V3 mRNA we were generated (data not shown). Additionally, to maximize the translational potential of the V3 cDNA and increase protein production, a codon optimized cDNA sequence for human V3 (hsoptV3) was used (GenScript; see Table 1). A control vector was generated to express tdTomato fluorescent protein only. In spite of promising results showing successful transduction of HEK cells as determined by QPCR using probes against V3 (FIG. 4C), V3-containing constructs failed to generate a high fluorescent signal while controls generated a strong fluorescent signal. It was hypothesized, therefore, that the IRES was rendered nonfunctional when placed downstream of the target sequence, an apparently random, and therefore unpredictable occurrence (Mansha, M., et al. (2012) Problems encountered in bicistronic IRES-GFP expression vectors employed in functional analyses of GC-induced genes. *Molecular Biology Reports* 39, 10227-10234).

TABLE 1

| GPLss-hsoptV3HA-TS cDNA sequence |
|---|
| ATGTTCATCAATATCAAGTCCATACTGTGGATGTGTAGTACCCTCATTGTG |
| ACACATGCATTGCACAAAGTAAAAGTTGGAAAGAGTCCGCCTGTGAGGGGA |
| TCACTGAGTGGCAAAGTGTCACTGCCCTGTCACTTTTCCACTATGCCAACT |
| CTCCCACCCTCTTATAACACATCCGAGTTTCTCCGCATAAAGTGGTCCAAA |
| ATCGAGGTAGACAAGAACGGCAAAGACCTCAAAGAGACTACTGTGCTCGTG |
| GCACAGAATGGAAACATCAAGATTGGGCAGGACTATAAGGGTCGTGTCAGC |
| GTGCCAACTCACCCAGAAGCCGTTGGCGACGCCAGCTTGACAGTTGTGAAA |
| CTGCTTGCCAGCGACGCCGGACTGTATCGCTGCGATGTCATGTATGGTATC |
| GAAGATACACAGGACACAGTGAGCCTGACCGTGGATGGGGTAGTCTTTCAC |
| TATAGAGCCGCCACATCTAGATACACCCTGAATTTTGAGGCAGCTCAGAAG |
| GCCTGCTTGGATGTGGGCGCCGTGATTGCAACGCCTGAGCAACTGTTCGCC |
| GCCTACGAAGATGGATTCGAGCAGTGTGACGCAGGATGGCTGGCCGATCAG |
| ACCCTTCGGTACCCTATCAGAGCTCCCCGAGTAGGGTGCTATGGCGATAAA |
| ATGGGCAAGGCTGGCGTGAGGACCTACGGCTTCAGGTCACCTCAGGAAACC |
| TATGACGTGTACTGTTATGTGGACCACTTGGATGGCGATGTCTTTCATCTC |
| ACGGTCCCCTCTAAATTTACGTTCGAAGAAGCGGCCAAGGAGTGCGAGAAT |
| CAGGACGCCAGGCTGGCAACTGTGGGAGAACTGCAGGCTGCCTGGCGCAAT |
| GGGTTCGACCAGTGCGATTATGGGTGGCTGAGTGACGCTTCTGTCCGCCAT |
| CCCGTTACCGTCGCTAGGGCGCAATGCGGTGGAGGACTTCTGGGCGTTAGA |
| ACCCTCTATCGCTTTGAGAATCAGACTGGGTTTCCGCCACCAGATTGTCGG |
| TTCGATGCGTATTGCTTCAAACGTCCCGACCGTTGTAAGATGAACCCATGC |
| CTTAACGGCGGAACCTGTTACCCAACAGAAACGAGCTATGTTTGCACCTGT |
| GTGCCCGGGTACTCAGGCGACCAGTGTGAACTGGACTTTGACGAATGCCAC |
| TCTAATCCGTGCAGAAATGGCGCTACGTGCGTGGACGGGTTCAACACTTTC |
| CGATGTCTGTGTCTGCCTAGCTACGTCGGGGCACTGTGCGAGCAGGATACC |
| GAAACCTGTGATTACGGGTGGCACAAGTTTCAGGGTCAGTGCTACAAGTAC |
| TTTGCGCATAGAAGAACATGGGATGCCGCAGAGCGAGAGTGTAGGCTGCAA |
| GGGGCTCATCTGACATCCATCCTTAGCCATGAGGAACAAATGTTTGTCAAC |
| AGAGTTGGCCACGACTATCAATGGATCGGCTTGAATGACAAGATGTTCGAG |
| CACGACTTCAGGTGGACAGACGGCTCCAGCCTCCAGTACGAGAACTGGAGG |
| CCTAATCAGCCCGACAGCTTCTTCAGTGCAGGAGAGGATTGCGTAGTCATA |
| ATCTGGCACGAAAACGGTCAGTGGAACGATGTGCCATGCAACTATCATCTG |
| ACCTACACATGCAAGAAAGGTACTGTGGCCTGTGGCCAACCTCCTGTCGTG |
| GAGAATGCCAAAACATTTGGTAAGATGAAACCCAGGTACGAGATTAACTCC |
| CTTATTCGCTACCACTGTAAGGATGGTTTCATTCAACGGCATCTGCCCACT |
| ATTCGGTGCCTGGGAAATGGGCGGTGGGCAATTCCGAAGATAACCTGTATG |
| AACCCCTCTGCTTACCAGCGAACCTACTCCATGAAGTACTTCAAGAACTCC |
| AGTTCAGCTAAAGACAATAGCATCAACACTTCAAAACACGATCATCGCTGG |
| AGCCGGCGGTGGCAGGAAAGCAGACGGTATCCTTATGACGTGCCTGATTAC |
| GCTTGGAGCCACCCCCAGTTCGAGAAGGGTGGAGGTTCTGGCGGTGGATCG |
| GGAGGTTCAGCGTGGAGCCACCCGCAGTTCGAGAAA | rhV3 sequence must be placed downstream of fluorescent proteins in a bicistronic system: Bicistronic expression of proteins can also be achieved using a viral 2A self-cleaving peptide element. Since the IRES appeared non-functional in our previous construct, subsequent lentiviral constructs were generated to contain either a T2A or P2A element as well as the UCOE element. HEK cells were successfully transduced with a vector in which green fluorescent protein (GFP) was placed upstream and the HA-tagged hsoptV3 was placed downstream of the 2A element. Fluorescent protein, as well as secreted soluble rhV3, was successfully produced as visualized by immunohistochemistry (FIGS. 5A and 5B). Surprisingly, placing hsoptV3 upstream of the 2A peptide was not successful, resulting in lower-than-normal levels of GFP and extremely low levels of V3 expression. The reason for this positional specificity around the 2A peptide sequence is unknown.

In an effort to further enhance the amount of rhV3 made and secreted by the HEK cell cultures and to make purifying it more efficient, the pCVLU expression construct was further modified to include a matrix attachment region (MAR), which helps to localize the cDNA to the nuclear matrix where it facilitates the assembly of transcriptional machinery (Puttini, S., et al. (2013) MAR-mediated integration of plasmid vectors for in vivo gene transfer and regulation. *BMC Molecular Biology* 14, 26). The MAR element is followed by a stabilizing anti-repressor element (STAR) which has been shown to enhance protein expression levels (Kwaks, T. H., et al. (2003) Identification of anti-repressor elements that confer high and stable protein production in mammalian cells. *Nature Biotechnology* 21, 553-558). The signal peptide was also considered as a potential reason for the relatively moderate levels of V3 secretion. Analysis of the signal peptide sequence (SignalP 4.1) predicted it to be a relatively weak signal peptide, thus the native V3 signal peptide sequence was substituted with the highly efficient *Gaussia princeps* luciferase signal peptide (see Table 1) (Petersen, T. N., et al. (2011) SignalP 4.0: discriminating signal peptides from transmembrane regions. *Nature Methods* 8.785-786).

To aid in the isolation and purification of rhV3, a Twin-Strep-Tag® (Schmidt, T. G., et al. (2013) Development of the Twin-Strep-Tag® and its application for purification of recombinant proteins from cell culture supernatants. *Protein Expression and Purification* 92, 54-61) was added after the C-terminal HA-tag (FIGS. 6A and 6B). This allowed for the rapid isolation and purification of rhV3 directly from the HEK cell culture media into physiological buffers for use in tissue culture applications and further analysis. When adherent serum-requiring HEK cells were used for production, some albumin was detected in the isolate (FIG. 6A, lower band). Average yields ranged from 80-100 μg/L of conditioned media. The protein remained soluble for up to a week at 4° C. in buffers maintained at pH 8.0. However, freezing the isolates resulted in 75% loss to precipitation. In later experiments, HEK cells were adapted to serum-free, biotin-free suspension cultures to allow for greater scalability. Yields were further increased to 1-1.5 mg/L through use of PES membrane concentrators rather than nitrocellulose and streptactin-conjugated methacrylate beads instead of sepharose.

Elastin fiber networks are enhanced in cells exposed to rhV3 in vitro: The large CS-containing isoforms of versican accumulate in adult tissues in regions of injury and inflammation where they act to facilitate the infiltration of inflammatory cells and the disruption of elastin fiber networks. The proteases released by inflammatory cells break down existing elastin fibers, while the CS-chains of versican directly inhibit the interaction of newly synthesized tropoelastin with the elastin binding protein complex, thus preventing assembly of new elastin fibers. V3 overexpression in smooth muscle cells and dermal fibroblasts restores their ability to generate new, functional elastin fiber networks in part by reducing the expression of CS-containing versican. To determine if administration of rhV3 would have similar effects in vitro. Fischer rat smooth muscle cells (FRSMC) were cultured on tissue culture plastic coated with gelatin, impregnated with or without 5 μg/ml of rhV3, and in culture media supplemented with 0, 2.5, or 5 μg/ml rhV3. Cells were cultured for 2 weeks and given fresh media every 3 days without any additional rhV3. QPCR analysis of our cultures demonstrated a dose-dependent reduction in total versican expression (FIG. 7A), while expression of elastin and the microfibrillar molecules fibulin-5 and fibrillin-1 remained unaffected (FIGS. 7B-7D). Immunohistochemical analysis of elastin, however, clearly demonstrated a dose-dependent increase in elastin fiber network formation (FIGS. 7E-7H). This finding is consistent with gene overexpression studies, in which an increase in elastin message is not always observed, yet unfailingly enhanced elastin fiber network formation is found after 2 weeks of culture.

Soluble rhV3 dampens TLR3-stimulated inflammatory response: The inventors have shown that V3-expressing FRSMC exhibit dampened inflammatory response phenotypes via modulation of TGFβ and NFκB signaling. Therefore, it was investigated whether rhV3 would impart similar anti-inflammatory benefits. To investigate this, a previously published in vitro model was used in which a 24-h treatment of polyinosine-polycytidylic acid (poly I:C), a Toll-like receptor (TLR3) agonist, was used to stimulate an immune response in murine lung fibroblasts (Kang. I., et al. (2017) Versican deficiency significantly reduces lung inflammatory response induced by polyinosine-polycytidylic acid stimulation. *J Biol Chem* 292, 51-63). When cells were treated with 5 μg/ml of rhV3 for the same 24-h period, we did not observe a significant impact on versican expression (FIG. 8A), however rhV3 treatment significantly dampened the expression of the chemokine CCL2 and cytokines IL1β and TNFα (FIGS. 8B-8D respectively), demonstrating that the recombinant protein has similar anti-inflammatory properties in vitro as gene overexpression. These properties support the development of rhV3 as an anti-inflammatory therapeutic.

Secreted soluble rhV3 deposited onto surfaces inhibits monocyte adhesion: One of the surprising findings and potentially useful properties of secreted rhV3 is the observation that it coats tissue culture and other surfaces (see FIG. 6B, last lane). Although direct cellular deposition of rhV3 generates the most V3-rich ECM coatings, isolated rhV3 added back to culture media will evenly coat surfaces as well. Interestingly, HEK cells that deposit an rhV3-rich ECM coating on the tissue culture plate, subsequently avoid growing on that surface (FIG. 8E). This led to an inquiry of whether rhV3-coated surfaces might enhance the anti-inflammatory potential of this molecule by inhibiting inflammatory cell adhesion. Although it was demonstrated that rhV3 acted directly in cells to dampen their response to pro-inflammatory agonists, the role of rhV3 as an independent anti-adhesive molecule was not previously contemplated. Indeed, surfaces coated with 5 μg/ml rhV3 showed significantly less U937 monocyte/macrophage adhesion than surfaces coated with an equivalent amount of full length versican (V0V1) (FIG. 8F).

Taken together, these data show that rhV3 protein is functional and capable of recapitulating the biological effects previously observed in conditions where V3 was overexpressed. Use of this protein as a therapeutic represents a novel approach to promote elastic fiber network integrity while simultaneously dampening inflammation in damaged and diseased tissues where versican is a major contributor to pathogenesis. This establishes utility of rhV3 for use as a protein-based biologic that, like antibody-based treatments, is expected to be of sufficient molecular weight to prolong systemic residence times and to have favorable pharmacokinetics.

Materials and Methods:

Bacterial Expression System: Human V3 cDNA with C-terminal HA and pHis tags was cloned into the pGEX 4T1 (Pharmacia) bacterial expression vector to express V3 as a C-terminal fusion with GST (GST-HuV3-HApHis), and a thrombin cleavage site to remove the N-terminal GST moiety from the recombinant fusion protein. Under standard induction conditions. BL21 (IPTG-inducible strain containing T7 RNAP (DE3) (ThermoFisher)) competent *E. coli* transformed with the expression vector produced significant amounts of rhV3.

Coomassie Staining and Western Blotting: Cells were lysed in Laemmle buffer containing 100 mM DTT or 5% β-mercaptoethanol and separated on 10% SDS-PAGE gels. For Coomassie staining, gels were incubated in 0.1% Coomassie Blue R250 in 10% acetic acid and 50% methanol. Gels were destained in water, air dried and digitally imaged. For western blotting, gels were transferred to 0.22 μm nitrocellulose, membranes were blocked with 1% fish serum in TBST (Tris-Buffered Saline Tween-20, pH 7.4) and incubated at 4° C. overnight with primary antibodies, including polyclonal rabbit anti-hemagglutinin-tag antibody (1:3000; Sigma Aldrich), polyclonal goat anti GFP (1:3000; Novus Biologicals), and a custom, specific chicken anti-V3 raised against bacterial recombinant V3. Membranes were washed three times in TBST and incubated with fluorescently-labeled secondary antibodies (1:20,000; Li-Cor Biosystems) for 1 h. Membranes were washed again and scanned in a Li-Cor Odyssey CLx.

Plant Expression System: The V3 sequence cloned into Agrenvec's proprietary viral expression system contained the core protein of 641aa (21-655 aa) plus a 6-histidine tag at N-terminal where the signal peptide was removed. *Nicotiana benthamiana* plants were then inoculated with V3 viral expression clones and which were allowed to infect the plants for up to 10 days. Total protein was extracted from 0.5-1 kg of plant tissue and the soluble fraction was collected over nickel affinity resin. Protein was run on SDS-PAGE gels and stained with Coomassie or transferred to nitrocellulose for western blotting. Blots were incubated with antibodies against versican (AAH50524.1, 1 aa~354 aa full-length human protein-Abnova) and an anti-histidine antibody (6×His Monoclonal Antibody, Clontech).

HEK Cell Culture: HEK293 cells were purchased from ATCC (ATCC® CRL 1573™). HEK293LTV cells were purchased from Cell Biolabs, Inc. (LTV-100). Both cell types were maintained under standard culture conditions in DMEM 10% (DMEM high glucose supplemented with non-essential amino acids, Gluta-MAX, pen-strep antibiotics (Thermo Fisher) and 10% v/v fetal bovine serum (FBS; Atlanta Biologicals).

Transient Mammalian HEK Cell Expression System: Human V3 sequence (NM_001126336.2) with C-terminal HA and pHis tags were cloned into the pCEP-Pu (31) vector (huV3-HApHis) and the vector used to transfect HEK cells. After puromycin selection, cells were grown to confluence, 72 h HEK cell conditioned media was collected and cell layer detergent extracts were prepared and clarified by centrifugation.

Lentiviral Transfection: HEK293LTV cells were transfected with 25 kDa PEI-based transfection reagent (made in-house) and a mixture of the transfer vector, psPAX2 and pMD2G at a ratio of 3:2:1. Transfected cells were cultured in DMEM 10% supplemented with 8 mM butyrate overnight (~16 h), and then cultured further in DMEM 10% (DMEM with 10% fetal bovine serum, penicillin/streptomycin, non-essential amino acids, sodium pyruvate and GlutaMax™) with 1 mM butyrate for an additional 24 h. The virus-containing conditioned media was harvested and cells and debris were removed by centrifugation. Virus was concentrated by centrifugation at 13,000×g through a 10% sucrose cushion for 4 h and transferred to target cultures of 50% confluent HEK293 cells in DMEM 10% supplemented with 1 mg/ml Synperonic F-108 and 5 µg/ml DEAE-dextran for 6-12 h. Cultures were fed with DMEM 10% and cultured until near confluent at which time cells were sorted for high expression of GFP to enrich the cultures for V3-expressing cells. Gentamicin (Thermo Fisher; 10 µg/ml) was added to sorted cell cultures to reduce possibility of bacterial contamination during the sorting process.

Isolation of rhV3 using Twin-Strep-Tag® system: Adherent HEK cells transduced with the #15 lentiviral vector expressing rhV3 containing both HA and Twin-Strep® tags were cultured for up to 48 h in 0.1% FBS DMEM. The conditioned media was collected, protease inhibitors were added and the pH was adjusted to 8.0, after which the media was centrifuged to remove cell debris. Media was stored short-term, up to a week, at 4° C. or frozen at −20° C. for later use. Strep-Tactin® Super Flow resin (iba) was used to isolate the rhV3 according to manufacturer's directions. When the rhV3 was to be used in cell culture experiments, rhV3 was eluted directly into phenol red-free DMEM containing 2.5 mM desthiobiotin at pH 8.0. Isolated rhV3 remained soluble for up to a week at 4° C.

Gene Expression Analysis: Cultured cell monolayers were lysed in 0.5 ml Trizol followed by the addition of 0.1 ml chloroform and vigorous mixing. The solution was incubated at room temperature for 5 min and spun at 14,000 RPM for 10 min at 4° C. The aqueous phase was collected, mixed with equal volume of 70% ethanol, and purified using EconoSpin™ columns (Epoch Life Science). cDNA was prepared from the isolated RNA with a High Capacity cDNA Reverse Transcription Kit (Life Technologies) according to manufacturer's instructions. Real-time PCR was carried out with SYBR Select Master Mix or TaqMan® Gene Expression Master Mix (Life Technologies), as directed by the manufacturer, on an Applied Biosystems 7900HT Fast Real-Time PCR System. For each sample, assays were run as technical duplicates. cDNA levels were then expressed as estimated copy numbers of mRNA using the master-template approach (32). TaqMan® and SYBR® primer information is listed in Table 2.

TABLE 2 qPCR primer sequences.

| Target | Primer Type | RefSeq ID | Sequence |
|---|---|---|---|
| 18S rRNA | TaqMan ® | | 4319413E-1403063 |
| V3 Versican Isoform | SYBR | NM_001126336.2 | F: CAGGCTTCCCTCCCCCTGATAGC<br>R: GCTGTATCCTGGCACACAGGTGC |
| Total Versican | TaqMan ® | | Mm01283063_m1 |
| Elastin | TaqMan ® | | Rn01499783_m1 |
| Fibulin-5 | TaqMan ® | | Mm01336252_m1 |
| Fibrilin-1 | TaqMan ® | | Rn00582774_m1 |
| CCL2 | SYBR | NM_011333.3 | F: TGCAGGTCCCTGTCATGCTT<br>R: GAATGAGTAGCAGCAGGTGAGT |
| CXCL1 | SYBR | NM_008176.3 | F: AACCGAAGTCATAGCCACAC<br>R: TTTCTCCGTTACTTGGGGACA |
| TNFα | TaqMan ® | | Mm00443258_m1 |

Immunohistochemistry: HEK cells were grown on glass coverslips and then fixed with neutral buffered formalin (NBF) for 10 min at room temperature. Cells were washed with Tris-buffered saline containing 0.02% Tween 20 (TBST), blocked with 10% AquaBlock (EastCoast Bio. Inc.) in TBST for 1 h at room temperature and stained with a polyclonal rabbit anti-HA-tag antibody (1:1000; Sigma Aldrich) and mouse anti-GFP (1:1000; Abcam) overnight at 4° C. Alexa fluor-labeled secondary antibodies were obtained from Life Technologies and used at 1:400. Nuclei were labeled with DAPI (ThermoFisher). In other studies, FRSMC were grown on gelatin-coated glass coverslips and then fixed with 10% formalin, 70% ethanol, and 5% acetic acid for 10 min at room temperature, washed with PBS, and incubated in 10% AquaBlock in TBST for 1 h. Fixed coverslips were stained for tropoelastin (1:1000; rabbit polyclonal, a kind gift from Dr. Robert Mechan (St. Louis, MO)). All fluorescence imaging was carried out using a Leica DMIRB inverted microscope and a SPOT 5 digital camera.

Lung Fibroblast Isolation from Mice: C57Bl/6J mice at 10-12 weeks of age were deeply anesthetized with IP injection of tribromoethanol (500 mg/kg) and sacrificed by cardiac exsanguination. Lung fibroblasts were explanted from the minced lung tissues dissected from the animals in DMEM culture media supplemented with 20% FBS, GlutaMAX, sodium pyruvate, penicillin-streptomycin, and antibiotic/antimycotic (Gibco, ThermoFisher Scientific). All cells were used up to passage 4.

Poly I:C Stimulation of Murine Lung Fibroblasts: Isolated lung fibroblasts were plated on tissue culture plates at 2.0×10/cm² density for 24 h, growth arrested in low serum culture media supplemented with 0.1% FBS for 48 h, and treated with or without 40 μg/ml poly I:C and/or 5 μg/ml rhV3 in culture media containing 10% FBS for 24 h. Monolayers were then harvested for RNA isolation and gene expression analysis as described above.

Monocyte Adhesion Assay: Wells of a 96-well tissue culture plate were coated with 36 μl of either 1 or 5 μg/ml full-length purified bovine versican (V0/V1) or purified rhV3 diluted in PBS, or PBS alone. Plates were incubated at 4° C. overnight and then allowed to air-dry overnight at room temperature in sterile conditions. The human monocytic cells, U937 (ATCC) labeled with 300 nM MitoTracker™ Red (Invitrogen) for 45 min, were added to the wells allowed to bind for 60 min on ice. Non-bound monocytic cells were removed by washing with cold PBS. Monocyte binding was measured by exciting the fluorophore at 579 nm and reading absorbance at 599 nm using an EnSpire® MultiMode Plate Reader (Perkin Elmer) is presented in arbitrary fluorescence units.

Study 2: "The Synthesis and Secretion of Versican Isoform V3 by Mammalian Cells: A Role for N-linked Glycosylation."

Introduction:

Detection of V3 protein in tissues or cells has been a challenge due to the lack of an antibody that specifically recognizes V3 and not the other isoforms. Secretion of V3 protein by primary human skeletal muscle cells was recently detected by proteomic analysis. Also, some success has been achieved in localizing V3 in tissues, such as in the myocardium proximal to the outflow track in developing heart using tagged primer constructs in forced expression systems. Other studies have demonstrated that expression of V3 can have prominent effects on the proliferation and migration of different cell types such as chondrocytes, arterial SMCs, fibroblasts, melanoma cells, and fibrosarcoma cells. One particularly impressive consequence of expressing V3 in a variety of cells is dramatic ECM remodeling, including promoting the synthesis of tropoelastin and the assembly of elastic fibers. Additionally, several point mutations in a splice acceptor site of the VCAN gene have been identified as the cause of erosive vitreoretinopathy and Wagner disease. The most often detected exon 7 point mutation, 1Z8861540309529236c.4004-5T→C, results in an imbalance of versican splice variants in the eye, with a strong expression of V2 and V3 and an insufficiency in expression of V0 and V1, indicating possible involvement of V3 in this disease.

While there is abundant information on the expression and accumulation of the CS-containing isoforms of versican, little is known about the V3 isoform. Therefore, in this study, the synthesis, secretion, and processing of V3 in a mammalian in vitro system is explored. Using lentiviral generation of doxycycline (Dox)-inducible V3 in stable NIH 3T3 cell lines, it is demonstrated that V3 is secreted through the classical secretory pathway and uses N-linked glycosylation to establish efficient secretion and maintain solubility. The sites of N-linked glycosylation are determined and exons 11-13 (see FIG. 10A for exon/domain map of V3) are established as critical for V3 secretion. Once outside the cell, V3 associates with HA present at the surface of the cell, as well as within the surrounding ECM. These results establish critical parameters for processing, solubility, and targeting of this versican isoform and enhance the ability to use this enigmatic form of versican as a therapeutic.

Results:

V3 is Secreted Through the Classical Secretory Pathway

Figures 10A, 10B, 10C, 10D:
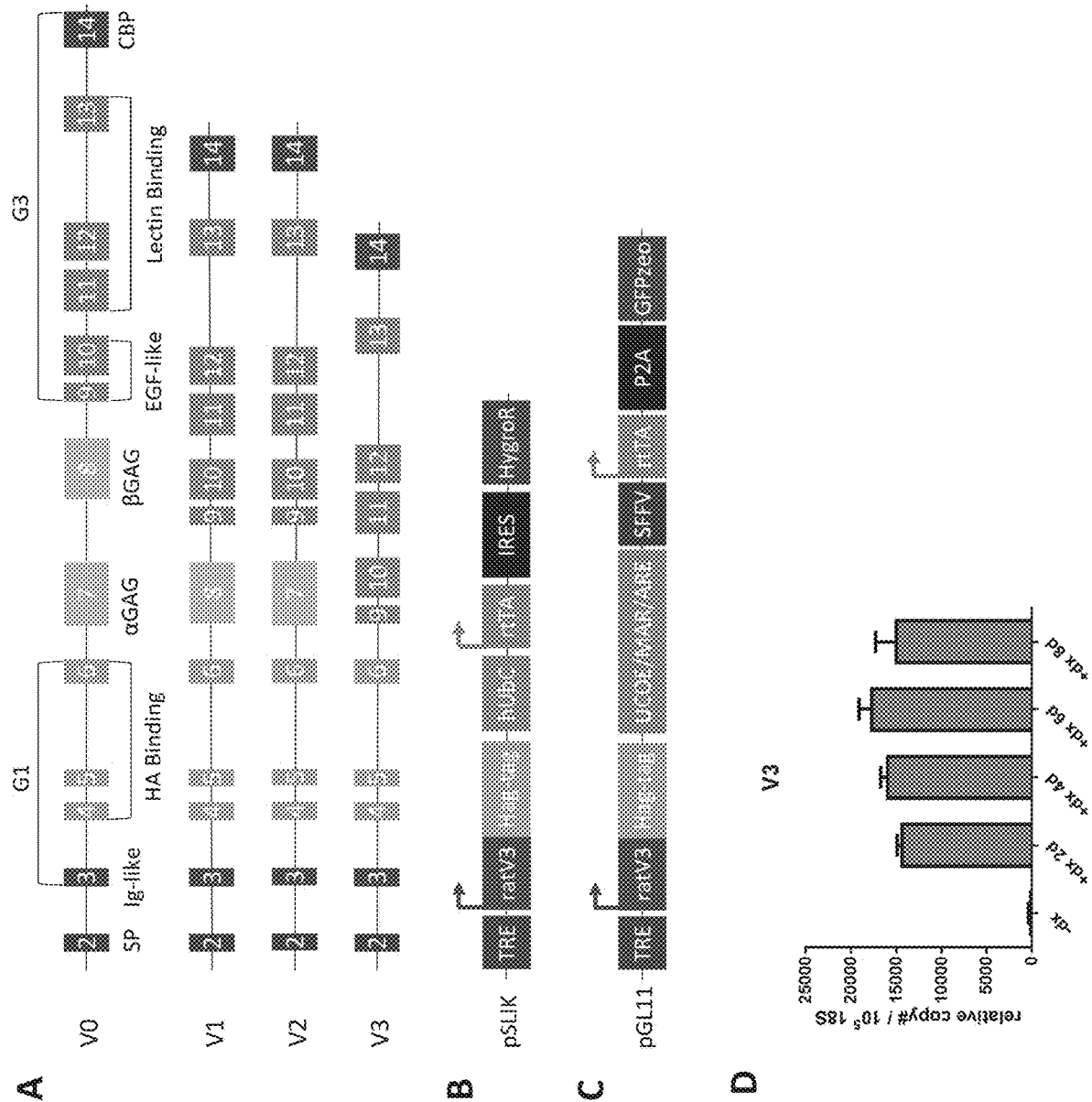
FIGS. 10A-10D illustrate the structure of the domain structure of the major isoforms of versican and lentiviral transfer plasmids used to generate stable cell lines with doxycycline-inducible V3 expression.

Although it has been speculated that V3 is secreted in a similar manner as the larger versican splice variants V0, V1, and V2, V3 has never been specifically identified in the extracellular space, except when using tagged V3 expression systems. This is, in part, due to its low expression level under normal conditions and a lack of effective immunohistochemistry (IHC) tools to detect native V3 in cells and tissues. Therefore, to specifically determine the synthesis and secretion kinetics as well as the cellular localization of V3, a stable cell line which overexpresses V3 was generated. Previous attempts to create stable cell lines constitutively expressing V3 driven by viral (CMV, SFFV) or mammalian (EF-1 alpha) promoters using lentiviral transduction were unsuccessful. After strong initial expression and selection for the respective antibiotic resistance, the polyclonal lines showed a rapid loss of V3 expression even under persistent and stringent selection pressure resulting in almost undetectable protein levels after two to three weeks (data not shown). Therefore, a tetracycline-inducible expression systems with constitutive co-expression of the selection markers hygromycin (Hygro) or GFP-Zeocin fusion protein (GFPzeo) were used to establish stable cell lines (pSLIK-Hygro or PGL11-GFPzeo). NIH 3T3 fibroblasts were transduced with pSLIK-rV3-Hygro (FIG. 10B) or pGL11-rV3-GFPzeo (FIG. 10C) and were induced to express c-terminal hemagglutinin-tagged V3 with 500 ng/ml Dox for 48 h. Consistent levels of V3 mRNA were apparent up to 8 days after each induction with Dox (FIG. 10D).

In order to determine whether V3 is secreted through the classical secretory pathway. V3-expressing cells were treated with Brefeldin A (BrefA). BrefA inhibits protein transport from the endoplasmic reticulum (ER) to the Golgi indirectly by preventing the formation of COPII-mediated transport vesicles, thereby preventing the movement of secretory proteins out of the ER. In this study, cells were treated with or without addition of 50 μM BrefA. Secretion of V3 into the culture medium was detected via western blotting using an antibody directed against the c-terminal hemagglutinin tag (FIGS. 11A-11F). As expected, when the cells were induced with Dox alone, V3 could be detected (FIG. 11A), however treatment of Dox-induced cells with BrefA inhibited the secretion of V3 into the culture medium. No V3 was secreted in the absence of Dox.

Figures 11A, 11B, 11C, 11D, 11E, 11F:
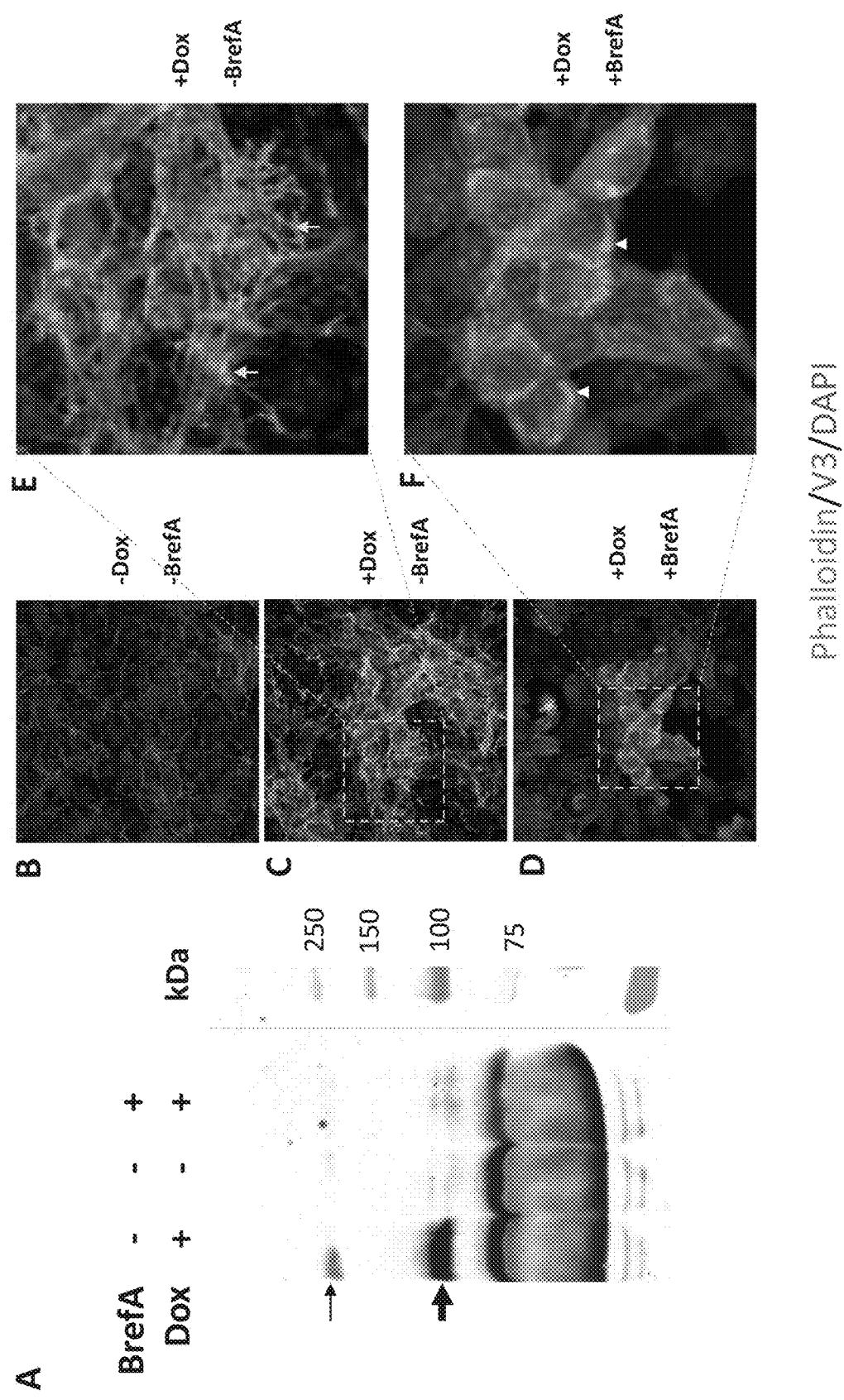
FIGS. 11A-11F illustrate that V3 is secreted into the culture medium through the classical secretion pathway.

These results were confirmed by IHC using the same antibody against the c-terminal hemagglutinin tag (FIG. 11B-F). NIH 3T3 cells were grown on glass coverslips and treated with Dox and BrefA, as described above. The cells were then probed for hemagglutinin-tagged V3 (orange) and F-actin (green), and the nuclei were counterstained (blue). The untreated cells showed no positive staining for V3 (FIG. 11B), whereas the Dox-induced cells showed a strong extracellular staining of secreted V3 (FIGS. 11C and 11E). This prominent extracellular V3 staining could not be observed in the BrefA-treated cells, where positive V3 staining could only be detected in vesicular intracellular regions, suggesting retention in the ER/Golgi (FIGS. 11D and 11F). These results support the conclusion that V3 similar to other versican splice variants, is secreted via the classical secretory pathway into the extracellular space.

G3 Domain Contains Critical Elements for V3 Expression and Secretion

Figures 12A, 12B, 12C:
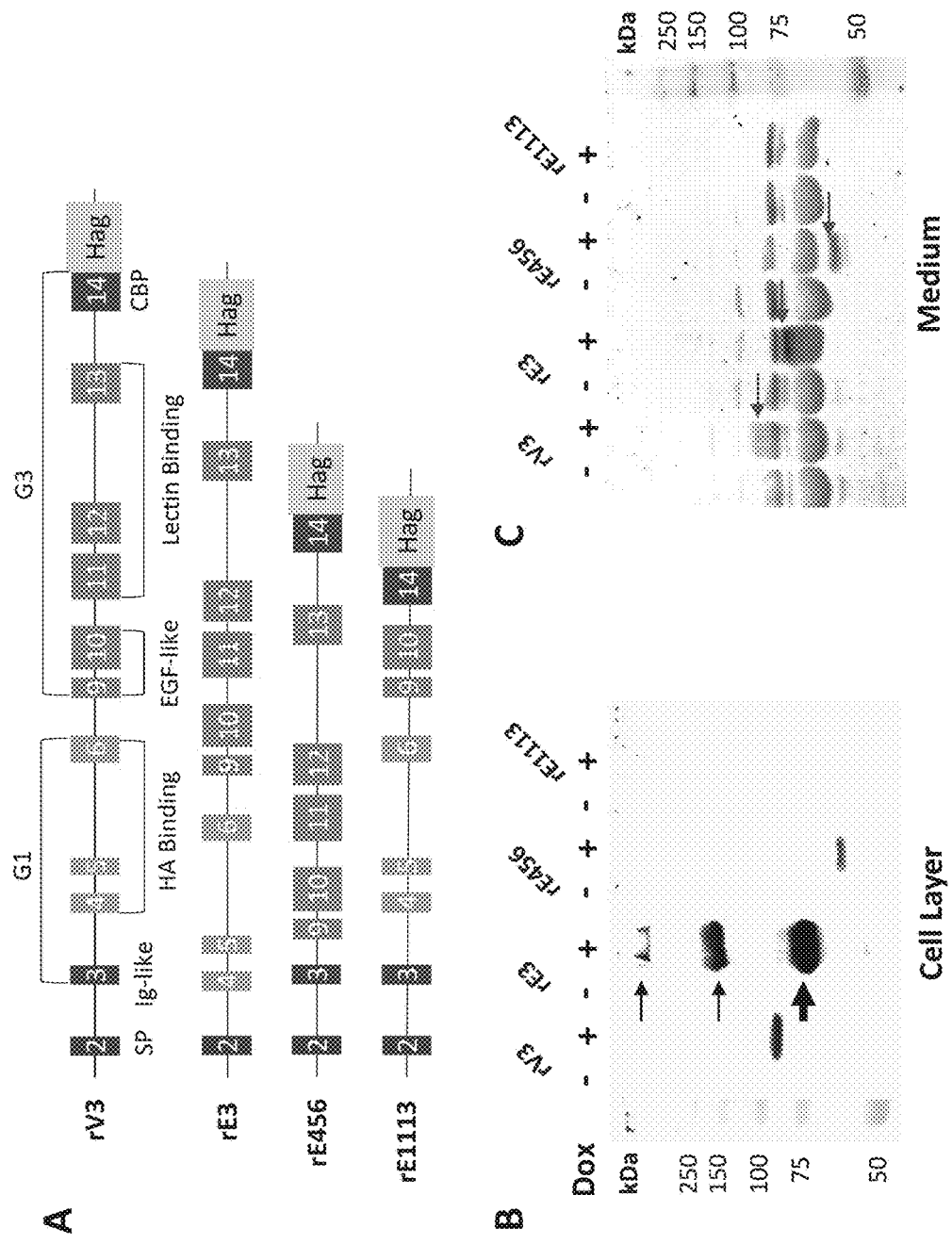
FIGS. 12A-12C illustrate that exon deletion mutants highlight G3 domain as being critical for expression and secretion.

To determine which exons are critical for generating soluble, secreted V3 in stable NIH 3T3 cell lines, different exon-deletion mutants expressed using the same Dox-inducible lentiviral system were tested as described above for native, full-length V3, including the addition of the c-terminal hemagglutinin tag for detection. The mutants generated by site-directed mutagenesis of native V3 contained deletions of exon 3 (rE3), exons 4-6 (rE456), and exons 11-13 (rE1113) (FIG. 12A) and expressed similar levels of mRNA under Dox-induced conditions (not shown). As anticipated, native V3 was expressed in the cell layer and the conditioned media, as were mutants rE3 and rE456 (FIGS. 12B and 12C). Only rE1113 failed to express any V3, indicating that these exons, as part of the G3 domain of the molecule, contain critical elements for successful V3 expression and secretion.

V3 is N-Glycosylated

Figure 13:
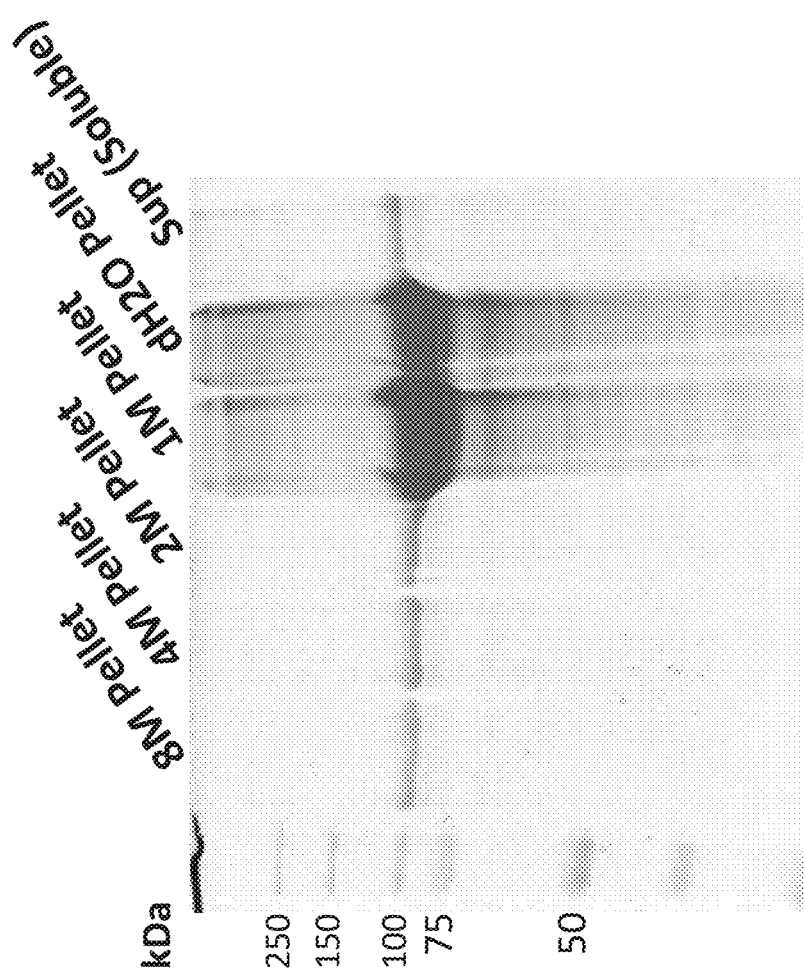
FIG. 13 illustrates that bacterial V3 is insoluble. An aliquot of TALON-isolated recombinant GST-V3 fusion protein containing c-terminal hemagglutinin and His tags from solubilized bacterial inclusion bodies was sequentially dialyzed from 6M GdnHCl dissociative elution buffer in 8 M, 4M, 2M and 1M urea buffer, and then in PBS. Prior to each dialysis change, insoluble protein was collected by centrifugation (pellet) and run on SDS-PAGE gel with the final supernatant (sol). Note that virtually all V3 was present in insoluble pellets, with little recombinant protein remaining in the soluble fraction.

Since the lack of glycosaminoglycan (GAG) side chains does not affect either secretion or solubility of V3, the glycosylation status of V3 was addressed. Attempts to express V3 in a bacterial system in which proteins are not glycosylated resulted in the production of a completely insoluble product located exclusively in the inclusion bodies (FIG. 13). This led to question whether V3, previously thought to be non-glycosylated, was in fact glycosylated and whether such modification was necessary for solubility and secretion.

Figures 14A, 14B:
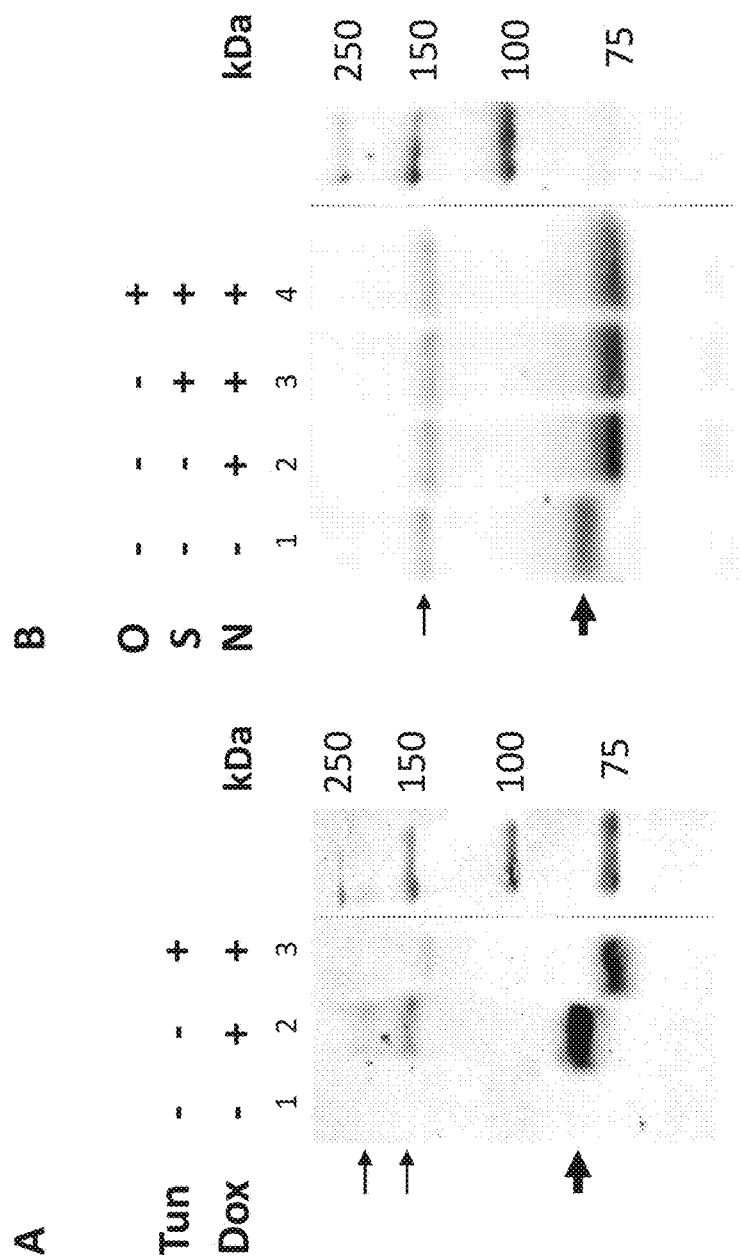
FIGS. 14A and 14B illustrate that V3 is N-glycosylated.

In order to test if V3 is N-glycosylated, tunicamycin (Tun) was used to block the N-glycosylation during V3 synthesis. Tun inhibits, among others, the enzyme GlcNAc phosphotransferase, which catalyzes the transfer of N-acetylglucosamine-1-phosphate from UDP-N-acetylglucosamine to dolichol phosphate in the first step of glycoprotein synthesis. In this experiment, V3 expression was induced in V3-transduced NIH 3T3 fibroblasts by treatment with 500 ng/ml Dox for 48 h with or without addition of 10 µM Tun. Secretion of V3 into the culture medium was detected via western blotting with an antibody directed against the c-terminal hemagglutinin tag. Cells treated with Dox and Tun were found to express V3 at a lower molecular weight than seen by cells which were treated with Dox alone (FIG. 14A). Untreated cells without Dox or Tun showed no detectable V3 expression (FIG. 14A). These results indicate that V3 is N-glycosylated when expressed in a mammalian system.

Next, V3 was investigated for possible O-glycosylation. Cellular protein harvested from V3-expressing NIH 3T3 fibroblasts was subjected to enzymatic deglycosylation with PNGase F, sialidase, and O-glycanase for 24 h (FIG. 14B). Western blotting and antibody detection against the c-terminal hemagglutinin tag revealed that enzymatic removal of all N-glycosylation moieties with PNGase F reduces the V3 band by approximately 6 kDa compared to non-digested cell lysate from Dox-induced cells (FIG. 14B). No further shift in the V3 band size was detected after digestion with sialidase and O-glycanase in combination with PNGase F (FIG. 14B), indicating that V3 is exclusively N-glycosylated.

Glycosylation is not Essential for Secretion, but is Important for the Solubility of V3

Figures 15A, 15B, 15C, 15D:
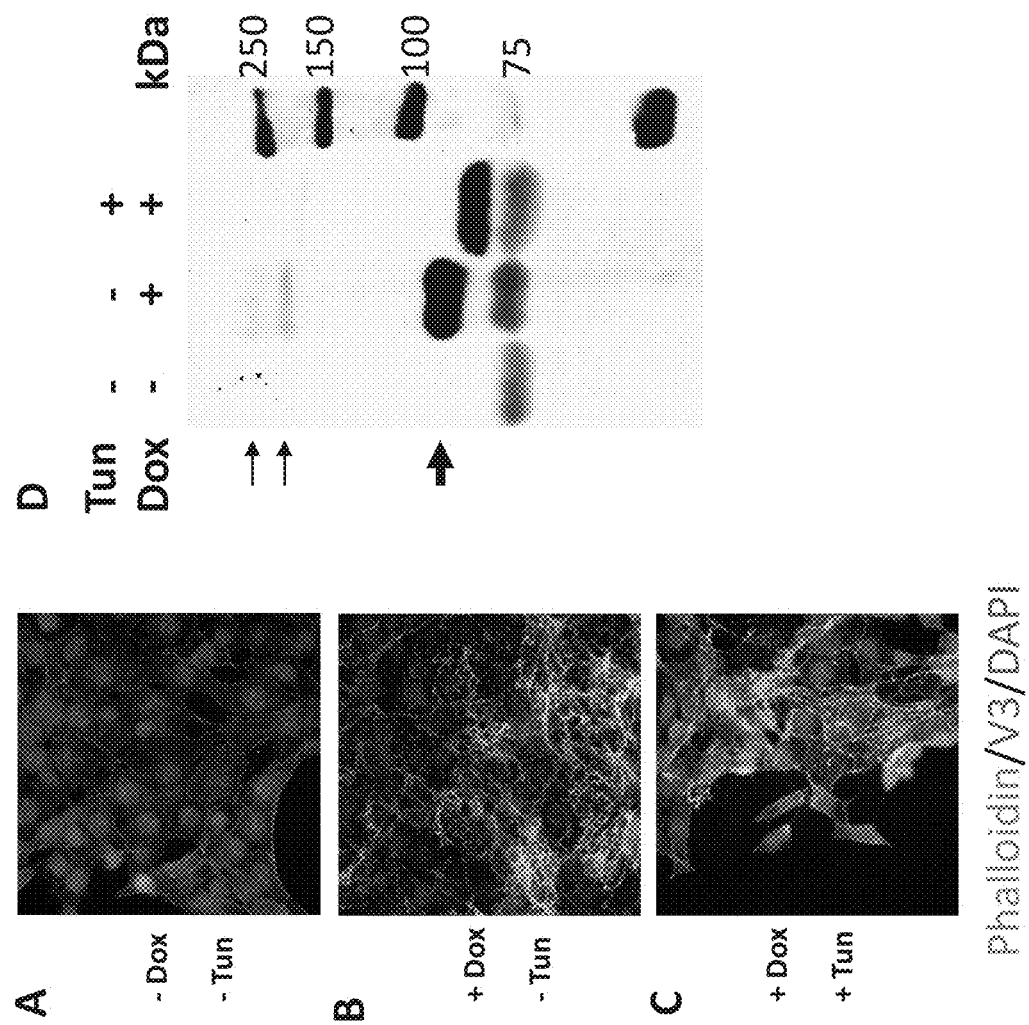
FIGS. 15A-15D illustrate that glycosylation is not necessary for secretion, but is important for the solubility of V3.

To directly determine if N-glycosylation affects the solubility of V3, NIH 3T3 cells grown on glass coverslips were induced to express V3 with 500 ng/ml Dox for 48 h with or without addition of 10 µM Tun to block N-glycosylation. Using an immunocytochemical approach, the cells were probed for hemagglutinin-tagged V3 (red), F-actin (green), and nuclei (blue) (FIGS. 15A-15C). Cells receiving Dox showed strong positive extracellular V3 staining (FIG. 14B). When the cells were treated with Dox and Tun (FIG. 15B), the extracellular staining pattern for V3 was minimally altered, suggesting that V3 was reaching the outside of the cell.

However, cells transduced with a lentivirus engineered to maximize secreted recombinant protein (FIG. 10C) still showed a slight 12% reduction in secreted V3 in the presence of Dox and Tun, compared to Dox alone, as measured by digital pixel densitometry of the western blot (FIG. 15D). These data indicate that N-glycosylation is not essential for extracellular targeting of V3, but does have an impact on the quantity of protein secreted from the cell, which could suggest an impact on protein stability and/or solubility.

Soluble V3 Expressed in Mammalian Cells Aggregates and Precipitates Over Time

Figures 16A, 16B:
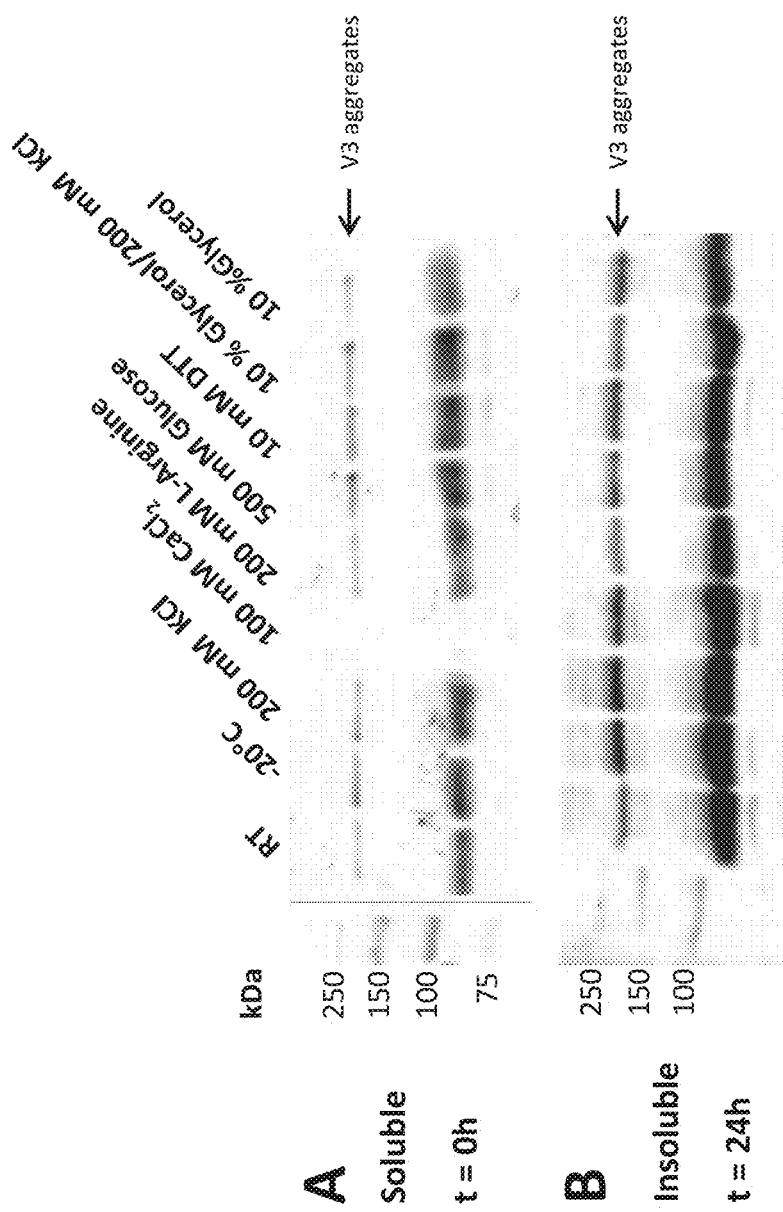
FIGS. 16A and 16B illustrate that V3 expressed in mammalian cells is initially soluble, but aggregates and precipitates over time. For FIG. 16A, V3 expressed in NIH 3T3 fibroblasts was harvested by homogenization of the cell layer in TBS. After centrifugation, the cleared supernatant was filtered through a 0.2 µm filter and the solution supplemented with various additives in an attempt to retard or prevent aggregation and precipitation of V3. Aliquots of supernatant were run in a 10% SDS-PAGE gel and blotted with an anti-hemagglutinin tag antibody to detect V3. For FIG. 16B, samples were stored for 24 h at the indicated temperatures and then centrifuged. Precipitates were solubilized in Laemmli sample buffer and again blotted and probed with anti-hemagglutinin tag. All lanes contained equivalent volumes of sample.

Although V3 from either conditioned media or cell lysates is initially soluble, we observed that over time (as early as 24 h) it becomes insoluble. Indeed, western blotting revealed the reproducible presence of high molecular weight, hemagglutinin-tag positive bands that correspond in size to aggregated multimers of V3 (FIG. 11A, small arrow). In an attempt to preserve the solubility of V3 when stored, a variety of additives commonly used to enhance solubility and prevent protein aggregation were tested (e.g., 10% glycerol or 10 mM DTT) in the same setting (FIGS. 16A and 16B). Lysates from Dox-induced NIH 3T3 cells were ultracentrifuged and the cleared supernatants were filtered and then supplemented with anti-aggregation additives. Samples were loaded in equal volumes onto an SDS-PAGE gel and V3 was detected by western blotting using an anti-hemagglutinin tag antibody (FIGS. 16A and 16B). An additional aliquot of each sample was stored for 24 h at either room temperature or at −20° C. with and without additives and V3 was visualized by western blotting the next day. Regardless of the additive used, all samples exhibited marked aggregation and precipitation after 24 h of storage. These results indicate that V3 has a natural tendency towards aggregation and insolubility. This characteristic represents a major challenge for the successful purification of recombinant V3.

Native V3 is N-Glycosylated at Amino Acids 57 and 330 in the G1 Domain

Figure 17:
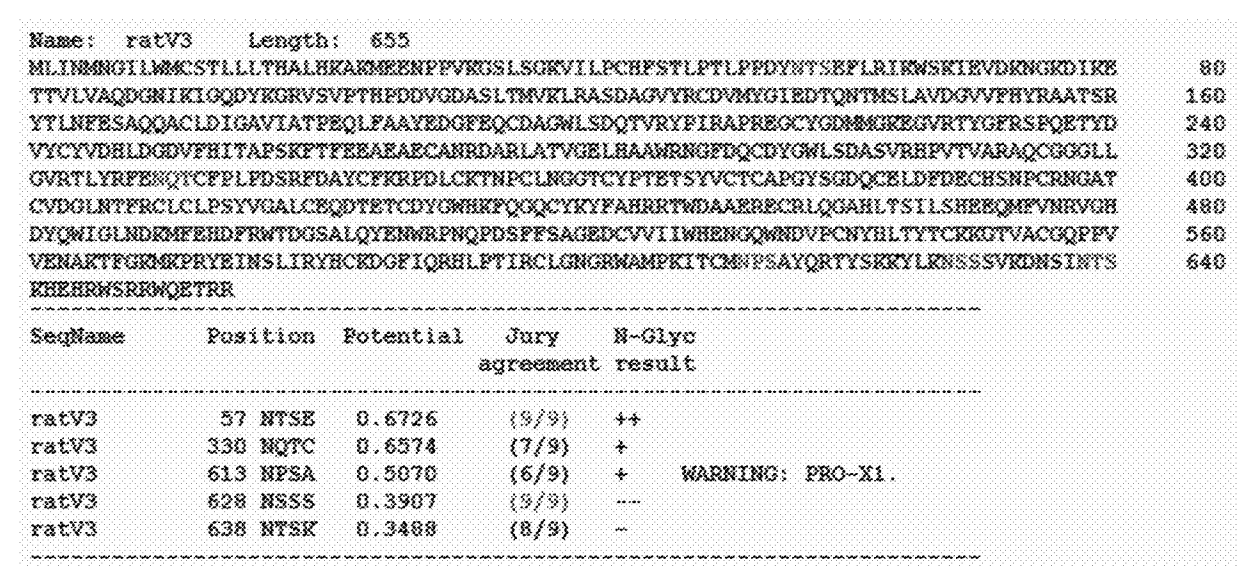

As the Tun treatment of the cells revealed that V3 is N-glycosylated, the exact location of the glycosylation sites was addressed. Sequence analysis of full-length rat V3 revealed that it contains a total of twelve possible N-glycosylation sites. Three of these sites, at amino acid (AA) positions 57, 330, and 613 relative to the initial methionine, were predicted to be potential N-glycosylation sites by NetNGlyc, a web-based N-glycosylation prediction algorithm (FIG. 17). Of these predicted attachment sites, only AA position 57 was expected to be glycosylated by two other prediction algorithms (GlycoEP and NGlycPred). To determine if AA position 57 is the only N-glycosylated attachment point, rat V3 was mutated at position 57 from an asparagine to a glutamine (N57Q) and expressed in Dox-inducible NIH 3T3 fibroblasts (FIG. 17). As a comparison, AA 330 was also mutated in the same fashion (N330Q).

Figure 18:
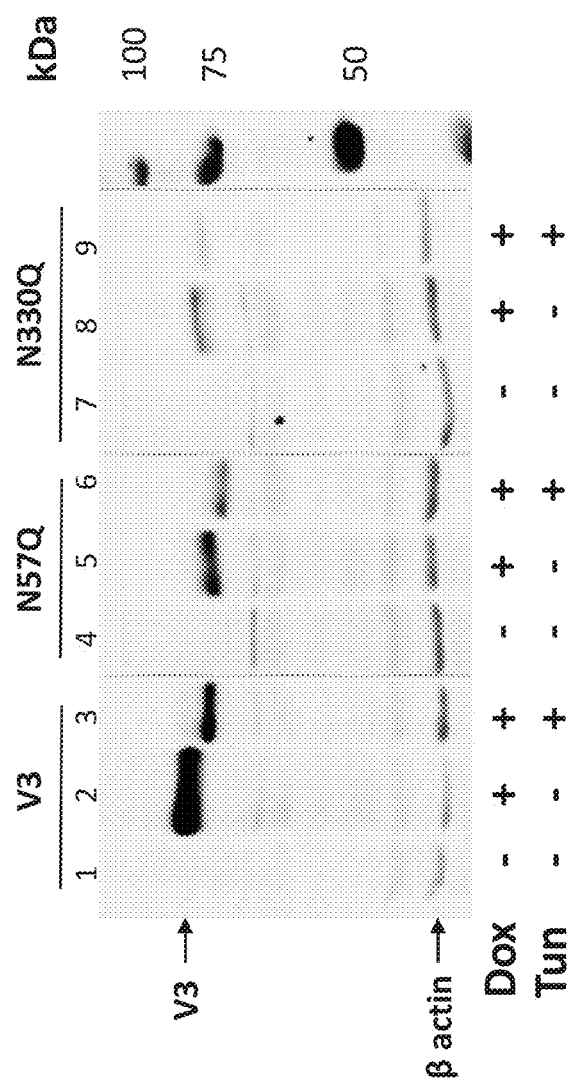
FIG. 18 illustrates that mutation of putative N-glycosylation sites in V3 prevents glycosylation. AA 57 in the Ig-like V-type domain and AA 330 in the Link 2 domain were mutated to glutamine (N57Q and N330Q, respectively) and expressed in a Dox-inducible fashion in NIH 3T3 fibroblasts. Apparent shift in molecular weight suggests correct identification of both N-glycosylation sites. V3+Dox and V3+Dox+Tun samples were diluted to ensure equal band intensity, as mutations in V3 resulted in marked reduction in protein expression compared to control.
Figures 19A, 19B:
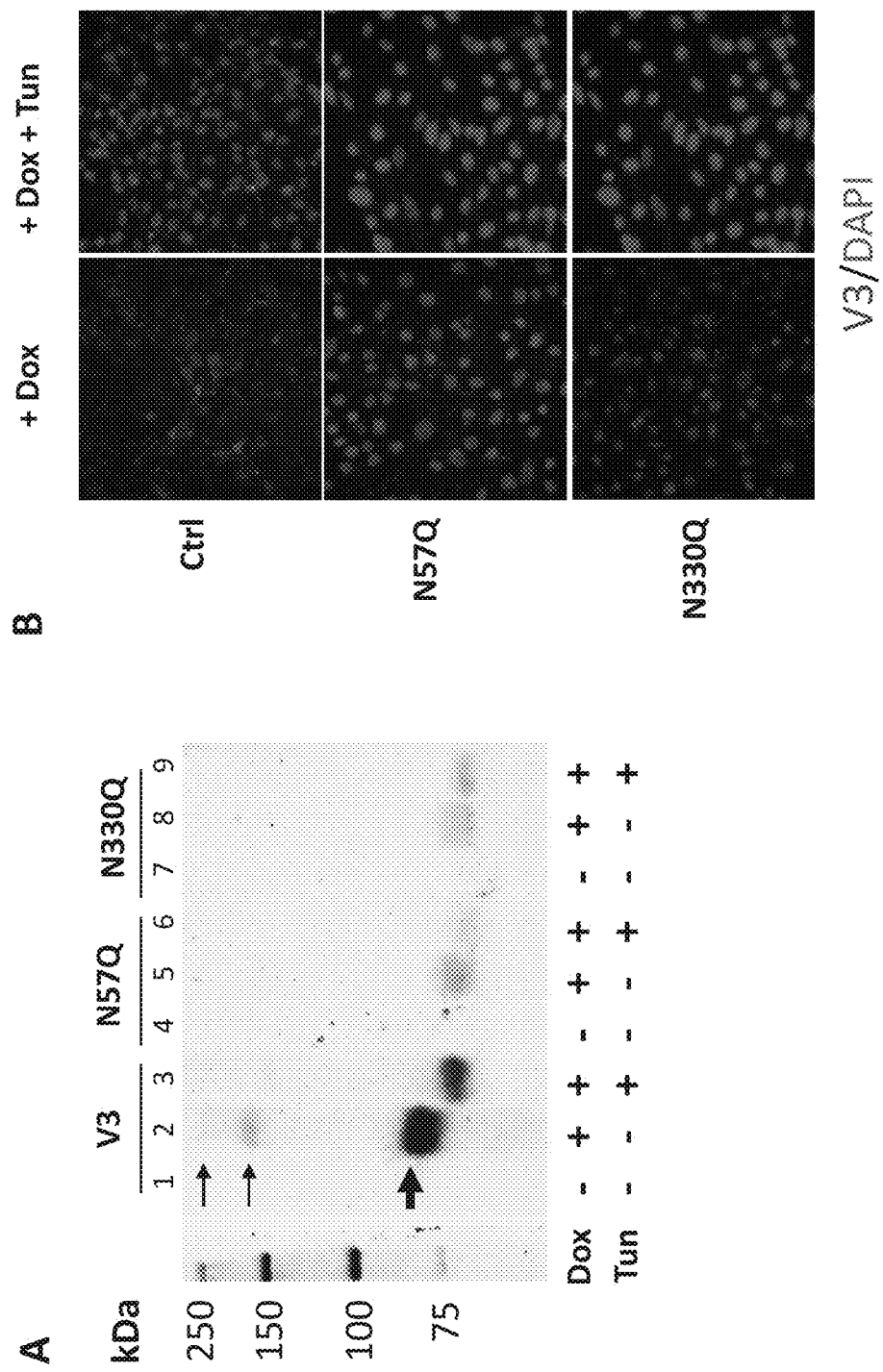
FIGS. 19A and 19B illustrate that loss of N-glycosylation at either site prevents secretion of V3.

When cell lysates were analyzed by western blotting, mutant N57Q ran at a lower apparent molecular weight compared to native V3, indicating that this is indeed an active N-glycosylation site (FIG. 17). Further treatment of the N57Q mutant with Tun resulted in a V3 band of even lower molecular weight, suggesting that V3 is glycosylated at more than just AA 57. Similar results were found with the N330Q V3 mutant, indicating that V3 is N-glycosylated at both sites. Total inhibition of glycosylation with Tun treatment resulted in a modest reduction in the production (1.8-5.3-fold; FIGS. 14A and 18) and secretion (0.12-1.9-fold; FIGS. 15D and 19A) of native V3 as measured by western blot densitometric analysis. However, in the absence of Tun treatment, even partial loss of N-glycosylation was able to reduce cellular production as well as secretion of V3. Cell lysates from N57Q and N330Q mutants displayed a reduction in overall V3 production (2.2- and 11.8-fold, respectively; FIG. 18, lanes 5 and 8), suggesting that N-glycosylation is important for protein stability during processing. Furthermore, western blotting demonstrated a marked reduction in soluble V3 in the conditioned media of the N57Q and N330Q mutant V3 cultures (10.2- and 37.6-fold, respectively; FIG. 19A, lanes 5 and 8). Dox-induced cells, grown on coverslips and probed for tagged V3 (red) clearly demonstrate this marked reduction in V3 production and secretion by the glycosylation mutants compared to native V3 (FIG. 19B), which manifested as reduced accumulation of V3 in the extracellular space. Further treatment with Tun for 24 h nearly abolished the presence of pericellular V3 in the glycosylation mutant cultures (FIG. 19A, lanes 6 and 9; and FIG. 19B, right panels). Taken together, these results demonstrate that V3 is N-glycosylated at multiple sites in its G1 domain and that proper glycosylation at these sites is necessary for maximal secretion of the protein into the ECM.

Expression of V3 Increases the Amount of Exogenous HA Bound to the Cell Surface

V3 has a G1 domain common to all versican splice variants, containing link domains that allow versican to bind hyaluronic acid (HA), which is an important process for ECM organization during development, inflammation, and disease progression. However, it is not known whether the G3 domain of V3 impacts its ability to bind HA.

In order to determine the binding capacity of V3 for HA, NIH 3T3 cells transduced with native V3 were grown on glass coverslips for 24 h in the presence or absence of Dox and incubated with high molecular weight HA (>106 250 kDa) labeled with fluorescein for an additional 24 h. In the absence of Dox, no positive staining for V3 (red) was detected, as expected, and the exogenous HA (green) was not retained in the pericellular ECM (FIG. 20A, C). In contrast, when the cells were treated with Dox to induce V3 expression, the pericellular ECM showed a bright, positive co-staining for V3 and HA confirming that the link domains in the G1 region of V3 retain their ability to bind and organize HA near the cell surface. Cells expressing N57Q glycosylation mutant V3, which secreted ~10-fold less V3, did not retain any more HA at the cell surface than the −Dox controls, which expressed no V3 (FIG. 20B, D), indicating that the quantity of secreted V3 had a direct impact on the ability of the cells to organize the exogenous HA in their pericellular ECM.

Discussion

In this study, lentiviral generation of Dox-inducible V3 with C-terminal hemagglutinin tag in NIH 3T3 stable cell lines was used to demonstrate that V3 travels through the classical secretory pathway to the extracellular space and uses N-linked glycosylation to establish efficient secretion and maintain solubility. By site directed mutagenesis, AA 57 and 330 were confirmed as active N-linked glycosylation sites in V3, demonstrating that loss of glycosylation at either site had deleterious effects on V3 secretion. Furthermore, exon deletion constructs revealed that exons 11-13, which are part of the G3 domain, were essential for V3 processing and secretion. Once outside the cell, V3 associates with HA along the cell membrane and within the ECM. These results establish critical parameters for proper processing, solubility, and targeting of this versican V3 isoform in mammalian cells.

Since V3 contains no CS chains, it should be considered a glycoprotein and not a proteoglycan (PG), however, it is commonly grouped with PGs and is characterized as such. RNA splicing occurs in the two large exons, 7 and 8, which encode the GAG attachment sites, giving rise to the distinct isoforms of versican. These variants differ in the length of the core proteins and number of attached GAGs. Regulation of versican core protein and CS synthesis can be at transcriptional or post-transcriptional levels and may involve similar or different signaling pathways regulating both core protein and CS synthesis of versican separately. The majority of studies have focused on the synthesis and secretion of the CS-carrying isoforms of versican, V0, V1, and V2. The fact that V3 contains no CS chains indicates that this isoform may function very differently in the ECM than the other isoforms. Little is known about the secretion and trafficking of V3.

The inventors have shown that V3 expression by a variety of cell types induces significant changes in cell phenotypes. For example, V3 expression significantly decreased proliferation of melanoma cells and cardiomyocytes and increased cell-cell association. In melanoma cells, this reduction in cell proliferation was partly due to the inhibition of EGF-dependent signaling pathways. In Splotch mice, which have mutations in the Pax3 gene, versican expression was associated with defective neural crest migration characterized by altered expression of V3. In chondrocytes, V3 expression reduced the expression of aggrecan, the principal PG present in cartilage. Expression of V3 in tumor cells in a fibrosarcoma tumor model inhibited tumor cell growth. Similarly, the inventors have shown that controlled expression of V3 alters phenotypes of fibroblasts and arterial SMCs such that cell growth and migration are reduced while cell adhesion is enhanced. Moreover. V3 expression in arterial SMCs induced a significant change in ECM composition, including a reduction of the larger isoforms of versican V0/V1, and HA, whereas elastic fiber deposition was greatly enhanced. Furthermore. V3-expressing arterial SMCs exhibited a reduced capacity to bind monocytes in vitro and in vivo, by altering TGFβ-, EGF-, and NFκB-dependent signaling pathways. Despite these mechanistic and functional experiments, studies investigating pathways involved in the synthesis, secretion, and targeting of V3 have not been done.

V3. like other members of the lectican family of PGs including versican, aggrecan, brevican, and neurocan, is characterized by having N-terminal (G1) and C-terminal (G3) globular domains, with variable GAG binding domains in between (see FIG. 10A). The V3 molecule consists of the N- and C-terminal globular domains of versican spliced together with the variable region of protein carrying the CS chains spliced out. The globular domains of the lecticans each have distinctive motifs with their own folded structures. The G1 domain contains two PG binding tandem repeats and one immunoglobulin motif. The folded domain in the tandem repeat of G1 defines the HA binding site. This site engages HA after the PG is secreted. The G3 domain bears homologies to EGF, C-type lectin and sushi or CRP with the number of EGF repeats variable among the lecticans. A number of early studies showed that each of the globular domains can have different activities. For example, the importance of the globular domains of the lecticans was recognized in nanomelia, a lethal autosomal recessive mutation in chickens caused by a premature stop codon in aggrecan. The truncated aggrecan protein accumulates within the cell due to the absence of the G3 domain. Other studies have focused on the importance of the globular domains in the secretion of aggrecan and versican. In vitro, the G domain tended to inhibit secretion, while G3 tended to promote secretion. The findings of the current study highlight exons 11-13 of V3, which code for a portion of G3 containing the C-type lectin domain, as critical for V3 secretion and processing. This finding supports the importance of this portion of the G3 region in facilitating versican secretion. Likewise, the loss of exon 3 in the G1 region enhanced V3 secretion verifying that this region of G1 inhibits secretion. The mechanisms by which these regions modulate V3 secretion are yet to be elucidated.

When expressed independently, the two globular domains appear to have different effects on cellular phenotypes such as influencing cell proliferation, migration, and cell survival. Interestingly, when expressed separately in cultured cells, both the G1 and G3 domains promote proliferation. In contrast, V3 containing the G1 and G3 domains together, reduces proliferation. Such opposing activities between individually expressed domains and intact V3 may also have an impact on inflammation. Through its ability to self-associate into multimers via intermolecular disulfide bonds. G3 expression enhances the production of an ECM which promotes leukocyte binding and aggregation, while we have shown that expression of intact V3 organizes an ECM which resists leukocyte binding and dampens inflammatory signaling.

In other ways, the individual globular domains appear to act similarly to intact V3 while opposing the activity of full-length, CS-containing forms of versican. It was demonstrated that adding recombinant G1 to dermal fibroblast cultures promoted the formation of HA cable-like structures, whereas V0/V1 had no effect on HA organization. The data presented herein likewise show that V3 expression enhances HA organization at the surface of the cell. Furthermore, it was previously shown that expression of V3 reduces the expression and accumulation of the CS-containing isoforms of versican, V0/V1, which may be a partial explanation for the opposing effects that V3 and V0/V1 have on cell phenotypes. Also, the tendency of V3 to self-aggregate points to the possibility that V3 directly interacts with other versican isoforms and perhaps other lecticans, thus altering the organization of the ECM and changing its interaction with the cell.

While it is well-known that the CS-bearing isoforms are degraded by a variety of proteases, V3 lacks consensus sequences for the ADAMTS proteases which are the major proteases that degrade versican. Whether V3 is non-cleavable awaits confirmation, but this suggests positive qualities for V3 as an effective therapeutic reagent.

The importance of N-linked glycosylation of glycoproteins is clear. However, little is known about the importance of N-linked oligosaccharides in the processing and trafficking of PGs. Earlier studies revealed that the protein core of the CS-carrying isoforms versican. V0 and V1, also contained N-linked and O-linked oligosaccharides in addition to the CS GAG chains, but it was not clear at the time if the V3 isoform contained N- and O-linked sugars. It was also not clear what role these N- and O-linked oligosaccharides played in the processing and trafficking of V0/V1. The results from the current study establish that V3 does contain N-linked sugars but not O-linked sugars and that the N-linked sugars have a role in establishing proper trafficking and solubility of this isoform. Previously, it was suggested that a truncated portion of G1 containing the HA binding domain expressed alone in COS-7 cells might be glycosylated in some form based on western blot data, without confirming such. Interestingly, it was later shown that N-linked glycosylation of G1 was not necessary for binding to HA or the formation of ternary complexes; however, it is now shown that it does appear to be necessary for efficient secretion. It remains to be determined if this is a general property of all versican isoforms, or whether it reflects differences in the structure of the isoforms which relate to differences in function.

The variants of versican are emerging as potential targets for therapeutic intervention across a variety of conditions. Interestingly and seemingly paradoxically, the variant without the GAG chains. V3, acts to counter pathological changes induced by the parent GAG containing versican isoforms, V0. V1 and V2, highlighting the potential therapeutic importance of V3 in the treatment of disease.

Experimental Procedures

Plasmid Construction

The open reading frame of rat V3 (NM_001170559.1) was PCR-amplified with primers rV3SpeIF and rV3XbaIR (Table 3) introducing SpeI and XbaI restriction sites and a c-terminal hemagglutinin tag and cloned into pEN_TTG-miRc2 (Addgene #25753) cut with SpeI and XbaI to remove the green fluorescent protein and CDDB. The resulting expression cassette consisting of the TRE-tight promoter and rV3 flanked by attL sites was cloned into pSLIK-Hygro (Addgene #25737) by gateway cloning to produce pSLIK-rV3-Hygro (FIG. 10B). This construct was further modified to generate the pGLI1-rV3-GFPzeo configuration (FIG. 10C) by inserting a Gateway destination cassette amplified from pSLIK-Hygro into the pCVL-A backbone upstream of the SFFV promoter. The third-generation doxycycline reverse transcriptional transactivator (rtTA3) from pSLIK-Hygro was linked to a GFP Sh ble fusion protein (conferring Zeocin resistance; GFPzeo) using the P2A peptide and cloned downstream of the SFFV promoter using XhoI and XbaI restriction sites. To confer additional resistance to silencing of the tetracycline-inducible CMV promoter, a minimal matrix attachment region (MAR) derived from the Ig kappa locus and the murine anti-repressor element 40 (ARE) residing upstream of the 400 IL17R gene were fused and inserted upstream of the attR site by In-Fusion® cloning (Clontech). All plasmid and insert sequences were verified by sequencing.

All deletion mutants of rat V3 were generated by PCR using the Agilent QuikChange Mutagenesis Kit. Because the N- and C-terminal sequences are retained in all deletion construct primers, rV3SpeIF and rV3XbaIR (Table 3) were used to amplify and sub clone the deletions shown in FIG. 12A with the same strategy that was used for the full length V3.

TABLE 3

Primer Sequences for V3 Construct Assembly

| Primer | Sequence |
| --- | --- |
| rV3SpeIF | TTTTACTAGTGCCACCATGTTGATAAATATGAACGGCATCCTATGG |
| rV3XbaIR | TTTTTCTAGATCAAGCGTAATCTGGAACATCGTATGGGTAGCGCCTCGTTTCCTGCCACC |

Viral Production and Transduction

HEK 297 LTV cells (Cell BioLabs) were plated 48 h prior to transfection in Dulbecco's modified Eagle medium (DMEM) 10% (DMEM high glucose supplemented with non-essential amino acids, Gluta-MAX, pen-strep antibiotics [Life Technologies] and 10% v/v fetal bovine serum [FBS; Atlanta Biologicals]). Cells were transfected with 25 kDa PEI-based transfection reagent (made in-house) and a mixture of the transfer vector, psPAX2 and pMD2G at a ratio of 3:2:1. Transfected cells were cultured in DMEM 10% supplemented with 8 mM butyrate overnight (~16 h), and then cultured further in DMEM 10% with 1 mM butyrate for an additional 24 h. The virus-containing conditioned media was harvested and cells and debris were removed by centrifugation. Virus was concentrated by centrifugation at 13,000×g through a 10% sucrose cushion for 4 h and transferred to target cultures of 50% confluent NIH 3T3 cells in DMEM 10% supplemented with 1 mg/ml Synperonic F-108 and 5 μg/ml DEAE-dextran for 6-12 h. Successfully transduced cells were then selected with 500 μg/ml hygromycin for seven days.

Cell Culture

NIH 3T3 cells (ATCC) transduced with pSLIK-rV3-Hygro were grown in DMEM 10% and induced to express hemagglutinin-tagged rV3 by treatment with 500 ng/ml Dox (Sigma Aldrich) for 48 h. In some experiments, movement of secreted proteins through the secretory pathway was inhibited with the addition of 50 μM BrefA (Sigma Aldrich) to the culture medium together with Dox for 24-48 h. In an independent set of experiments. N-glycosylation was blocked by the addition of 10 μM Tun (Sigma Aldrich). Fluoresceinated HA was added to some cultures at a concentration of 1 428 μg/ml.

Immunocytochemistry

Cells were grown on glass coverslips and fixed with neutral buffered formalin (NBF) for 2 h. Cells were washed with Tris-buffered saline containing 0.02% TWEEN® 20 (TBST) and stained with a polyclonal rabbit anti-hemagglutinin-tag antibody (1:1000; Sigma Aldrich). Alexa fluor-labeled secondary antibodies were obtained from Life Technologies. Affinity histochemistry of HA was performed with biotinylated HA binding protein and detected with Alexa fluor-labeled streptavidin (1 μg; Life Technologies). For standard fluorescence microscopy, nuclei were labeled with DAPI (ThermoFisher), for images taken with a confocal microscope (Leica TCS SP5), TO-PRO (Life Technologies) was used instead of DAPI.

Western Blotting

Cells were lysed in Laemmli buffer containing 100 mM DTT and equal protein amounts for each condition were separated on 10% SDS-PAGE gels. Volumes of conditioned media normalized to equal cellular protein were ethanol precipitated, dissolved in Laemmli buffer containing 100 mM DTT and separated on 10% SDS-PAGE gels. After semi-dry transfer of protein gels to nitrocellulose, membranes were blocked with 1% fish serum in Tris-buffered saline containing 0.02% TWEEN® 20 (TBST) and incubated with polyclonal rabbit anti-hemagglutinin-tag antibody (1:3000; Sigma-Aldrich) and, in the case of cell layer protein, mouse anti-β-actin (1:4000; Abcam) at 4° C. overnight. Membranes were washed three times in TBST and incubated with fluorescently-labeled secondary antibodies (1:20,000; Li-Cor Biosystems) for 1 h. bMembranes were washed again and scanned in a Li-Cor Odyssey CLx. Desitometric analysis of V3 bands was carried out using the Image Studio software provided by Li-Cor. Cellular protein loading was normalized to β-actin.

Enzymatic Digestion of Glycans

Cultures of V3-expressing cells were lysed with RIPA buffer, and 100 μg of total protein were subjected to deglycosylation with PNGase F, sialidase and O-glycanase (PROZYME™) under denaturing conditions for 24 h according to the manufacturer's instructions. After enzymatic digestion, samples were analyzed for V3 via western blotting using the anti-hemagglutinin-tag antibody.

Gene Expression Analysis

Cultured cell monolayers were lysed in 0.5 ml TRIZOL™ Trizol followed by the addition of 0.1 ml chloroform and vigorous mixing. The solution was incubated at room temperature for 5 min and spun at 14,000 RPM for 10 min at 4° C. The aqueous phase was collected, mixed with equal volume of 70% ethanol, and RNA was purified using ECONOSPIN™ columns (Epoch Life Science). cDNA was prepared from the isolated RNA with a High Capacity cDNA Reverse Transcription Kit (Life 453 Technologies) according to manufacturer's instructions. Real-time PCR was carried out with SYBR® Select Master Mix (Life Technologies), as directed by the manufacturer, on an Applied Biosystems 7900HT Fast Real-Time PCR System. For each sample, assays were run as technical duplicates. cDNA levels were then expressed as estimated copy numbers of mRNA using the master-template approach. SYBR® primers: rV3F AGCAGATTTGATGCCTACTGCTTT (SEQ ID NO: 38) and rV3R GCACAGGTGCACACATAGGA (SEQ ID NO:39).

Web-Based N-Glycosylation Site Prediction

Rat V3 protein sequence (NP 001164030.1) was analyzed by NetNGlyc (cbs.dtu.dk/services/NetNGlyc/), GlycoEP (imtech.res.in/raghava/glycoep/), and NGlycPred (exon-.niaid.nih.gov/nglycpred/) to determine the most likely sites to be N-glycosylated.

Study 3: "Recombinant Human Protein Restoring de novo Elastic Fiber Network Formation in Healing Skin"

In another study, entitled "Recombinant Human Protein Restoring de novo Elastic Fiber Network Formation in Healing Skin", three different rhV3 compositions were administered in vivo. A mouse dermal splinted wound healing model was utilized to determine the safety of the rhV3 compositions and their efficacy in improving the quality of healed wound tissue.

Introduction:

Organized elastic fiber networks are essential to the elasticity, resilience, and quality of skin, but are lost and not regenerated in adult skin after injury. Their absence during healing, in conjunction with inflammation and fibrosis, lead to scar tissue formation, further negatively impacting skin integrity and tissue function. Although the inflammatory process is necessary for wound healing, chronic inflammation contributes to healing failure, resulting in slow healing and chronic wounds, and contributing to tissue scarring. Utilizing recombinant human V3 (rhV3) compositions, we sought to restore tissue integrity, elasticity, and function to healing skin by addressing these issues. Restoring de novo generated mature organized elastic fiber networks to healing tissue represents a paradigm shift in wound care, differentiating rhV3 from other products Methods Mice: Male Balb/c mice were purchased from Charles River (Wilmington, MA) and were housed in a temperature-controlled facility (23° C.) with a 12-hour light/dark cycle, with water and food provided ad libitum, and nesting material provided. Animals were purchased at 8-10 weeks of age and used for experiments between 12 and 16 weeks of age.

Surgery: Prior to surgery, mice were acclimated to wearing a protective elastic veterinary wrap "jacket" (Vet Wrap, 3M) for at least 48 h. On the day of surgery, mice were deeply anesthetized with 3% isoflurane and provided with analgesics buprenorphine and meloxicam. Mice were maintained on a 37° C. heating pad until recovery to minimize potential for hypothermic stress. To prepare the surgical area, all fur was removed from the dorsal region by shaving and depilatory cream. The skin was then treated with chlorhexidine. Mice were laid on their sides and a flap of skin was pulled away from the fascia roughly midway down the spine. A 5 mm punch was used to simultaneously generate two contralateral full-thickness dermal wounds on either size of the spine about 1 cm below the shoulders. The mice were then covered in a surgical drape exposing inly the area containing the wounds. Sterile silicone washers, with an outer diameter of 14.27 mm and an inner diameter of 7.92 mm, 0.03 in. thickness and durometer hardness 40 (Acme Rubber), were glued to the skin centered around the punch wounds with medical-grade cyanoacrylate glue (Vet Bond; 3M). The splints were further secured through the full thickness of the skin with 8-10 monofilament nylon (6-0) sutures. After administration of rhV3 or control compositions, wounds were covered with a Tegaderm (3M) and wrapped with the veterinary elastic wrap for protection.

rhV3 compositions: One wound on each animal was treated with a single dose of one of 3 compositions of rhV3. 1) 50 µl of 8 µg/ml rhV3 in pH 8 buffered Dulbecco's Modified Eagle's Medium (DMEM) without phenol red 2) 50 µl 8 µg/ml rhV3 in 0.5% a thiolated hyaluronan gel (Glycosil; ESI Bio) and 3) a 6 mm diameter disk of the acellular skin substitute Endoform (Aroa Biosurgery) soaked with 8 µg/ml rhV3 in pH 8 buffered DMEM. Contralateral wounds were treated with matching compositions lacking the rhV3 component. Cohorts of 3-4 mice were treated with each formulation of rhV3. The concentration of rhV3 used was determined based on results of in vitro dose response studies of the ability of rhV3 treated dermal fibroblasts to form organized elastic fibers in culture (see FIGS. 7E-7H).

Wound Monitoring: Mice were weighed and wounds were digitally imaged 3 times per week for 3 weeks until wounds were completely closed. The images were composed such that the outer diameter of each silicone splint essentially filled the image frame. Each imaged was standardized to a size of 932×932 pixels and NIH Image J was used to draw a region of interest around the visible wound margin. Measurements of wound area were expressed as a percent of initial wound size.

Cell Culture: Human dermal fibroblasts around passage 10 were maintained in DMEM with 10% fetal bovine serum, and 1× nonessential amino acids, pen/strep, and GlutaMax additives (Thermo Fisher). For experiments, cells were plated in dishes coated with 1% gelatin with or without 5 ug/ml rhV3. Cells were then given DMEM media either with or without 5 ug/ml rhV3. After the initial 3 days, media without rhV3 was replenished every 3-4 days. Cells were harvested on day 7 for gene expression analysis.

Tissue Harvest: On day 23 after surgery, mice were euthanized and the fur was again removed from the dorsal region. Final images were taken and healed wounds were excised with an 8 mm punch with the scar centrally located. An equivalent portion of non-wounded skin was also taken for comparison. Half of the wound was fixed in formalin for histological examination and one quarter each of the wound was snap frozen in liquid nitrogen for gene expression and elastin analyses, respectively.

Gene Expression Analysis: Total mRNA was extracted from wound pieces using 1.5 mm triziconium bead agitation into Trizol and cultured cells lysed in Trizol. RNA was isolated and purified using commercially available mRNA extraction kits. cDNA was prepared from the isolated RNA with a High Capacity cDNA Reverse Transcription Kit (Life Technologies) according to manufacturer's instructions. Real-time PCR was carried out with SYBR Select Master Mix or TaqMan® Gene Expression Master Mix (Life Technologies), as directed by the manufacturer, on an Applied Biosystems 7900HT Fast Real-Time PCR System. For each sample, assays were run as technical duplicates. cDNA levels were then expressed as estimated copy numbers of mRNA using the master-template approach (32). TaqMan® and SYBR® primers included Elastin, Fibrillin 1, fibulinn 2, fibulin 5, Acta2 and Col1a1.

Results

Treatment of Wounds with rhV3 Compositions In Vivo had No Deleterious Effects on Wound Closure Rate.

Figures 22A, 22B:
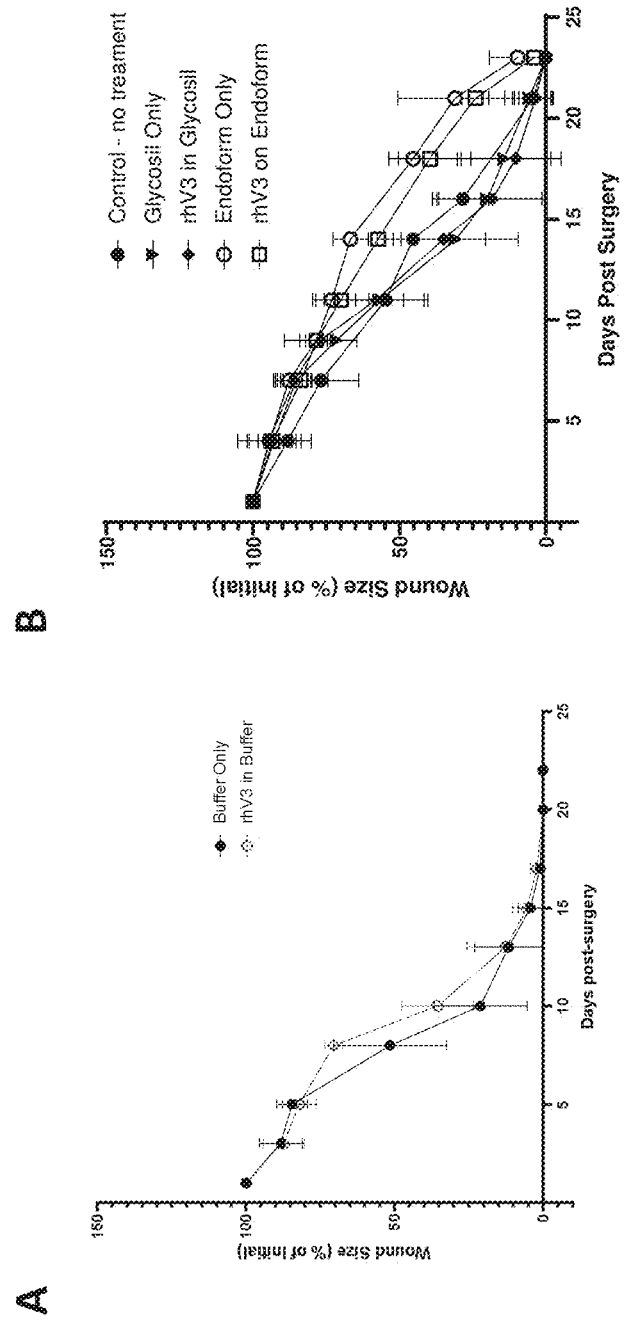
FIGS. 22A and 22B illustrate that administration of rhV3 in vivo does not impair rate of wound healing.

Wounds treated with rhV3 protein administered in DMEM buffer (FIG. 22A). Glycosil or on Endoform (FIG. 22B) were able to heal at a nearly identical rate to wounds treated with vehicle only, thus indicating that the use of rhV3 protein isolated in the method of this invention is safe to use in vivo and does not have deleterious effects on dermal wound healing, such as inflammatory reactivity. Wounds were imaged every 2-3 days for the entire course of wound healing and digital image analysis (ImageJ) was used to measure the area of the wounds on each day. Wound size data are expressed as a percentage of initial wound size.

Wounds Treated with rhV3 in Buffer Showed Trends Toward Increased Elastin Expression.

Figures 23A, 23B, 23C, 23D:
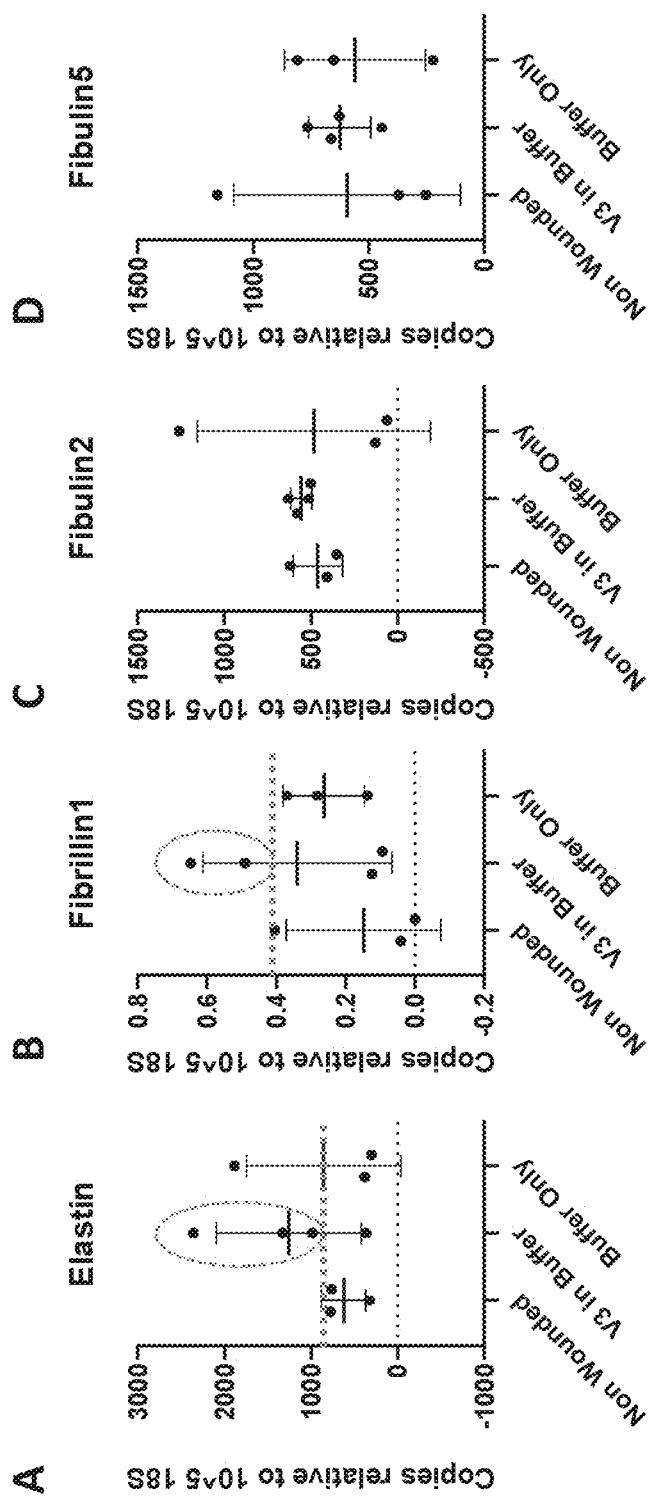
FIGS. 23A-23D illustrate that tissue from healed wounds treated with rhV3 administered in DMEM buffer show trends towards increased elastin and microfibrillar protein fibrillin 1 expression (see orange dashed lines), while microfibrillar proteins Fibulin 2 and 5 appear less affected. This suggests that rhV3 may be acting to increase elastin fiber networks within the healed wound tissue. RNA was extracted from snap-frozen healed wound tissue and analyzed via QPCR. Data are expressed as copy number relative to the 18S housekeeping gene.

Tissue from healed wounds treated with rhV3 administered in DMEM buffer show trends towards increased elastin and microfibrillar protein fibrillin 1 expression (see FIGS. 23A & 23B: red dashed lines), while microfibrillar proteins Fibulin 2 and 5 appear less affected (FIGS. 23C & 23D). This suggests that rhV3 may be acting to increase elastin fiber networks within the healed wound tissue. RNA was extracted from snap-frozen healed wound tissue and analyzed via QPCR. Data are expressed as copy number relative to the 18S housekeeping gene.

Cultured Human Dermal Fibroblasts Exhibited Reduced Expression of Markers of Fibrosis.

Figures 24A, 24B:
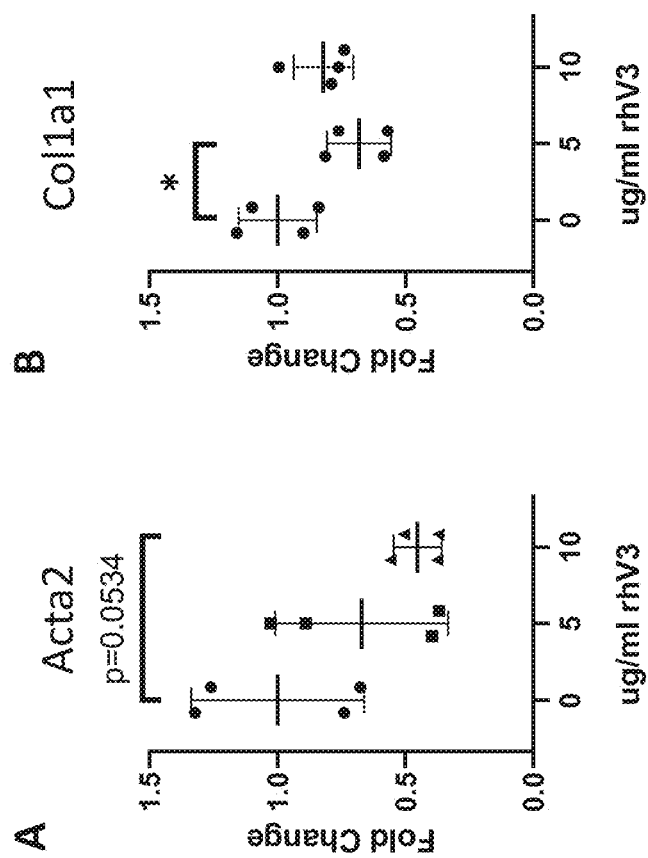
FIGS. 24A & 24B illustrate that cultured human dermal fibroblasts cultured in the presence of rhV3 exhibit reduced gene expression of markers of fibrosis, Acta2 and Col1a1, which code for smooth muscle α actin, a differentiation marker for myofibroblasts, and Type1 collagen, the major ECM protein component of fibrosis. Data are expressed as fold change in gene expression compared to untreated cultures.

Cultured human dermal fibroblasts cultured in the presence of rhV3 exhibit reduced gene expression of markers of inflammation. Acta2 and Col1a1, which code for smooth muscle α actin, a differentiation marker for myofibroblasts, and Type1 collagen, the major ECM protein component of fibrosis (FIGS. 24A & 24B). Data are expressed as fold change in gene expression compared to untreated cultures.

Discussion

Taken together these results indicate that rhV3 appears safe to use in vivo and demonstrates early stage in vivo efficacy in a model of dermal wound healing. The administration of rhV3 in vivo did not increase markers of inflammation, exhibited trends towards increased elastin expression, and reduced expression of markers of fibrosis, without adversely affecting the rate of wound closure. Thus, in vivo administration of rhV3 can be useful in improving tissue healing.

BIBLIOGRAPHY

The references and patents cited below, as well as any additional references and patents cited throughout this application, are hereby incorporated by reference.

1. Bode-Lesniewska B, Dours-Zimmermann M T, Odermatt B F, Briner J, Heitz P U, Zimmermann D R. Distribution of the large aggregating proteoglycan versican in adult human tissues. J Histochem Cytochem. 1996; 44:303-12.
2. Wight T N. Versican: a versatile extracellular matrix proteoglycan in cell biology. Curr Opin Cell Biol. 2002; 14:617-23.

3. Wight T N. Kinsella M G, Evanko S P, Potter-Perigo S. Merrilees M J. Versican and the regulation of cell phenotype in disease. Biochim Biophys Acta. 2014; 1840: 2441-51.
4. Wu Y J, La Pierre D P, Wu J, Yee A J, Yang B B. The interaction of versican with its binding partners. Cell Res. 2005; 15:483-94.
5. Mayanil C S, George D, Freilich L, Miljan E J. Mania-Farnell B, McLone D G, et al. Microarray analysis detects novel Pax3 downstream target genes. J Biol Chem. 2001: 276:49299-309.
6. Mjaatvedt C H, Yamamura H, Capehart A A. Turner D. Markwald R R. The Cspg2 gene, disrupted in the hdf mutant, is required for right cardiac chamber and endocardial cushion formation. Dev Biol. 1998; 202:56-66.
7. Wight T N. Kang I, Merrilees M J. Versican and the control of inflammation. Matrix Biol. 2014:35:152-61.
8. Merrilees M J, Kang I. Hinek A, Wight T N. Regulating elastogenesis using proteoglycans. In: Ramamurthi A. Kothapalli C, editors. Elastic Fiber Matrices: Biomemetic Approaches to Regeneration and Repair. Boca Raton, FL: CRC Press/Taylor & Francis; 2016. p. 255-84.
9. Zimmermann D. Versican. In: Iozzo R, editor. Proteoglycans: Structure. Biology and Molecular Interactions. New York: Marcel Dekker. Inc; 2000. p. 327-41.
10. Zimmermann D R, Ruoslahti E. Multiple domains of the large fibroblast proteoglycan, versican. EMBO J. 1989; 8:2975-81.
11. Lemire J M. Braun K R, Maurel P. Kaplan E D. Schwartz S M. Wight T N. Versican/PG-M isoforms in vascular smooth muscle cells. Arterioscler Thromb Vasc Biol. 1999:19:1630-9.
12. Kang I, Barth J L, Sproul E P. Yoon D W. Braun K R, Argraves W S, et al. Expression of V3 versican by rat arterial smooth muscle cells promotes differentiated and anti-inflammatory phenotypes. J Biol Chem. 2015; 290: 21629-41.
13. Kang I. Yoon D W, Braun K R, Wight T N. Expression of versican V3 by arterial smooth muscle cells alters tumor growth factor beta (TGFbeta)-, epidermal growth factor (EGF)-, and nuclear factor kappaB (NFkappaB)-dependent signaling pathways, creating a microenvironment that resists monocyte adhesion. J Biol Chem. 2014; 289:15393-404.
14. Merrilees M J, Lemire J M, Fischer J W, Kinsella M G, Braun K R, Clowes A W, et al. Retrovirally mediated overexpression of versican v3 by arterial smooth muscle cells induces tropoelastin synthesis and elastic fiber formation in vitro and in neointima after vascular injury. Circ Res. 2002; 90:481-7.
15. Merrilees M J, Wight T N. Targeting the matrix: potential benefits for versican therapeutics: Elsevier; 2012. Available from: http://www.elsevierblogs.com/currentcomments/?p=519.
16. Hinek A. Braun K R, Liu K, Wang Y, Wight T N. Retrovirally mediated overexpression of versican v3 reverses impaired elastogenesis and heightened proliferation exhibited by fibroblasts from Costello syndrome and Hurler disease patients. Am J Pathol. 2004; 164:119-31.
17. Wight T N. A role for proteoglycans in vascular disease. Matrix Biol. 2018; 71-72:396-420.
18. Wight T N. Frevert C W, Debley J S, Reeves S R. Parks W C, Ziegler S F. Interplay of extracellular matrix and leukocytes in lung inflammation. Cell Immunol. 2017; 312:1-14.
19. Zimmermann D R, Dours-Zimmermann M T. Extracellular matrix of the central nervous system: from neglect to challenge. Histochem Cell Biol. 2008; 130:635-53.
20. Keire P A. Kang I, Wight T N. Versican: Role in cancer tumorigenesis. In: Brekken R A. Stupack D G, editors. Extracellular Matrix in Tumor Biology. Biology of Extracellular Matrix. Cham. Switzerland: Springer International Publishing A G; 2017. p. 51-74.
21. Ricciardelli C, Sakko A J. Ween M P, Russell D L, Horsfall D J. The biological role and regulation of versican levels in cancer. Cancer Metastasis Rev. 2009:28: 233-45.
22. Wilbur W J. Lipman D J. Rapid similarity searches of nucleic acid and protein data banks. Proc Natl Acad Sci USA. 1983; 80:726-30.
23. Carillo H. Lipton D. The Multiple Sequence Alignment Problem in Biology. SIAM Applied Math. 1988; 48:1073-82.
24. Devereux J, Haeberli P. Smithies 0. A comprehensive set of sequence analysis programs for the VAX. Nucleic Acids Res. 1984; 12:387-95.
25. Altschul S F, Gish W, Miller W. Myers E W, Lipman D J. Basic local alignment search tool. J Mol Biol. 1990: 215:403-10.
26. Karlin S, Altschul S F. Methods for assessing the statistical significance of molecular sequence features by using general scoring schemes. Proc Natl Acad Sci USA. 1990; 87:2264-8.
27. Karlin S, Altschul S F. Applications and statistics for multiple high-scoring segments in molecular sequences. Proc Natl Acad Sci USA. 1993; 90:5873-7.
28. Altschul S F, Madden T L, Schaffer A A, Zhang J, Zhang Z. Miller W. et al. Gapped BLAST and PSI-BLAST: a new generation of protein database search programs. Nucleic Acids Res. 1997; 25:3389-402.
29. Altschul S F. Lipman D J. Protein database searches for multiple alignments. Proc Natl Acad Sci USA. 1990; 87:5509-13.
30. LeBaron R G. Zimmermann D R, Ruoslahti E. Hyaluronate binding properties of versican. J Biol Chem. 1992; 267:10003-10.
31. Bano F, Tammi M I. Kang D W, Harris E N, Richter R P. Single-Molecule Unbinding Forces between the Polysaccharide Hyaluronan and Its Binding Proteins. Biophys J. 2018; 114:2910-22.
32. Hudson K S, Andrews K, Early J, Mjaatvedt C H. Capehart A A. Versican G1 domain and V3 isoform overexpression results in increased chondrogenesis in the developing chick limb in ovo. Anat Rec (Hoboken). 2010; 293:1669-78.
33. Seyfried N T, McVey G F, Almond A, Mahoney D J, Dudhia J, Day A J. Expression and purification of functionally active hyaluronan-binding domains from human cartilage link protein, aggrecan and versican: formation of ternary complexes with defined hyaluronan oligosaccharides. J Biol Chem. 2005; 280:5435-48.
34. Isogai Z. Aspberg A, Keene D R. Ono R N. Reinhardt D P, Sakai L Y. Versican interacts with fibrillin-1 and links extracellular microfibrils to other connective tissue networks. J Biol Chem. 2002; 277:4565-72.
35. Olin A I, Morgelin M, Sasaki T, Timp R, Heinegard D, Aspberg A. The proteoglycans aggrecan and Versican form networks with fibulin-2 through their lectin domain binding. J Biol Chem. 2001; 276:1253-61.
36. Wu Y, Chen L. Cao L, Sheng W, Yang B B. Overexpression of the C-terminal PG-M/versican domain impairs growth of tumor cells by intervening in the interaction between epidermal growth factor receptor and β1-integrin. J Cell Sci. 2004; 117:2227-37.
37. Hope C, Foulcer S. Jagodinsky J. Chen S X, Jensen J L, Patel S, et al. Immunoregulatory roles of versican proteolysis in the myeloma microenvironment. Blood. 2016; 128:680-5.
38. Merrilees M J, Falk B A. Zuo N, Dickinson M E. May B C H, Wight T N. Use of versican variant V3 and versican antisense expression to engineer cultured human skin containing increased content of insoluble elastin. J Tiss Eng Regen Med. 2017; 11:295-305.
39. Lemire J M. Merrilees M J, Braun K R, Wight T N. Overexpression of the V3 variant of versican alters arterial smooth muscle cell adhesion, migration, and proliferation in vitro. J Cell Physiol. 2002; 190:38-45.
40. Merrilees M J. Beaumont B W, Braun K R, Thomas A C, Kang I. Hinek A, et al. Neointima formed by arterial smooth muscle cells expressing versican variant v3 is resistant to lipid and macrophage accumulation. Arterioscler Thromb Vasc Biol. 2011:31:1309-16.
41. Serra M, Miquel L. Domenzain C, Docampo M J, Fabra A. Wight T N, et al. V3 versican isoform expression alters the phenotype of melanoma cells and their tumorigenic potential. Int J Cancer. 2005; 114:879-86.
42. Kiani C. Lee V, Cao L. Chen L. Wu Y. Zhang Y, et al. Roles of aggrecan domains in biosynthesis, modification by glycosaminoglycans and product secretion. Biochem J. 2001; 354:199-207.
43. Clark M A, Hammond F R. Papaioannou A, Hawkins N J, Ward R L. Regulation and expression of human Fabs under the control of the *Escherichia coli* arabinose promoter, PBAD. Immunotechnology. 1997:3:217-26.
44. Merrilees M J, Zuo N, Evanko S P, Day A J, Wight T N. G1 domain of versican regulates hyaluronan organization and the phenotype of cultured human dermal fibroblasts. J Histochem Cytochem. 2016; 64:353-63.
45. Hofmann A, Kessler B. Ewerling S. Kabermann A, Brem G, Wolf E. et al. Epigenetic regulation of lentiviral transgene vectors in a large animal model. Mol Ther. 2006; 13:59-66.
46. Bandaranayake A D, Correnti C, Ryu B Y, Brault M, Strong R K, Rawlings D J. Daedalus: a robust, turnkey platform for rapid production of decigram quantities of active recombinant proteins in human cell lines using novel lentiviral vectors. Nucleic Acids Res. 2011; 39:e143.
47. Mansha M, Wasim M, Ploner C, Hussain A. Latif A A, Tariq M, ct al. Problems encountered in bicistronic IRES-GFP expression vectors employed in functional analyses of G C-induced genes. Mol Biol Rep. 2012:39:10227-34.
48. Puttini S, van Zwieten R W, Saugy D, Lekka M, Hogger F, Ley D. et al. MAR-mediated integration of plasmid vectors for in vivo gene transfer and regulation. BMC Mol Biol. 2013; 14:26.
49. Kwaks T H, Barnett P, Hemrika W, Siersma T, Sewalt R G, Satijn D P, et al. Identification of anti-repressor elements that confer high and stable protein production in mammalian cells. Nat Biotechnol. 2003; 21:553-8.
50. Petersen T N, Brunak S, von Heijne G. Nielsen H. SignalP 4.0: discriminating signal peptides from transmembrane regions. Nat Methods. 2011; 8:785-6.
51. Schmidt T G, Batz L. Bonet L, Carl U, Holzapfel G. Kiem K, et al. Development of the Twin-Strep-Tag® and its application for purification of recombinant proteins from cell culture supernatants. Protein Expr Purif. 2013; 92:54-61.
52. Keire P A. L'Heureux N, Vernon R B, Merrilces M J. Starcher B. Okon E. et al. Expression of versican isoform V3 in the absence of ascorbate improves elastogenesis in engineered vascular constructs. Tissue Eng Part A. 2010; 16:501-12.
53. Kang I, Harten I A, Chang M Y, Braun K R. Sheih A, Nivison M P. et al. Versican deficiency significantly reduces lung inflammatory response induced by polyinosine-polycytidylic acid stimulation. J Biol Chem. 2017; 292:51-63.
54. Kohfeldt E. Maurer P, Vannahme C, Timpl R. Properties of the extracellular calcium binding module of the proteoglycan testican. FEBS Lett. 1997; 414:557-61.
55. Shih S C. Smith L E. Quantitative multi-gene transcriptional profiling using real-time PCR with a master template. Exp Mol Pathol. 2005; 79:14-22.
56. Zako M. Shinomura T. Ujita M, Ito K. Kimata K. Expression of PG-M (V3), an alternatively spliced form of PG-M without a chondroitin sulfate attachment region in mouse and human tissues. J Biol Chem. 1995; 270: 3914-8.
57. Hartwig S, Raschke S, Knebel B, Scheler M. Irmler M, Passlack W, et al. Secretome profiling of primary human skeletal muscle cells. Biochim Biophys Acta. 2014; 1844: 1011-7.
58. Kern C B, Norris R A, Thompson R P, Argraves W S, Fairey S E, Reyes L, et al. Versican proteolysis mediates myocardial regression during outflow tract development. Dev Dyn. 2007:236:671-83.
59. Kamiya N, Watanabe H, Habuchi H, Takagi H, Shinomura T, Shimizu K, et al. Versican/PG-M regulates chondrogenesis as an extracellular matrix molecule crucial for mesenchymal condensation. J Biol Chem. 2006:281: 2390-400.
60. Potter-Perigo S, Johnson P Y, Evanko S P, Chan C K, Braun K R, Wilkinson T S, et al. Polyinosine-polycytidylic acid stimulates versican accumulation in the extracellular matrix promoting monocyte adhesion. Am J Respir Cell Mol Biol. 2010; 43:109-20.
61. Hernandez D. Miquel-Serra L. Docampo M J. Marco-Ramell A, Cabrera J, Fabra A. et al. V3 versican isoform alters the behavior of human melanoma cells by interfering with CD44/ErbB-dependent signaling. J Biol Chem. 2011; 286:1475-85.
62. Miquel-Serra L, Serra M, Herndndez D, Domenzain C, Docampo M J, Rabanal R, et al. V3 versican isoform expression has a dual role in human melanoma tumor growth and metastasis. Lab Invest. 200686:889-901.
63. Fanhchaksai K, Okada F, Nagai N, Pothacharoen P, Kongtawelert P, Hatano S, et al. Host stromal versican is essential for cancer-associated fibroblast function to inhibit cancer growth. Int J Cancer. 2016; 138:630-41.
64. Perveen R, Hart-Holden N, Dixon M J. Wiszniewski W, Fryer A E, Brunner H G, et al.
Refined genetic and physical localization of the Wagner disease (WGN1) locus and the genes CRTL1 and CSPG2 to a 2- to 2.5-cM region of chromosome 5q14.3. Genomics. 1999:57:219-26.
65. Mukhopadhyay A, Nikopoulos K. Maugeri A, de Brouwer A P, van Nouhuys C E, Boon C J. et al. Erosive vitreoretinopathy and wagner disease are caused by intronic mutations in CSPG2/Versican that result in an imbalance of splice variants. Invest Ophthalmol Vis Sci. 2006; 47:3565-72.
66. Lebendiker M. Danieli T. Production of prone-to-aggregate proteins. FEBS Lett. 2014:588:236-46.

67. Gill S. Wight T N, Frevert C W. Proteoglycans: key regulators of pulmonary inflammation and the innate immune response to lung infection. Anat Rec (Hoboken). 2010; 293:968-81.
68. Andersson-Sjoland A, Hallgren O, Rolandsson S. Weitoft M, Tykesson E. Larsson-Callerfelt A K, et al. Versican in inflammation and tissue remodeling: the impact on lung disorders. Glycobiology. 2015; 25:243-51.
69. Ito K. Shinomura T. Zako M. Ujita M. Kimata K. Multiple forms of mouse PG-M, a large chondroitin sulfate proteoglycan generated by alternative splicing. J Biol Chem. 1995; 270:958-65.
70. Rahmani M. Read J T. Carthy J M, McDonald P C, Wong B W, Esfandiarei M, et al. Regulation of the versican promoter by the beta-catcnin-T-cell factor complex in vascular smooth muscle cells. J Biol Chem. 2005; 280: 13019-28.
71. Cardoso L E, Little P J. Ballinger M L. Chan C K, Braun K R. Potter-Perigo S. et al. Platelet-derived growth factor differentially regulates the expression and post-translational modification of versican by arterial smooth muscle cells through distinct protein kinase C and extracellular signal-regulated kinase pathways. J Biol Chem. 2010; 285:6987-95.
72. Lemire J M, Chan C K. Bressler S, Miller J, LeBaron R G, Wight T N. Interleukin-Ibeta selectively decreases the synthesis of versican by arterial smooth muscle cells. J Cell Biochem. 2007; 101:753-66.
73. Henderson D J, Copp A J. Role of the extracellular matrix in neural crest cell migration. J Anat. 1997; 191: 507-15.
74. Yamaguchi Y. Chondroitin sulfate proteoglycans in the nervous system. In: Iozzo R, editor. Proteoglycans: Structure. Biology, and Molecular Interactions. New York: Marcel Dekker; 2000. p. 379-402.
75. Luo W. Guo C, Zheng J, Chen T L. Wang P Y, Vertel B M, et al. Aggrecan from start to finish. J Bone Miner Metab. 2000; 18:51-6.
76. Luo W, Kuwada T S, Chandrasekaran L. Zheng J, Tanzer M L. Divergent secretory behavior of the opposite ends of aggrecan. J Biol Chem. 1996; 271:16447-50.
77. Perkins S J, Nealis A S, Dudhia J. Hardingham T E. Immunoglobulin fold and tandem repeat structures in proteoglycan N-terminal domains and link protein. J Mol Biol. 1989; 206:737-53.
78. Watanabe H. Cheung S C, Itano N, Kimata K, Yamada Y. Identification of hyaluronan-binding domains of aggrecan. J Biol Chem. 1997; 272:28057-65.
79. Brissett N C, Perkins S J. Conserved basic residues in the C-type lectin and short complement repeat domains of the G3 region of proteoglycans. Biochem J. 1998:329 (Pt 2):415-24.
80. Perkins S J, Nealis, A. S., Dunham, D. G., Hardingham. T. E., Muir I H. Molecular modeling of the multidomain structures of the proteoglycan binding region and the link protein of cartilage by neutron and synchrotron X-ray scattering. Biochemistry. 1991; 30:10708-16.
81. Zheng J, Luo W Tanzer M L. Aggrecan synthesis and secretion. A paradigm for molecular and cellular coordination of multiglobular protein folding and intracellular trafficking. J Biol Chem. 1998; 273:12999-3006.
82. Vertel B M, Walters L M. Grier B. Maine N, Goetinck P F. Nanomelic chondrocytes synthesize, but fail to translocate, a truncated aggrecan precursor. J Cell Sci. 1993; 104:939-48.
83. Chen T L, Wang P Y. Luo W, Gwon S S, Flay N W, Zheng J. et al. Aggrecan domains expected to traffic through the exocytic pathway are misdirected to the nucleus. Exp Cell Res. 2001; 263:224-35.
84. Vertel B M. The ins and outs of aggrecan. Trends Cell Biol. 1995; 5:458-64.
85. Cao L, Yang B B. Chondrocyte apoptosis induced by aggrecan G1 domain as a result of decreased cell adhesion. Exp Cell Res. 1999; 246:527-37.
86. Chen L, Wu Y, Lee V Kiani C. Adams M E, Yao Y, et al. The folded modules of aggrecan G3 domain exert two separable functions in glycosaminoglycan modification and product secretion. J Biol Chem. 2002:277:2657-65.
87. Chen L. Yang B L, Wu Y, Yee A, Yang B B. G3 domains of aggrecan and PG-M/versican form intermolecular disulfide bonds that stabilize cell-matrix interaction. Biochemistry. 2003; 42:8332-41.
88. Du W W, Fang L, Yang W. Sheng W. Zhang Y, Seth A, et al. The role of versican G3 domain in regulating breast cancer cell motility including effects on osteoblast cell growth and differentiation in vitro—evaluation towards understanding breast cancer cell bone metastasis. BMC Cancer. 2012; 12:341.
89. Zhang Y. Cao L, Yang B L, Yang B B. The G3 domain of versican enhances cell proliferation via epidermal growth factor-like motifs. J Biol Chem. 1998; 273:21342-51.
90. Ang L C, Zhang Y. Cao L, Yang B L, Young B, Kiani C, et al. Versican enhances locomotion of astrocytoma cells and reduces cell adhesion through its G1 domain. J Neuropathol Exp Neurol. 1999; 58:597-605.
91. Apte S S. A disintegrin-like and metalloprotease (reprolysin-type) with thrombospondin type 1 motif (AD-AMTS) superfamily: functions and mechanisms. J Biol Chem. 2009; 284:31493-7.
92. Freeze H H. Understanding human glycosylation disorders: biochemistry leads the charge. J Biol Chem. 2013: 288:6936-45.
93. Ohtsubo K. Marth J D. Glycosylation in cellular mechanisms of health and disease. Cell. 2006; 126:855-67.
94. Rudd P M, Elliott T, Cresswell P, Wilson I A, Dwek R A. Glycosylation and the immune system. Science. 2001; 291:2370-6.
95. Shriver Z, Raguram S, Sasisekharan R. Glycomics: a pathway to a class of new and improved therapeutics. Nat Rev Drug Discov. 2004; 3:863-73.
96. Spiro R G. Protein glycosylation: nature, distribution, enzymatic formation, and disease implications of glycopeptide bonds. Glycobiology. 2002; 12:43R-56R.
97. Chang Y, Yanagishita M, Hascall V C, Wight T N. Proteoglycans synthesized by smooth muscle cells derived from monkey (Macaca nemestrina) aorta. J Biol Chem. 1983; 258:5679-88.
98. Yang B L, Cao L, Kiani C, Lee V, Zhang Y, Adams M E, et al. Tandem repeats are involved in G1 domain inhibition of versican expression and secretion and the G3 domain enhances glycosaminoglycan modification and product secretion via the complement-binding protein-like motif. J Biol Chem. 2000:275:21255-61.
99. Harten I A, Kaber G, Agarwal K J, Kang I. Ibarrientos S R, Workman G, Chan C K, Nivison M P, Nagy N, Braun K R, Kinsella M G, Merrilees M J, Wight T N. The synthesis and secretion of versican isoform V3 by mammalian cells: A role for N-linked glycosylation. Matrix Biol. 2020 July; 89:27-42.

SEQUENCE LISTING

List of SEQ IDS
Amino Acid Sequences
1. SEQ ID NO:1: Consensus human V3 amino acid sequence with native signal peptide (CCDS47242.1 including RefSeq. NP_001119808.1)

2. SEQ ID NO:2: Consensus human V3 amino acid sequence without signal peptide
3. SEQ ID NO:3: Consensus rat V3 amino acid sequence without signal peptide (NP_001164030.1)
4. SEQ ID NO:4: Consensus murine V3 amino acid sequence without signal peptide (CCDS 49322.1 including RefSeq NP_01127947.1)
5. SEQ ID NO:5: Consensus porcine V3 amino acid sequence without signal peptide (BAK09351.1)
6. SEQ ID NO:6: Consensus bovine V3 amino acid sequence without signal peptide (AAC24361.1)
7. SEQ ID NO:7: Consensus rhesus monkey V3 amino acid sequence without signal peptide (assembled from XP_014995845.1)
8. SEQ ID NO:8: Consensus canine V3 amino acid sequence without signal peptide (assembled from XP_022272456.1)
9. SEQ ID NO:9: Consensus human V3 amino acid sequence with Vint tail without signal peptide
10. SEQ ID NO:10: Consensus *Gaussia princeps* luciferase signal peptide amino acid sequence (AAG54095.1)—example of non-native signal peptide for V3

Nucleic Acid Sequences

11. SEQ ID NO:11: Consensus human V3 nucleotide sequence with native signal peptide (CCDS47242.1 including RefSeq. NM_001126336.3)
12. SEQ ID NO:12: Consensus human V3 nucleotide sequence without signal peptide
13. SEQ ID NO:13: Human codon-optimized V3 nucleotide sequence of consensus with signal peptide
14. SEQ ID NO:14: Human codon-optimized V3 nucleotide sequence without signal peptide
15. SEQ ID NO:15: Consensus rat V3 nucleotide sequence without signal peptide (NM_001170559.1)
16. SEQ ID NO:16: Consensus mouse V3 nucleotide sequence without signal peptide (NM_001134475.1)
17. SEQ ID NO:17: Consensus pig V3 nucleotide sequence without signal peptide (AB558523.1)
18. SEQ ID NO:18: Consensus cow V3 nucleotide sequence without signal peptide (AF060459.1)
19. SEQ ID NO:19: Consensus rhesus monkey V3 nucleotide sequence without signal peptide (assembled from XM_015140359.1)
20. SEQ ID NO:20: Consensus dog V3 nucleotide sequence without signal peptide (assembled from XM_022416748.1)
21. SEQ ID NO:21: Vint tail version of human V3
22. SEQ ID NO:22: STAR, UCOE, SFFV, optGPLuc, hsoptV3 nucleotide sequence (BASE CASE
23. SEQ ID NO:23: MAR, STAR. UCOE, SFFV, GFPz, P2A, optGPLuc, hsoptV3, HA tag, Twin-Strep nucleotide sequence—constitutive expressor
24. SEQ ID NO:24: MAR, STAR. TRE, optGPLuc, hsoptV3, UCOE, SFFV, rtTA nucleotide sequence-inducible expressor
25. SEQ ID NO:25: Consensus *Gaussia princeps* luciferase signal peptide nucleotide sequence (AY015993.1)
26. SEQ ID NO:26: Sequence optimized *Gaussia princeps* luciferase signal peptide nucleotide sequence NON-native to V3

Amino Acid Sequences

```
SEQ ID NO: 1:
Consensus human V3 amino acid sequence with native signal peptide
(CCDS47242.1 including RefSeq. NP_001119808.1)
MFINIKSILWMCSTLIVTHALHKVKVGKSPPVRGSLSGKVSLPCHFSTMPTLPPSYNTSEFLRIKWSKIEVDK

NGKDLKETTVLVAQNGNIKIGQDYKGRVSVPTHPEAVGDASLTVVKLLASDAGLYRCDVMYGIEDTQDT

VSLTVDGVVFHYRAATSRYTLNFEAAQKACLDVGAVIATPEQLFAAYEDGFEQCDAGWLADQTVRYPIRA

PRVGCYGDKMGKAGVRTYGFRSPQETYDVYCYVDHLDGDVFHLTVPSKFTFEEAAKECENQDARLATVG

ELQAAWRNGFDQCDYGWLSDASVRHPVTVARAQCGGGLLGVRTLYRFFNQTGFPPPDSRFDAYCFKRPD

RCKMNPCLNGGTCYPTETSYVCTCVPGYSGDQCELDFDECHSNPCRNGATCVDGFNTFRCLCLPSYVGAL

CEQDTETCDYGWHKFQGQCYKYFAHRRTWDAAERECRLQGAHLTSILSHEEQMFVNRVGHDYQWIGLN

DKMFEHDFRWTDGSTLQYENWRPNQPDSFFSAGEDCVVIIWHENGQWNDVPCNYHLTYTCKKGTVACG

QPPVVENAKTFGKMKPRYEINSLIRYHCKDGFIQRHLPTIRCLGNGRWAIPKITCMNPSAYQRTYSMKYFK

NSSSAKDNSINTSKHDHRWSRRWQESRR

SEQ ID NO: 2:
Consensus human V3 amino acid sequence without signal peptide
LHKVKVGKSPPVRGSLSGKVSLPCHFSTMPTLPPSYNTSEFLRIKWSKIEVDKNGKDLKETTVLVAQNGNIK

IGQDYKGRVSVPTHPEAVGDASLTVVKLLASDAGLYRCDVMYGIEDTQDTVSLTVDGVVFHYRAATSRYT

LNFEAAQKACLDVGAVIATPEQLFAAYEDGFEQCDACWLADQTVRYPIRAPRVGCYGDKMGKAGVRTY

GFRSPQETYDVYCYVDHLDGDVFHLTVPSKFTFEEAAKECENQDARLATVGELQAAWRNGFDQCDYGWL

SDASVRHPVTVARAQCGGGLLGVRTLYRFENQTGFPPPDSRFDAYCFKRPDRCKMNPCLNGGTCYPTETS

YVCTCVPGYSGDQCELDFDECHSNPCRNGATCVDGFNTFRCLCLPSYVGALCEQDTETCDYGWHKFQGQ

CYKYFAHRRTWDAAERECRLQGAHLTSILSHEEQMFVNRVGHDYQWIGLNDKMFEHDFRWTDGSTLQYE
```

```
NWRPNQPDSFFSAGEDCVVIIWHENGQWNDVPCNYHLTYTCKKGTVACGQPPVVENAKTFGKMKPRYEI

NSLIRYHCKDGFIQRHLPTIRCLGNGRWAIPKITCMNPSAYQRTYSMKYFKNSSSAKDNSINTSKHDHRWSR

RWQESRR

SEQ ID NO: 3:
Consensus rat V3 amino acid sequence without signal peptide
(NP_001164030.1)
LHKAKMEENPPVKGSLSGKVILPCHFSTLPTLPPDYNTSEFLRIKWSKIEVDKNGKDIKETTVLVAQDGNIKI

GQDYKGRVSVPTHPDDVGDASLTMVKLRASDAGVYRCDVMYGIEDTQNTMSLAVDGVVFHYRAATSRY

TLNFESAQQACLDIGAVIATPEQLFAAYEDGFEQCDAGWLSDQTVRYPIRAPREGCYGDMMGKEGVRTYG

FRSPQETYDVYCYVDHLDGDVFHITAPSKFTFEEAEAECANRDARLATVGELHAAWRNGFDQCDYGWLS

DASVRHPVTVARAQCGGGLLGVRTLYRFENQTCFPLPDSRFDAYCFKRPDLCKTNPCLNGGTCYPTETSYV

CTCAPGYSGDQCELDFDECHSNPCRNGATCVDGLNTFRCLCLPSYVGALCEQDTETCDYGWHKFQGQCY

KYFAHRRTWDAAERECRLQGAHLTSILSHEEQMFVNRVGHDYQWIGLNDKMFEHDFRWTDGSALQYEN

RPNQPDSFFSAGEDCVVIIWHENGQWNDVPCNYHLTYTCKKGTVACGQPPVVENAKTFGKMKPRYEINSL

IRYHCKDGFIQRHLPTIRCLGNGRWAMPKITCMNPSAYQRTYSKKYLKNSSSVKDNSINTSKHEHRWSRR

WQETRR

SEQ ID NO: 4:
Consensus murine V3 amino acid sequence without signal peptide
(CCDS 49322.1 including RefSeq NP_001127947.1)
LHQAKMETSPPVKGSLSGKVVLPCHFSTLPTLPPNYNTSEFLRIKWSKMEVDKNGKDIKETTVLVAQNGNI

KIGQDYKGRVSVPTHPDDVGDASLTMVKLRASDAGVYRCDVMYGIEDTQDTMSLAVDGVVFHYRAATS

RYTLNFAAAQQACLDIGAVIASPEQLFAAYEDGFEQCDAGWLSDQTVRYPIRAPREGCYGDMMGKEGVR

TYGFRSPQETYDVYCYVDHLDGDVFHITAPSKFTFEEAEAECTSRDARLATVGELQAAWRNGFDQCDYG

WLSDASVRHPVTVARAQCGGGLLGVRTLYRFENQTCFPLPDSRFDAYCFKRPDLCKTNPCLNGTCYPLTE

TSYVCTCAPGYSGDQCELDFDECHSNPCRNGATCVDGFNTFRCLCLPSYVGALCEQDTETCDYGWHKFQG

QCYKYFAHRRTWDAAERECRLQGAHLTSILSHEEQMFVNRVGHDYQWIGLNDKMFEHDFRWTDGSALQ

YENWRPNQPDSFFSAGEDCVVIIWHENGQWNDVPCNYHLTYTCKKGTVACGQPPVVENAKTFGKMKPRY

EINSLIRYHCKDGFIQRHLPTIRCLGNGRWAMPKITCMNPSAYQRTYSKKYLKNSSSAKDNSINTSKHEHR

WSRRRQETRR

SEQ ID NO: 5:
Consensus porcine V3 amino acid sequence without signal peptide
(BAK09351.1)
LHKVKVEKSPPVKGSLSGKVNLPCHFSTMPTLPPSYNTTSEFLRIKWSKIELDKSGKDLKETTVLVAQNGNI

KIGQGYKGRVSVPTHPEDVGDASLTMVKLLASDAGLYRCDVMYGIEDTQDSVSLAVDGVVFHYRAATSR

YTLNFEAAQKACLDIGAVIATPEQLHAAYEDGFEQCDAGWLSDQTVRYPIRTPREGCYGDMMGKEGVRT

YGFRAPHETYDVYCYVDHLDGDVFHITAPNKFTFEEAEEECENQDARLATVGELQAAWRNGFDQCDYGW

LLDASVRHPVTVPRAQCGGGLLGVRTLYRFENQTGFPSPDSRFDAYCYKRPDRCKTNPCLNGGTCYPTETS

YVCTCVPGYSGDQCELDFDECHSNPCRNGATCVDGFNTFRCLCLPSYVGALCEQDTETCDYGWHKFQGQ

CYKYFAHRRTWDAAERECRLQGAHLTSILSHEEQMFVNRVGHDYQWIGLNDKMFEHDFRWTDGSTLQYE

NWRPNQPDSFFSSGEDCVVIIWHENGQWNDVPCNYHLTYTCKKGTVACGQPPVVENAKTFGKMKPRYEI

NSLIRYHCKDGFIQRHPPTIRCLGNGRWAMPKITCLNPSAYQRTYSKKYFKNSSSAKDNSINTSKHDHRWS

RRWQESRR

SEQ ID NO: 6:
Consensus bovine V3 amino acid sequence without signal peptide
(AAC24361.1)
LQKVNMEKSPPVKGSLSGKVNLPCHFSTMPTLPPSYNTTSEFLRIKWSKIELDKTGKDLKETTVLVAQNGNI

KIGQDYKGRVSVPTHPEDVGDASLTMVKLLASDAGRYRCDVMYGIEDTQDTVSLTVEGVVTHYRAATSR
```

YTLNFEMAQKACVDIGAVIATPEQLHAAYEDGFEQCDAGWLSDQTVRYPIRVPREGCYGDMMGKEGVRT

YGFRAPHETYDVYCYVDHLDGDVFHITAPNKFTEEAGEECKTQDARLATVGELQAAWRNGFDRCDYGW

LLDASVRHPVTVARAQCGGGLLGVRTLYRFENQTGFPTPDSRFDAYCFKRPDRCKMNPCLNGGTCYPTET

SYVCTCVPGYSGDRCELDFDECHSNPCRNGATCIDGFNTFRCLCLPSYVGALCEQDTETCDYGWHKFQGQ

CYKYFAHRRTWDAAERECRLQGAHLTSILSHEEQMFVNRVGHDYQWIGLNDKMFEHDFRWTDGSTLQYE

NWRPNQPDSFFSTGEDCVVIIWHENGQWNDVPCNYHLTYTCKKGTVACGQPPVVENAKTFGKMKPRYEI

NSLIRYHCKDGFIQRHLPTIRCLGNGRWAMPKITCLNPSAYQRTYSKKYFKNSSSAKDNSINTSKHDHRWS

RRWQESRR

SEQ ID NO: 7:
Consensus rhesus monkey V3 amino acid sequence without signal peptide
(assembled from XP_014995845.1)
LHKVKVGKSPPLRGSLSGKVSLPCHFSTMPTLPPSYNTSEFLRIKWSKIEVDKNGKDLKETTVLVAQNGNIK

IGQDYKGRVSVPTHPEAVGDASLTVVKLLASDAGLYRCDVMYGIDDTQDTVSLAVDGVVFHYRASTSRY

TLNFEAAQKACLDIGAVIATPEQLFAAYEDGFEQCDAGWLADQTVRYPIRAPRVGCYGDMMGKAGVRTY

GFRSPQETYDVYCYVDHLDGDVFHLTAPSKFTFEEAAKECENQDARLATVGELQAAWRNGFDQCDYGWL

SDASVRHPVTVARAQCGGGLLGVRTLYRFENQTGFPPPDSRFDAYCFKRPDRCKMNPCLNGGTCYPTETS

YVCTCVPGYSGDQCELDFDECHSNPCRNGATCVDGFNTFRCLCLPSYVGALCEQDTETCDYGWHKFQGQ

CYKYFAHRRTWDAAERECRLQGAHLTSILSHEEQTFVNRVGHDYQWIGLNDKMFEHDFRWTDGSTLQYE

NWRPNQPDSFFSAGEDCVVIIWHENGQWNDVPCNYHLTYTCKKGTVACGQPPVVENAKTFGKMKPRYEI

NSLIRYHCKDGFIQRHLPTIRCLGNGRWAIPKITCMNPSAYQRTYSMKYFKNSSSAKDNSINTSKHDHRWSR

RWQETRR

SEQ ID NO: 8:
Consensus canine V3 amino acid sequence without signal peptide
(assembled from XP_022272456.1)
LHKAKVEKSPPVKGSLSGKVNLPCHFSTMPTLPPSYNTSSEFLRIKWSKIELDKNGKDLKETTVLVAQNGN

VKIGQGYQGRVSVPTHAEVVGDASLTMVKLRASDAGQYRCDVMYGIEDTQDTVSLAVDGVVFHYRAAT

SRYTLNFEAAQKACLDIGAVIATPEQLYAAYEDGFEQCDAGWLSDQTVRYPIRAPRVGCYGDMMGKEGV

RTYGFRSPHETYDVYCYVDHLDGDVFHITAPNKFTFEEAEEECENQDARLATVGELQAAWRNGFDQCDY

GWLSDASVRHPVTVARAQCGGGLLGVRTLYRFENQTGFPPPDSRFDAYCFKRPDRCKTNPCLNGGTCYPT

ETSYVCTCVPGFSGDQCELDFDECHSNPCRNGATCVDGFNTFRCLCLPSYVGALCEQDTETCDYGWHKFQ

GQCYKYFAHRRTWDAAERECRLQGAHLTSILSHEEQMFVNRVGHDYQWIGLNDKMFEHDFRWTDGSTL

QYENWRPNQPDSFFSAGEDCVVIIWHENGQWNDVPCNYHLTYTCKKGTVACGQPPVVENAKTFGKMKPR

YEINSLIRYHCKDGFIQRHLPTIRCLGNGRWAMPKITCMNPSAYQRTYSKKYFKNSSSAKDNSINTSKHDHR

WSRRWQESRR

SEQ ID NO: 9:
Consensus human V3 amino acid sequence with Vint tail without signal peptide
LHKVKVGKSPPVRGSLSGKVSLPCHFSTMPTLPPSYNTSEFLRIKWSKIEVDKNGKDLKETTVLVAQNGNIK

IGQDYKGRVSVPTHPEAVGDASLTVVKLLASDAGLYRCDVMYGIEDTQDTVSLTVDGVVFHYRAATSRYT

LNFEAAQKACLDVGAVIATPEQLFAAYEDGFEQCDAGWLADQTVRYPIRAPRVGCYGDKMGKAGVRTY

GFRSPQETYDVYCYVDHLDGDVFHLTVPSKFTFEEAAKECENQDARLATVGELQAAWRNGFDQCDYGWL

SDASVRHPVTVARAQCGGGLLGVRTLYRFENQTGFPPPDSRFDAYCFKRPDRCKMNPCLNGGTCYPTETS

YVCTCVPGYSGDQCELDFDECHSNPCRNGATCVDGFNTFRCLCLPSYVGALCEQDTETCDYGWHKFQGQ

CYKYFAHRRTWDAAERECRLQGAHLTSILSHEEQMFVNRVGHDYQWIGLNDKMFEHDFRWTDGSTLQYE

NWRPNQPDSFFSAGEDCVVIIWHENGQWNDVPCNYHLTYTCKKGTVACGQPPVVENAKTFGKMKPRYEI

NSLIRYHCKDGFIQRHLPTIRCLGNGRWAIPKITCMNRKWSFRKNGLPCYNNY

SEQ ID NO: 10:
Consensus *Gaussia princeps* luciferase signal peptide amino acid sequence
(AAG54095.1)
MGVKVLFALICIAVAEA Nucleotide Sequences
All nucleotide SEQ ID sequences below are cDNA.

SEQ ID NO: 11:
Consensus human V3 nucleotide sequence including native signal peptide
(CCDS47242.1 including RefSeq. NM_001126336.2)
ATGTTCATAAATATAAAGAGCATCTTATGGATGTGTTCAACCTTAATAGTAACCCATGCGCTACATAA

AGTCAAAGTGGGAAAAAGCCCACCGGTGAGGGGCTCCCTCTCTGGAAAAGTCAGCCTACCTTGTCATT

TTTCAACGATGCCTACTTTGCCACCCAGTTACAACACCAGTGAATTTCTCCGCATCAAATGGTCTAAGA

TTGAAGTGGACAAAAATGGAAAAGATTTGAAAGAGACTACTGTCCTTGTGGCCCAAAATGGAAATAT

CAAGATTGGTCAGGACTACAAAGGGAGAGTGTCTGTGCCCACACATCCCGAGGCTGTGGGCGATGCCT

CCCTCACTGTGGTCAAGCTGCTGGCAAGTGATGCGGGTCTTTACCGCTGTGACGTCATGTACGGGATTG

AAGACACACAAGACACGGTGTCACTGACTGTGGATGGGGTTGTGTTTCACTACAGGGCGGCAACCAGC

AGGTACACACTGAATTTTGAGGCTGCTCAGAAGGCTTGTTTGGACGTTGGGGCAGTCATAGCAACTCC

AGAGCAGCTCTTTGCTGCCTATGAAGATGGATTTGAGCAGTGTGACGCAGGCTGGCTGGCTGATCAGA

CTGTCAGATATCCCATCCGGGCTCCCAGAGTAGGCTGTTATGGAGATAAGATGGGAAAGGCAGGAGTC

AGGACTTATGGATTCCGTTCTCCCCAGGAAACTTACGATGTGTATTGTTATGTGGATCATCTGGATGGT

GATGTGTTCCACCTCACTGTCCCCAGTAAATTCACCTTCGAGGAGGCTGCAAAAGAGTGTGAAAACCA

GGATGCCAGGCTGGCAACAGTGGGGGAACTCCAGGCGGCATGGAGGAACGGCTTTGACCAGTGCGAT

TACGGGTGGCTGTCGGATGCCAGCGTGCGCCACCCTGTGACTGTGGCCAGGGCCCAGTGTGGAGGTGG

TCTACTTGGGGTGAGAACCCTGTATCGTTTTGAGAACCAGACAGGCTTCCCTCCCCCTGATAGCAGATT

TGATGCCTACTGCTTTAAACGACCTGATCGCTGCAAAATGAACCCGTGCCTTAACGGAGGCACCTGTT

ATCCTACTGAAACTTCCTACGTATGCACCTGTGTGCCAGGATACAGCGGAGACCAGTGTGAACTTGAT

TTTGATGAATGTCACTCTAATCCCTGTCGTAATGGAGCCACTTGTGTTGATGGTTTTAACACATTCAGG

TGCCTCTGCCTTCCAAGTTATGTTGGTGCACTTTGTGAGCAAGATACCGAGACATGTGACTATGGCTGG

CACAAATTCCAAGGGCAGTGCTACAAATACTTTGCCCATCGACGCACATGGGATGCAGCTGAACGGGA

ATGCCGTCTGCAGGGTGCCCATCTCACAAGCATCCTGTCTCACGAAGAACAAATGTTTGTTAATCGTGT

GGGCCATGATTATCAGTGGATAGGCCTCAATGACAAGATGTTTGAGCATGACTTCCGTTGGACTGATG

GCAGCACACTGCAATACGAGAATTGGAGACCCAACCAGCCAGACAGCTTCTTTTCTGCTGGAGAAGAC

TGTGTTGTAATCATTTGGCATGAGAATGGCCAGTGGAATGATGTTCCCTGCAATTACCATCTCACCTAT

ACGTGCAAGAAAGGAACAGTCGCTTGCGGCCAGCCCCCTGTTGTAGAAAATGCCAAGACCTTTGGAA

AGATGAAACCTCGTTATGAAATCAACTCCCTGATTAGATACCACTGCAAAGATGGTTTCATTCAACGT

CACCTTCCAACTATCCGGTGCTTAGGAAATGGAAGATGGGCTATACCTAAAATTACCTGCATGAACCC

ATCTGCATACCAAAGGACTTATTCTATGAAATACTTTAAAAATTCCTCATCAGCAAAGGACAATTCAA

TAAATACATCCAAACATGATCATCGTTGGAGCCGGAGGTGGCAGGAGTCGAGGCGCTGA

-continued

SEQ ID NO: 12:
Consensus human V3 nucleotide sequence without signal peptide
CTACATAAAGTCAAAGTGGGAAAAAGCCCACCGGTGAGGGGCTCCCTCTCTGGAAAAGTCAGCCTAC

CTTGTCATTTTTCAACGATGCCTACTTTGCCACCCAGTTACAACACCAGTGAATTTCTCCGCATCAAAT

GGTCTAAGATTGAAGTGGACAAAAATGGAAAAGATTTGAAAGAGACTACTGTCCTTGTGGCCCAAAA

TGGAAATATCAAGATTGGTCAGGACTACAAAGGGAGAGTGTCTGTGCCCACACATCCCGAGGCTGTGG

GCGATGCCTCCCTCACTGTGGTCAAGCTGCTGGCAAGTGATGCGGGTCTTTACCGCTGTGACGTCATGT

ACGGGATTGAAGACACACAAGACACGGTGTCACTGACTGTGGATGGGGTTGTGTTTCACTACAGGGCG

GCAACCAGCAGGTACACACTGAATTTTGAGGCTGCTCAGAAGGCTTGTTTGGACGTTGGGGCAGTCAT

AGCAACTCCAGAGCAGCTCTTTGCTGCCTATGAAGATGGATTTGAGCAGTGTGACGCAGGCTGGCTGG

CTGATCAGACTGTCAGATATCCCATCCGGGCTCCCAGAGTAGGCTGTTATGGAGATAAGATGGGAAAG

GCAGGAGTCAGGACTTATGGATTCCGTTCTCCCCAGGAAACTTACGATGTGTATTGTTATGTGGATCAT

CTGGATGGTGATGTGTTCCACCTCACTGTCCCCAGTAAATTCACCTTCGAGGAGGCTGCAAAAGAGTG

TGAAAACCAGGATGCCAGGCTGGCAACAGTGGGGGAACTCCAGGCGGCATGGAGGAACGGCTTTGAC

CAGTGCGATTACGGGTGGCTGTCGGATGCCAGCGTGCGCCACCCTGTGACTGTGGCCAGGGCCCAGTG

TGGAGGTGGTCTACTTGGGGTGAGAACCCTGTATCGTTTTGAGAACCAGACAGGCTTCCCTCCCCCTG

ATAGCAGATTTGATGCCTACTGCTTTAAACGACCTGATCGCTGCAAAATGAACCCGTGCCTTAACGGA

GGCACCTGTTATCCTACTGAAACTTCCTACGTATGCACCTGTGTGCCAGGATACAGCGGAGACCAGTG

TGAACTTGATTTTGATGAATGTCACTCTAATCCCTGTCGTAATGGAGCCACTTGTGTTGATGGTTTTAA

CACATTCAGGTGCCTCTGCCTTCCAAGTTATGTTGGTGCACTTTGTGAGCAAGATACCGAGACATGTGA

CTATGGCTGGCACAAATTCCAAGGGCAGTGCTACAAATACTTTGCCCATCGACGCACATGGGATGCAG

CTGAACGGGAATGCCGTCTGCAGGGTGCCCATCTCACAAGCATCCTGTCTCACGAAGAACAAATGTTT

GTTAATCGTGTGGGCCATGATTATCAGTGGATAGGCCTCAATGACAAGATGTTTGAGCATGACTTCCG

TTGGACTGATGGCAGCACACTGCAATACGAGAATTGGAGACCCAACCAGCCAGACAGCTTCTTTTCTG

CTGGAGAAGACTGTGTTGTAATCATTTGGCATGAGAATGGCCAGTGGAATGATGTTCCCTGCAATTAC

CATCTCACCTATACGTGCAAGAAAGGAACAGTCGCTTGCGGCCAGCCCCCTGTTGTAGAAAATGCCAA

GACCTTTGGAAAGATGAAACCTCGTTATGAAATCAACTCCCTGATTAGATACCACTGCAAAGATGGTT

TCATTCAACGTCACCTTCCAACTATCCGGTGCTTAGGAAATGGAAGATGGGCTATACCTAAAATTACCT

GCATGAACCCATCTGCATACCAAAGGACTTATTCTATGAAATACTTTAAAAATTCCTCATCAGCAAAG

GACAATTCAATAAATACATCCAAACATGATCATCGTTGGAGCCGGAGGTGGCAGGAGTCGAGGCGCT

GA

SEQ ID NO: 13:
Codon-optimized human V3 nucleotide sequence of consensus with
signal peptide
ATGTTCATCAATATCAAGTCCATACTGTGGATGTGTAGTACCCTCATTGTGACACATGCATTGCACAAA

GTAAAAGTTGGAAAGAGTCCGCCTGTGAGGGGATCACTGAGTGGCAAAGTGTCACTGCCCTGTCACTT

TTCCACTATGCCAACTCTCCCACCCTCTTATAACACATCCGAGTTTCTCCGCATAAAGTGGTCCAAAAT

CGAGGTAGACAAGAACGGCAAAGACCTCAAAGAGACTACTGTGCTCGTGGCACAGAATGGAAACATC

AAGATTGGGCAGGACTATAAGGGTCGTGTCAGCGTGCCAACTCACCCAGAAGCCGTTGGCGACGCCA

GCTTGACAGTTGTGAAACTGCTTGCCAGCGACGCCGGACTGTATCGCTGCGATGTCATGTATGGTATC

GAAGATACACAGGACACAGTGAGCCTGACCGTGGATGGGGTAGTCTTTCACTATAGAGCCGCCACATC

TAGATACACCCTGAATTTTGAGGCAGCTCAGAAGGCCTGCTTGGATGTGGGCGCCGTGATTGCAACGC

CTGAGCAACTGTTCGCCGCCTACGAAGATGGATTCGAGCAGTGTGACGCAGGATGGCTGGCCGATCAG

-continued

```
ACCGTTCGGTACCCTATCAGAGCTCCCCGAGTAGGGTGCTATGGCGATAAAATGGGCAAGGCTGGCGT

GAGGACCTACGGCTTCAGGTCACCTCAGGAAACCTATGACGTGTACTGTTATGTGGACCACTTGGATG

GCGATGTCTTTCATCTCACGGTCCCCTCTAAATTTACGTTCGAAGAAGCGGCCAAGGAGTGCGAGAAT

CAGGACGCCAGGCTGGCAACTGTGGGAGAACTGCAGGCTGCCTGGCGCAATGGGTTCGACCAGTGCG

ATTATGGGTGGCTGAGTGACGCTTCTGTCCGCCATCCCGTTACCGTCGCTAGGGCGCAATGCGGTGGA

GGACTTCTGGGCGTTAGAACCCTCTATCGCTTTGAGAATCAGACTGGGTTTCCGCCACCAGATTCTCGG

TTCGATGCGTATTGCTTCAAACGTCCCGACCGTTGTAAGATGAACCCATGCCTTAACGGCGGAACCTGT

TACCCAACAGAAACGAGCTATGTTTGCACCTGTGTGCCCGGGTACTCAGGCGACCAGTGTGAACTGGA

CTTTGACGAATGCCACTCTAATCCGTGCAGAAATGGCGCTACGTGCGTGGACGGGTTCAACACTTTCC

GATGTCTGTGTCTGCCTAGCTACGTCGGGGCACTGTGCGAGCAGGATACCGAAACCTGTGATTACGGG

TGGCACAAGTTTCAGGGTCAGTGCTACAAGTACTTTGCGCATAGAAGAACATGGGATGCCGCAGAGCG

AGAGTGTAGGCTGCAAGGGGCTCATCTGACATCCATCCTTAGCCATGAGGAACAAATGTTTGTCAACA

GAGTTGGCCACGACTATCAATGGATCGGCTTGAATGACAAGATGTTCGAGCACGACTTCAGGTGGACA

GACGGCTCCACCCTCCAGTACGAGAACTGGAGGCCTAATCAGCCCGACAGCTTCTTCAGTGCAGGAGA

GGATTGCGTAGTCATAATCTGGCACGAAAACGGTCAGTGGAACGATGTGCCATGCAACTATCATCTGA

CCTACACATGCAAGAAAGGTACTGTGGCCTGTGGCCAACCTCCTGTCGTGGAGAATGCCAAAACATTT

GGTAAGATGAAACCCAGGTACGAGATTAACTCCCTTATTCGCTACCACTGTAAGGATGGTTTCATTCA

ACGGCATCTGCCCACTATTCGGTGCCTGGGAAATGGGCGGTGGGCAATTCCGAAGATAACCTGTATGA

ACCCCTCTGCTTACCAGCGAACCTACTCCATGAAGTACTTCAAGAACTCCAGTTCAGCTAAAGACAAT

AGCATCAACACTTCAAAACACGATCATCGCTGGAGCCGGCGGTGGCAGGAAAGCAGACGGTGA
```

SEQ ID NO: 14:
Codon-optimized human V3 nucleotide sequence of SEQ ID NO: 13: without signal peptide

```
TTGCACAAAGTAAAAGTTGGAAAGAGTCCGCCTGTGAGGGGATCACTGAGTGGCAAAGTGTCACTGC

CCTGTCACTTTTCCACTATGCCAACTCTCCCACCCTCTTATAACACATCCGAGTTTCTCCGCATAAAGTG

GTCCAAAATCGAGGTAGACAAGAACGGCAAAGACCTCAAAGAGACTACTGTGCTCGTGGCACAGAAT

GGAAACATCAAGATTGGGCAGGACTATAAGGGTCGTGTCAGCGTGCCAACTCACCCAGAAGCCGTTG

GCGACGCCAGCTTGACAGTTGTGAAACTGCTTGCCAGCGACGCCGGACTGTATCGCTGCGATGTCATG

TATGGTATCGAAGATACACAGGACACAGTGAGCCTGACCGTGGATGGGGTAGTCTTTCACTATAGAGC

CGCCACATCTAGATACACCCTGAATTTTGAGGCAGCTCAGAAGGCCTGCTTGGATGTGGGCGCCGTGA

TTGCAACGCCTGAGCAACTGTTCGCCGCCTACGAAGATGGATTCGAGCAGTGTGACGCAGGATGGCTG

GCCGATCAGACCGTTCGGTACCCTATCAGAGCTCCCCGAGTAGGGTGCTATGGCGATAAAATGGGCAA

GGCTGGCGTGAGGACCTACGGCTTCAGGTCACCTCAGGAAACCTATGACGTGTACTGTTATGTGGACC

ACTTGGATGGCGATGTCTTTCATCTCACGGTCCCCTCTAAATTTACGTTCGAAGAAGCGGCCAAGGAGT

GCGAGAATCAGGACGCCAGGCTGGCAACTGTGGGAGAACTGCAGGCTGCCTGGCGCAATGGGTTCGA

CCAGTGCGATTATGGGTGGCTGAGTGACGCTTCTGTCCGCCATCCCGTTACCGTCGCTAGGGCGCAAT

GCGGTGGAGGACTTCTGGGCGTTAGAACCCTCTATCGCTTTGAGAATCAGACTGGGTTTCCGCCACCA

GATTCTCGGTTCGATGCGTATTGCTTCAAACGTCCCGACCGTTGTAAGATGAACCCATGCCTTAACGGC

GGAACCTGTTACCCAACAGAAACGAGCTATGTTTGCACCTGTGTGCCCGGGTACTCAGGCGACCAGTG

TGAACTGGACTTTGACGAATGCCACTCTAATCCGTGCAGAAATGGCGCTACGTGCGTGGACGGGTTCA

ACACTTTCCGATGTCTGTGTCTGCCTAGCTACGTCGGGGCACTGTGCGAGCAGGATACCGAAACCTGT

GATTACGGGTGGCACAAGTTTCAGGGTCAGTGCTACAAGTACTTTGCGCATAGAAGAACATGGGATGC
```

```
CGCAGAGCGAGAGTGTAGGCTGCAAGGGGCTCATCTGACATCCATCCTTAGCCATGAGGAACAAATGT

TTGTCAACAGAGTTGGCCACGACTATCAATGGATCGGCTTGAATGACAAGATGTTCGAGCACGACTTC

AGGTGGACAGACGGCTCCACCCTCCAGTACGAGAACTGGAGGCCTAATCAGCCCGACAGCTTCTTCAG

TGCAGGAGAGGATTGCGTAGTCATAATCTGGCACGAAAACGGTCAGTGGAACGATGTGCCATGCAAC

TATCATCTGACCTACACATGCAAGAAAGGTACTGTGGCCTGTGGCCAACCTCCTGTCGTGGAGAATGC

CAAAACATTTGGTAAGATGAAACCCAGGTACGAGATTAACTCCCTTATTCGCTACCACTGTAAGGATG

GTTTCATTCAACGGCATCTGCCCACTATTCGGTGCCTGGGAAATGGGCGGTGGGCAATTCCGAAGATA

ACCTGTATGAACCCCTCTGCTTACCAGCGAACCTACTCCATGAAGTACTTCAAGAACTCCAGTTCAGCT

AAAGACAATAGCATCAACACTTCAAAACACGATCATCGCTGGAGCCGGCGGTGGCAGGAAAGCAGAC

GGTGA

SEQ ID NO: 15:
Consensus rat V3 nucleotide sequence without signal peptide
(NM_001170559.1)
CTGCATAAAGCCAAATGGAAGAAAACCCACCTGTTAAAGGCTCTCTGTCTGGAAAAGTGATCCTACC

TTGTCATTTTTCAACCTTGCCCACCTTACCACCCGATTACAACACGAGTGAATTTCTCAGAATCAAATG

GTCTAAAATAGAAGTGGACAAAAATGGAAAAGACATAAAGGAGACTACTGTCCTGGTGGCCCAAGAC

GGGAACATCAAGATTGGTCAGGACTACAAGGGGCGGGTATCAGTGCCTACGCATCCCGATGACGTAG

GCGATGCCTCTCTCACCATGGTCAAACTCCGTGCTAGTGACGCAGGTGTCTACCGCTGTGATGTCATGT

ATGGCATTGAAGACACTCAGAACACGATGTCGCTGGCCGTGGACGGTGTCGTGTTTCACTACAGGGCA

GCGACCAGCAGATACACTCTGAACTTCGAGTCTGCTCAACAGGCTTGTTTGGACATCGGGGCGGTCAT

AGCAACCCCAGAGCAGCTGTTCGCTGCCTATGAGGATGGATTTGAGCAGTGTGATGCAGGATGGCTGT

CTGACCAAACTGTCAGATATCCCATACGGGCTCCCCGAGAGGGCTGTTATGGAGACATGATGGGGAAG

GAAGGGGTCCGGACCTATGGATTCCGCTCTCCCCAGGAAACCTATGATGTGTATTGCTATGTGGATCA

TCTGGACGGCGATGTGTTCCACATCACTGCTCCCAGTAAATTCACCTTCGAGGAGGCCGAAGCAGAGT

GTGCAAACCGGGATGCCAGGCTGGCGACTGTTGGGGAACTTCACGCAGCTTGGAGGAACGGCTTTGAC

CAGTGCGATTACGGCTGGCTGTCGGATGCCAGCGTGCGGCACCCTGTGACTGTGGCCAGGGCCCAGTG

TGGAGGTGGTCTACTTGGGGTGAGAACCCTGTATCGTTTTGAGAACCAGACATGCTTCCCTCTCCCTGA

TAGCAGATTTGATGCCTACTGCTTTAAACGACCTGATCTCTGCAAAACAAACCCATGCCTCAATGGAG

GCACCTGCTATCCTACTGAGACTTCCTATGTGTGCACCTGTGCACCTGGCTACAGTGGAGACCAGTGTG

AACTGGATTTTGATGAATGTCACTCTAACCCTTGTCGGAATGGAGCCACCTGTGTGGACGGTCTGAAT

ACATTTAGATGCCTCTGCCTTCCGAGTTATGTCGGTGCACTCTGCGAACAAGACACTGAGACATGCGA

CTATGGCTGGCACAAATTCCAAGGGCAATGCTACAAGTACTTTGCTCATCGCCGTACATGGGATGCTG

CTGAAAGGGAGTGTCGCCTGCAGGGTGCCCACCTCACAAGCATCCTTTCTCATGAGGAACAAATGTTT

GTGAATCGTGTGGGCCATGATTACCAGTGGATTGGCCTCAATGACAAGATGTTTGAACATGACTTCCG

CTGGACTGACGGCAGCGCACTGCAATATGAGAACTGGAGACCCAACCAGCCAGACAGCTTCTTTTCTG

CTGGAGAAGACTGCGTTGTGATCATTTGGCATGAGAATGGCCAGTGGAATGACGTCCCCTGCAACTAC

CACCTCACCTACACCTGCAAGAAGGGAACAGTTGCTTGCGGCCAACCCCCTGTTGTAGAAAATGCCAA

GACCTTTGGAAAGATGAAACCACGTTATGAAATCAACTCCTTGATTAGATACCACTGCAAAGATGGTT

TCATTCAGCGTCACCTTCCAACTATCCGGTGCCTAGGAAATGGGAGATGGGCAATGCCTAAAATAACC

TGCATGAACCCATCTGCATACCAAAGGACTTATTCTAAGAAATACTTAAAAAATTCCTCATCAGTCAA

GGACAATTCTATAAATACGTCAAAACATGAGCATCGCTGGAGCCGGAGGTGGCAGGAAACGAGGCGC

TGA
```

-continued

SEQ ID NO: 16:
Consensus mouse V3 nucleotide sequence without signal peptide
(NM_001134475.1)
CTACATCAAGCCAAAATGGAAACCAGCCCACCTGTTAAAGGCTCTCTGTCTGGAAAAGTGGTCCTACC

TTGTCATTTTTCAACCTTACCTACCTTACCACCCAATTACAACACGAGTGAATTTCTCAGAATCAAATG

GTCTAAGATGGAAGTGGACAAAAATGGAAAAGATATAAAGGAGACGACTGTCTTGGTGGCCCAGAAC

GGAAATATCAAGATTGGTCAGGACTACAAGGGGCGAGTGTCCGTGCCTACACATCCCGATGATGTAGG

TGATGCTTCCCTCACCATGGTCAAACTCCGGGCTAGTGATGCAGGCGTCTACCGATGTGATGTCATGTA

TGGGATTGAAGACACTCAGGACACCATGTCACTGGCTGTGGATGGTGTTGTGTTTCACTACAGGGCAG

CCACCAGCAGGTACACTCTGAACTTTGCCGCTGCTCAACAGGCTTGTTTGGATATCGGGGCGGTCATA

GCAAGCCCAGAGCAGCTGTTTGCCGCCTATGAGGATGGATTTGAGCAGTGTGATGCAGGATGGCTGTC

TGATCAAACTGTCAGATATCCCATACGGGCTCCCCGAGAGGGCTGTTACGGAGACATGATGGGGAAG

GAAGGGGTTCGGACCTATGGATTCCGCTCTCCCCAGGAAACCTATGATGTGTATTGTTATGTGGATCAT

CTGGATGGCGATGTGTTCCACATCACTGCTCCCAGTAAGTTCACCTTCGAGGAGGCCGAAGCAGAGTG

TACAAGCAGGGATGCGAGGCTGGCGACTGTTGGAGAACTTCAGGCAGCTTGGAGAAATGGCTTTGAC

CAATGCGATTACGGCTGGCTGTCGGATGCCAGCGTGCGGCACCCTGTGACTGTGGCCAGGGCCCAGTG

TGGAGGAGGTCTACTTGGGGTGAGAACCCTGTATCGTTTTGAGAACCAGACATGCTTCCCTCTCCCTGA

TAGCAGATTTGATGCCTACTGCTTTAAACGACCTGATCTCTGCAAAACAAACCCATGCCTCAACGGAG

GCACCTGTTATCCTACCGAGACTTCCTATGTGTGCACCTGTGCACCTGGATACAGCGGAGACCAGTGT

GAACTTGATTTTGATGAATGTCACTCTAACCCTTGTCGGAATGGTGCCACCTGTGTGGATGGTTTTAAT

ACATTTAGATGTCTCTGTCTCCCAAGTTATGTTGGTGCACTCTGTGAACAAGACACTGAGACATGTGAC

TATGGCTGGCACAAAATTCCAAGGACAGTGCTACAAGTACTTTGCTCATCGACGCACATGGGATGCTGC

TGAAAGGGAGTGTCGCCTGCAGGGTGCCCACCTCACAAGCATCCTTTCTCATGAGGAACAAATGTTTG

TGAATCGTGTGGGCCATGATTACCAGTGGATCGGCCTCAATGACAAGATGTTTGAACATGACTTCCGC

TGGACTGACGGCAGTGCACTGCAATATGAGAACTGGAGACCCAACCAGCCAGACAGTTTCTTTTCTGC

AGGAGAAGACTGCGTTGTGATCATTTGGCATGAAAATGGTCAGTGGAATGACGTCCCCTGCAATTACC

ACCTCACCTACACTTGCAAGAAGGGAACAGTTGCTTGCGGCCAACCCCCTGTTGTAGAAAATGCCAAG

ACCTTTGGAAAGATGAAACCACGCTATGAAATCAACTCCTTGATTAGATATCACTGCAAAGATGGTTT

CATTCAGCGACACCTTCCAACTATCCGGTGCCTAGGAAACGGGAGATGGGCAATGCCTAAAATAACCT

GCATGAACCCATCTGCATACCAAAGGACTTATTCTAAGAAATACTTAAAAAATTCCTCATCCGCAAAG

GACAATTCTATAAATACATCAAAACATGAGCATCGCTGGAGCCGGAGGCGGCAGGAAACCAGGCGCT
GA

SEQ ID NO: 17:
Consensus pig V3 nucleotide sequence without signal peptide
(AB558523.1)
CTACATAAAGTCAAAGTGGAAAAAAGCCCACCTGTCAAGGGCTCCCTCTCTGGAAAAGTCAACCTACC

TTGTCATTTTTCAACTATGCCTACCTTACCACCCAGTTACAACACCACCAGTGAATTTCTCCGAATTAA

ATGGTCTAAGATTGAATTGGACAAGAGTGGAAAAGATTTAAAGGAGACTACTGTTCTTGTGGCCCAAA

ATGGGAATATCAAGATTGGTCAGGGCTACAAAGGAAGAGTGTCGGTGCCTACACATCCGGAGGATGT

GGGTGATGCCTCACTCACCATGGTCAAACTCCTTGCCAGTGATGCAGGCCTTTACCGCTGTGATGTCAT

GTATGGGATAGAAGACACACAAGACTCCGTGTCATTGGCTGTGGATGGAGTTGTGTTTCACTACAGGG

CAGCGACGAGCAGGTACACTCTGAATTTTGAGGCTGCRCAGAAGGCTTGTCTGGATATCGGAGCAGTC

ATAGCAACCCCAGAGCAGCTCCATGCCGCCTATGAAGACGGATTTGAGCAATGTGATGCAGGCTGGCT

-continued

```
GTCTGATCAGACTGTTAGATATCCCATCCGGACTCCCCGAGAAGGCTGTTACGGAGATATGATGGGGA

AGGAAGGAGTCAGGACCTACGGATTCCGTGCTCCCCATGAGACTTACGATGTGTATTGTTACGTGGAC

CATCTGGATGGTGATGTGTTCCACATCACTGCTCCCAATAAATTCACCTTTGAGGAGGCTGAAGAAGA

GTGTGAAAACCAGGATGCCCGCCTGGCAACAGTGGGGGAACTCCAAGCAGCGTGGAGGAACGGCTTT

GACCAGTGTGATTACGGGTGGCTATTGGATGCCAGTGTTCGCCACCCTGTGACTGTGCCCAGGGCCCA

GTGTGGAGGTGGTTTACTTGGGGTGAGAACCCTGTATCGTTTTGAGAACCAGACAGGCTTCCCTTCCCC

TGATAGCAGATTTGATGCCTACTGCTATAAACGACCCGATCGTTGCAAAACCAACCCGTGCCTTAATG

GGGGCACCTGCTACCCTACTGAAACGTCCTATGTGTGCACCTGCGTGCCAGGATACAGTGGCGACCAA

TGTGAACTTGATTTTGATGAATGTCACTCTAACCCCTGTCGCAACGGAGCCACATGCGTTGACGGTTTT

AATACCCTTAGGTGTCTCTGCCTCCCGAGCTATGTAGGTGCACTTTGTGAGCAAGACACGGAGACATG

TGACTATGGCTGGCACAAATTTCAAGGGCAGTGCTACAAGTACTTCGCCCACCGACGTACGTGGGATG

CAGCTGAACGGGAGTGCCGTCTTCAGGGTGCCCATCTCACCAGCATTCTGTCTCATGAGGAACAAATG

TTTGTGAATCGTGTGGGCCATGATTATCAGTGGATTGGTCTCAATGACAAGATGTTTGAGCATGACTTC

CGTTGGACCGATGGCAGCACACTGCAATATGAGAACTGGAGGCCCAACCAGCCAGACAGCTTCTTTTC

TTCTGGAGAAGACTGCGTTGTGATCATATGGCATGAGAATGGCCAGTGGAATGATGTTCCCTGCAATT

ACCATCTCACCTACACCTGCAAGAAAGGAACAGTTGCTTGCGGCCAGCCCCCTGTTGTAGAAAATGCC

AAGACCTTTGGAAAGATGAAACCTCGTTATGAAATCAACTCCCTGATTAGATATCACTGCAAAGATGG

TTTCATTCAACGCCACCCTCCAACTATCCGTTGCCTAGGAAATGGAAGATGGGCTATGCCCAAAATTA

CCTGCCTGAACCCATCCGCATACCAAAGGACTTATTCTAAGAAATACTTTAAAAATTCCTCATCAGCA

AAGGACAATTCAATAAACACATCCAAACATGATCACCGTTGGAGTCGGAGGTGGCAAGAGTCAAGGC

GCTGA

SEQ ID NO: 18:
Consensus cow V3 nucleotide sequence without signal peptide
(AF060459.1)
CTACAGAAAGTCAACATGGAAAAAAGCCCACCTGTTAAGGGCTCCCTCTCTGGAAAAGTCAACCTACC

TTGTCATTTCTCAACCATGCCTACCTTACCACCCAGTTATAACACCACCAGTGAATTTCTGCGAATCAA

ATGGTCTAAGATTGAATTGGACAAGACGGGAAAAGATTTAAAGGAGACTACTGTTCTCGTGGCCCAAA

ATGGGAATATCAAGATCGGTCAAGACTACAAAGGGAGAGTGTCGGTGCCTACACATCCCGAGGATGT

GGGCGATGCCTCACTCACCATGGTCAAACTGCTGGCCAGTGATGCAGGCCGCTACCGCTGTGACGTCA

TGTACGGGATTGAAGACACACAGGACACGGTGTCACTGACCGTGGAGGGGGTTGTGTTTGACTACAGG

GCGGCAACCAGCAGGTACACCCTGAACTTTGAGATGGCACAGAAGGCTTGTGTGGACATCGGGGCCG

TCATAGCCACCCCAGAGCAGCTGCATGCCGCCTATGAAGATGGTTTTGAGCAGTGTGATGCAGGATGG

CTGTCAGATCAGACTGTTAGGTATCCCATCCGGGTTCCCCGAGAAGGCTGCTATGGAGACATGATGGG

GAAGGAAGGAGTCCGGACCTACGGATTCCGTGCTCCTCATGAAACTTACGATGTGTATTGTTACGTGG

ACCATCTGGATGGTGATGTGTTCCACATCACTGCTCCCAACAAGTTCACCTTTGAGGAAGCTGGAGAA

GAGTGTAAAACCCAGGACGCCCGCCTGGCGACCGTGGGGGAGCTCCAAGCAGCGTGGAGGAACGGCT

TCGACCGGTGTGATTACGGGTGGCTGTTGGACGCCAGCGTTCGCCACCCTGTGACTGTGGCCAGGGCC

CAGTGTGGAGGTGGTTTACTTGGGGTGAGAACCCTGTATCGTTTTGAGAACCAGACAGGCTTCCCTAC

CCCTGATAGCAGATTTGATGCCTACTGCTTTAAACGACCTGATCGTTGCAAAATGAACCCGTGCCTCAA

TGGGGGCACCTGTTATCCTACTGAAACTTCCTACGTGTGCACCTGCGTGCCAGGATACAGTGGTGATC

GGTGTGAACTTGATTTTGATGAATGTCATTCTAATCCTTGTCGCAATGGAGCCACATGTATTGACGGTT

TTAATACCTTCAGGTGTCTCTGCCTCCCGAGCTACGTTGGTGCGCTTTGTGAGCAAGACACGGAGACAT
```

-continued

```
GTGACTATGGCTGGCACAAATTTCAAGGGCAGTGCTACAAGTACTTTGCCCATCGACGGACGTGGGAT

GCAGCTGAACGGGAATGCCGTCTGCAGGGCGCCCATCTCACCAGTATCCTGTCTCACGAGGAACAAAT

GTTTGTGAATCGTGTGGGCCATGATTATCAGTGGATAGGTCTCAATGACAAGATGTTTGAGCATGACTT

CCGTTGGACTGATGGCAGCACACTGCAATATGAGAACTGGAGGCCGAACCAACCAGACAGCTTCTTTT

CTACTGGAGAAGATTGTGTTGTGATTATATGGCATGAGAATGGCCAGTGGAATGACGTTCCCTGCAAT

TACCATCTCACCTACACCTGCAAGAAAGGAACAGTTGCTTGCGGCCAGCCCCTGTTGTAGAAAATGC

CAAGACCTTTGGAAAGATGAAACCTCGTTATGAAATCAACTCCTTGATTAGATATCACTGCAAAGATG

GTTTCATTCAACGCCACCTTCCAACTATCCGTTGCCTAGGAAATGGAAGATGGGCTATGCCTAAAATTA

CCTGCCTGAACCCATCTGCATACCAAAGGACTTATTCTAAGAAATATTTTAAAAATTCCTCATCAGGAA

AGGACAATTCAATAAATACATCAAAACATGATCACCGTTGGAGCCGAAGGTGGCAAGAATCAAGGCG

CTGA

SEQ ID NO: 19:
Consensus rhesus monkey V3 nucleotide sequence without signal peptide
(assembled from XM_015140359.1)
CTACATAAAGTCAAAGTGGGAAAAAGCCCACCTCTGAGGGGCTCCCTCTCTGGAAAAGTCAGCCTACC

TTGTCATTTTTCAACCATGCCTACTTTGCCACCCAGTTACAACACCAGTGAATTTCTCCGCATCAAATG

GTCTAAGATTGAAGTGGACAAAAATGGAAAAGATTTGAAAGAAACTACTGTCCTTGTGGCCCAAAAT

GGAAATATCAAGATTGGTCAGGACTACAAAGGGAGAGTGTCTGTGCCCACACATCCCGAGGCCGTGG

GCGATGCCTCCCTCACTGTGGTCAAGCTGCTGGCAAGTGATGCGGGCCTCTACCGCTGTGATGTCATGT

ACGGGATTGATGACACGCAAGACACGGTGTCACTGGCTGTGGATGGGGTTGTGTTTCACTACAGGGCG

TCAACCAGCAGGTACACACTGAATTTTGAGGCTGCTCAGAAGGCTTGTTTGGACATTGGGCGGTCAT

AGCAACTCCAGAGCAGCTCTTTGCCGCCTATGAAGATGGATTTGAGCAGTGTGACGCAGGCTGGCTGG

CTGATCAGACTGTCAGATATCCCATCCGGGCTCCCCGAGTAGGCTGTTACGGAGATATGATGGGAAAG

GCAGGAGTCAGGACCTATGGATTCCGTTCTCCCCAGGAAACTTACGATGTGTATTGTTATGTGGATCAT

CTGGATGGTGATGTGTTCCACCTCACTGCCCCCAGTAAATTCACCTTCGAGGAGGCCGCAAAAGAGTG

TGAAAACCAGGACGCCAGGCTGGCAACAGTGGGGAACTCCAGGCGGCGTGGAGGAACGGCTTTGAC

CAGTGCGATTACGGGTGGCTGTCGGATGCCAGCGTGCGCCACCCTGTGACTGTGGCCAGGGCCCAGTG

TGGAGGTGGTCTACTTGGGGTGAGAAGCCTGTATCGTTTTGAGAACCAGACAGGCTTCCCTCCCCCTG

ATAGCAGATTTGATGCCTACTGCTTTAAACGACCTGATCGTTGCAAAATGAACCCGTGCCTTAACGGA

GGCACCTGTTATCCTACTGAAACTTCCTATGTATGCACCTGTGTGCCAGGATACAGTGGAGACCAGTGT

GAACTTGATTTTGATGAATGTCACTCTAATCCCTGTCGGAATGGAGCCACTTGTGTTGATGGTTTTAAC

ACATTCAGGTGCCTCTGCCTTCCAAGTTATGTTGGTGCACTTTGTGAACAAGACACTGAGACATGTGAC

TATGGCTGGCACAAATTCCAAGGGCAGTGCTACAAATACTTTGCCCATCGACGCACATGGGATGCAGC

TGAACGGGAATGCCGTCTGCAGGGTGCCCATCTCACAAGCATCCTGTCTCACGAAGAACAAACGTTTG

TTAATCGTGTGGGCCATGATTATCAGTGGATAGGCCTCAATGACAAGATGTTTGAGCATGACTTCCGCT

GGACTGATGGCAGCACACTGCAATACGAGAATTGGAGGCCCAACCAGCCAGACAGCTTCTTTTCTGCT

GGAGAAGACTGTGTTGTAATCATTTGGCATGAGAATGGCCAGTGGAATGATGTTCCCTGCAATTACCA

TCTCACCTATGTGCAAGAAAGGAACAGTTGCTTGCGGCCAGCCCCTGTTGTAGAAAATGCCAAGA

CCTTTGGAAAGATGAAACCTCGTTATGAAATCAACTCCCTGATTAGATACCACTGCAAAGATGGTTTC

ATTCAACGTCACCTTCCAACCATCCGGTGCCTAGGAAATGGAAGATGGGCTATACCTAAAATTACCTG
```

CATGAACCCATCTGCATACCAAAGGACTTATTCTATGAAATACTTTAAAAATTCCTCATCAGCAAAGG

ACAATTCAATAAATACATCCAAACATGATCATCGTTGGAGCCGGAGGTGGCAGGAGACGAGGCGCTG

A

SEQ ID NO: 20:
Consensus dog V3 nucleotide sequence without signal peptide
(assembled from XM_022416748.1)
CTACATAAAGCCAAAGTGGAAAAAAGCCCACCTGTTAAGGGCTCCCTGTCTGGAAAAGTCAACCTACC

TTGCCATTTTTCCACTATGCCTACCTTACCGCCCAGTTACAACACCTCCAGCGAATTTCTCAGAATCAA

ATGGTCTAAGATTGAATTGGACAAGAATGGAAAGGATTTGAAGGAGACTACCGTCCTTGTAGCCCAAA

ATGGGAATGTCAAGATTGGTCAGGGCTATCAAGGAAGGGTGTCCGTGCCTACACATGCTGAGGTGGTG

GGTGATGCCTCCCTCACCATGGTCAAACTGCGTGCCAGTGACGCGGGCCAGTACCGCTGCGACGTCAT

GTACGGGATTGAAGACACACAAGACACGGTATCGTTGGCGGTGGACGGGGTTGTGTTTCACTACAGAG

CGGCAACCAGCAGGTATACACTGAATTTTGAGGCTGCACAGAAGGCTTGTTTGGATATTGGAGCAGTC

ATAGCAACCCCAGAGCAGCTCTATGCTGCCTACGAAGATGGATTTGAGCAGTGTGATGCAGGCTGGCT

GTCTGATCAGACCGTCAGATATCCCATCCGGGCTCCCCGAGTAGGCTGTTACGGAGATATGATGGGGA

AGGAAGGAGTCAGGACCTACGGATTCCGTTCGCCTCATGAGACTTACGATGTGTACTGCTACGTGGAC

CACCTGGATGGTGATGTGTTCCATATCACTGCTCCCAATAAATTTACCTTTGAGGAGGCCGAAGAAGA

GTGTGAGAACCAGGACGCCCGGCTGGCGACAGTGGGGGAACTCCAAGCAGCTTGGAGGAATGGCTTT

GACCAGTGCGATTATGGGTGGCTGTCCGACGCCAGCGTTCGCCACCCTGTGACTGTGGCCAGGGCCCA

GTGTGGAGGTGGTTTGCTTGGGGTGAGAACCCTGTATCGTTTTGAGAACCAGACAGGCTTCCCTCCCCC

TGATAGCAGATTTGATGCCTACTGCTTTAAACGACCCGATCGTTGTAAAACGAACCCGTGCCTTAATG

GAGGCACCTGTTATCCTACTGAAACTTCCTACGTATGTACCTGTGTGCCAGGATTCAGTGGCGACCAGT

GTGAGCTTGATTTCGATGAATGTCACTCTAACCCCTGTCGCAATGGAGCCACGTGTGTGGATGGTTTTA

ATACGTTCAGGTGCCTCTGCCTTCCGAGCTACGTTGGTGCACTTTGTGAACAAGACACAGAGACGTGT

GACTACGGCTGGCACAAATTCCAAGGCCAGTGCTACAAATACTTCGCCCATCGGCGCACGTGGGACGC

AGCTGAACGGGAATGCCGTCTGCAGGGCGCGCATCTCACAAGCATCCTGTCTCACGAGGAACAGATGT

TTGTGAACCGTGTGGGGCATGATTATCAGTGGATAGGCCTCAATGACAAGATGTTTGAACATGACTTC

CGTTGGACCGATGGCAGCACACTGCAATATGAGAACTGGAGGCCCAACCAGCCAGACAGCTTCTTTTC

TGCTGGAGAGGACTGTGTTGTAATCATTTGGCATGAGAATGGCCAGTGGAATGATGTTCCCTGCAATT

ATCATCTCACTTATACCTGCAAGAAAGGAACAGTTGCTTGCGGCCAGCCCCCTGTTGTAGAAAATGCC

AAGACCTTTGGAAAGATGAAACCTCGTTATGAAATCAACTCCCTGATTAGATATCACTGCAAAGATGG

TTTCATTCAACGCCACCTTGCAACTATCCGTTGCCTAGGAAATGGAAGATGGGCTATGCCTAAAATTAC

CTGCATGAACCCGTCTGCATACCAAAGGACTTACTCTAAGAAATACTTTAAAAATTCTTCATCAGCAA

AGGACAATTCAATAAATACATCAAAACATGATCACCGTTGGAGCCGAAGGTGGCAGGAGTCCAGGCG

CTGA

SEQ ID NO: 21:
Consensus human V3 nucleotide sequence with Vint tail, without signal
peptide
CTACATAAAGTCAAAGTGGAAAAAAGCCCACCGGTGAGGGGCTCCCTCTCTGGAAAAGTCAGCCTAC

CTTGTCATTTTTCAACGATGCCTACTTTGCCACCCAGTTACAACACCAGTGAATTTCTCCGCATCAAAT

GGTCTAAGATTGAAGTGGACAAAAATGGAAAAGATTTGAAAGAGACTACTGTCCTTGTGGCCCAAAA

TGGAAATATCAAGATTGGTCAGGACTACAAAGGGAGAGTGTCTGTGCCCACACATCCCGAGGCTGTGG

GCGATGCCTCCCTCACTGTGGTCAAGCTGCTGGCAAGTGATGCGGGTCTTTACCGCTGTGACGTCATGT

-continued

```
ACGGGATTGAAGACACACAAGACACGGTGTCACTGACTGTGGATGGGGTTGTGTTTCACTACAGGGCG
GCAACCAGCAGGTACACACTGAATTTTGAGGCTGCTCAGAAGGCTTGTTTGGACGTTGGGGCAGTCAT
AGCAACTCCAGAGCAGCTCTTTGCTGCCTATGAAGATGGATTTGAGCAGTGTGACGCAGGCTGGCTGG
CTGATCAGACTGTCAGATATCCCATCCGGGCTCCCAGAGTAGGCTGTTATGGAGATAAGATGGGAAAG
GCAGGAGTCAGGACTTATGGATTCCGTTCTCCCCAGGAAACTTACGATGTGTATTGTTATGTGGATCAT
CTGGATGGTGATGTGTTCCACCTCACTGTCCCCAGTAAATTCACCTTCGAGGAGGCTGCAAAAGAGTG
TGAAAACCAGGATGCCAGGCTGGCAACAGTGGGGGAACTCCAGGCGGCATGGAGGAACGGCTTTGAC
CAGTGCGATTACGGGTGGCTGTCGGATGCCAGCGTGCGCCACCCTGTGACTGTGGCCAGGGCCCAGTG
TGGAGGTGGTCTACTTGGGGTGAGAACCCTGTATCGTTTTGAGAACCAGACAGGCTrCCCTCCCCCTG
ATAGCAGATTTGATGCCTACTGCTTTAAACGACCTGATCGCTGCAAAATGAACCCGTGCCTTAACGGA
GGCACCTGTTATCCTACTGAAACTTCCTACGTATGCACCTGTGTGCCAGGATACAGCGGAGACCAGTG
TGAACTTGATTTTGATGAATGTCACTCTAATCCCTGTCGTAATGGAGCCACTTGTGTTGATGGTTTTAA
CACATTCAGGTGCCTCTGCCTTCCAAGTTATGTTGGTGCACTTTGTGAGCAAGATACCGAGACATGTGA
CTATGGCTGGCACAAATTCCAAGGGCAGTGCTACAAATACTTTGCCCATCGACGCACATGGGATGCAG
CTGAACGGGAATGCCGTCTGCAGGGTGCCCATCTCACAAGCATCCTGTCTCACGAAGAACAAATGTTT
GTTAATCGTGTGGGCCATGATTATCAGTGGATAGGCCTCAATGACAAGATGTTTGAGCATGACTTCCG
TTGGACTGATGGCAGCACACTGCAATACGAGAATTGGAGACCCAACCAGCCAGACAGCTTCTTTTCTG
CTGGAGAAGACTGTGTTGTAATCATTTGGCATGAGAATGGCCAGTGGAATGATGTTCCCTGCAATTAC
CATCTCACCTATACGTGCAAGAAAGGAACAGTCGCTTGCGGCCAGCCCCTGTTGTAGAAAATGCCAA
GACCTTTGGAAAGATGAAACCTCGTTATGAAATCAACTCCCTGATTAGATACCACTGCAAAGATGGTT
TCATTCAACGTCACCTTCCAACTATCCGGTGCTTAGGAAATGGAAGATGGGCTATACCTAAAATTACCT
GCATGAACCGTAAGTGGTCCTTTAGAAAGAATGGACTACCGTGCTATAACAACTACTAGA
SEQ ID NO: 22:
STAR, UCOE, SFFV, optGPLuc, hsoptV3 nucleotide sequence
CTGCAGCTAGACAGCGTCCTACAGGTGCTTTACGTGTGAAATTTTGGTTTTTATGGTGCTTTGCTCTGA
GCCAGCCCACCAGTTTGGAATGACTCCTTTTTATGACTTGAATTTTCAAGTATAAAGTCTAGTGCTAAA
TTTAATTTGAACAACTGTATAGTTTTTGCTGGTTGGGGGAAGGAAAAAAAATGGTGGCAGTGTTTTTTT
CAGAATTAGAAGTGAAATGAAAACTTGTTGTGTGTGAGGATTTCTAATGACATGTGGTGGTTGCATAC
TGAGTGAAGCCGGTGAGCATTCTGCCATGTCACCCCCTCGTGCTCAGTAATGTACTTTACAGAAATCCT
AAACTCAAAAGATTGATATAAACCATGCTTCTTGTGTATATCCGGTCTCTTCTCTGGGTAGTCTCACTC
AGCCTGCATTTCTGCCAACGCGTGTGGCATCTGAAGCACCACCAGCGAGCGAGAGCTAGAGAGAAGG
AAAGCCACCGACTTCACCGCCTCCGAGCTGCTCCGGGTCGCGGGTCTGCAGCGTCTCCGGCCCTCCGC
GCCTACAGCTCAAGCCACATCCGAAGGGGGAGGGAGCCGGGAGCTGCGCGCGGGGCCGCCGGGGGG
AGGGGTGGCACCGCCCACGCCGGGCGGCCACGAAGGGCGGGGCAGCGGGCGCGCGCCCGGCGGGGG
GAGGGGCCGCGCGCCGCGCCCGCTGGGAATTGGGGCCCTAGGGGAGGGCGGAGGCGCCGACGACCG
CGGCACTTACCGTTCGCGGCGTGGCGCCCGGTGGTCCCCAAGGGGAGGGAAGGGGGAGGCGGGGCGA
GGACAGTGACCGGAGTCTCCTCAGCGGTGGCTTTTCTGCTTGGCAGCCTCAGCGGCTGGCGCCAAAAC
CGGACTCCGCCCACTTCCTCGCCCCTGCGGTGCGAGGGTGTGGAATCCTCCAGACGCTGGGGGAGGGG
GAGTTGGGAGCTTAAAAACTAGTACCCCTTTGGGACCACTTTCAGCAGCGAACTCTCCTGTACACCAG
GGGTCAGTTCCACAGACGCGGGCCAGGGGTGGGTCATTGCGGCGTGAACAATAATTTGACTAGAAGTT
GATTCGGGTGTTTCCGGAATTCCTAGCTGCAGTAACGCCATTTTGCAAGGCATGGAAAAATACCAAAC
CAAGAATAGAGAAGTTCAGATCAAGGGCGGGTACATGAAAATAGCTAACGTTGGGCCAAACAGGATA
```

-continued

```
TCTGCGGTGAGCAGTTTCGGCCCCGGCCCGGGGCCAAGAACAGATGGTCACCGCAGTTTCGGCCCCGG

CCCGAGGCCAAGAACAGATGGTCCCCAGATATGGCCCAACCCTCAGCAGTTTCTTAAGACCCATCAGA

TGTTTCCAGGCTCCCCCAAGGACCTGAAATGACCCTGCGCCTTATTTGAATTAACCAATCAGCCTGCTT

CTCGCTTCTGTTCGCGCGCTTCTGCTTCCCGAGCTCTATAAAAGAGCTCACAACCCCTCACTCGGCGCG

CCAGTCCTCCGACAGACTGAGTCATGGGCGTGAAGGTGCTGTTCGCCCTGATCTGCATCGCCGTGGCC

GAGGCCTTGCACAAAGTAAAAGTTGGAAAGAGTCCGCCTGTGAGGGGATCACTGAGTGGCAAAGTGT

CACTGCCCTGTCACTTTTCCACTATGCCAACTCTCCCACCCTCTTATAACACATCCGAGTTTCTCCGCAT

AAAGTGGTCCAAAATCGAGGTAGACAAGAACGGCAAAGACCTCAAAGAGACTACTGTGCTCGTGGCA

CAGAATGGAAACATCAAGATTGGGCAGGACTATAAGGGTCGTGTCAGCGTGCCAACTCACCCAGAAG

CCGTTGGCGACGCCAGCTTGACAGTTGTGAAACTGCTTGCCAGCGACGCCGGACTGTATCGCTGCGAT

GTCATGTATGGTATCGAAGATACACAGGACACAGTGAGCCTGACCGTGGATGGGGTAGTCTTTCACTA

TAGAGCCGCCACATCTAGATACACCCTGAATTTTGAGGCAGCTCAGAAGGCCTGCTTGGATGTGGGCG

CCGTGATTGCAACGCCTGAGCAACTGTTCGCCGCCTACGAAGATGGATTCGAGCAGTGTGACGCAGGA

TGGCTGGCCGATCAGACCGTTCGGTACCCTATCAGAGCTCCCCGAGTAGGGTGCTATGGCGATAAAAT

GGGCAAGGCTGGCGTGAGGACCTACGGCTTCAGGTCACCTCAGGAAACCTATGACGTGTACTGTTATG

TGGACCACTTGGATGGCGATGTCTTTCATCTCACGGTCCCCTCTAAATTTACGTTCGAAGAAGCGGCCA

AGGAGTGCGAGAATCAGGACGCCAGGCTGGCAACTGTGGGAGAACTGCAGGCTGCCTGGCGCAATGG

GTTCGACCAGTGCGATTATGGGTGGCTGAGTGACGCTTCTGTCCGCCATCCCGTTACCGTCGCTAGGGC

GCAATGCGGTGGAGGACTTCTGGGCGTTAGAACCCTCTATCGCTTTGAGAATCAGACTGGGTTTCCGC

CACCAGATTCTCGGTTCGATGCGTATTGCTTCAAACGTCCCGACCGTTGTAAGATGAACCCATGCCTTA

ACGGCGGAACCTGTTACCCAACAGAAACGAGCTATGTTTGCACCTGTGTGCCCGGGTACTCAGGCGAC

CAGTGTGAACTGGACTTTGACGAATGCCACTCTAATCCGTGCAGAAATGGCGCTACGTGCGTGGACGG

GTTCAACACTTTCCGATGTCTGTGTCTGCCTAGCTACGTCGGGGCACTGTGCGAGCAGGATACCGAAA

CCTGTGATTACGGGTGGCACAAGTTTCAGGGTCAGTGCTACAAGTACTTTGCGCATAGAAGAACATGG

GATGCCGCAGAGCGAGAGTGTAGGCTGCAAGGGGCTCATCTGACATCCATCCTTAGCCATGAGGAAC

AAATGTTTGTCAACAGAGTTGGCCACGACTATCAATGGATCGGCTTGAATGACAAGATGTTCGAGCAC

GACTTCAGGTGGACAGACGGCTCCACCCTCCAGTACGAGAACTGGAGGCCTAATCAGCCCGACAGCTT

CTTCAGTGCAGGAGAGGATTGCGTAGTCATAATCTGGCACGAAAACGGTCAGTGGAACGATGTGCCAT

GCAACTATCATCTGACCTACACATGCAAGAAAGGTACTGTGGCCTGTGGCCAACCTCCTGTCGTGGAG

AATGCCAAAACATTTGGTAAGATGAAACCCAGGTACGAGATTAACTCCCTTATTCGCTACCACTGTAA

GGATGGTTTCATTCAACGGCATCTGCCCACTATTCGGTGCCTGGGAAATGGGCGGTGGGCAATTCCGA

AGATAACCTGTATGAACCCCTCTGCTTACCAGCGAACCTACTCCATGAAGTACTTCAAGAACTCCAGTT

CAGCTAAAGACAATAGCATCAACACTTCAAAACACGATCATCGCTGGAGCCGGCGGTGGCAGGAAAG

CAGACGG

SEQ ID NO: 23:
MAR, STAR, UCOE, SFFV, GFPz, P2A, GPLuc, hsoptV3, HA tag, Twin-STREP
nucleotide sequence
AGAAAGGGCATAAACTGCTTTATCCAGTGTTATATTAAAAGCTTAATGTATATAATCTTTTAGAGGTAA

AATCTACAGCCAGCAAAAGTCATGGTAAATATTCTTTGACTGAACTCTCACTAAACTCCTCTAAATTAT

ATGTCATATTAACTGGTTAAATTAATATAAATTTGTGACATGACCTTAACTGGTTAGCTTAGGATATTTT

TCTTCATGCAAAATATGACTAATAATAATTTAGCACAAAATATTTCCCAATACTTTAATTCTGTGAT

AGAAAAATGTTTAACTCAGCTACTATAATCCCATAATTTTGAAAACTATTTATTAGCTTTTGTGTTTGA
```

```
CCCTTCCCTAGCCAAAGGCAACTATTTAAGGACCCTTTAAAACTCTTGAAACTACTTTAGAGTCATTAA

GTTCTGCAGCTAGACAGCGTCCTACAGGTGCTTTACGTGTGAAATTTTGGTTTTTATGGTGCTTTGCTCT

GAGCCAGCCCACCAGTTTGGAATGACTCCTTTTTATGACTTGAATTTTCAAGTATAAAGTCTAGTGCTA

AATTTAATTTGAACAACTGTATAGTTTTTGCTGGTTGGGGGAAGGAAAAAAAATGGTGGCAGTGTTTT

TTTCAGAATTAGAAGTGAAATGAAAACTTGTTGTGTGTGAGGATTTCTAATGACATGTGGTGGTTGCAT

ACTGAGTGAAGCCGGTGAGCATTCTGCCATGTCACCCCTCGTGCTCAGTAATGTACTTTACAGAAATC

CTAAACTCAAAAGATTGATATAAACCATGCTTCTTGTGTATATCCGGTCTCTTCTCTGGGTAGTCTCAC

TCAGCCTGCATTTCTGCCAACGCGTGTGGCATCTGAAGCACCACCAGCGAGCGAGAGCTAGAGAGAA

GGAAAGCCACCGACTTCACCGCCTCCGAGCTGCTCCGGGTCGCGGGTCTGCAGCGTCTCCGGCCCTCC

GCGCCTACAGCTCAAGCCACATCCGAAGGGGGAGGGAGCCGGGAGCTGCGCGCGGGGCCGCCGGGGG

GAGGGGTGGCACCGCCCACGCCGGGCGGCCACGAAGGGCGGGGCAGCGGGCGCGCGCCCGGCGGGG

GGAGGGGCCGCGCGCCGCGCCCGCTGGGAATTGGGGCCCTAGGGGCAGGGCGGAGGCGCCGACGACC

GCGGCACTTACCGTTCGCGGCGTGGCGCCCGGTGGTCCCCAAGGGGAGGGAAGGGGGAGGCGGGGCG

AGGACAGTGACCGGAGTCTCCTCAGCGGTGGCTTTTCTGCTTGGCAGCCTCAGCGGCTGGCGCCAAAA

CCGGACTCCGCCCACTTCCTCGCCCCTGCGGTGCGAGGGTGTGGAATCCTCCAGACGCTGGGGGAGGG

GGAGTTGGGAGCTTAAAAACTAGTACCCCTTTGGGACCACTTTCAGCAGCGAACTCTCCTGTACACCA

GGGGTCAGTTCCACAGACGCGGGCCAGGGGTGGGTCATTGCGGCGTGAACAATAATTTGACTAGAAG

TTGATTCGGGTGTTTCCGGAATTCCTAGCTGCAGTAACGCCATTTTGCAAGGCATGGAAAAATACCAA

ACCAAGAATAGAGAAGTTCAGATCAAGGGCGGGTACATGAAAATAGCTAACGTTGGGCCAAACAGGA

TATCTGCGGTGAGCAGTTTCGGCCCCGGCCCGGGGCAAGAACAGATGGTCACCGCAGTTTCGGCCCC

GGCCCGAGGCCAAGAACAGATGGTCCCCAGATATGGCCCAACCCTCAGCAGTTTCTTAAGACCCATCA

GATGTTTCCAGGCTCCCCCAAGGACCTGAAATGACCCTGCGCCTTATTTGAATTAACCAATCAGCCTGC

TTCTCGCTTCTGTTCGCGCGCTTCTGCTTCCCGAGCTCTATAAAAGAGCTCACAACCCCTCACTCGGCG

CGCCAGTCCTCCGACAGACTGAGTCGCCCGCTCGAGGTCGACGGTATCGATAAGCTTGCCACCATGGT

GAGCAAGGGCGAGGAGCTGTTCACCGGGGTGGTGCCCATCCTGGTCGAGCTGGACGGCGACGTAAAC

GGCCACAAGTTCAGCGTGTCCGGCGAGGGCGAGGGCGATGCCACCTACGGCAAGCTGACCCTGAAGT

TCATCTGCACCACCGGCAAGCTGCCCGTGCCCTGGCCCACCCTCGTGACCACCCTGACCTACGGCGTG

CAGTGCTTCAGCCGCTACCCCGACCACATGAAGCAGCACGACTTCTTCAAGTCCGCCATGCCCGAAGG

CTACGTCCAGGAGCGCACCATCTTCTTCAAGGACGACGGCAACTACAAGACCCGCGCCGAGGTGAAGT

TCGAGGGCGACACCCTGGTGAACCGCATCGAGCTGAAGGGCATCGACTTCAAGGAGGACGGCAACAT

CCTGGGGCACAAGCTGGAGTACAACTACAACAGCCACAACGTCTATATCATGGCCGACAAGCAGAAG

AACGGCATCAAGGTGAACTTCAAGATCCGCCACAACATCGAGGACGGCAGCGTGCAGCTCGCCGACC

ACTACCAGCAGAACACCCCCATCGGCGACGGCCCCGTGCTGCTGCCCGACAACCACTACCTGAGCACC

CAGTCCGCCCTGAGCAAAGACCCCAACGAGAAGCGCGATCACATGGTCCTGCTGGAGTTCGTGACCGC

CGCCGGGATCACTCTCGGCATGGACGAGCTGTACAAGCATATGGCCAAGTTGACCAGTGCCGTTCCGG

TGCTCACCGCGCGCGACGTCGCCGGAGCGGTCGAGTTCTGGACCGACCGGCTCGGGTTCTCCCGGGAC

TTCGTGGAGGACGACTTCGCCGGTGTGGTCCGGGACGACGTGACCCTGTTCATCAGCGCGGTCCAGGA

CCAGGTGGTGCCGGACAACACCCTGGCCTGGGTGTGGGTGCGCGGCCTGGACGAGCTGTACGCCGAGT

GGTCGGAGGTCGTGTCCACGAACTTCCGGGACGCCTCCGGGCCGGCCATGACCGAGATCGGCGAGCA

GCCGTGGGGGCGGGAGTTCGCCCTGCGCGACCCGGCCGGCAACTGCGTGCACTTCGTGGCCGAGGAG
```

```
CAGGACGGAAGCGGAGCTACTAACTTCAGCCTGCTGAAGCAGGCTCGTGACGTGGAGGAGAATCCCG

GCCCTAGCATGGGCGTGAAGGTGCTGTTCGCCCTGATCTGCATCGCCGTGGCCGAGGCCTTGCACAAA

GTAAAAGTTGGAAAGAGTCCGCCTGTGAGGGGATCACTGAGTGGCAAAGTGTCACTGCCCTGTCACTT

TTCCACTATGCCAACTCTCCCACCCTCTTATAACACATCCGAGTTTCTCCGCATAAAGTGGTCCAAAAT

CGAGGTAGACAAGAACGGCAAAGACCTCAAAGAGACTACTGTGCTCGTGGCACAGAATGGAAACATC

AAGATTGGGCAGGACTATAAGGGTCGTGTCAGCGTGCCAACTCACCCAGAAGCCGTTGGCGACGCCA

GCTTGACAGTTGTGAAACTGCTTGCCAGCGACGCCGGACTGTATCGCTGCGATGTCATGTATGGTATC

GAAGATACACAGGACACAGTGAGCCTGACCGTGGATGGGGTAGTCTTTCACTATAGAGCCGCCACATC

TAGATACACCCTGAATTTTGAGGCAGCTCAGAAGGCCTGCTTGGATGTGGGCGCCGTGATTGCAACGC

CTGAGCAACTGTTCGCCGCCTACGAAGATGGATTCGAGCAGTGTGACGCAGGATGGCTGGCCGATCAG

ACCGTTCGGTACCCTATCAGAGCTCCCCGACTAGGGTGCTATGGCGATAAAATGGGCAAGGCTGGCGT

GAGGACCTACGGCTTCAGGTCACCTCAGGAAACCTATGACGTGTACTGTTATGTGGACCACTTGGATG

GCGATGTCTTTCATCTCACGGTCCCCTCTAAATTTACGTTCGAAGAAGCGGCCAAGGAGTGCGAGAAT

CAGGACGCCAGGCTGGCAACTGTGGGAGAACTGCAGGCTGCCTGGCGCAATGGGTTCGACCAGTGCG

ATTATGGGTGGCTGAGTGACGCTTCTGTCCGCCATCCCGTTACCGTCGCTAGGGCGCAATGCGGTGGA

GGACTTCTGGGCGTTAGAACCCTCTATCGCTTTGAGAATCAGACTGGGTTTCCGCCACCAGATTCTCGG

TTCGATGCGTATTGCTTCAAACGTCCCGACCGTTGTAAGATGAACCCATGCCTTAACGGCGGAACCTGT

TACCCAACAGAAACGAGCTATGTTTGCACCTGTGTGCCCGGGTACTCAGGCGACCAGTGTGAACTGGA

CTTTGACGAATGCCACTCTAATCCGTGCAGAAATGGCGCTACGTGCGTGGACGGGTTCAACACTTTCC

GATGTCTGTGTCTGCCTAGCTACGTCGGGGCACTGTGCGAGCAGGATACCGAAACCTGTGATTACGGG

TGGCACAAGTTTCAGGGTCAGTGCTACAAGTACTTTGCGCATAGAAGAACATGGGATGCCGCAGAGCG

AGAGTGTAGGCTGCAAGGGGCTCATCTGACATCCATCCTTAGCCATGAGGAACAAATGTTTGTCAACA

GAGTTGGCCACGACTATCAATGGATCGGCTTGAATGACAAGATGTTCGAGCACGACTTCAGGTGGACA

GACGGCTCCACCCTCCAGTACGAGAACTGGAGGCCTAATCAGCCCGACAGCTTCTTCAGTGCAGGAGA

GGATTGCGTAGTCATAATCTGGCACGAAAACGGTCAGTGGAACGATGTGCCATGCAACTATCATCTGA

CCTACACATGCAAGAAAGGTACTGTGGCCTGTGGCCAACCTCCTGTCGTGGAGAATGCCAAAACATTT

GGTAAGATGAAACCCAGGTACGAGATTAACTCCCTTATTCGCTACCACTGTAAGGATGGTTTCATTCA

ACGGCATCTGCCCACTATTCGGTGCCTGGGAAATGGGCGGTGGGCAATTCCGAAGATAACCTGTATGA

ACCCCTCTGCTTACCAGCGAACCTACTCCATGAAGTACTTCAAGAACTCCAGTTCAGCTAAAGACAAT

AGCATCAACACTTCAAAACACGATCATCGCTGGAGCCGGCGGTGGCAGGAAAGCAGACGGTATCCTT

ATGACGTGCCTGATTACGCTTGGAGCCACCCCCAGTTCGAGAAGGGTGGAGGTTCTGGCGGTGGATCG

GGAGGTTCAGCGTGGAGCCACCCGCAGTTCGAGAAAT

SEQ ID NO: 24:
STAR, TRE, hsoptV3, HA tag, Twin-STREP, UCOE, SFFV, rtTA nucleotide
sequence
AGAAAGGGCATAAACTGCTTTATCCAGTGTTATATTAAAAGCTTAATGTATATAATCTTTTAGAGGTAA

AATCTACAGCCAGCAAAAGTCATGGTAAATATTCTTTGACTGAACTCTCACTAAACTCCTCTAAATTAT

ATGTCATATTAACTGGTTAAATTAATATAAATTTGTGACATGACCTTAACTGGTTAGGTAGGATATTTT

TCTTCATGCAAAAATATGACTAATAATAATTTAGCACAAAAATATTTCCCAATACTTTAATTCTGTGAT

AGAAAAATGTTTAACTCAGCTACTATAATCCCATAATTTTGAAAACTATTTATTAGCTTTTGTGTTTGA

CCCTTCCCTAGCCAAAGGCAACTATTTAAGGACCCTTTAAAACTCTTGAAACTACTTTAGAGTCATTAA

GTTCTGCAGCTAGACAGCGTCCTACAGGTGCTTTACGTGTGAAATTTTGGTTTTTATGGTGCTTTGCTCT
```

-continued

```
GAGCCAGCCCACCAGTTTGGAATGACTCCTTTTTATGACTTGAATTTTCAAGTATAAAGTCTAGTGCTA
AATTTAATTTGAACAACTGTATAGTTTTTGCTGGTTGGGGGAAGGAAAAAAAATGGTGGCAGTGTTTT
TTTCAGAATTAGAAGTCAAATGAAAACTTGTTGTGTGTGAGGATTTCTAATGACATGTGGTGGTTGCAT
ACTGAGTGAAGCCGGTGAGCATTCTGCCATGTCACCCCCTCGTGCTCAGTAATGTACTTTACAGAAATC
CTAAACTCAAAAGATTGATATAAACCATGCTTCTTGTGTATATCCGGTCTCTTCTCTGGGTAGTCTCAC
TCAGCCTGCATTTCTGCCACGAGTTTACTCCCTATCAGTGATAGAGAACGTATCTCGAGTTTACTCCCT
ATCAGTGATAGAGAACGATGTCGAGTTTACTCCCTATCAGTGATAGAGAACGTATGTCGAGTTTACTC
CCTATCAGTGATAGAGAACGTATGTCGAGTTTACTCCCTATCAGTGATAGAGAACGTATGTCGAGTTT
ATCCCTATCAGTGATAGAGAACGTATGTCGAGTTTACTCCCTATCAGTGATAGAGAACGTATGTCGAG
GTAGGCGTGTACGGTGGGAGGCCTATATAAGCAGAGCTCGTTTAATGGGCGTGAAGGTGCTGTTCGCC
CTGATCTGCATCGCCGTGGCCGAGGCCTTGCACAAAGTAAAAGTTGGAAAGAGTCCGCCTGTGAGGGG
ATCACTGAGTGGCAAAGTGTCACTGCCCTGTCACTTTTCCACTATGCCAACTCTCCCACCCTCTTATAA
CACATCCGAGTTTCTCCGCATAAAGTGGTCCAAAATCGAGGTAGACAAGAACGGCAAAGACCTCAAA
GAGACTACTGTGCTCGTGGCACAGAATGGAAACATCAAGATTGGGCAGGACTATAAGGGTCGTGTCA
GCGTGCCAACTCACCCAGAAGCCGTTGGCGACGCCAGCTTGACAGTTGTGAAACTGCTTGCCAGCGAC
GCCGGACTGTATCGCTGCGATGTCATGTATGGTATCGAAGATACACAGGACACAGTGAGCCTGACCGT
GGATGGGGTAGTCTTTCACTATAGAGCCGCCACATCTAGATACACCCTGAATTTTGAGGCAGCTCAGA
AGGCCTGCTTGGATGTGGGCGCCGTGATTGCAACGCCTGAGCAACTGTTCGCCGCCTACGAAGATGGA
TTCGAGCAGTGTGACGCAGGATGGCTGGCCGATCAGACCGTTCGGTACCCTATCAGAGCTCCCCGAGT
AGGGTGCTATGGCGATAAAATGGGCAAGGCTGGCGTGAGGACCTACGGCTTCAGGTCACCTCAGGAA
ACCTATGACGTGTACTGTTATGTGGACCACTTGGATGGCGATGTCTTTCATCTCACGGTCCCCTCTAAA
TTTACGTTCGAAGAAGCGGCCAAGGAGTGCGAGAATCAGGACGCCAGGCTGGCAACTGTGGGAGAAC
TGCAGGCTGCCTGGCGCAATGGGTTCGACCAGTGCGATTATGGGTGGCTGAGTGACGCTTCTGTCCGC
CATCCCGTTACCGTCGCTAGGGCGCAATGCGGTGGAGGACTTCTGGGCGTTAGAACCCTCTATCGCTTT
GAGAATCAGACTGGGTTTCCGCCACCAGATTCTCGGTTCGATGCGTATTGCTTCAAACGTCCCGACCGT
TGTAAGATGAACCCATGCCTTAACGGCGGAACCTGTTACCCAACAGAAACGAGCTATGTTTGCACCTG
TGTGCCCGGGTACTCAGGCGACCAGTGTGAACTGGACTTTGACGAATGCCACTCTAATCCGTGCAGAA
ATGGCGCTACGTGCGTGGACGGGTTCAACACTTTCCGATGTCTGTGTCTGCCTAGCTACGTCGGGGCAC
TGTGCGAGCAGGATACCGAAACCTGTGATTACGGGTGGCACAAGTTTCAGGGTCAGTGCTACAAGTAC
TTTGCGCATAGAAGAACATGGGATGCCGCAGAGCGAGAGTGTAGGCTGCAAGGGGCTCATCTGACAT
CCATCCTTAGCCATGAGGAACAAATGTTTGTCAACAGAGTTGGCCACGACTATCAATGGATCGGCTTG
AATGACAAGATGTTCGAGCACGACTTCAGGTGGACAGACGGCTCCACCCTCCAGTACGAGAACTGGA
GGCCTAATCAGCCCGACAGCTTCTTCAGTGCAGGAGAGGATTGCGTAGTCATAATCTGGCACGAAAAC
GGTCAGTGGAACGATGTGCCATGCAACTATCATCTGACCTACACATGCAAGAAAGGTACTGTGGCCTG
TGGCCAACCTCCTGTCGTGGAGAATGCCAAAACATTTGGTAAGATGAAACCCAGGTACGAGATTAACT
CCCTTATTCGCTACCACTGTAAGGATGGTTTCATTCAACGGCATCTGCCCACTATTCGGTGCCTGGGAA
ATGGGCGGTGGGCAATTCCGAAGATAACCTGTATGAACCCCTCTGCTTACCAGCGAACCTACTCCATG
AAGTACTTCAAGAACTCCAGTTCAGCTAAAGACAATAGCATCAACACTTCAAAACACGATCATCGCTG
GAGCCGGCGGTGGCAGGAAAGCAGACGGCGCGTGTGGCATCTGAAGCACCACCAGCGAGCGAGAGCT
AGAGAGAAGGAAAGCCACCGACTTCACCGCCTCCGAGCTGCTCCGGGTCGCGGGTCTGCAGCGTCTCC
GGCCCTCCGCGCCTACAGCTCAAGCCACATCCGAAGGGGGAGGGAGCCGGGAGCTGCGCGCGGGGCC
```

-continued

```
GCCGGGGGGAGGGGTGGCACCGCCCACGCCGGGCGGCCACGAAGGGCGGGGCAGCGGGCGCGCGCC
CGGCGGGGGGAGGGGCCGCGCGCCGCGCCCGCTGGGAATTGGGGCCCTAGGGGGAGGGCGGAGGCG
CCGACGACCGCGGCACTTACCGTTCGCGGCGTGGCGCCCGGTGGTCCCCAAGGGGAGGGAAGGGGGA
GGCGGGGCGAGGACAGTGACCGGAGTCTCCTCAGCGGTGGCTTTTCTGCTTGGCAGCCTCAGCGGCTG
GCGCCAAAACCGGACTCCGCCCACTTCCTCGCCCCTGCGGTGCGAGGGTGTGGAATCCTCCAGACGCT
GGGGGAGGGGGAGTTGGGAGCTTAAAAACTAGTACCCCTTTGGGACCACTTTCAGCAGCGAACTCTCC
TGTACACCAGGGGTCAGTTCCACAGACGCGGGCCAGGGGTGGGTCATTGCGGCGTGAACAATAATTTG
ACTAGAAGTTGATTCGGGTGTTTCCGGTATCCTTATGACGTGCCTGATTACGCTTGGAGCCACCCCCAG
TTCGAGAAGGGTGGAGGTTCTGGCGGTGGATCGGGAGGTTCAGCGTGGAGCCACCCGCAGTTCGAGA
AATCTAGCTGCAGTAACGCCATTTTGCAAGGCATGGAAAAATACCAAACCAAGAATAGAGAAGTTCA
GATCAAGGGCGGGTACATGAAAATAGCTAACGTTGGGCCAAACAGGATATCTGCGGTGAGCAGTTTC
GGCCCCGGCCCGGGGCCAAGAACAGATGGTCACCGCAGTTTCGGCCCCGGCCCGAGGCCAAGAACAG
ATGGTCCCCAGATATGGCCCAACCCTCAGCAGTTTCTTAAGACCCATCAGATGTTTCCAGGCTCCCCCA
AGGACCTGAAATGACCCTGCGCCTTATTTGAATTAACCAATCAGCCTGCTTCTCGCTTCTGTTCGCGCG
CTTCTGCTTCCCGAGCTCTATAAAAGAGCTCACAACCCCTCACTCGGCGCGCCAGTCCTCCGACAGACT
GAGTCATGTCCAGACTGGACAAGAGCAAAGTCATAAACGGAGCTCTGGAATTACTCAATGGTGTCGGT
ATCGAAGGCCTGACGACAAGGAAACTCGCTCAAAAGCTGGGAGTTGAGCAGCCTACCCTGTACTGGC
ACGTGAAGAACAAGCGGGCCCTGCTCGATGCCCTGCCAATCGAGATGCTGGACAGGCATCATACCCAC
TTCTGCCCCCTGGAAGGCGAGTCATGGCAAGACTTTCTGCGGAACAACGCCAAGTCATACCGCTGTGC
TCTCCTCTCACATCGCGACGGGGCTAAAGTGCATCTCGGCACCCGCCCAACAGAGAAACAGTACGAAA
CCCTGGAAAATCAGCTCGCGTTCCTGTGTCAGCAAGGCTTCTCCCTGGAGAACGCACTGTACGCTCTGT
CCGCCGTGGGCCACTTTACACTGGGCTGCGTATTGGAGGAACAGGAGCATCAAGTAGCAAAAGAGGA
AAGAGAGACACCTACCACCGATTCTATGCCCCCACTTCTGAGACAAGCAATTGAGCTGTTCGACCGGC
AGGGAGCCGAACCTGCCTTCCTTTTCGGCCTGGAACTAATCATATGTGGCCTGGAGAAACAGCTAAAG
TGCGAAAGCGGCGGGCCGACCGACGCCCTTGACGATTTTGACTTAGACATGCTCCCAGCCGATGCCCT
TGACGACTTTGACCTTGATATGCTGCCTGCTGACGCTCTTGACGATTTTGACCTTGACATGCTCCCCGG
G
```

SEQ ID NO: 25:
Consensus *Gaussia princeps* luciferase signal peptide
nucleotide sequence (AY015993.1)
ATGGGAGTGAAAGTTCTTTTTGCCCTTATTTGTATTGCTGTGGCCGAGGCC SEQ ID NO: 26:
Codon-optimized *Gaussia princeps* luciferase signal peptide
nucleotide sequence
ATGGGCGTGAAGGTGCTGTTCGCCCTGATCTGCATCGCCGTGGCCGAGGCC Percent Identity Matrix—created by Clustal2.1—Sequences are SEQ ID NOs:2-8 as compared to SEQ ID NO:2

| | | | | | | | |
|---|---|---|---|---|---|---|---|
| 1: Rat | 100.00 | 97.32 | 92.76 | 92.91 | 92.13 | 92.91 | 93.86 |
| 2: Mouse | 97.32 | 100.00 | 92.91 | 93.07 | 92.28 | 93.07 | 94.02 |
| 3: Human | 92.76 | 92.91 | 100.00 | 98.58 | 93.86 | 94.65 | 95.43 |
| 4: Monkey | 92.91 | 93.07 | 98.58 | 100.00 | 93.39 | 94.49 | 95.28 |
| 5: Cow | 92.13 | 92.28 | 93.86 | 93.39 | 100.00 | 96.23 | 94.81 |
| 6: Pig | 92.91 | 93.07 | 94.65 | 94.49 | 96.23 | 100.00 | 96.54 |
| 7: Dog | 93.86 | 94.02 | 95.43 | 95.28 | 94.81 | 96.54 | 100.00 |

% Nucleic Acid Sequence Identity compared to human created using BLASTN-sequences are SEQ ID Nos: 11, and 14-19 compared to SEQ ID NO:11

| | |
|---|---|
| Monkey | 98% |
| Dog | 91% |
| Pig | 91% |
| Cow | 91% |
| Mouse | 89% |
| Rat | 89% |

Statements of the Invention

1. A method for increasing production of soluble rV3 comprising the steps of providing an expression vector comprising an expression cassette, the cassette further comprising cDNA sequences coding for i. recombinant V3 (rV3), ii. an efficient signal peptide, operatively linked to, contiguous with and upstream of the rV3 sequence, iii. a strong promoter, operatively linked to and upstream of the rV3 sequence, and iv. a chromatin function modifying element, further comprising a universal chromatin opening element (UCOE) operatively linked to and upstream of the strong promoter sequence, and transfecting a host cell or tissue with an expression vector, wherein the host cell or tissue is capable of N-glycosylating rV3 at one or more glycosylation sites, and wherein N-glycosylation of that one or more sites increases the levels of rV3 secretion and/or solubility of the expressed rV3 in aqueous solution, as compared to levels of secretion and/or solubility of a non-N-glycosylated form of the rV3 protein.

2. The method of statement 1, wherein the cDNA sequence coding for V3 codes for human rV3.

3. The method of statement 2, wherein the cDNA sequence coding for humanV3 comprises codons optimized for expression of human rV3.

4. The method of statement 1, wherein the cDNA sequence has at least about 85%, at least about 90%, or at least about 95% sequence identity to at least one of SEQ ID NOs: 12, 14-21.

5. The method of statement 2, wherein the signal peptide and contiguous V3 cDNA have at least about 85%, at least about 90%, or at least about 95% sequence identity to at least one of SEQ ID NOs: 11 and 13.

6. The method of statement 1, wherein the strong promoter is SFFV, CMV, EF1, or TRE.

7. The method of statement 2 or 3, further comprising the step of isolating and purifying the expressed rV3 from the host cell or organism.

8. The method of statement 2, wherein the signal peptide is a *Gaussia princeps* luciferase signal peptide.

9. The method of statement 7, wherein the signal peptide has a sequence at least about 85%, or at least about 90%, or at least about 95% sequence identity to SEQ ID NOs 25 or 26.

10. The method of statement 1, wherein the expression cassette further comprises a cDNA sequence coding for a selection marker operatively positioned and linked to and downstream of the promoter cDNA sequence in the expression cassette.

11. The method of statement 10, wherein the selection marker is one that confers antibiotic and/or drug resistance and/or fluorescence.

12. The method of statement 1, wherein the expression cassette further comprises cDNA coding for an additional chromatin function modifying element operatively positioned in the cassette and upstream of the promoter, 13. The method of statement 12, wherein the additional chromatin function modifying element is one or more MAR. STAR, cHS4 and the V3 cDNA is human.

14. The method of statement 13, wherein the expression cassette further comprises a cDNA sequence coding for a purification tag and/or an identification tag operatively and contiguously linked to the rV3 cDNA.

15. The method of statement 14, wherein the purification tag is Twin-Strep-Tag®

16. The method of statement 14, wherein the identification tag is a Hemagglutinin tag.

17. The method of statement 8, wherein the expression cassette is bicistronic and further comprises a cDNA sequence coding for a self-cleaving peptide operatively linked to and downstream of the selection marker.

18. The method of statement 17, wherein the strong promoter is SFFV, CMV, EF1 or TRE.

19. The method of statement 17, wherein the self-cleaving peptide is P2A

20. The method of statement 1, wherein the host cells are non-adherent and grown in suspension culture in animal protein-free media.

21. The method of statement 19, wherein the additional elements are MAR and STAR.

22. The expression vector of statements 1-19.

23. The method of statement 1, wherein the rV3 encoded for has at least about 85%, at least about 90%, or at least about 95% amino acid sequence identity with at least one of the SEQ ID NO. 2-9.

24. The method of statement 20, wherein the host cells are mammalian.

25. The method of statement 20, wherein the pH of the suspension culture is not at or near the protein's isoelectric point, and further comprising the step of isolating the recombinant mammalian V3 protein.

26. The method of statement 24, wherein the host cells are HEK cells.

27. The expression cassette of statements 1-17.

28. A composition comprising the rV3 of statement 23 in pharmaceutical acceptable carrier.

29. The isolated rV3 protein of the method of statement 25, wherein the protein is stored in aqueous solution.

30. The isolated rV3 protein of the method of statement 25, wherein the protein is lyophilized.

31. The isolated rV3 protein of the method of statement 25, wherein the protein is in frozen solution.

32. The isolated rV3 protein of the method of statement 7, wherein the protein is detectably labeled.

33. An isolated and purified rV3 protein obtained according to the method of statement 7 having at least about 80% purity.

34. An antibody or antigen binding fragment or derivative thereof, that binds to the recombinant protein of statement 7.

35. An rV3 expression system comprising the expression vector and the host cells or tissue transfected by the vector of statement 1.

36. The expression system of statement 35, where the host cells or tissue are mammalian.

37. The expression system of statement 36, wherein the cDNA coding for rV3 has at least about 85%, at least about 90%, or at least about 95% sequence identity with SEQ IDs 12, 14-21.

38. A nucleic acid having at least 85%, at least 90%, or at least 95% sequence identity to SEQ ID NO:13, 22, 23, or 24.

39. A composition comprising a molecular complex of a rV3 molecule, or a portion thereof, bound to or complexed to a hyaluronan molecule, or a portion thereof, capable of binding to the rV3 or rV3 portion.

40. The composition of statement 39, wherein the rV3 and hyaluronan of the complex are exogenously produced, complexed and the composition further comprises a pharmaceutically acceptable carrier.

41. The molecular complex of statement 40, wherein the secreted rV3 molecule has at least about 85%, or at least about 90%, or at least about 95% sequence identity to SEQ IDs 2-9.

42. The molecular complex of statement 39, wherein the hyaluronan or portion thereof has an average molecular weight greater than 250 kDa.

43. The molecular complex of statement 40, wherein the hyaluronan molecule comprises high molecular weight hyaluronan.

44. A composition comprising the molecular complex of statement 40, further comprising a gel, lotion, foam, cream or ointment.

45. The molecular complex of statement 40 in aqueous solution.

46. The composition of statement 41, wherein the composition comprises a cosmetic for dermal use.

47. The composition of statement 44, wherein the gel is impregnated with the hyaluronan or portion thereof.

48. The molecular complex of statement 41, further comprising a link protein bound to the complex.

49. A composition comprising the molecular complex of statement 42, wherein the composition further comprises a carrier for the complex.

50. The composition of statement 40, wherein the carrier comprises a wound dressing, biodressing or skin substitute, cellular or decellularized extracellular matrix, a synthetic or naturally derived scaffold, layer, gel or sheet.

51. A method of making an endogenous molecular complex of rV3 and hyaluronan comprising the steps of: providing an exogenously produced rV3 molecule or a portion thereof, providing a hyaluronan molecule or a portion thereof capable of binding to the rV3 or portion thereof, and complexing the rV3 or portion thereof to the hyaluronan or portion thereof under conditions favorable to the complexing the rV3 and hyaluronan.

52. The method of statement 51, wherein the method further comprises the step of combining the complex with a pharmaceutically acceptable carrier.

53. The method of statement 52, wherein the pharmaceutically acceptable carrier is gel, lotion, foam, cream or ointment.

54. A method to improve tissue healing, reduce the signs of aging, and/or treat conditions where elastic fiber formation is inadequate or disrupted comprising administering the composition of claim 40 to a subject in need thereof.

55. The method of claim 54, wherein said tissue healing improvement is a reduction in inflammation, reduction in fibrosis and/or scarring, and/or an increase in organized elastic fiber network formation.

56. The method of claim 54, wherein the administration is topical.

57. The method of claim 54, wherein the carrier comprises a wound dressing, biodressing or skin substitute, cellular or decellularized extracellular matrix, a synthetic or naturally derived scaffold, layer, gel or sheet.

58. A method to improve tissue healing, reduce the signs of aging, and/or treat conditions where elastic fiber formation is inadequate or disrupted comprising administering the composition of claim 28 to a subject in need thereof.

While illustrative embodiments/statements have been illustrated and described, it will be appreciated that various changes can be made therein without departing from the spirit and scope of the invention.

---

What is claimed is:

1. A method for increasing production of soluble rV3 comprising providing an expression vector comprising an expression cassette, the cassette further comprising cDNA sequences coding for
   recombinant V3 (rV3),
   a signal peptide, operatively linked to, contiguous with and upstream of the rV3 sequence,
   a promoter, operatively linked to and upstream of the rV3 sequence, and
   a chromatin function modifying element comprising a universal chromatin opening element (UCOE) operatively linked to and upstream of the promoter sequence,
   and transfecting a host cell or tissue with the expression vector, wherein the host cell or tissue N-glycosylates rV3 at one or more glycosylation sites, and wherein N-glycosylation of said one or more sites increases the levels of rV3 secretion and/or solubility of the expressed rV3 in aqueous solution, as compared to levels of secretion and/or solubility of a non-N-glycosylated form of the rV3 protein, wherein the host cell or tissue is selected from the group consisting of mammalian, plant, insect, yeast, fungal or bacterial cell or tissue.

2. The method of claim 1, wherein the cDNA sequence coding for V3 codes for human rV3.

3. The method of claim 2, wherein the cDNA sequence coding for human V3 comprises codons optimized for expression of human rV3.

4. The method of claim 1, wherein the cDNA sequence has at least about 85%, at least about 90%, or at least about 95% sequence identity to at least one of SEQ ID NOs: 12, 14-21.

5. The method of claim 1, wherein the rV3 encoded for has at least about 85%, at least about 90%, or at least about 95% amino acid sequence identity with at least one of the SEQ ID NO. 2-9.

6. The method of claim 1, wherein the host cell is a mammalian cell.

* * * * *